(12) United States Patent
Baker et al.

(10) Patent No.: US 8,632,980 B2
(45) Date of Patent: Jan. 21, 2014

(54) GENE EXPRESSION MARKERS FOR PREDICTION OF PATIENT RESPONSE TO CHEMOTHERAPY

(75) Inventors: Joffre B. Baker, Montara, CA (US); Wayne Cowens, Tiburon, CA (US); Kim Langone, Sunnyvale, CA (US); James Hackett, San Jose, CA (US); Drew Watson, Los Altos, CA (US); Soonmyung Paik, Pittsburgh, PA (US)

(73) Assignees: Genomic Health, Inc., Redwood City, CA (US); NSABP Foundation, Inc, Pittsburgh, PA (US)

(\*) Notice: Subject to any disclaimer, the term of this patent is extended or adjusted under 35 U.S.C. 154(b) by 4 days.

(21) Appl. No.: 13/278,934

(22) Filed: Oct. 21, 2011

(65) Prior Publication Data

US 2012/0040842 A1 Feb. 16, 2012

Related U.S. Application Data

(62) Division of application No. 12/404,268, filed on Mar. 13, 2009, now Pat. No. 8,067,178.

(60) Provisional application No. 61/069,373, filed on Mar. 14, 2008.

(51) Int. Cl.
*C12Q 1/68* (2006.01)

(52) U.S. Cl.
USPC ........................................ 435/6.14; 435/6.12

(58) Field of Classification Search
None
See application file for complete search history.

(56) References Cited

U.S. PATENT DOCUMENTS

| | | | |
|---|---|---|---|
| 7,695,913 B2 | 4/2010 | Cowens et al. |
| 8,026,060 B2 | 9/2011 | Watson et al. |
| 8,029,995 B2 | 10/2011 | Watson et al. |
| 8,067,178 B2 | 11/2011 | Baker et al. |
| 8,114,597 B2 | 2/2012 | Liew |
| 8,153,378 B2 | 4/2012 | Cowens et al. |
| 8,153,379 B2 | 4/2012 | Watson et al. |
| 8,153,380 B2 | 4/2012 | Watson et al. |
| 8,198,024 B2 | 6/2012 | Watson et al. |
| 2007/0099209 A1 | 5/2007 | Clarke et al. |
| 2007/0105133 A1 | 5/2007 | Clarke et al. |
| 2009/0023149 A1 | 1/2009 | Knudsen |
| 2009/0258795 A1 | 10/2009 | Cowens et al. |
| 2010/0124745 A1 | 5/2010 | Liew |
| 2010/0285980 A1 | 11/2010 | Shak et al. |
| 2010/0291573 A1 | 11/2010 | Cowens et al. |
| 2011/0059447 A1 | 3/2011 | Liew |
| 2011/0097759 A1 | 4/2011 | Cowens et al. |
| 2012/0136583 A1 | 5/2012 | Lazar et al. |

FOREIGN PATENT DOCUMENTS

| | | |
|---|---|---|
| EP | 1522594 A2 | 4/2005 |
| WO | WO2006081248 A2 | 8/2006 |
| WO | WO2007082099 | 7/2007 |
| WO | WO2008115419 A3 | 9/2008 |
| WO | WO2012024543 A1 | 2/2012 |

OTHER PUBLICATIONS

Strausberg et al, in Microarrays and Cancer Research, 2002, Warrington et al (eds.), Eaton Publishing, Westborough, MA, pp. xi-xvi.\*
or Notterman et al, in Microarrays and Cancer Research, 2002, Warrington et al (eds.), Eaton Publishing, Westborough, MA, pp. 81-111.\*
Callagy et al., "Bcl-2 is a Prognostic Marker in Brast Cancer Independently of the Nottingham Prognostic Index," Clin. Cancer Res. 2006; 12(8):2468-75.
Glinsky et al., "Microarray Analysis Identifies a Death-From-Cancer Signature Predicting Therapy Failure in Patients with Multiple Types of Cancer," J. Clin. Investigation 2005; 115(6):1503-21.
Miyoshi et al., "Association of Centrosomal Kinase STK15/BTAK mRNA Expression with Chromosomal Instability in Human Breast Cancers," Int. J. Cancer 2001; 92:370-3.
Modlich et al., "Predictors of Primary Breast Cancers Responsiveness to Preoperative Epirubicin/Cyclophosphamide-Based Chemotherapy: Translation of Microarray Data Into Clinically Useful Predictive Signatures," J. Translational Medicine 2005; 3:32.
Nakopoulou et al., "Stromelysin-3 Protein Expression in Invasive Breast Cancer: Relation to Proliferation, Cell survival and Patients' Outcome," Modern Pathology 2002; 15(11):1154-61.
Nessling et al., "Candidate Genes in Breast Cancer Revealed by Microarray-Based Comparative Genomic Hybridization of Archived Tissue," Cancer Res. 2005; 65(2):439-47.
Notterman et al., "Transcriptional Gene Expression Profiles of Colorectal Adenoma Adenocarcinoma and Normal Tissue Examined by Oligonucleotide Arrays", Cancer Research, 2001; 61:3124-30.
Tanaka et al., "Centrosomal Kinase AIK1 is Overexpressed in Invasive Ductal Carcinoma of the Breast," Cancer Res. 1999; 59:2041-4.
Urruticoechea et al., "Proliferation Marker Ki-67 in Early Breast Cancer," J. Clin. Oncology 2005; 23:7212-20.
Valkovic et al., "Correlation Between Vascular Endothelial Growth Factor, Angiogenesis, and Tumor-Associated Marcophages in Invasive Ductal Breast Carcinoma," Virchows Arch. 2002; 440:583-8.
Bonin et al., "Multicenter Validation Study of Nucleic Acids Extraction from FFPE Tissues," Virchows Arch 457:309-317 (2010).
Farragher et al., "RNA Expression Analysis from Formalin Fixed Paraffin Embedded Tissues," Histochem. Cell Biol. 130:435-445 (2008).
Davison, A.C., Statistical Models, Cambridge University Press (2003), p. 1-57.
Lehmann, E. L., Theory of Point Estimation, Wiley: New York. (1983), p. 1-2.

\* cited by examiner

*Primary Examiner* — James Martinell
(74) *Attorney, Agent, or Firm* — Finnegan, Henderson, Farabow, Garrett & Dunner, L.L.P.

(57) ABSTRACT

The present invention relates to gene sets useful in assessing prognosis and/or predicting the response of cancer, e.g. colorectal cancer to chemotherapy. In addition, the invention relates to a clinically validated cancer test, e.g. colorectal test, for assessment of prognosis and/or prediction of patient response to chemotherapy, using expression analysis. The present invention accommodates the use of archived paraffin embedded biopsy material for assay of all markers in the relevant gene sets and therefore is compatible with the most widely available type of biopsy material.

18 Claims, No Drawings

GENE EXPRESSION MARKERS FOR PREDICTION OF PATIENT RESPONSE TO CHEMOTHERAPY

CROSS-REFERENCE TO RELATED APPLICATION

This application is a divisional application of U.S. application Ser. No. 12/404,268, filed Mar. 13, 2009, and claims the benefit of U.S. Provisional Application. No. 61/069,373, filed Mar. 14, 2008, the entire disclosures of which are incorporated herein by reference in their entirety.

TECHNICAL FIELD

The present invention provides genes and gene sets, the expression levels of which are useful for predicting response of cancer patients to chemotherapy.

INTRODUCTION

Colorectal cancer is the number two cause of cancer-related death in the United States and the European Union, accounting for 10% of all cancer-related deaths. Although colon cancer and rectal cancer may represent identical or similar disease at the molecular level, surgery for rectal cancer is complicated by anatomical issues. Possibly for this reason, the rate of local recurrence for rectal cancer is significantly higher than for colon cancer, and so the treatment approach is significantly different. Approximately 100,000 colon cancers are newly diagnosed each year in the United States, with about 65% of these being diagnosed as stage II/III as discussed below.

Refining a diagnosis of colorectal cancer involves evaluating the progression status of the cancer using standard classification criteria. Two classification systems have been widely used in colorectal cancer, the modified Duke's (or Astler-Coller) staging system (Stages A-D) (Astler V B, Coller F A., *Ann Surg* 1954; 139:846-52), and more recently TNM staging (Stages I-IV) as developed by the American Joint Committee on Cancer (*AJCC Cancer Staging Manual*, 6th Edition, Springer-Verlag, New York, 2002). Both systems evaluate tumor progression by applying measures of the spread of the primary tumor through layers of colon or rectal wall to adjacent organs, lymph nodes and distant sites. Estimates of recurrence risk and treatment decisions in colon cancer are currently based primarily on tumor stage.

There are approximately 33,000 newly diagnosed Stage II colorectal cancers each year in the United States. Nearly all of these patients are treated by surgical resection of the tumor and, in addition, about 40% are currently treated with chemotherapy based on 5-fluorouracil (5-FU). The decision whether to administer adjuvant chemotherapy is not straightforward. The five-year survival rate for Stage II colon cancer patients treated with surgery alone is approximately 80%. Standard adjuvant treatment with 5-FU+leucovorin (leucovorin-mediated fluorouracil) produces an only 2-4% absolute improvement in 5-year survival in this population. Such treatment also shows significant toxicity, including a rate of toxic death from chemotherapy as high as 1%. Thus, a large number of patients receive toxic therapy from which only a few benefit. A test capable of quantifying likelihood of patient benefit from chemotherapy to more accurately identify Stage II patients for treatment would be extremely useful.

The benefit of chemotherapy in Stage III colon cancer is even more evident than in Stage II. A large proportion of the 31,000 patients annually diagnosed with Stage III colon cancer receive 5-FU-based adjuvant chemotherapy. The absolute benefit of treatment in this setting ranges, depending on the particular regimen employed, from about 18% (5-FU+leucovorin) to about 24% (5-FU+leucovorin+oxaliplatin). Current standard-of-care chemotherapy treatment for Stage III colon cancer patients is moderately effective, achieving an improvement in 5-year survival rate from about 50% (surgery alone) to about 65% (5-FU+leucovorin) or 70% (5-FU+leucovorin+oxaliplatin). Treatment with 5-FU+leucovorin alone or in combination with oxaliplatin is accompanied by a range of adverse side-effects, including toxic death in approximately 1% of patients treated. It has not been established whether a subset of Stage III patients (overall untreated 5-year survival about 50%) exists for which recurrence risk resembles that observed for Stage II patients (overall untreated 5-year survival about 80%).

A test capable of quantifying likelihood of patient benefit from chemotherapy to more accurately identify Stage III patients for treatment would be extremely useful. A patient having a low recurrence risk resembling that of a Stage II patient and a low likelihood of benefit from chemotherapy might elect to forego chemotherapy. A patient with a high recurrence risk and a low likelihood of benefit from 5-FU based chemotherapy might elect an alternative treatment.

Staging of rectal tumors is carried out based on similar criteria as for colon tumor staging, although there are some differences resulting for example from differences in the arrangement of the draining lymph nodes. As a result, Stage II/III rectal tumors bear a reasonable correlation to Stage II/III colon tumors as to their state of progression. As noted above, the rate of local recurrence and other aspects of prognosis differ between rectal cancer and colon cancer, and these differences may arise from difficulties in accomplishing total resection of rectal tumors. Nevertheless, there is no compelling evidence that there is a difference between colon cancer and rectal cancer as to the molecular characteristics of the respective tumors.

Tests able to predict chemotherapy treatment benefit for rectal cancer patients would have utility similar in nature as described for colon cancer tests and the same markers might well have utility in both cancer types. Tests that identify patients more likely to be those that fail to respond to standard-of-care are useful in drug development, for example in identifying patients for inclusion in clinical trials testing the efficacy of alternative drugs. For example, 30-35% of Stage III colon cancer patients fail to survive five years when treated with fluorouracil-based chemotherapy after surgical resection of tumor. Preferential inclusion of these patients in a clinical trial for a new Stage III colon cancer treatment could substantially improve the efficiency and reduce the costs of such a clinical trial.

SUMMARY

The present invention relates to gene sets useful in assessing prognosis and/or predicting the response of cancer, e.g. colorectal cancer to chemotherapy. In addition, the invention relates to a clinically validated cancer test, e.g. colorectal test, for assessment of prognosis and/or prediction of patient response to chemotherapy, using expression analysis. The present invention accommodates the use of archived paraffin embedded biopsy material for assay of all markers in the relevant gene sets and therefore is compatible with the most widely available type of biopsy material.

In one aspect, the present disclosure concerns a method of predicting the likelihood of positive response to treatment with chemotherapy of a subject diagnosed with cancer involving determining the normalized expression level of at least one gene listed in Table 5, or its expression product, in a tumor sample obtained from said subject, and using the normalized expression level to calculate a likelihood of a positive clinical response to chemotherapy, wherein increased normalized expression of one or more of the genes selected from the group consisting of ABCB1, AMFR, ANXA1, APC, B-Catenin, BGN, CALD1, CD44E, CD44s, CD44v6, CD68, CDH11, CHFR, CLDN1, CLTC, COL1A1, COL1A2, CREBBP, CTSB, CTSL, CXCL12, EFNB2, ENO1, EPAS1, FGF18, FOXO3A, FPGS, FZD1, GJB2, GPX1, HIF1A, HNRPD, HSD17B2, HoxA5, IGFBP3, IGFBP5, IGFBP7, IL6ST, ITGA5, KLF5, KLK10, KRT8, LEF, LOX, MADH7, MCM3, MCP1, MMP1, MMP2, Maspin, NRP1, PDGFC, PDGFD, PDGFRa, PFN2, PKR2, RUNX1, SEMA4B, SIAT4A, SKP2, SPARC, SPRY1, THBS1, TIMP1, UPP1, and VDAC2, or their corresponding product, indicates that said subject is predicted to have a decreased likelihood of a positive clinical response to the chemotherapy, and wherein increased normalized expression of one or more of the genes selected from the group consisting of AURKB, Axin 2, BIK, BRAF, BRCA2, BUB1, C20 orf1, C20ORF126, CASP9, CCNE2 variant 1, CDC2, CDC4, CENPA, CENPF, CLIC1, CYR61, Cdx2, Chk1, DLC1, DUSP1, E2F1, EGR3, EI24, ESPL1, FBXO5, FGF2, FOS, FUT6, GSK3B, Grb10, HES6, HLA-G, HNRPAB, HOXB13, HSPE1, KIF22, KIFC1, KLRK1, Ki-67, LAT, LMYC, MAD2L1, MSH2, MSH3, NR4A1, PDGFA, PRDX2, RAB32, RAD54L, RANBP2, RCC1, ROCK2, RhoB, S100P, SAT, SOD1, SOS1, STK15, TCF-1, TOP2A, TP53BP1, UBE2C, VCP, and cMYC, or their corresponding products, indicates that said subject has an increased likelihood of a positive clinical response to chemotherapy.

In another aspect, the present disclosure concerns methods of predicting the likelihood of a positive clinical outcome of treatment with chemotherapy of a subject diagnosed with cancer by determining the normalized expression level of one or more genes listed in Table 5, or their expression products, in a tumor sample obtained from said subject, using the normalized expression level to calculate a likelihood of a positive clinical outcome of treatment with chemotherapy, wherein increased normalized expression of one or more of the genes selected from the group consisting of ABCB1, AMFR, ANXA1, APC, B-Catenin, BGN, CALD1, CD44E, CD44s, CD44v6, CD68, CDH11, CHFR, CLDN1, CLTC, COL1A1, COL1A2, CREBBP, CTSB, CTSL, CXCL12, EFNB2, ENO1, EPAS1, FGF18, FOXO3A, FPGS, FZD1, GJB2, GPX1, HIF1A, HNRPD, HSD17B2, HoxA5, IGFBP3, IGFBP5, IGFBP7, IL6ST, ITGA5, KLF5, KLK10, KRT8, LEF, LOX, MADH7, MCM3, MCP1, MMP1, MMP2, Maspin, NRP1, PDGFC, PDGFD, PDGFRa, PFN2, PKR2, RUNX1, SEMA4B, SIAT4A, SKP2, SPARC, SPRY1, THBS1, TIMP1, UPP1, and VDAC2, or their corresponding products, indicates that said subject is predicted to have a decreased likelihood of a positive clinical outcome, and wherein increased expression of one or more of the genes selected from the group consisting of AURKB, Axin 2, BIK, BRAF, BRCA2, BUB1, C20 orf1, C20ORF126, CASP9, CCNE2 variant 1, CDC2, CDC4, CENPA, CENPF, CLIC1, CYR61, Cdx2, Chk1, DLC1, DUSP1, E2F1, EGR3, EI24, ESPL1, FBXO5, FGF2, FOS, FUT6, GSK3B, Grb10, HES6, HLA-G, HNRPAB, HOXB13, HSPE1, KIF22, KIFC1, KLRK1, Ki-67, LAT, LMYC, MAD2L1, MSH2, MSH3, NR4A1, PDGFA, PRDX2, RAB32, RAD54L, RANBP2, RCC1, ROCK2, RhoB, S100P, SAT, SOD1, SOS1, STK15, TCF-1, TOP2A, TP53BP1, UBE2C, VCP, and cMYC, or their corresponding products, indicates that said subject has an increased likelihood of a positive clinical outcome.

The clinical outcome of the methods of the present disclosure may be expressed, for example, in terms of Recurrence-Free Interval (RFI), Overall Survival (OS), Disease-Free Survival (DFS), or Distant Recurrence-Free Interval (DRFI).

In one embodiment, the cancer is selected from the group of cancers including colorectal cancer, breast cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma and brain cancer. In one embodiment the cancer is colorectal cancer. In another embodiment, the colorectal cancer is invasive colorectal cancer or Dukes B (stage II) or Dukes C (stage III) colorectal cancer.

In a particular embodiment, the chemotherapy is adjuvant chemotherapy. In another embodiment, the chemotherapy is neoadjuvant chemotherapy. In a particular embodiment the chemotherapy is 5-fluorouracil with leucovorin. The chemotherapy may further include administration of an additional anti-cancer agent.

In another aspect the present disclosure provides methods of predicting a positive clinical response of a colorectal cancer patient to treatment with 5-fluorouracil involving determining the normalized expression level of one or more of the genes listed in Table 5, or their products, in a tumor sample obtained from said patient, using the normalized expression level to calculate a likelihood of a positive clinical response, wherein increased normalized expression of one or more of the genes selected from the group consisting of ABCB1, AMFR, ANXA1, APC, B-Catenin, BGN, CALD1, CD44E, CD44s, CD44v6, CD68, CDH11, CHFR, CLDN1, CLTC, COL1A1, COL1A2, CREBBP, CTSB, CTSL, CXCL12, EFNB2, ENO1, EPAS1, FGF18, FOXO3A, FPGS, FZD1, GJB2, GPX1, HIF1A, HNRPD, HSD17B2, HoxA5, IGFBP3, IGFBP5, IGFBP7, IL6ST, ITGA5, KLF5, KLK10, KRT8, LEF, LOX, MADH7, MCM3, MCP1, MMP1, MMP2, Maspin, NRP1, PDGFC, PDGFD, PDGFRa, PFN2, PKR2, RUNX1, SEMA4B, SIAT4A, SKP2, SPARC, SPRY1, THBS1, TIMP1, UPP1, and VDAC2, or their corresponding product, indicates a decreased likelihood of clinical response; and increased normalized expression of one or more of the genes selected from the group consisting of AURKB, Axin 2, BIK, BRAF, BRCA2, BUB1, C20 orf1, C20ORF126, CASP9, CCNE2 variant 1, CDC2, CDC4, CENPA, CENPF, CLIC1, CYR61, Cdx2, Chk1, DLC1, DUSP1, E2F1, EGR3, EI24, ESPL1, FBXO5, FGF2, FOS, FUT6, GSK3B, Grb10, HES6, HLA-G, HNRPAB, HOXB13, HSPE1, KIF22, KIFC1, KLRK1, Ki-67, LAT, LMYC, MAD2L1, MSH2, MSH3, NR4A1, PDGFA, PRDX2, RAB32, RAD54L, RANBP2, RCC1, ROCK2, RhoB, S100P, SAT, SOD1, SOS1, STK15, TCF-1, TOP2A, TP53BP1, UBE2C, VCP, and cMYC, or their corresponding product, indicates an increased likelihood of clinical response, and generating a report based on the likelihood of a positive clinical response to chemotherapy.

In another aspect the present disclosure provides methods of predicting an effect of treatment with a 5-fluorouracil (5-FU)-based therapy on duration of a Recurrence-Free Interval (RFI) in a subject diagnosed with colorectal cancer by determining the normalized expression level of one or more of the genes listed in Table 5, or their expression products, in a tumor sample obtained from said subject, using the normalized expression level to calculate a predicted RFI for the subject after treatment with a 5-FU-based therapy, wherein evidence of increased normalized expression of one or more of the genes selected from the group consisting of ABCB1, AMFR, ANXA1, APC, B-Catenin, BGN, CALD1, CD44E, CD44s, CD44v6, CD68, CDH11, CHFR, CLDN1, CLTC, COL1A1, COL1A2, CREBBP, CTSB, CTSL, CXCL12, EFNB2, ENO1, EPAS1, FGF18, FOXO3A, FPGS, FZD1, GJB2, GPX1, HIF1A, HNRPD, HSD17B2, HoxA5, IGFBP3, IGFBP5, IGFBP7, IL6ST, ITGA5, KLF5, KLK10, KRT8, LEF, LOX, MADH7, MCM3, MCP1, MMP1, MMP2, Maspin, NRP1, PDGFC, PDGFD, PDGFRa, PFN2, PKR2, RUNX1, SEMA4B, SIAT4A, SKP2, SPARC, SPRY1, THBS1, TIMP1, UPP1, and VDAC2, or their corresponding product, indicates that said RFI is predicted to be shorter; and evidence of increased normalized expression of one or more of the genes listed elected from the group consisting of AURKB, Axin 2, BIK, BRAF, BRCA2, BUB1, C20 orf1, C20ORF126, CASP9, CCNE2 variant 1, CDC2, CDC4, CENPA, CENPF, CLIC1, CYR61, Cdx2, Chk1, DLC1, DUSP1, E2F1, EGR3, EI24, ESPL1, FBXO5, FGF2, FOS, FUT6, GSK3B, Grb10, HES6, HLA-G, HNRPAB, HOXB13, HSPE1, KIF22, KIFC1, KLRK1, Ki-67, LAT, LMYC, MAD2L1, MSH2, MSH3, NR4A1, PDGFA, PRDX2, RAB32, RAD54L, RANBP2, RCC1, ROCK2, RhoB, S100P, SAT, SOD1, SOS1, STK15, TCF-1, TOP2A, TP53BP1, UBE2C, VCP, and cMYC, or their corresponding product, indicates that said RFI is predicted to be longer.

For all aspects of the method of the present disclosure, determining the expression level of one or more genes may be obtained, for example, by a method of gene expression profiling. The method of gene expression profiling may be, for example, a PCR-based method.

The expression level of said genes can be determined, for example, by RT-PCR (reverse transcriptase PCR) or an other PCR-based method, immunohistochemistry, proteomics techniques, an array-based method, or any other methods known in the art or their combination. In one aspect the RNA trancripts are fragmented.

For all aspects of the methods disclosed herein, the RNA transcript may be detected by assaying for an exon-baed sequence or an intron-based sequence, the expression of which correlates with the expression of a corresponding exon sequence.

In an embodiment, the assay for the measurement of said genes, or its expression products, is provided in the form of a kit or kits.

For all aspects of the present disclosure, the expression levels of the genes may be normalized relative to the expression levels of one or more reference genes, or their expression products.

The tumor sample may be e.g. a tissue sample containing cancer cells, or portion(s) of cancer cells, where the tissue can be fixed, paraffin-embedded or fresh or frozen tissue. In a particular embodiment, the tissue is from fine needle, core or other types of biopsy. For example, the tissue sample can be obtained by fine needle aspiration, or by obtaining body fluid containing a cancer cell, e.g. urine, blood, etc.

For all aspects of the present disclosure, the subject preferably is a human patient.

For all aspects of the present disclosure, the methods may further include determining the expression levels of at least two of said genes, or their expression products. It is further contemplated that the method of the present disclosure may further include determining the expression levels of at least three of said genes, or their expression products. It is also contemplated that the method of the present disclosure may further include determining the expression levels of at least four of said genes, or their expression products. It is also contemplated that the method of the present disclosure may further include determining the expression levels of at least five of said genes, or their expression products. The method may involve determination of the expression levels of at least ten (10) or at least fifteen (15) of the transcripts listed above or their products. Thus, for all aspects of the present disclosure, the method may further include determining the expression levels of, e.g., STK15, B1K, or MAD2L1 and at least one other of said genes, or their expression products. Thus, it is further contemplated that the method of the present disclosure may further include determining the expression levels of, e.g., STK15, B1K, or MAD2L1 and at least two others of said genes, or their expression products. Thus, it is also contemplated that the method of the present disclosure may further include determining the expression levels of, e.g., STK15, B1K, or MAD2L1 and at least three others of said genes, or their expression products. Thus, it is also contemplated that the method of the present disclosure may further include determining the expression levels of, e.g., STK15, B1K, or MAD2L1 and at least four others of said genes, or their expression products. Thus, the method may involve determination of the expression levels of, e.g., STK15, B1K, or MAD2L1 and at least nine others totaling ten (10) or at least fourteen others totaling fifteen (15) of the transcripts listed above or their products. It is contemplated that the method will include determining the expression levels of a gene and at least one additional gene that co-expresses with a significant pairwise correlation co-efficient, e.g. a Pearson correlation of ≥0.4.

For all aspects of the methods of the present disclosure, it is contemplated that for every increment of an increase in the level of one or more genes or their expression products, the patient is identified to show an incremental increase in clinical outcome.

For all aspects of the methods of the present disclosure, the determination of expression levels may occur more than one time.

For all aspects of the methods of the present disclosure, the determination of expression levels may occur before the patient is subjected to any therapy following surgical resection.

For all aspects of the methods of the present disclosure, the methods may further include the step of creating a report summarizing said likelihood.

In another aspect the present disclosure provides methods of producing reports that include gene expression information about a tumor sample obtained from a patient that includes the steps of determining information indicative of the expression levels of the genes listed in Table 5, or their expression products, in said tumor sample; and creating a report summarizing said information. In one aspect of the method, if increased expression of AURKB, Axin 2, BIK, BRAF, BRCA2, BUB1, C20 orf1, C20ORF126, CASP9, CCNE2 variant 1, CDC2, CDC4, CENPA, CENPF, CLIC1, CYR61, Cdx2, Chk1, DLC1, DUSP1, E2F1, EGR3, EI24, ESPL1, FBXO5, FGF2, FOS, FUT6, GSK3B, Grb10, HES6, HLA-G, HNRPAB, HOXB13, HSPE1, KIF22, KIFC1, KLRK1, Ki-67, LAT, LMYC, MAD2L1, MSH2, MSH3, NR4A1, PDGFA, PRDX2, RAB32, RAD54L, RANBP2, RCC1, ROCK2, RhoB, S100P, SAT, SOD1, SOS1, STK15, TCF-1, TOP2A, TP53BP1, UBE2C, VCP, and cMYC, or the corresponding expression product, is determined, said report includes a prediction that said subject has an increased likelihood of response to treatment with 5-fluorouracil. In another aspect of the method, if increased expression of one or more of ABCB1, AMFR, ANXA1, APC, B-Catenin, BGN, CALD1, CD44E, CD44s, CD44v6, CD68, CDH11, CHFR, CLDN1, CLTC, COL1A1, COL1A2, CREBBP, CTSB, CTSL, CXCL12, EFNB2, ENO1, EPAS1, FGF18, FOXO3A, FPGS, FZD1, GJB2, GPX1, HIF1A, HNRPD, HSD17B2, HoxA5, IGFBP3, IGFBP5, IGFBP7, IL6ST, ITGA5, KLF5, KLK10, KRT8, LEF, LOX, MADH7, MCM3, MCP1, MMP1, MMP2, Maspin, NRP1, PDGFC, PDGFD, PDGFRa, PFN2, PKR2, RUNX1, SEMA4B, SIAT4A, SKP2, SPARC, SPRY1, THBS1, TIMP1, UPP1, and VDAC2, or the corresponding expression product, is determined, said report includes a prediction that said subject has an decreased likelihood of response to treatment with 5-fluorouracil.

In one aspect the report includes information to support a treatment recommendation for said patient. For example, the information can include a recommendation for adjuvant chemotherapy and/or neoadjuvant chemotherapy, a likelihood of chemotherapy benefit score, or other such data.

In another aspect the present disclosure provides reports for a patient containing a summary of the expression levels of the one or more genes listed in Table 5, or their expression products, in a tumor sample obtained from said patient. In one aspect the report is in electronic form.

In one aspect the report indicates that if increased expression of one or more of ABCB1, AMFR, ANXA1, APC, B-Catenin, BGN, CALD1, CD44E, CD44s, CD44v6, CD68, CDH11, CHFR, CLDN1, CLTC, COL1A1, COL1A2, CREBBP, CTSB, CTSL, CXCL12, EFNB2, ENO1, EPAS1, FGF18, FOXO3A, FPGS, FZD1, GJB2, GPX1, HIF1A, HNRPD, HSD17B2, HoxA5, IGFBP3, IGFBP5, IGFBP7, IL6ST, ITGA5, KLF5, KLK10, KRT8, LEF, LOX, MADH7, MCM3, MCP1, MMP1, MMP2, Maspin, NRP1, PDGFC, PDGFD, PDGFRa, PFN2, PKR2, RUNX1, SEMA4B, SIAT4A, SKP2, SPARC, SPRY1, THBS1, TIMP1, UPP1, and VDAC2, or their corresponding expression products, is determined, said report includes a prediction that said subject has an increased likelihood of cancer recurrence at 10 years.

In another aspect the report indicates that if increased expression of one or more of AURKB, Axin 2, BIK, BRAF, BRCA2, BUB1, C20 orf1, C20ORF126, CASP9, CCNE2 variant 1, CDC2, CDC4, CENPA, CENPF, CLIC1, CYR61, Cdx2, Chk1, DLC1, DUSP1, E2F1, EGR3, EI24, ESPL1, FBXO5, FGF2, FOS, FUT6, GSK3B, Grb10, HES6, HLA-G, HNRPAB, HOXB13, HSPE1, KIF22, KIFC1, KLRK1, Ki-67, LAT, LMYC, MAD2L1, MSH2, MSH3, NR4A1, PDGFA, PRDX2, RAB32, RAD54L, RANBP2, RCC1, ROCK2, RhoB, S100P, SAT, SOD1, SOS1, STK15, TCF-1, TOP2A, TP53BP1, UBE2C, VCP, and cMYC, or their corresponding expression products, is determined, said report includes a prediction that said subject has a decreased likelihood of cancer recurrence at 10 years.

In some embodiments, the report further includes a recommendation for a treatment modality for said patient. In all aspects the report may include a classification of a subject into a risk group. In all aspects a report may include a prediction of the likelihood that said patient will respond positively to treatment with chemotherapy.

In another aspect, the present disclosure concerns methods of preparing a personalized genomics profile for a patient by a) determining the normalized expression levels of at least one gene listed in Table 5, or its expression product, in a tumor sample obtained from said patient; and (b) creating a report summarizing the data obtained by the gene expression analysis.

In another embodiment, the present disclosure provides an array comprising polynucleotides hybridizing to a plurality of the genes listed in Table 5. In another aspect the present disclosure provides arrays having polynucleotides hybridizing to a plurality of the following genes: ABCB1, AMFR, ANXA1, APC, B-Catenin, BGN, CALD1, CD44E, CD44s, CD44v6, CD68, CDH11, CHFR, CLDN1, CLTC, COL1A1, COL1A2, CREBBP, CTSB, CTSL, CXCL12, EFNB2, ENO1, EPAS1, FGF18, FOXO3A, FPGS, FZD1, GJB2, GPX1, HIF1A, HNRPD, HSD17B2, HoxA5, IGFBP3, IGFBP5, IGFBP7, IL6ST, ITGA5, KLF5, KLK10, KRT8, LEF, LOX, MADH7, MCM3, MCP1, MMP1, MMP2, Maspin, NRP1, PDGFC, PDGFD, PDGFRa, PFN2, PKR2, RUNX1, SEMA4B, SIAT4A, SKP2, SPARC, SPRY1, THBS1, TIMP1, UPP1, and VDAC2. In another aspect the present disclosure provides arrays having polynucleotides hybridizing to a plurality of the following genes: AURKB, Axin 2, BIK, BRAF, BRCA2, BUB1, C20 orf1, C20ORF126, CASP9, CCNE2 variant 1, CDC2, CDC4, CENPA, CENPF, CLIC1, CYR61, Cdx2, Chk1, DLC1, DUSP1, E2F1, EGR3, EI24, ESPL1, FBXO5, FGF2, FOS, FUT6, GSK3B, Grb10, HES6, HLA-G, HNRPAB, HOXB13, HSPE1, KIF22, KIFC1, KLRK1, Ki-67, LAT, LMYC, MAD2L1, MSH2, MSH3, NR4A1, PDGFA, PRDX2, RAB32, RAD54L, RANBP2, RCC1, ROCK2, RhoB, S100P, SAT, SOD1, SOS1, STK15, TCF-1, TOP2A, TP53BP1, UBE2C, VCP, and cMYC.

The present disclosure also provides methods for analyzing a colorectal cancer tissue sample to determine whether the sample contains cancer cells likely to respond to a chemotherapy, where the method includes determining a normalized expression value for at least one gene from Table 5, or its expression product, in a colorectal cancer tissue sample obtained from the patient; inputting the normalized expression value of the least one gene from Table 5, or a gene co-expressed with a gene of Table 5, into a computer programmed to execute an algorithm to convert the value to a score indicative of a likelihood of the patient to respond to chemotherapy, wherein expression of one or more of the genes selected from the group consisting of AURKB, Axin 2, BIK, BRAF, BRCA2, BUB1, C20 orf1, C20ORF126, CASP9, CCNE2 variant 1, CDC2, CDC4, CENPA, CENPF, CLIC1, CYR61, Cdx2, Chk1, DLC1, DUSP1, E2F1, EGR3, EI24, ESPL1, FBXO5, FGF2, FOS, FUT6, GSK3B, Grb10, HES6, HLA-G, HNRPAB, HOXB13, HSPE1, KIF22, KIFC1, KLRK1, Ki-67, LAT, LMYC, MAD2L1, MSH2, MSH3, NR4A1, PDGFA, PRDX2, RAB32, RAD54L, RANBP2, RCC1, ROCK2, RhoB, S100P, SAT, SOD1, SOS1, STK15, TCF-1, TOP2A, TP53BP1, UBE2C, VCP, and cMYC, or a gene co-expressed with one or more of said genes, is positively correlated with an increased likelihood of a positive clinical response to treatment with chemotherapy; and expression of one or more of the genes selected from the group consisting of ABCB1, AMFR, ANXA1, APC, B-Catenin, BGN, CALD1, CD44E, CD44s, CD44v6, CD68, CDH11, CHFR, CLDN1, CLTC, COL1A1, COL1A2, CREBBP, CTSB, CTSL, CXCL12, EFNB2, ENO1, EPAS1, FGF18, FOXO3A, FPGS, FZD1, GJB2, GPX1, HIF1A, HNRPD, HSD17B2, HoxA5, IGFBP3, IGFBP5, IGFBP7, IL6ST, ITGA5, KLF5, KLK10, KRT8, LEF, LOX, MADH7, MCM3, MCP1, MMP1, MMP2, Maspin, NRP1, PDGFC, PDGFD, PDGFRa, PFN2, PKR2, RUNX1, SEMA4B, SIAT4A, SKP2, SPARC, SPRY1, THBS1, TIMP1, UPP1, and VDAC2, or a gene co-expressed with one or more of said genes, is negatively correlated with an increased likelihood of a positive response to treatment with chemotherapy; and generating a report comprising the score.

In related embodiments, the tumor sample is obtained from a solid tumor, e.g., a colorectal cancer. In further related embodiments, the chemotherapy is a 5-fluorouracil (5-FU)-based treatment.

DETAILED DESCRIPTION OF THE EXEMPLARY EMBODIMENTS

Definitions

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

The term "tumor," as used herein, refers to any neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth. Examples of cancer include, but are not limited to, colorectal cancer, breast cancer, ovarian cancer, lung cancer, prostate cancer, hepatocellular cancer, gastric cancer, pancreatic cancer, cervical cancer, liver cancer, bladder cancer, cancer of the urinary tract, thyroid cancer, renal cancer, carcinoma, melanoma, and brain cancer. In one embodiment the cancer is colorectal cancer. In another embodiment the cancer is invasive colorectal cancer or Dukes B (stage II) or Dukes C (stage III) colorectal cancer.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

The term "colorectal cancer" is used in the broadest sense and refers to (1) all stages and all forms of cancer arising from epithelial cells of the large intestine and/or rectum and/or (2) all stages and all forms of cancer affecting the lining of the large intestine and/or rectum. In the staging systems used for classification of colorectal cancer, the colon and rectum are treated as one organ.

According to the tumor, node, metastatis (TNM) staging system of the American Joint Committee on Cancer (AJCC) (Greene et al. (eds.), AJCC Cancer Staging Manual. 6th Ed. New York, N.Y.: Springer; 2002), the various stages of colorectal cancer are defined as follows:

Tumor: T1: tumor invades submucosa; T2: tumor invades muscularis propria; T3: tumor invades through the muscularis propria into the subserose, or into the pericolic or perirectal tissues; T4: tumor directly invades other organs or structures, and/or perforates.

Node: N0: no regional lymph node metastasis; N1: metastasis in 1 to 3 regional lymph nodes; N2: metastasis in 4 or more regional lymph nodes.

Metastasis: M0: mp distant metastasis; M1: distant metastasis present.

Stage groupings: Stage I: T1 N0 M0; T2 N0 M0; Stage II: T3 N0 M0; T4 N0 M0; Stage III: any T, N1-2; M0; Stage 1V: any T, any N, M1.

According to the Modified Duke Staging System, the various stages of colorectal cancer are defined as follows:

Stage A: the tumor penetrates into the mucosa of the bowel wall but not further. Stage B: tumor penetrates into and through the muscularis propria of the bowel wall; Stage C: tumor penetrates into but not through muscularis propria of the bowel wall, there is pathologic evidence of colorectal cancer in the lymph nodes; or tumor penetrates into and through the muscularis propria of the bowel wall, there is pathologic evidence of cancer in the lymph nodes; Stage D: tumor has spread beyond the confines of the lymph nodes, into other organs, such as the liver, lung or bone.

Prognostic factors are those variables related to the natural history of colorectal cancer, which influence the recurrence rates and outcome of patients once they have developed colorectal cancer. Clinical parameters that have been associated with a worse prognosis include, for example, lymph node involvement, and high grade tumors. Prognostic factors are frequently used to categorize patients into subgroups with different baseline relapse risks.

The term "prognosis" is used herein to refer to the prediction of the likelihood of cancer-attributable death or progression, including recurrence, metastatic spread, and drug resistance, of a neoplastic disease, such as colon cancer. "Prognosis" thus encompasses prediction of response to chemotherapy.

The term "prediction" is used herein to refer to the likelihood that a patient will have a particular clinical outcome, whether positive or negative, following treatment with chemotherapy and, optionally, surgical removal of the primary tumor. The predictive methods of the present disclosure can be used clinically to make treatment decisions by choosing the most appropriate treatment modalities for any particular patient. The predictive methods of the present disclosure are valuable tools in predicting if a patient is likely to respond favorably to a treatment regimen, such as chemotherapy, surgical intervention, or both.

The term "positive clinical response" can be assessed using any endpoint indicating a benefit to the patient, including, without limitation, (1) inhibition, to some extent, of tumor growth, including slowing down and complete growth arrest; (2) reduction in the number of tumor cells; (3) reduction in tumor size; (4) inhibition (i.e., reduction, slowing down or complete stopping) of tumor cell infiltration into adjacent peripheral organs and/or tissues; (5) inhibition of metastasis; (6) enhancement of anti-tumor immune response, possibly resulting in regression or rejection of the tumor; (7) relief, to some extent, of one or more symptoms associated with the tumor; (8) increase in the length of survival following treatment; and/or (9) decreased mortality at a given point of time following treatment. Positive clinical response may also be expressed in terms of various measures of clinical outcome. Positive clinical outcome can also be considered in the context of an individual's outcome relative to an outcome of a population of patients having a comparable clinical diagnosis, and can be assessed using various endpoints such as an increase in the duration of Recurrence-Free interval (RFI), an increase in the time of survival as compared to Overall Survival (OS) in a population, an increase in the time of Disease-Free Survival (DFS), an increase in the duration of Distant Recurrence-Free Interval (DRFI), and the like. An increase in the likelihood of positive clinical response corresponds to a decrease in the likelihood of cancer recurrence.

The term "long-term" survival is used herein to refer to survival for at least 3 years, or for at least 5 years.

The term "Recurrence-Free Interval (RFI)" is used herein to refer to time in years to first colon cancer recurrence. RFI excludes the identification of a second primary cancer or death without evidence of recurrence.

The term "Overall Survival (OS)" is used herein to refer to time in years from surgery to death from any cause.

The term "Disease-Free Survival (DFS)" is used herein to refer to the length of time (in years) after treatment for colon cancer during which a patient survives with no sign of recurrence.

The term "Distant Recurrence-Free Interval (DRFI)" is used herein to refer to the time (in years) from surgery to the first cancer recurrence that is regionally distant from the primary tumor.

The term "microarray" refers to an ordered arrangement of hybridizable array elements, preferably polynucleotide probes, on a substrate.

The term "polynucleotide," when used in singular or plural, generally refers to any polyribonucleotide or polydeoxyribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. The term "polynucleotide" specifically includes cDNAs. The term includes DNAs (including cDNAs) and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

The terms "differentially expressed gene," "differential gene expression" and their synonyms, which are used interchangeably, refer to a gene whose expression is activated to a higher or lower level in a subject suffering from a disease, specifically cancer, such as colon cancer, relative to its expression in a normal or control subject. The terms also include genes whose expression is activated to a higher or lower level at different stages of the same disease. It is also understood that a differentially expressed gene may be either activated or inhibited at the nucleic acid level or protein level, or may be subject to alternative splicing to result in a different polypeptide product. Such differences may be evidenced by a change in mRNA levels, surface expression, secretion or other partitioning of a polypeptide, for example. Differential expression includes both quantitative, as well as qualitative, differences in the temporal or cellular expression pattern in a gene, for example, normal and diseased cells, or among cells which have undergone different disease events or disease stages.

The term "increased expression" or "increased normalized expression" with regard to a gene or an RNA transcript or other expression prodocut (e.g., protein) is used to refer to the level of the transcript (or fragmented RNA) determined by normalization to the level of reference mRNAs, which might be all measured transcripts in the specimen or a particular reference set of mRNAs. A gene exhibits "increased expression" in a subpopulation of subjects when the normalized expression level of an RNA transcript (or its gene product) is higher in one clinically relevant subpopulation of patients (e.g., patients who are responsive to chemotherapy treatment) than in a related subpopulation (e.g., patients who are not responsive to said chemotherapy). In the context of an analysis of a normalized expression level of a gene in tissue obtained from an individual subject, a gene is exhibits "increased expression" when the normalized expression level of the gene trends toward or more closely approximates the normalized expression level characteristic of such a clinically relevant subpopulation of patients. Thus, for example, when the gene analyzed is a gene that shows increased expression in responsive subjects as compared to non-responsive subjects, then if the expression level of the gene in the patient sample trends toward a level of expression characteristic of a responsive subject, then the gene expression level supports a determination that the individual patient is likely to be a responder. Similarly, where the gene analyzed is a gene that is increased in expression in non-responsive patients as compared to responsive patients, then if the expression level of the gene in the patient sample trends toward a level of expression characteristic of a non-responsive subject, then the gene expression level supports a determination that the individual patient will be nonresponsive. Thus normalized expression of a given gene as disclosed herein can be described as being positively correlated with an increased likelihood of positive clinical response to chemotherapy or as being positively correlated with a decreased likelihood of a positive clinical response to chemotherapy.

The phrase "gene amplification" refers to a process by which multiple copies of a gene or gene fragment are formed in a particular cell or cell line. The duplicated region (a stretch of amplified DNA) is often referred to as "amplicon." Usually, the amount of the messenger RNA (mRNA) produced, i.e., the level of gene expression, also increases in the proportion of the number of copies made of the particular gene expressed.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, typically: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide, followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

In the context of the present disclosure, reference to "at least one," "at least two," "at least five," etc. of the genes listed in any particular gene set means any one or any and all combinations of the genes listed.

The term "node negative" cancer, such as "node negative" colon cancer, is used herein to refer to cancer that has not spread to the lymph nodes.

The terms "splicing" and "RNA splicing" are used interchangeably and refer to RNA processing that removes introns and joins exons to produce mature mRNA with continuous coding sequence that moves into the cytoplasm of an eukaryotic cell.

In theory, the term "exon" refers to any segment of an interrupted gene that is represented in the mature RNA product (B. Lewin. *Genes IV* Cell Press, Cambridge Mass. 1990). In theory the term "intron" refers to any segment of DNA that is transcribed but removed from within the transcript by splicing together the exons on either side of it. Operationally, exon sequences occur in the mRNA sequence of a gene as defined by Ref. SEQ ID numbers. Operationally, intron sequences are the intervening sequences within the genomic DNA of a gene, bracketed by exon sequences and having GT and AG splice consensus sequences at their 5' and 3' boundaries.

The term "expression cluster" is used herein to refer to a group of genes which co-express, e.g., tend to exhibit a similar change in expression level across different samples, when studied within samples from a defined set of patients. As used herein, the genes within an expression cluster show similar expression patterns when studied within samples from patients with Stage II and/or Stage III cancers of the colon and/or rectum.

Reference to markers for prediction of response to 5-fluorouracil (5-FU) and like expressions encompass within their meaning response to treatment comprising 5-FU as monotherapy, or in combination with other agents, or as prodrugs, or together with local therapies such as surgery and radiation, or as adjuvant or neoadjuvant chemotherapy, or as part of a multimodal approach to the treatment of neoplastic disease. The general mechanism of action of 5-FU is its activity as a pyrimidine antimetabolite. In 5-FU, the smaller fluorine at position 5 allows the molecule to mimic uracil biochemically. However, the fluorine-carbon bond is much tighter than that of C-H and prevents methylation of the 5 position of 5-FU by thymidylate synthase. Instead, in the presence of the physiological cofactor 5,10-methylene tetrahydrofolate, the fluoropyrimidine locks the enzyme in an inhibited state and prevents the synthesis of thymidylate, a required DNA precursor.

A 5-FU combination or 5-FU combination therapy refers to a combination of 5-FU and another agent. A number of agents have been combined with 5-FU to enhance the cytotoxic activity through biochemical modulation. Addition of exogenous folate in the form of 5-formyl-tetrahydrofolate (leucovorin) sustains inhibition of thymidylate synthase. Methotrexate, by inhibiting purine synthesis and increasing cellular pools of certain substrates for reactivity with 5-FU, enhances the activation of 5-FU. The combination of cisplatin and 5-FU increases the antitumor activity of 5-FU. Oxaliplatin is commonly used with 5-FU and leucovorin for treating colorectal cancer, and it may inhibit catabolism of 5-FU, perhaps by inhibiting dihydropyrimidine dehydrogenase (the enzyme that is responsible for the catabolism of 5-FU), and may also inhibit expression of thymidylate synthase. The combination of 5-FU and irinotecan, a topoisomerase-1 inhibitor, is a treatment that combines 5-FU with an agent that has a different mechanism of action. Eniluracil, which is an inactivator of dihydropyrimidine dehydrogenase, leads to another strategy for improving the efficacy of 5-FU.

A number of 5-FU prodrugs have been developed. One is capecitabine (N4-pentoxycarbonyl-5'-deoxy-5-fluorcytidine). This orally administered agent is converted to 5'-deoxy-5-fluorcytidine by the ubiquitous enzyme cytidine deaminase. The final step in its activation occurs when thymidine phosphorylase cleaves off the 5'-deoxy sugar, leaving intracellular 5-FU. Capecitabine (Xeloda®) is approved by the FDA for certain treatments including colorectal cancer. Another fluoropyrimidine that acts as a prodrug for 5-FU is ftorafur.

As used herein, the terms "5-FU-based therapy", "5-FU based treatment", and "5-FU therapy" are used interchangeably to refer to encompass administration of 5-FU or a prodrug thereof and further encompasses administion of 5-FU combination or 5-FU combination therapy (e.g., 5-FU with the agents exemplified above).

General Description

The practice of the methods and compositions of the present disclosure will employ, unless otherwise indicated, conventional techniques of molecular biology (including recombinant techniques), microbiology, cell biology, and biochemistry, which are within the skill of the art. Such techniques are explained fully in the literature, such as, "Molecular Cloning: A Laboratory Manual", $2^{nd}$ edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", $4^{th}$ edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); and "PCR: The Polymerase Chain Reaction", (Mullis et al., eds., 1994).

Based on evidence of differential expression of a gene (e.g., as deteted by assaying for an RNA transcript or expression product threof) in cancer cells that positively respond to chemotherapy and non-responsive cancer cells, the present disclosure provides prognostic and/or predictive gene markers for colorectal cancer. Thus, in a particular aspect, the present disclosure provides prognostic and/or predictive gene markers of Stage II and/or Stage III colorectal cancer. The prognostic and/or predictive markers and associated information provided by the present disclosure allow physicians to make more intelligent treatment decisions, and to customize the treatment of colorectal cancer to the needs of individual patients, thereby maximizing the benefit of treatment and minimizing the exposure of patients to unnecessary treatments, which do not provide any significant benefits and often carry serious risks due to toxic side-effects.

The prognostic and/or predictive markers and associated information provided by the present disclosure predicting the clinical outcome in Stage II and/or Stage III cancers of the colon and/or rectum has utility in the development of drugs to treat Stage II and/or Stage III cancers of the colon and/or rectum.

The prognostic and/or predictive markers and associated information provided by the present disclosure predicting the clinical outcome of treatment with 5-FU/leucovorin of Stage II and/or Stage III cancers of the colon and/or rectum also have utility in screening patients for inclusion in clinical trials that test the efficacy of other drug compounds. The predictive markers and associated information provided by the present disclosure predicting the clinical outcome of treatment with 5-FU/leucovorin of Stage II and/or Stage III cancers of the colon and/or rectum are useful as inclusion criterion for a clinical trial. For example, a patient is more likely to be included in a clinical trial if the results of the test indicate that the patient will have a poor clinical outcome if treated with surgery and 5-FU/leucovorin and a patient is less likely to be included in a clinical trial if the results of the test indicate that the patient will have a good clinical outcome if treated with surgery alone or with surgery and 5-FU/leucovorin.

In a particular embodiment, prognostic and/or predictive markers and associated information are used to design or produce a reagent that modulates the level or activity of the gene's transcript (i.e., RNA transcript) or its expression product. Said reagents may include but are not limited to an antisense RNA, a small inhibitory RNA, a ribozyme, a monoclonal or polyclonal antibody.

In various embodiments of the methods of the present disclosure, various technological approaches are available for determination of expression levels of the disclosed genes, including, without limitation, RT-PCR, microarrays, serial analysis of gene expression (SAGE) and Gene Expression Analysis by Massively Parallel Signature Sequencing (MPSS), which will be discussed in detail below. In particular embodiments, the expression level of each gene may be determined in relation to various features of the expression products of the gene including exons, introns, protein epitopes and protein activity Gene Expression Profiling Methods of gene expression profiling include methods based on hybridization analysis of polynucleotides, methods based on sequencing of polynucleotides, and proteomics-based methods. The most commonly used methods known in the art for the quantification of mRNA expression in a sample include northern blotting and in situ hybridization (Parker & Barnes, Methods in Molecular Biology 106:247-283 (1999)); RNAse protection assays (Hod, Biotechniques 13:852-854 (1992)); and PCR-based methods, such as reverse transcription polymerase chain reaction (RT-PCR) (Weis et al., Trends in Genetics 8:263-264 (1992)). Alternatively, antibodies may be employed that can recognize sequence-specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS).

Reverse Transcriptase PCR (RT-PCR)

The first step is the isolation of mRNA from a target sample. The starting material is typically total RNA isolated from human tumors or tumor cell lines, and, optionally, corresponding normal tissues or cell lines as a control, respectively. If the source of mRNA is a primary tumor, mRNA can be extracted, for example, from frozen or archived paraffin-embedded and fixed (e.g. formalin-fixed) tissue samples.

General methods for mRNA extraction are well known in the art and are disclosed in standard textbooks of molecular biology, including Ausubel et al., *Current Protocols of Molecular Biology*, John Wiley and Sons (1997). Methods for RNA extraction from paraffin embedded tissues are disclosed, for example, in Rupp and Locker, Lab Invest. 56:A67 (1987), and De Andrés et al., *BioTechniques* 18:42044 (1995). In particular, RNA isolation can be performed using a purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include Master-Pure™ Complete DNA and RNA Purification Kit (EPICENTRE®, Madison, Wis.), and Paraffin Block RNA Isolation Kit (Ambion, Inc.). Total RNA from tissue samples can be isolated using RNA Stat-60 (Tel-Test). RNA prepared from tumor can be isolated, for example, by cesium chloride density gradient centrifugation.

As RNA cannot serve as a template for PCR, the first step in gene expression profiling by RT-PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, Taq-Man® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® RT-PCR can be performed using commercially available equipment, such as, for example, ABI PRISM 7700™ Sequence Detection System™ (Perkin-Elmer-Applied Biosystems, Foster City, Calif., USA), or Lightcycler (Roche Molecular Biochemicals, Mannheim, Germany). In a preferred embodiment, the 5' nuclease procedure is run on a real-time quantitative PCR device such as the ABI PRISM 7700™ Sequence Detection System™. The system consists of a thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

5'-Nuclease assay data are initially expressed as $C_t$, or the threshold cycle. As discussed above, fluorescence values are recorded during every cycle and represent the amount of product amplified to that point in the amplification reaction. The point when the fluorescent signal is first recorded as statistically significant is the threshold cycle ($C_t$).

To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and β-actin.

A more recent variation of the RT-PCR technique is the real time quantitative PCR, which measures PCR product accumulation through a dual-labeled fluorigenic probe (i.e., TaqMan® probe). Real time PCR is compatible both with quantitative competitive PCR, where internal competitor for each target sequence is used for normalization, and with quantitative comparative PCR using a normalization gene contained within the sample, or a housekeeping gene for RT-PCR. For further details see, e.g. Held et al., *Genome Research* 6:986-994 (1996).

The steps of a representative protocol for profiling gene expression using fixed, paraffin-embedded tissues as the RNA source, including mRNA isolation, purification, primer extension and amplification are given in various published journal articles (for example: T. E. Godfrey et al. J. Molec. Diagnostics 2: 84-91 (2000); K. Specht et al., Am. J. Pathol. 158: 419-29 (2001)). Briefly, a representative process starts with cutting about 10 μm thick sections of paraffin-embedded tumor tissue samples. The RNA is then extracted, and protein and DNA are removed. After analysis of the RNA concentration, RNA repair and/or amplification steps may be included, if necessary, and RNA is reverse transcribed using gene specific primers followed by RT-PCR.

MassARRAY System

In the MassARRAY-based gene expression profiling method, developed by Sequenom, Inc. (San Diego, Calif.) following the isolation of RNA and reverse transcription, the obtained cDNA is spiked with a synthetic DNA molecule (competitor), which matches the targeted cDNA region in all positions, except a single base, and serves as an internal standard. The cDNA/competitor mixture is PCR amplified and is subjected to a post-PCR shrimp alkaline phosphatase (SAP) enzyme treatment, which results in the dephosphorylation of the remaining nucleotides. After inactivation of the alkaline phosphatase, the PCR products from the competitor and cDNA are subjected to primer extension, which generates distinct mass signals for the competitor- and cDNA-derived PCR products. After purification, these products are dispensed on a chip array, which is pre-loaded with components needed for analysis with matrix-assisted laser desorption ionization time-of-flight mass spectrometry (MALDI-TOF MS) analysis. The cDNA present in the reaction is then quantified by analyzing the ratios of the peak areas in the mass spectrum generated. For further details see, e.g. Ding and Cantor, Proc. Natl. Acad. Sci. USA 100:3059-3064 (2003).

Other PCR-Based Methods

Further PCR-based techniques include, for example, differential display (Liang and Pardee, Science 257:967-971 (1992)); amplified fragment length polymorphism (iAFLP) (Kawamoto et al., Genome Res. 12:1305-1312 (1999)); BeadArray™ technology (Illumina, San Diego, Calif.; Oliphant et al., Discovery of Markers for Disease (Supplement to Biotechniques), June 2002; Ferguson et al., Analytical Chemistry 72:5618 (2000)); BeadsArray for Detection of Gene Expression (BADGE), using the commercially available Luminex 100 LabMAP system and multiple color-coded microspheres (Luminex Corp., Austin, Tex.) in a rapid assay for gene expression (Yang et al., Genome Res. 11:1888-1898 (2001)); and high coverage expression profiling (HiCEP) analysis (Fukumura et al., Nucl. Acids. Res. 31(16) e94 (2003)).

Microarrays

Differential gene expression can also be identified, or confirmed using the microarray technique. Thus, the expression profile of colorectal cancer-associated genes can be measured in either fresh or paraffin-embedded tumor tissue, using microarray technology. In this method, polynucleotide sequences of interest (including cDNAs and oligonucleotides) are plated, or arrayed, on a microchip substrate. The arrayed sequences are then hybridized with specific DNA probes from cells or tissues of interest. Just as in the RT-PCR method, the source of mRNA typically is total RNA isolated from human tumors or tumor cell lines, and corresponding normal tissues or cell lines. Thus RNA can be isolated from a variety of primary tumors or tumor cell lines. If the source of mRNA is a primary tumor, mRNA can be extracted, for example, from frozen or archived paraffin-embedded and fixed (e.g. formalin-fixed) tissue samples, which are routinely prepared and preserved in everyday clinical practice.

In a specific embodiment of the microarray technique, PCR amplified inserts of cDNA clones are applied to a substrate in a dense array. Preferably at least 10,000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pair wise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., *Proc. Natl. Acad. Sci. USA* 93(2):106-149 (1996)). Microarray analysis can be performed by commercially available equipment, following manufacturer's protocols, such as by using the Affymetrix GenChip technology, or Incyte's microarray technology.

The development of microarray methods for large-scale analysis of gene expression makes it possible to search systematically for molecular markers of outcome predictions for a variety of chemotherapy treatments for a variety of tumor types.

Serial Analysis of Gene Expression (SAGE)

Serial analysis of gene expression (SAGE) is a method that allows the simultaneous and quantitative analysis of a large number of gene transcripts, without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. For more details see, e.g. Velculescu et al., *Science* 270:484-487 (1995); and Velculescu et al., *Cell* 88:243-51 (1997).

Gene Expression Analysis by Massively Parallel Signature Sequencing (MPSS)

This method, described by Brenner et al., *Nature Biotechnology* 18:630-634 (2000), is a sequencing approach that combines non-gel-based signature sequencing with in vitro cloning of millions of templates on separate 5 µm diameter microbeads. First, a microbead library of DNA templates is constructed by in vitro cloning. This is followed by the assembly of a planar array of the template-containing microbeads in a flow cell at a high density (typically greater than $3 \times 10^6$ microbeads/cm$^2$). The free ends of the cloned templates on each microbead are analyzed simultaneously, using a fluorescence-based signature sequencing method that does not require DNA fragment separation. This method has been shown to simultaneously and accurately provide, in a single operation, hundreds of thousands of gene signature sequences from a yeast cDNA library.

Immunohistochemistry

Immunohistochemistry methods are also suitable for detecting the expression levels of the prognostic and/or predictive markers of the present disclosure. Thus, antibodies or antisera, preferably polyclonal antisera, and most preferably monoclonal antibodies specific for each marker are used to detect expression. The antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. Immunohistochemistry protocols and kits are well known in the art and are commercially available.

Proteomics

The term "proteome" is defined as the totality of the proteins present in a sample (e.g. tissue, organism, or cell culture) at a certain point of time. Proteomics includes, among other things, study of the global changes of protein expression in a sample (also referred to as "expression proteomics"). Proteomics typically includes the following steps: (1) separation of individual proteins in a sample by 2-D gel electrophoresis (2-D PAGE); (2) identification of the individual proteins recovered from the gel, e.g. by mass spectrometry or N-terminal sequencing, and (3) analysis of the data using bioinformatics. Proteomics methods are valuable supplements to other methods of gene expression profiling, and can be used, alone or in combination with other methods, to detect the products of the prognostic and/or predictive markers of the present disclosure.

Promoter Methylation Analysis

A number of methods for quantization of RNA transcripts (gene expression analysis) or their protein translation products are discussed herein. The expression level of genes may also be inferred from information regarding chromatin structure, such as for example the methylation status of gene promoters and other regulatory elements and the acetylation status of histones.

In particular, the methylation status of a promoter influences the level of expression of the gene regulated by that promoter. Aberrant methylation of particular gene promoters has been implicated in expression regulation, such as for example silencing of tumor suppressor genes. Thus, examination of the methylation status of a gene's promoter can be utilized as a surrogate for direct quantization of RNA levels.

Several approaches for measuring the methylation status of particular DNA elements have been devised, including methylation-specific PCR (Herman J. G. et al. (1996) Methylation-specific PCR: a novel PCR assay for methylation status of CpG islands. Proc. Natl Acad. Sci. USA. 93, 9821-9826) and bisulfite DNA sequencing (Frommer M. et al. (1992) A genomic sequencing protocol that yields a positive display of 5-methylcytosine residues in individual DNA strands. Proc. Natl Acad. Sci. USA. 89, 1827-1831). More recently, microarray-based technologies have been used to characterize promoter methylation status (Chen C. M. (2003) Methylation target array for rapid analysis of CpG island hypermethylation in multiple tissue genomes. Am. J. Pathol. 163, 37-45).

General Description of the mRNA Isolation, Purification and Amplification

The steps of a representative protocol for profiling gene expression using fixed, paraffin-embedded tissues as the RNA source, including mRNA isolation, purification, primer extension and amplification are provided in various published journal articles (for example: T. E. Godfrey et al., *J. Molec. Diagnostics* 2: 84-91 (2000); K. Specht et al., *Am. J. Pathol.* 158: 419-29 (2001)). Briefly, a representative process starts with cutting about 10 µm thick sections of paraffin-embedded tumor tissue samples. The RNA is then extracted, and protein and DNA are removed. After analysis of the RNA concentration, RNA repair and/or amplification steps may be included, if necessary, and the RNA is reverse transcribed using gene specific primers followed by RT-PCR. Finally, the data are analyzed to identify and/or facilitate selection of treatment option(s) available to the patient on the basis of the characteristic gene expression pattern identified in the tumor sample examined, dependent on the predicted likelihood of response of the cancer to treatment.

Colon Cancer Gene Set, Assayed Gene Subsequences, and Clinical Application of Gene Expression Data The measured expression of certain genes by colon cancer tissue to provide prognostic and/or predictive information which is indicative of a likelihood of clinical benefit of treatment of a patient having cancer, particularly a colorectal cancer, with chemotherapy, particularly 5-FU therapy.

It is desirable to correct for (normalize away) both differences in the amount of RNA assayed and variability in the quality of the RNA used. Therefore, the assay typically measures, and expression analysis of a marker gene incorporates analysis of, the expression of certain reference genes (or "normalizing genes"), including well known housekeeping genes, such as GAPDH. Alternatively, normalization can be based on the mean or median signal (Ct) of all of the assayed genes or a large subset thereof (often referred to as a "global normalization" approach). On a gene-by-gene basis, measured normalized amount of a patient tumor mRNA may be compared to the amount found in a colon cancer tissue reference set. See M. Cronin, et al., Am. Soc. Investigative Pathology 164:35-42 (2004).

The genes assayed can include one or more (e.g., two or more, three or more, etc.) of the genes listed in Table 5, and/or a gene that is co-expressed with a gene listed in Table 5. As shown in the Examples below, increased expression of AURKB, Axin 2, BIK, BRAF, BRCA2, BUB1, C20 orf1, C20ORF126, CASP9, CCNE2 variant 1, CDC2, CDC4, CENPA, CENPF, CLIC1, CYR61, Cdx2, Chk1, DLC1, DUSP1, E2F1, EGR3, EI24, ESPL1, FBXO5, FGF2, FOS, FUT6, GSK3B, Grb10, HES6, HLA-G, HNRPAB, HOXB13, HSPE1, KIF22, KIFC1, KLRK1, Ki-67, LAT, LMYC, MAD2L1, MSH2, MSH3, NR4A1, PDGFA, PRDX2, RAB32, RAD54L, RANBP2, RCC1, ROCK2, RhoB, S100P, SAT, SOD1, SOS1, STK15, TCF-1, TOP2A, TP53BP1, UBE2C, VCP, and cMYC is positively correlated to an increased likelihood of a positive clinical response to treatment with chemotherapy; and increased expression of one or more of the genes selected from the group consisting of ABCB1, AMFR, ANXA1, APC, B-Catenin, BGN, CALD1, CD44E, CD44s, CD44v6, CD68, CDH11, CHFR, CLDN1, CLTC, COL1A1, COL1A2, CREBBP, CTSB, CTSL, CXCL12, EFNB2, ENO1, EPAS1, FGF18, FOXO3A, FPGS, FZD1, GJB2, GPX1, HIF1A, HNRPD, HSD17B2, HoxA5, IGFBP3, IGFBP5, IGFBP7, IL6ST, ITGA5, KLF5, KLK10, KRT8, LEF, LOX, MADH7, MCM3, MCP1, MMP1, MMP2, Maspin, NRP1, PDGFC, PDGFD, PDGFRa, PFN2, PKR2, RUNX1, SEMA4B, SIAT4A, SKP2, SPARC, SPRY1, THBS1, TIMP1, UPP1, and VDAC2 is negatively correlated to an increased likelihood of a positive response to treatment with chemotherapy.

Genes that exhibit an expression pattern that directly correlates with that of a gene of Table 5 are referred to herein as "co-expressed genes" or "substitute genes". Such genes can be assayed in lieu of the gene with which it exhibits co-expression, or can be assayed in combination with the gene with which it is co-expressed (e.g., as an internal control or to increase statistical power). Suitable co-expressed genes that exhibit co-expression with a gene of Table 5 are provided in Table C.

Design of Primers and Probes

Primers and probes (e.g., for use in PCR amplification-based methods) can be designed based upon exon sequence or upon intron sequences present in the gene to be amplified. Accordingly, the first step in the primer/probe design is the delineation of a target exon or intron sequence within the gene of interest. This can be done by publicly available software, such as the DNA BLAT software developed by Kent, W. J., *Genome Res.* 12(4):656-64 (2002), or by the BLAST software including its variations. Subsequent steps follow well established methods of PCR primer and probe design.

In order to avoid non-specific signals, repetitive sequences within the target sequence of the gene can be masked when designing the primers and probes. This can be easily accomplished by using the Repeat Masker program available on-line through the Baylor College of Medicine, which screens DNA sequences against a library of repetitive elements and returns a query sequence in which the repetitive elements are masked. The masked sequences can then be used to design primer and probe sequences using any commercially or otherwise publicly available primer/probe design packages, such as Primer Express (Applied Biosystems); MGB assay-by-design (Applied Biosystems); Primer3 (Steve Rozen and Helen J. Skaletsky (2000) Primer3 on the WWW for general users and for biologist programmers. In: Krawetz S, Misener S (eds) *Bioinformatics Methods and Protocols: Methods in Molecular Biology*. Humana Press, Totowa, N.J., pp 365-386).

The factors that to be considered in PCR primer design can include primer length, melting temperature (Tm), and G/C content, specificity, complementary primer sequences, and 3'-end sequence. In general, optimal PCR primers are generally 17-30 bases in length, and contain about 20-80%, such as, for example, about 50-60% G+C bases. Tm's between 50 and 80° C., e.g. about 50 to 70° C. are typically preferred.

For further guidelines for PCR primer and probe design see, e.g. Dieffenbach, C. W. et al., "General Concepts for PCR Primer Design" in: *PCR Primer, A Laboratory Manual*, Cold Spring Harbor Laboratory Press, New York, 1995, pp. 133-155; Innis and Gelfand, "Optimization of PCRs" in: *PCR Protocols, A Guide to Methods and Applications*, CRC Press, London, 1994, pp. 5-11; and Plasterer, T. N. Primerselect: Primer and probe design. *Methods Mol. Biol.* 70:520-527 (1997), the entire disclosures of which are hereby expressly incorporated by reference.

Kits

The materials for use in the methods of the present disclosure are suited for preparation of kits produced in accordance with well known procedures. The present disclosure thus provides kits comprising agents, which may include gene-specific or gene-selective probes and/or primers, for quantitating the expression of the disclosed genes for predicting clinical outcome or response to treatment. Such kits may optionally contain reagents for the extraction of RNA from tumor samples, in particular fixed paraffin-embedded tissue samples and/or reagents for RNA amplification. In addition, the kits may optionally comprise the reagent(s) with an identifying description or label or instructions relating to their use in the methods of the present disclosure. The kits may comprise containers (including microtiter plates suitable for use in an automated implementation of the method), each with one or more of the various reagents (typically in concentrated form) utilized in the methods, including, for example, prefabricated microarrays, buffers, the appropriate nucleotide triphosphates (e.g., dATP, dCTP, dGTP and dTTP; or rATP, rCTP, rGTP and UTP), reverse transcriptase, DNA polymerase, RNA polymerase, and one or more probes and primers of the present disclosure (e.g., appropriate length poly(T) or random primers linked to a promoter reactive with the RNA polymerase). Mathematical algorithms used to estimate or quantify prognostic and/or predictive information are also properly potential components of kits.

The methods provided by the present disclosure may also be automated in whole or in part.

Reports

The methods of the present disclosure are suited for the preparation of reports summarizing the predictions resulting from the methods of the present disclosure. A "report," as described herein, is an electronic or tangible document which includes report elements that provide information of interest relating to a likelihood assessment and its results. A subject report includes at least a likelihood assessment, e.g., an indication as to the likelihood that a cancer patient will exhibit a beneficial clinical response to a 5FU treatment regimen. A subject report can be completely or partially electronically generated, e.g., presented on an electronic display (e.g., computer monitor). A report can further include one or more of: 1) information regarding the testing facility; 2) service provider information; 3) patient data; 4) sample data; 5) an interpretive report, which can include various information including: a) indication; b) test data, where test data can include a normalized level of one or more genes of interest, and 6) other features.

The present disclosure thus provides for methods of creating reports and the reports resulting therefrom. The report may include a summary of the expression levels of the RNA transcripts, or the expression products of such RNA transcripts, for certain genes in the cells obtained from the patients tumor tissue. The report may include a prediction that said subject has an increased likelihood of response to treatment with a particular chemotherapy or the report may include a prediction that the subject has a decreased likelihood of response to the chemotherapy. The report may include a recommendation for treatment modality such as surgery alone or surgery in combination with chemotherapy. The report may be presented in electronic format or on paper.

Thus, in some embodiments, the methods of the present disclosure further includes generating a report that includes information regarding the patient's likelihood of response to chemotherapy, particularly an 5FU-based therapy. For example, the methods disclosed herein can further include a step of generating or outputting a report providing the results of a subject response likelihood assessment, which report can be provided in the form of an electronic medium (e.g., an electronic display on a computer monitor), or in the form of a tangible medium (e.g., a report printed on paper or other tangible medium).

A report that includes information regarding the likelihood that a patient will respond to treatment with chemotherapy, particularly a 5-FU-based therapy, is provided to a user. An assessment as to the likelihood that a cancer patient will respond to treatment with chemotherapy, particularly a 5FU-based therapy, is referred to below as a "response likelihood assessment" or, simply, "likelihood assessment." A person or entity who prepares a report ("report generator") will also perform the likelihood assessment. The report generator may also perform one or more of sample gathering, sample processing, and data generation, e.g., the report generator may also perform one or more of: a) sample gathering; b) sample processing; c) measuring a level of an indicator response gene product(s); d) measuring a level of a reference gene product(s); and e) determining a normalized level of a response indicator gene product(s). Alternatively, an entity other than the report generator can perform one or more sample gathering, sample processing, and data generation.

For clarity, it should be noted that the term "user," which is used interchangeably with "client," is meant to refer to a person or entity to whom a report is transmitted, and may be the same person or entity who does one or more of the following: a) collects a sample; b) processes a sample; c) provides a sample or a processed sample; and d) generates data (e.g., level of a response indicator gene product(s); level of a reference gene product(s); normalized level of a response indicator gene product(s)) for use in the likelihood assessment. In some cases, the person(s) or entity(ies) who provides sample collection and/or sample processing and/or data generation, and the person who receives the results and/or report may be different persons, but are both referred to as "users" or "clients" herein to avoid confusion. In certain embodiments, e.g., where the methods are completely executed on a single computer, the user or client provides for data input and review of data output. A "user" can be a health professional (e.g., a clinician, a laboratory technician, a physician (e.g., an oncologist, surgeon, pathologist), etc.).

In embodiments where the user only executes a portion of the method, the individual who, after computerized data processing according to the methods of the invention, reviews data output (e.g., results prior to release to provide a complete report, a complete, or reviews an "incomplete" report and provides for manual intervention and completion of an interpretive report) is referred to herein as a "reviewer." The reviewer may be located at a location remote to the user (e.g., at a service provided separate from a healthcare facility where a user may be located).

Where government regulations or other restrictions apply (e.g., requirements by health, malpractice, or liability insurance), all results, whether generated wholly or partially electronically, are subjected to a quality control routine prior to release to the user.

Computer-Based Systems and Methods

The methods and systems described herein can be implemented in numerous ways. In one embodiment of particular interest, the methods involve use of a communications infrastructure, for example the internet. Several embodiments of the invention are discussed below. It is also to be understood that the present invention may be implemented in various forms of hardware, software, firmware, processors, or a combination thereof. The methods and systems described herein can be implemented as a combination of hardware and software. The software can be implemented as an application program tangibly embodied on a program storage device, or different portions of the software implemented in the user's computing environment (e.g., as an applet) and on the reviewer's computing environment, where the reviewer may be located at a remote site associated (e.g., at a service provider's facility).

For example, during or after data input by the user, portions of the data processing can be performed in the user-side computing environment. For example, the user-side computing environment can be programmed to provide for defined test codes to denote a likelihood "score," where the score is transmitted as processed or partially processed responses to the reviewer's computing environment in the form of test code for subsequent execution of one or more algorithms to provide a results and/or generate a report in the reviewer's computing environment. The score can be a numerical score (representative of a numerical value) or a non-numerical score representive of a numerical value or range of numerical values (e.g., "A' representative of a 90-95% likelihood of an outcome; "high" respresentative of a greater than 50% chance of response (or some other selected threshold of likelihood); "low" representative of a less than 50% chance of response (or some other selected threshold of likelihood); and the like.

The application program for executing the algorithms described herein may be uploaded to, and executed by, a machine comprising any suitable architecture. In general, the machine involves a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the application program (or a combination thereof) which is executed via the operating system. In addition, various other peripheral devices may be connected to the computer platform such as an additional data storage device and a printing device.

As a computer system, the system generally includes a processor unit. The processor unit operates to receive information, which can include test data (e.g., level of a response indicator gene product(s); level of a reference gene product(s); normalized level of a response indicator gene product(s)); and may also include other data such as patient data. This information received can be stored at least temporarily in a database, and data analyzed to generate a report as described above.

Part or all of the input and output data can also be sent electronically; certain output data (e.g., reports) can be sent electronically or telephonically (e.g., by facsimile, e.g., using devices such as fax back). Exemplary output receiving devices can include a display element, a printer, a facsimile device and the like. Electronic forms of transmission and/or display can include email, interactive television, and the like. In an embodiment of particular interest, all or a portion of the input data and/or all or a portion of the output data (e.g., usually at least the final report) are maintained on a web server for access, preferably confidential access, with typical browsers. The data may be accessed or sent to health professionals as desired. The input and output data, including all or a portion of the final report, can be used to populate a patient's medical record which may exist in a confidential database at the healthcare facility.

A system for use in the methods described herein generally includes at least one computer processor (e.g., where the method is carried out in its entirety at a single site) or at least two networked computer processors (e.g., where data is to be input by a user (also referred to herein as a "client") and transmitted to a remote site to a second computer processor for analysis, where the first and second computer processors are connected by a network, e.g., via an intranet or internet). The system can also include a user component(s) for input; and a reviewer component(s) for review of data, generated reports, and manual intervention. Additional components of the system can include a server component(s); and a database(s) for storing data (e.g., as in a database of report elements, e.g., interpretive report elements, or a relational database (RDB) which can include data input by the user and data output. The computer processors can be processors that are typically found in personal desktop computers (e.g., IBM, Dell, Macintosh), portable computers, mainframes, minicomputers, or other computing devices.

The networked client/server architecture can be selected as desired, and can be, for example, a classic two or three tier client server model. A relational database management system (RDMS), either as part of an application server component or as a separate component (RDB machine) provides the interface to the database.

In one example, the architecture is provided as a database-centric client/server architecture, in which the client application generally requests services from the application server which makes requests to the database (or the database server) to populate the report with the various report elements as required, particularly the interpretive report elements, especially the interpretation text and alerts. The server(s) (e.g., either as part of the application server machine or a separate RDB/relational database machine) responds to the client's requests.

The input client components can be complete, stand-alone personal computers offering a full range of power and features to run applications. The client component usually operates under any desired operating system and includes a communication element (e.g., a modem or other hardware for connecting to a network), one or more input devices (e.g., a keyboard, mouse, keypad, or other device used to transfer information or commands), a storage element (e.g., a hard drive or other computer-readable, computer-writable storage medium), and a display element (e.g., a monitor, television, LCD, LED, or other display device that conveys information to the user). The user enters input commands into the computer processor through an input device. Generally, the user interface is a graphical user interface (GUI) written for web browser applications.

The server component(s) can be a personal computer, a minicomputer, or a mainframe and offers data management, information sharing between clients, network administration and security. The application and any databases used can be on the same or different servers.

Other computing arrangements for the client and server(s), including processing on a single machine such as a mainframe, a collection of machines, or other suitable configuration are contemplated. In general, the client and server machines work together to accomplish the processing of the present invention.

Where used, the database(s) is usually connected to the database server component and can be any device which will hold data. For example, the database can be a any magnetic or optical storing device for a computer (e.g., CDROM, internal hard drive, tape drive). The database can be located remote to the server component (with access via a network, modem, etc.) or locally to the server component.

Where used in the system and methods, the database can be a relational database that is organized and accessed according to relationships between data items. The relational database is generally composed of a plurality of tables (entities). The rows of a table represent records (collections of information about separate items) and the columns represent fields (particular attributes of a record). In its simplest conception, the relational database is a collection of data entries that "relate" to each other through at least one common field.

Additional workstations equipped with computers and printers may be used at point of service to enter data and, in some embodiments, generate appropriate reports, if desired. The computer(s) can have a shortcut (e.g., on the desktop) to launch the application to facilitate initiation of data entry, transmission, analysis, report receipt, etc. as desired.

Computer-Readable Storage Media

The present disclosure also contemplates a computer-readable storage medium (e.g. CD-ROM, memory key, flash memory card, diskette, etc.) having stored thereon a program which, when executed in a computing environment, provides for implementation of algorithms to carry out all or a portion of the results of a response likelihood assessment as described herein. Where the computer-readable medium contains a complete program for carrying out the methods described herein, the program includes program instructions for collecting, analyzing and generating output, and generally includes computer readable code devices for interacting with a user as described herein, processing that data in conjunction with analytical information, and generating unique printed or electronic media for that user.

Where the storage medium provides a program which provides for implementation of a portion of the methods described herein (e.g., the user-side aspect of the methods (e.g., data input, report receipt capabilities, etc.)), the program provides for transmission of data input by the user (e.g., via the internet, via an intranet, etc.) to a computing environment at a remote site. Processing or completion of processing of the data is carried out at the remote site to generate a report.

After review of the report, and completion of any needed manual intervention, to provide a complete report, the complete report is then transmitted back to the user as an electronic document or printed document (e.g., fax or mailed paper report). The storage medium containing a program according to the invention can be packaged with instructions (e.g., for program installation, use, etc.) recorded on a suitable substrate or a web address where such instructions may be obtained. The computer-readable storage medium can also be provided in combination with one or more reagents for carrying out response likelihood assessment (e.g., primers, probes, arrays, or other such kit components).

All aspects of the present disclosure may also be practiced such that a limited number of additional genes that are co-expressed with the disclosed genes, for example as evidenced by high Pearson correlation coefficients, are included in a prognostic and/or predictive test in addition to and/or in place of disclosed genes.

Having described the invention, the same will be more readily understood through reference to the following Examples, which are provided by way of illustration, and are not intended to limit the invention in any way. All citations throughout the disclosure are hereby expressly incorporated by reference.

Example 1

A Study to Identify Relationships Between Genomic Tumor Expression Profiles and the Likelihood of Recurrence in Dukes' B and Duke's C Colon Cancer Patients Treated with Resection of the Colon The primary objective of this study was to determine whether there is a significant relationship between the expression of each of 751 test genes identified in Table B and clinical outcome in stage II and stage III colon cancer patients who receive colon resection (surgery) without chemotherapy.

Table A shows qRT-PCR and primer and probe sequences for all test and reference genes included in the studies described in the Examples. Reagt=Reagent; FPr=Forward Primer; RPr=Reverse Primer Table B shows target amplicons for all test and reference genes included in the studies described in the Examples.

Study Design

This study used tissue and outcome data from National Surgical Adjuvant Breast and Bowel Project (NSABP) Studies C-01 and C-02 in up to 400 Dukes B (stage II) and Dukes C (stage III) patients who received colon resection (surgery) only or surgery and postoperative Bacillus Calmette-Guerin (BCG).

Inclusion Criteria

Patients enrolled in either NSABP Study C-01: "A Clinical Trial To Evaluate Postoperative Immunotherapy And Postoperative Systemic Chemotherapy In The Management Of Resectable Colon Cancer" or NSABP Study C-02: "A Protocol To Evaluate The Postoperative Portal Vein Infusion Of 5-Fluorouracil And Heparin In Adenocarcinoma Of The Colon" Details of C-01 and C-02 can be found on the NSABP Website at the following URL: www.nsabp.pitt.edu/NSABP_Protocols.htm#treatment%20closed Tissue samples from the surgery only and surgery+postoperative BCG arms of NSABP C01 and from the surgery only arm of NSABP C02 surgery were combined into one sample set.

Exclusion Criteria

Patients enrolled in NSABP Study C-01 or NSABP Study C-02 were excluded from the present study if one or more of the following applied:

No tumor block available from initial diagnosis in the NSABP archive.

Insufficient tumor in block as assessed by examination of hematoxylin and eosin (H&E) slide.

Insufficient RNA (<700 ng) recovered from tissue sections for RT-PCR analysis.

Of 1943 patients enrolled in NSABP Study C-01 or NSABP Study C-02, 270 patient samples were available after application of exclusion criteria and used in the gene expression study disclosed herein. The overall demographic and clinical characteristics of the 270 included samples were similar to the original NSABP combined cohorts.

Gene Panel

Seven hundred fifty-seven genes, including reference genes (ATP5E, CLTC, GPX1, NEDD8, PGK1, UBB), were chosen for expression analysis. These genes are listed in Table A together with the sequences of primers and probes used in qRT-PCR to determine expression level.

Experimental Materials and Methods

The expression of 751 cancer-related test genes and 6 genes designated for use as reference genes was quantitatively assessed for each patient using TaqMan® RT-PCR, which was performed in singlet with RNA input at 1 nanogram per reaction.

Data Analysis Methods

Reference Normalization

For normalization of extraneous effects, cycle threshold ($C_T$) measurements obtained by RT-PCR were normalized relative to the mean expression of a set of reference genes. The resulting reference-normalized expression measurements typically range from 0 to 15, where a one unit increase generally reflects a 2-fold increase in RNA quantity.

Comparison of Study Cohort to Original NSABP Study Populations

We compared the distribution of clinical and demographic variables for the current study cohort of evaluable tissue blocks versus the original NSABP C-01 and C-02 study populations. There were no clinically meaningful differences in the distributions.

Univariate Analysis

For each of the 751 genes under study, we used the Cox proportional hazard model to examine the relationship between gene expression and recurrence free interval (RFI). The likelihood ratio was used as the test of statistical significance. The method of Benjamini and Hochberg (Benjamini, Y. and Hochberg, Y. (1995). Controlling the false discovery rate: a practical and powerful approach to multiple testing. J. R. Statist. Soc. B 57, 289-300), as well as resampling and permutation based methods (Tusher V G, Tibshirani R, Chu G (2001) Significance analysis of microarrays applied to the ionizing radiation response. Proc Natl Acad Sci USA, 98:5116-5121; Storey J D, Tibshirani R (2001) Estimating false discovery rates under dependence, with applications to DNA microarrays. Stanford: Stanford University, Department of Statistics; Report No.: Technical Report 2001-28; Korn E L, Troendle J, McShane L, Simon R (2001) Controlling the number of false discoveries: Application to high-dimensional genomic data. Technical Report 003. 2001. National Cancer Institute) were applied to the resulting set of p-values to estimate false discovery rates All analyses were repeated for each of the alternative endpoints: distant recurrence free interval (DRFI), overall survival (OS), and disease free survival (DFS).

Study Results

Table 1A shows associations for those genes whose increased expression is predictive of shorter Recurrence-Free Interval (RFI) in untreated patients (surgical resection only) based on univariate proportional hazards analysis. Table 1A shows associations between clinical outcome and gene expression for those genes which demonstrated a Hazard Ratio>1.0 and for which p<0.1. Univariate Cox Proportional Hazards Regression analysis was applied in combined Stage II (Duke's B) and Stage III (Duke's C) patients using RFI as the metric for clinical outcome.

TABLE 1A

| Gene | Hazard Ratio | P Value | Official Symbol | Accession Number |
|---|---|---|---|---|
| RARB | 2.22 | 0.0294 | RARB | NM_016152 |
| ITGB1 | 2.04 | 0.0002 | ITGB1 | NM_002211 |
| ANXA2 | 1.78 | 0.0003 | ANXA2 | NM_004039 |
| CYP3A4 | 1.68 | 0.0075 | CYP3A4 | NM_017460 |
| COX2 | 1.64 | 0.0604 | PTGS2 | NM_000963 |
| KRAS2 | 1.62 | 0.0064 | KRAS | NM_004985 |
| TJP1 | 1.58 | 0.0751 | TJP1 | NM_003257 |
| KIAA0125 | 1.58 | 0.0889 | KIAA0125 | NM_014792 |
| RhoB | 1.57 | 0.0002 | RHOB | NM_004040 |
| RhoC | 1.56 | 0.0059 | RHOC | NM_175744 |
| NTN1 | 1.54 | 0.0336 | NTN1 | NM_004822 |
| ANXA5 | 1.52 | 0.0086 | ANXA5 | NM_001154 |
| TIMP1 | 1.52 | <.0001 | TIMP1 | NM_003254 |
| AKT3 | 1.50 | <.0001 | AKT3 | NM_005465 |
| CALD1 | 1.48 | 0.0007 | CALD1 | NM_004342 |
| IGFBP7 | 1.46 | 0.0023 | IGFBP7 | NM_001553 |
| CYP1B1 | 1.45 | 0.0222 | CYP1B1 | NM_000104 |
| BGN | 1.44 | 0.0002 | BGN | NM_001711 |
| VEGFC | 1.44 | 0.0151 | VEGFC | NM_005429 |
| DLC1 | 1.44 | 0.0014 | DLC1 | NM_006094 |
| SI | 1.42 | 0.0086 | SI | NM_001041 |
| TIMP2 | 1.42 | 0.0022 | TIMP2 | NM_003255 |
| CDC42BPA | 1.41 | 0.0038 | CDC42BPA | NM_003607 |
| LAMC2 | 1.40 | 0.0004 | LAMC2 | NM_005562 |
| ITGAV | 1.40 | 0.0019 | ITGAV | NM_002210 |
| CTSB | 1.40 | 0.0357 | CTSB | NM_001908 |
| DUSP1 | 1.39 | <.0001 | DUSP1 | NM_004417 |
| TLN1 | 1.39 | 0.0335 | TLN1 | NM_006289 |
| CCNE2 variant 1 | 1.39 | 0.0708 | CCNE2 | NM_057749 |
| TIMP3 | 1.38 | 0.0023 | TIMP3 | NM_000362 |
| GHI BRAF mut4 | 1.38 | 0.0537 | | GHI_BRAF_mut4 |
| HB-EGF | 1.38 | 0.0109 | HBEGF | NM_001945 |
| HSPG2 | 1.38 | 0.0258 | HSPG2 | NM_005529 |
| VIM | 1.37 | 0.0077 | VIM | NM_003380 |
| ROCK1 | 1.37 | 0.0168 | ROCK1 | NM_005406 |
| S100A1 | 1.36 | 0.0233 | S100A1 | NM_006271 |
| p21 | 1.36 | 0.0113 | CDKN1A | NM_000389 |
| CGB | 1.36 | 0.0023 | CGB | NM_000737 |
| UBC | 1.36 | 0.0137 | UBC | NM_021009 |
| GADD45B | 1.36 | 0.0003 | GADD45B | NM_015675 |
| INHBA | 1.35 | 0.0010 | INHBA | NM_002192 |
| VCL | 1.34 | 0.0286 | VCL | NM_003373 |
| SIR2 | 1.34 | 0.0049 | SIRT1 | NM_012238 |
| CD68 | 1.34 | 0.0042 | CD68 | NM_001251 |
| Maspin | 1.34 | <.0001 | SERPINB5 | NM_002639 |
| FST | 1.33 | 0.0326 | FST | NM_006350 |
| EPAS1 | 1.33 | 0.0306 | EPAS1 | NM_001430 |
| LOXL2 | 1.33 | 0.0076 | LOXL2 | NM_002318 |
| STC1 | 1.33 | 0.0119 | STC1 | NM_003155 |
| UNC5C | 1.32 | 0.0642 | UNC5C | NM_003728 |
| IGFBP5 | 1.32 | 0.0080 | IGFBP5 | NM_000599 |
| INHBB | 1.32 | 0.0643 | INHBB | NM_002193 |
| FAP | 1.32 | 0.0017 | FAP | NM_004460 |
| DKK1 | 1.31 | 0.0298 | DKK1 | NM_012242 |
| FYN | 1.31 | 0.0053 | FYN | NM_002037 |
| CTHRC1 | 1.31 | 0.0017 | CTHRC1 | NM_138455 |
| FOS | 1.31 | 0.0010 | FOS | NM_005252 |
| RBX1 | 1.31 | 0.0633 | RBX1 | NM_014248 |
| TAGLN | 1.31 | 0.0058 | TAGLN | NM_003186 |
| SBA2 | 1.31 | 0.0439 | WSB2 | NM_018639 |
| CYR61 | 1.30 | 0.0018 | CYR61 | NM_001554 |
| SPARC | 1.30 | 0.0117 | SPARC | NM_003118 |
| SNAI2 | 1.30 | 0.0076 | SNAI2 | NM_003068 |
| TMSB10 | 1.30 | 0.0757 | TMSB10 | NM_021103 |
| IGFBP3 | 1.30 | 0.0056 | IGFBP3 | NM_000598 |
| PDGFC | 1.29 | 0.0040 | PDGFC | NM_016205 |
| SLPI | 1.29 | 0.0026 | SLPI | NM_003064 |
| COL1A2 | 1.29 | 0.0087 | COL1A2 | NM_000089 |
| NRP2 | 1.29 | 0.0112 | NRP2 | NM_003872 |
| PRKCA | 1.29 | 0.0093 | PRKCA | NM_002737 |
| KLF6 | 1.29 | 0.0661 | KLF6 | NM_001300 |
| THBS1 | 1.28 | 0.0062 | THBS1 | NM_003246 |
| EGR1 | 1.28 | 0.0067 | EGR1 | NM_001964 |
| S100A4 | 1.28 | 0.0070 | S100A4 | NM_002961 |
| CXCR4 | 1.28 | 0.0089 | CXCR4 | NM_003467 |
| LAMA3 | 1.27 | 0.0024 | LAMA3 | NM_000227 |
| LOX | 1.26 | 0.0036 | LOX | NM_002317 |
| AKAP12 | 1.26 | 0.0046 | AKAP12 | NM_005100 |
| ADAMTS12 | 1.26 | 0.0109 | ADAMTS12 | NM_030955 |
| MCP1 | 1.25 | 0.0122 | CCL2 | NM_002982 |
| Grb10 | 1.25 | 0.0107 | GRB10 | NM_005311 |
| PTGER3 | 1.25 | 0.0240 | PTGER3 | NM_000957 |
| CRYAB | 1.25 | 0.0035 | CRYAB | NM_001885 |
| ANGPT2 | 1.25 | 0.0566 | ANGPT2 | NM_001147 |
| ANXA1 | 1.25 | 0.0353 | ANXA1 | NM_000700 |
| EphB6 | 1.24 | 0.0960 | EPHB6 | NM_004445 |
| PDGFB | 1.24 | 0.0139 | PDGFB | NM_002608 |
| COL1A1 | 1.24 | 0.0198 | COL1A1 | NM_000088 |
| TGFB3 | 1.23 | 0.0094 | TGFB3 | NM_003239 |
| CTGF | 1.23 | 0.0265 | CTGF | NM_001901 |
| PDGFA | 1.23 | 0.0312 | | NM_002607 |
| HSPA1A | 1.23 | 0.0027 | HSPA1A | NM_005345 |
| EFNB2 | 1.23 | 0.0331 | EFNB2 | NM_004093 |
| CAPG | 1.23 | 0.0724 | CAPG | NM_001747 |
| TGFBI | 1.22 | 0.0231 | TGFBI | NM_000358 |
| SIAT4A | 1.22 | 0.0253 | ST3GAL1 | NM_003033 |
| LAT | 1.22 | 0.0307 | LAT | NM_014387 |
| ITGA5 | 1.22 | 0.0224 | ITGA5 | NM_002205 |
| GBP2 | 1.22 | 0.0225 | GBP2 | NM_004120 |
| ANTXR1 | 1.22 | 0.0204 | ANTXR1 | NM_032208 |
| ID4 | 1.22 | 0.0512 | ID4 | NM_001546 |
| SFRP2 | 1.22 | 0.0039 | SFRP2 | NM_003013 |
| TMEPAI | 1.21 | 0.0170 | TMEPAI | NM_020182 |
| CTSL | 1.21 | 0.0388 | CTSL | NM_001912 |
| KLK10 | 1.21 | 0.0007 | KLK10 | NM_002776 |
| FXYD5 | 1.21 | 0.0547 | FXYD5 | NM_014164 |
| GJB2 | 1.21 | 0.0356 | GJB2 | NM_004004 |
| P14ARF | 1.21 | 0.0451 | | S78535 |
| DAPK1 | 1.21 | 0.0525 | DAPK1 | NM_004938 |
| SKP1A | 1.21 | 0.0663 | SKP1A | NM_006930 |
| SFRP4 | 1.21 | 0.0078 | SFRP4 | NM_003014 |
| KLK6 | 1.20 | 0.0048 | KLK6 | NM_002774 |
| GJA1 | 1.20 | 0.0345 | GJA1 | NM_000165 |
| HOXB7 | 1.20 | 0.0278 | HOXB7 | NM_004502 |
| NDRG1 | 1.20 | 0.0948 | NDRG1 | NM_006096 |
| PAI1 | 1.19 | 0.0061 | SERPINE1 | NM_000602 |
| CDH11 | 1.19 | 0.0762 | CDH11 | NM_001797 |
| EGR3 | 1.19 | 0.0149 | EGR3 | NM_004430 |
| EMP1 | 1.19 | 0.0533 | EMP1 | NM_001423 |
| FZD1 | 1.19 | 0.0671 | FZD1 | NM_003505 |
| ABCC5 | 1.19 | 0.0631 | ABCC5 | NM_005688 |
| S100P | 1.18 | 0.0160 | S100P | NM_005980 |
| OPN, osteopontin | 1.18 | 0.0030 | SPP1 | NM_000582 |
| p16-INK4 | 1.17 | 0.0503 | | L27211 |
| NR4A1 | 1.17 | 0.0332 | NR4A1 | NM_002135 |
| TUBB | 1.17 | 0.0950 | TUBB2 | NM_001069 |
| SIAT7B | 1.17 | 0.0352 | ST6GALNAC2 | NM_006456 |
| ALDH1A1 | 1.17 | 0.0299 | ALDH1A1 | NM_000689 |
| F3 | 1.16 | 0.0654 | F3 | NM_001993 |
| SLC2A1 | 1.15 | 0.0806 | SLC2A1 | NM_006516 |
| CXCL12 | 1.13 | 0.0986 | CXCL12 | NM_000609 |
| STMY3 | 1.13 | 0.0518 | MMP11 | NM_005940 |
| S100A2 | 1.13 | 0.0303 | S100A2 | NM_005978 |
| FABP4 | 1.13 | 0.0363 | FABP4 | NM_001442 |

TABLE 1A-continued

| Gene | Hazard Ratio | P Value | Official Symbol | Accession Number |
|---|---|---|---|---|
| REG4 | 1.11 | 0.0034 | REG4 | NM_032044 |
| pS2 | 1.09 | 0.0690 | TFF1 | NM_003225 |
| MUC2 | 1.06 | 0.0674 | MUC2 | NM_002457 |

Table 1B shows associations for those genes whose increased expression is predictive of longer Recurrence-Free Interval (RFI) in untreated patients (surgical resection only) based on univariate proportional hazards analysis. Table 1B shows associations between clinical outcome and gene expression for those genes which demonstrated a Hazard Ratio<1.0 and for which p<0.1. Univariate Cox Proportional Hazards Regression analysis was applied in combined Stage II (Duke's B) and Stage III (Duke's C) patients using RFI as the metric for clinical outcome.

TABLE 1B

| Gene | Hazard Ratio | P Value | Official Symbol | Accession Number |
|---|---|---|---|---|
| ORC1L | 0.41 | 0.0623 | ORC1L | NM_004153 |
| E2F1 | 0.63 | 0.0006 | E2F1 | NM_005225 |
| HSPA8 | 0.63 | 0.0346 | HSPA8 | NM_006597 |
| RAD54L | 0.65 | 0.0026 | RAD54L | NM_003579 |
| BRCA1 | 0.68 | 0.0001 | BRCA1 | NM_007295 |
| SLC25A3 | 0.70 | 0.0100 | SLC25A3 | NM_213611 |
| PPM1D | 0.71 | 0.0025 | PPM1D | NM_003620 |
| DHFR | 0.71 | 0.0106 | DHFR | NM_000791 |
| SKP2 | 0.72 | 0.0087 | SKP2 | NM_005983 |
| FASN | 0.73 | 0.0070 | FASN | NM_004104 |
| HNRPD | 0.73 | 0.0611 | HNRPD | NM_031370 |
| ENO1 | 0.74 | 0.0432 | ENO1 | NM_001428 |
| C20 orf1 | 0.74 | 0.0086 | TPX2 | NM_012112 |
| BRCA2 | 0.75 | 0.0515 | BRCA2 | NM_000059 |
| DDB1 | 0.75 | 0.0639 | DDB1 | NM_001923 |
| KIF22 | 0.76 | 0.0127 | KIF22 | NM_007317 |
| RPLPO | 0.76 | 0.0330 | RPLP0 | NM_001002 |
| Chk1 | 0.76 | 0.0164 | CHEK1 | NM_001274 |
| ST14 | 0.77 | 0.0392 | ST14 | NM_021978 |
| Bax | 0.77 | 0.0502 | BAX | NM_004324 |
| TCF-1 | 0.78 | 0.0023 | TCF1 | NM_000545 |
| LMNB1 | 0.78 | 0.0458 | LMNB1 | NM_005573 |
| RRM1 | 0.78 | 0.0693 | RRM1 | NM_001033 |
| CSEL1 | 0.79 | 0.0261 | CSE1L | NM_001316 |
| CDC20 | 0.79 | 0.0274 | CDC20 | NM_001255 |
| PRDX2 | 0.79 | 0.0930 | PRDX2 | NM_005809 |
| RPS13 | 0.79 | 0.0906 | RPS13 | NM_001017 |
| RAF1 | 0.80 | 0.0717 | RAF1 | NM_002880 |
| CMYC | 0.80 | 0.0095 | MYC | NM_002467 |
| UBE2M | 0.80 | 0.0390 | UBE2M | NM_003969 |
| CKS2 | 0.80 | 0.0596 | CKS2 | NM_001827 |
| NME1 | 0.80 | 0.0694 | NME1 | NM_000269 |
| c-myb (MYB official) | 0.80 | 0.0082 | MYB | NM_005375 |
| CD80 | 0.80 | 0.0688 | CD80 | NM_005191 |
| CDCA7 v2 | 0.81 | 0.0164 | CDCA7 | NM_145810 |
| EFP | 0.81 | 0.0387 | TRIM25 | NM_005082 |
| CCNE2 | 0.81 | 0.0405 | CCNE2 | NM_057749 |
| SURV | 0.81 | 0.0573 | BIRC5 | NM_001168 |
| RRM2 | 0.82 | 0.0181 | RRM2 | NM_001034 |
| ABCC6 | 0.82 | 0.0464 | ABCC6 | NM_001171 |
| UMPS | 0.82 | 0.0371 | UMPS | NM_000373 |
| PI3KC2A | 0.82 | 0.0855 | PIK3C2A | NM_002645 |
| NOTCH1 | 0.82 | 0.0222 | NOTCH1 | NM_017617 |
| EIF4E | 0.82 | 0.0928 | EIF4E | NM_001968 |
| EPHB2 | 0.82 | 0.0183 | EPHB2 | NM_004442 |
| AREG | 0.83 | 0.0012 | AREG | NM_001657 |
| EREG | 0.83 | 0.0059 | EREG | NM_001432 |
| MYBL2 | 0.83 | 0.0234 | MYBL2 | NM_002466 |
| ABCB1 | 0.83 | 0.0342 | ABCB1 | NM_000927 |
| HRAS | 0.83 | 0.0708 | HRAS | NM_005343 |
| SLC7A5 | 0.84 | 0.0547 | SLC7A5 | NM_003486 |
| MAD2L1 | 0.84 | 0.0653 | MAD2L1 | NM_002358 |
| ING5 | 0.85 | 0.0920 | ING5 | NM_032329 |

TABLE 1B-continued

| Gene | Hazard Ratio | P Value | Official Symbol | Accession Number |
|---|---|---|---|---|
| Ki-67 | 0.85 | 0.0562 | MKI67 | NM_002417 |
| MCM2 | 0.85 | 0.0671 | MCM2 | NM_004526 |
| Cdx2 | 0.88 | 0.0430 | CDX2 | NM_001265 |
| HES6 | 0.89 | 0.0966 | HES6 | NM_018645 |
| PTPRO | 0.89 | 0.0664 | PTPRO | NM_030667 |
| cripto (TDGF1 official) | 0.90 | 0.0781 | TDGF1 | NM_003212 |

The hazard ratios derived from the Cox proportional hazards regression model provided in Tables 1A and 1B provide an assessment of the contribution of the instantaneous risk of recurrence at time t conditional on a recurrence not occurring by time t. For an individual with gene expression measurement X, the instantaneous risk of recurrence at time t, $\lambda(t|X)$ is given by the relationship $\lambda(t|X)=\lambda_o(t) \cdot \exp[\beta \cdot X]$ where $\lambda_o(t)$ is the baseline hazard at time t and $\beta$ is the log hazard ratio ($\beta=\ln[HR]$) from Tables 1A or 1B. Furthermore, the survivor function at time t is given by $S(t|X)=S_o(t)^{\exp[\beta \cdot X]}$, where $=S_o(t)$ is the baseline survivor function at time t. Consequently, the risk of recurrence at time t for a patient with a gene expression measurement of X is given by $1-S(t|X)$. In this way, an individual patient's estimated risk of recurrence may be derived from an observed gene expression measurement. As an example, suppose the baseline estimate of survival at 3 years is 0.95. Then a patient with a gene expression measurement of 5 for INHBA would have an estimated risk of recurrence of approximately $1-0.95^{\exp[\ln(1.35) \cdot 4]}=0.205$.

Example 2

A Study to Identify Relationships Between Tumor Gene Expression Profiles and Recurrence-Free Interval in Dukes' B and Duke's C Colon Cancer Patients Treated with Leucovorin-Modulated Fluorouracil after Resection of the Colon The primary objective of this study was to determine whether there is a significant relationship between the expression of each of 751 test genes identified in Table B and clinical outcome in stage II and stage III colon cancer patients who received chemotherapy with leucovorin-modulated fluorouracil after colon resection surgery. Improvement in a clinical endpoint such as recurrence free interval reflects an increased likelihood of response to treatment with FU/LV and an increased likelihood of a positive clinical outcome.

Study Design

This study used tissue and outcome data from National Surgical Adjuvant Breast and Bowel Project (NSABP) Study C04 in up to 360 Dukes B (stage II) and Dukes C (stage III) patients who received colon resection and postoperative treatment with 5-fluorouracil and leucovorin.

Inclusion Criteria

Enrollment in NSABP Study C-04: "A Clinical Trial to Assess the Relative Efficacy of Fluorouracil and Leucovorin, Fluorouracil and Levamisole, and Fluorouracil, Leucovorin, and Levamisole in Patients With Dukes' B and C Carcinoma of the Colon" and randomization to leucovorin-modulated fluorouracil (LV+5-FU) arm of the study. Details of C-04 can be found on the NSABP Website at the following URL: www.nsabp.pittedu/NSABP_Protocols.htm#treatment%20closed.

Exclusion Criteria

Patients enrolled in NSABP Study C-04 were excluded from the present study if one or more of the following applied:
- No tumor block available from initial diagnosis in the NSABP archive.
- Insufficient tumor in block as assessed by examination of hematoxylin and eosin (H&E) slide.
- Insufficient RNA (<700 ng) recovered from tissue sections for RT-PCR analysis.
- Pathologically ineligible.
- Clinically ineligible.

Of 1943 patients enrolled in NSABP Study C-04, 308 patient samples were available after application of exclusion criteria and used in the gene expression study disclosed herein. The overall demographic and clinical characteristics of the 308 included samples were similar to the original NSABP combined cohorts.

Gene Panel

Seven hundred fifty-seven genes, including reference genes (ATP5E, CLTC, GPX1, NEDD8, PGK1, UBB), were chosen for expression analysis. These genes are listed in Table A together with the sequences of primers and probes used in qRT-PCR to determine expression level.

Experimental Materials and Methods

The expression of 751 cancer-related test genes plus six genes designated for use as reference genes was quantitatively assessed for each patient using TaqMan® RT-PCR, which was performed in singlet with RNA input at 1 nanogram per reaction.

Data Analysis Methods

Reference Normalization

For normalization of extraneous effects, cycle threshold ($C_T$) measurements obtained by RT-PCR were normalized relative to the mean expression of a set of reference genes. The resulting reference-normalized expression measurements typically range from 0 to 15, where a one unit increase generally reflects a 2-fold increase in RNA quantity.

Comparison of Study Cohort to Original NSABP Study Populations

The distribution of clinical and demographic variables for the current study cohort of evaluable tissue blocks was compared to the original NSABP C-04 study population. There were no clinically meaningful differences in the distributions.

Univariate Analysis

For each of the 751 genes under study, the Cox proportional hazard model was used to examine the relationship between gene expression and recurrence free interval (RFI). The likelihood ratio was used as the test of statistical significance. The method of Benjamini and Hochberg (Benjamini, Y. and Hochberg, Y. (1995). Controlling the false discovery rate: a practical and powerful approach to multiple testing. J. R. Statist. Soc. B 57, 289-300), as well as resampling and permutation based methods (Tusher V G, Tibshirani R, Chu G (2001) Significance analysis of microarrays applied to the ionizing radiation response. Proc Natl Acad Sci USA, 98:5116-5121; Storey J D, Tibshirani R (2001) Estimating false discovery rates under dependence, with applications to DNA microarrays. Stanford: Stanford University, Department of Statistics; Report No.: Technical Report 2001-28; Korn E L, Troendle J, McShane L, Simon R (2001) Controlling the number of false discoveries: Application to high-dimensional genomic data. Technical Report 003. 2001. National Cancer Institute) were applied to the resulting set of p-values to estimate false discovery rates.

Table 2A shows associations for those genes whose increased expression is predictive of shorter Recurrence-Free Interval (RFI) in treated patients (surgical resection and 5-FU/LV) based on univariate proportional hazards analysis.

TABLE 2A

| Gene | Hazard Ratio | P Value | Official Symbol | Accession Number |
|---|---|---|---|---|
| CYR61 | 1.44 | 0.0003 | CYR61 | NM_001554 |
| FABP4 | 1.20 | 0.0014 | FABP4 | NM_001442 |
| CTGF | 1.38 | 0.0024 | CTGF | NM_001901 |
| CYP1B1 | 1.54 | 0.0024 | CYP1B1 | NM_000104 |
| IGFBP3 | 1.40 | 0.0037 | IGFBP3 | NM_000598 |
| PDGFC | 1.40 | 0.0041 | PDGFC | NM_016205 |
| P14ARF | 1.32 | 0.0043 | | S78535 |
| MAP2 | 2.89 | 0.0044 | MAP2 | NM_031846 |
| ID4 | 1.41 | 0.0054 | ID4 | NM_001546 |
| P16-INK4 | 1.29 | 0.0060 | | L27211 |
| PAI1 | 1.25 | 0.0074 | SERPINE1 | NM_000602 |
| SFRP2 | 1.22 | 0.0079 | SFRP2 | NM_003013 |
| NMB | 1.72 | 0.0081 | NMB | NM_021077 |
| INHA | 2.63 | 0.0087 | INHA | NM_002191 |
| MMP9 | 1.29 | 0.0095 | MMP9 | NM_004994 |
| FAP | 1.31 | 0.0104 | FAP | NM_004460 |
| GJB2 | 1.32 | 0.0112 | GJB2 | NM_004004 |
| LEF | 1.34 | 0.0126 | LEF1 | NM_016269 |
| BGN | 1.31 | 0.0129 | BGN | NM_001711 |
| SFRP4 | 1.25 | 0.0138 | SFRP4 | NM_003014 |
| EphB6 | 1.35 | 0.0148 | EPHB6 | NM_004445 |
| INHBA | 1.34 | 0.0149 | INHBA | NM_002192 |
| STC1 | 1.41 | 0.0161 | STC1 | NM_003155 |
| EPAS1 | 1.55 | 0.0168 | EPAS1 | NM_001430 |
| DLC1 | 1.36 | 0.0174 | DLC1 | NM_006094 |
| CXCR4 | 1.34 | 0.0174 | CXCR4 | NM_003467 |
| THY1 | 1.37 | 0.0184 | THY1 | NM_006288 |
| EMP1 | 1.29 | 0.0193 | EMP1 | NM_001423 |
| MADH7 | 1.37 | 0.0195 | SMAD7 | NM_005904 |
| CREBBP | 1.61 | 0.0196 | CREBBP | NM_004380 |
| K-ras | 1.35 | 0.0202 | KRAS | NM_033360 |
| FOXO3A | 1.30 | 0.0207 | FOXO3A | NM_001455 |
| IMP-1 | 1.90 | 0.0210 | IMP-1 | NM_006546 |
| HoxA5 | 1.28 | 0.0224 | HOXA5 | NM_019102 |
| PADI4 | 2.03 | 0.0225 | PADI4 | NM_012387 |
| AKT3 | 1.33 | 0.0226 | AKT3 | NM_005465 |
| CXCL12 | 1.23 | 0.0227 | CXCL12 | NM_000609 |
| EGR3 | 1.22 | 0.0235 | EGR3 | NM_004430 |
| TGFB3 | 1.25 | 0.0250 | TGFB3 | NM_003239 |
| RUNX1 | 1.42 | 0.0250 | RUNX1 | NM_001754 |
| EGR1 | 1.26 | 0.0265 | EGR1 | NM_001964 |
| Nkd-1 | 1.14 | 0.0271 | NKD1 | NM_033119 |
| SHC1 | 1.47 | 0.0280 | SHC1 | NM_003029 |
| SPARC | 1.32 | 0.0285 | SPARC | NM_003118 |
| UNC5B | 1.39 | 0.0293 | UNC5B | NM_170744 |
| ITGB3 | 1.31 | 0.0301 | ITGB3 | NM_000212 |
| CHFR | 1.27 | 0.0313 | CHFR | NM_018223 |
| WWOX | 1.77 | 0.0328 | WWOX | NM_016373 |
| VIM | 1.34 | 0.0339 | VIM | NM_003380 |
| TIMP1 | 1.32 | 0.0340 | TIMP1 | NM_003254 |
| VEGF_altsplice2 | 1.27 | 0.0340 | | AF214570 |
| VEGF | 1.34 | 0.0342 | VEGF | NM_003376 |
| PTP4A3 v2 | 1.26 | 0.0352 | PTP4A3 | NM_032611 |
| NRP2 | 1.28 | 0.0352 | NRP2 | NM_003872 |
| ANTXR1 | 1.25 | 0.0354 | ANTXR1 | NM_032208 |
| OPN, osteopontin | 1.15 | 0.0359 | SPP1 | NM_000582 |
| CEBPB | 1.51 | 0.0370 | CEBPB | NM_005194 |
| GADD45B | 1.27 | 0.0377 | GADD45B | NM_015675 |
| IL10 | 2.82 | 0.0381 | IL10 | NM_000572 |
| LOXL2 | 1.32 | 0.0403 | LOXL2 | NM_002318 |
| BCL2L11 | 1.39 | 0.0421 | BCL2L11 | NM_138621 |
| ANGPT2 | 1.35 | 0.0462 | ANGPT2 | NM_001147 |
| TGFB2 | 1.21 | 0.0462 | TGFB2 | NM_003238 |
| ABCC5 | 1.28 | 0.0467 | ABCC5 | NM_005688 |
| WISP1 | 1.27 | 0.0469 | WISP1 | NM_003882 |
| VEGFB | 1.42 | 0.0475 | VEGFB | NM_003377 |
| CRYAB | 1.22 | 0.0477 | CRYAB | NM_001885 |
| HSPA1A | 1.20 | 0.0481 | HSPA1A | NM_005345 |
| MCP1 | 1.23 | 0.0486 | CCL2 | NM_002982 |
| COL1A1 | 1.23 | 0.0498 | COL1A1 | NM_000088 |

Table 2B shows associations between clinical outcome and gene expression for those genes which demonstrated a Hazard Ratio<1.0 and for which p<0.05. Univariate Cox Proportional Hazards Regression analysis was applied in combined Stage II (Duke's B) and Stage III (Duke's C) patients using RFI after treatment with 5-FU/LV as the metric for clinical outcome.

TABLE 2B

| Gene | Hazard Ratio | P Value | Official Symbol | Accession Number |
|---|---|---|---|---|
| VCP | 0.52 | 0.0003 | VCP | NM_007126 |
| CKS2 | 0.61 | 0.0005 | CKS2 | NM_001827 |
| CDC20 | 0.67 | 0.0006 | CDC20 | NM_001255 |
| CDC2 | 0.69 | 0.0008 | CDC2 | NM_001786 |
| LMNB1 | 0.62 | 0.0009 | LMNB1 | NM_005573 |
| EI24 | 0.51 | 0.0009 | EI24 | NM_004879 |
| MAD2L1 | 0.70 | 0.0011 | MAD2L1 | NM_002358 |
| HNRPAB | 0.54 | 0.0014 | HNRPAB | NM_004499 |
| CCNB1 | 0.69 | 0.0015 | CCNB1 | NM_031966 |
| STK15 | 0.68 | 0.0017 | STK6 | NM_003600 |
| cdc25A | 0.30 | 0.0038 | CDC25A | NM_001789 |
| Chk1 | 0.68 | 0.0054 | CHEK1 | NM_001274 |
| UBE2C | 0.72 | 0.0062 | UBE2C | NM_007019 |
| ITGB4 | 0.70 | 0.0070 | ITGB4 | NM_000213 |
| SAT | 0.64 | 0.0071 | SAT | NM_002970 |
| MCM6 | 0.67 | 0.0077 | MCM6 | NM_005915 |
| SNRPF | 0.72 | 0.0080 | SNRPF | NM_003095 |
| TUBA1 | 0.69 | 0.0097 | TUBA1 | NM_006000 |
| HSPA8 | 0.45 | 0.0100 | HSPA8 | NM_006597 |
| BIK | 0.78 | 0.0104 | BIK | NM_001197 |
| PRDX4 | 0.66 | 0.0106 | PRDX4 | NM_006406 |
| H2AFZ | 0.64 | 0.0115 | H2AFZ | NM_002106 |
| CENPA | 0.70 | 0.0116 | CENPA | NM_001809 |
| BUB1 | 0.73 | 0.0118 | BUB1 | NM_004336 |
| Bax | 0.66 | 0.0130 | BAX | NM_004324 |
| MCM2 | 0.74 | 0.0144 | MCM2 | NM_004526 |
| TOP2A | 0.68 | 0.0156 | TOP2A | NM_001067 |
| Ki-67 | 0.77 | 0.0164 | MKI67 | NM_002417 |
| SLC25A3 | 0.56 | 0.0172 | SLC25A3 | NM_213611 |
| NEK2 | 0.66 | 0.0181 | NEK2 | NM_002497 |
| CENPE | 0.39 | 0.0195 | CENPE | NM_001813 |
| E2F1 | 0.69 | 0.0198 | E2F1 | NM_005225 |
| HSPE1 | 0.71 | 0.0198 | HSPE1 | NM_002157 |
| ODC1 | 0.73 | 0.0203 | ODC1 | NM_002539 |
| CLDN7 | 0.75 | 0.0203 | CLDN7 | NM_001307 |
| CSEL1 | 0.71 | 0.0204 | CSE1L | NM_001316 |
| MMP7 | 0.82 | 0.0228 | MMP7 | NM_002423 |
| CD24 | 0.83 | 0.0242 | CD24 | NM_013230 |
| C20 orf1 | 0.74 | 0.0249 | TPX2 | NM_012112 |
| BAD | 0.72 | 0.0259 | BAD | NM_032989 |
| CLIC1 | 0.61 | 0.0272 | CLIC1 | NM_001288 |
| F3 | 0.79 | 0.0272 | F3 | NM_001993 |
| TRAIL | 0.71 | 0.0285 | TNFSF10 | NM_003810 |

TABLE 2B-continued

| Gene | Hazard Ratio | P Value | Official Symbol | Accession Number |
|---|---|---|---|---|
| NME1 | 0.73 | 0.0316 | NME1 | NM_000269 |
| GDF15 | 0.84 | 0.0317 | GDF15 | NM_004864 |
| c-myb (MYB official) | 0.79 | 0.0327 | MYB | NM_005375 |
| CD44E | 0.79 | 0.0335 | | X55150 |
| EIF4E | 0.69 | 0.0341 | EIF4E | NM_001968 |
| cMet | 0.80 | 0.0349 | MET | NM_000245 |
| AREG | 0.87 | 0.0377 | AREG | NM_001657 |
| CYP2C8 | 0.68 | 0.0392 | CYP2C8 | NM_000770 |
| PCNA | 0.77 | 0.0421 | PCNA | NM_002592 |
| SLC31A1 | 0.72 | 0.0437 | SLC31A1 | NM_001859 |
| MSH2 | 0.72 | 0.0450 | MSH2 | NM_000251 |
| PRDX2 | 0.67 | 0.0476 | PRDX2 | NM_005809 |
| TUFM | 0.77 | 0.0499 | TUFM | NM_003321 |

Analysis of Combined Study Results (Example 1 and Example 2)

The study presented in Example 1 identified genes for which a significant association was found between gene expression and recurrence-free interval in colon cancer patients treated solely by surgical resection of tumor. The study presented in Example 2 identified genes for which a significant association was found between gene expression and recurrence-free interval in colon cancer patients treated with 5-FU/LV (leucovorin-modulated fluorouracil) after surgical resection of tumor. In order to identify genes whose expression is associated specifically with response to 5-FU/LV, a test was performed to evaluate whether the Hazard Ratio associated with gene expression in surgery-only patients is sufficiently different from the Hazard Ratio associated with gene expression in surgery+5-FU/LV to conclude that gene expression is informative regarding response to 5-FU.

The results are shown in Table 3, which show Hazard Ratios and 75% Confidence Intervals for association between normalized expression values for a particular gene and the likelihood of response to 5-FU treatment. A gene with interaction HR>1 indicates higher recurrence risk after treatment and therefore a decreased likelihood of beneficial response as gene expression increases. A gene with interaction HR<1 indicates lower recurrence risk after treatment and therefore increased likelihood of beneficial response as gene expression increases. Results are shown for all genes for which the 75% Confidence Interval for Hazard Ratio doe not include HR=1. LCL and UCL indicate the lower confidence limit and the upper confidence limit respectively.

TABLE 3

Hazard Ratios and 75% Confidence Intervals for Prediction of Treatment Response Based on Gene Expression Levels

| Gene | Hazard Ratio (HR) | HR 75% LCL | HR 75% UCL | Official Symbol | Accession Number |
|---|---|---|---|---|---|
| ABCB1 | 1.16 | 1.003 | 1.346 | ABCB1 | NM_000927 |
| ABCC6 | 1.24 | 1.018 | 1.521 | ABCC6 | NM_001171 |
| AKAP12 | 0.84 | 0.724 | 0.979 | AKAP12 | NM_005100 |
| ANXA2 | 0.54 | 0.415 | 0.705 | ANXA2 | NM_004039 |
| BAD | 0.68 | 0.550 | 0.835 | BAD | NM_032989 |
| BCL2L11 | 1.28 | 1.023 | 1.611 | BCL2L11 | NM_138621 |
| BIK | 0.80 | 0.694 | 0.923 | BIK | NM_001197 |
| BRCA1 | 1.24 | 1.025 | 1.490 | BRCA1 | NM_007295 |
| BUB1 | 0.82 | 0.694 | 0.970 | BUB1 | NM_004336 |
| CCNB1 | 0.74 | 0.627 | 0.882 | CCNB1 | NM_031966 |
| CD24 | 0.84 | 0.739 | 0.948 | CD24 | NM_013230 |
| CDC2 | 0.71 | 0.608 | 0.840 | CDC2 | NM_001786 |
| CDCA7 v2 | 1.27 | 1.080 | 1.501 | CDCA7 | NM_145810 |
| CENPA | 0.67 | 0.552 | 0.823 | CENPA | NM_001809 |
| CENPE | 0.29 | 0.164 | 0.515 | CENPE | NM_001813 |
| CHFR | 1.20 | 1.019 | 1.418 | CHFR | NM_018223 |

TABLE 3-continued

Hazard Ratios and 75% Confidence Intervals for Prediction of
Treatment Response Based on Gene Expression Levels

| Gene | Hazard Ratio (HR) | HR 75% LCL | HR 75% UCL | Official Symbol | Accession Number |
|---|---|---|---|---|---|
| CKS2 | 0.78 | 0.636 | 0.965 | CKS2 | NM_001827 |
| CLDN7 | 0.77 | 0.636 | 0.926 | CLDN7 | NM_001307 |
| CLIC1 | 0.51 | 0.362 | 0.722 | CLIC1 | NM_001288 |
| CREBBP | 1.42 | 1.076 | 1.861 | CREBBP | NM_004380 |
| CTSL | 0.80 | 0.668 | 0.949 | CTSL | NM_001912 |
| CYP2C8 | 0.67 | 0.493 | 0.901 | CYP2C8 | NM_000770 |
| CYP3A4 | 0.62 | 0.458 | 0.835 | CYP3A4 | NM_017460 |
| DKK1 | 0.76 | 0.626 | 0.935 | DKK1 | NM_012242 |
| DUSP1 | 0.84 | 0.723 | 0.973 | DUSP1 | NM_004417 |
| EI24 | 0.63 | 0.489 | 0.825 | EI24 | NM_004879 |
| ENO1 | 1.31 | 1.043 | 1.657 | ENO1 | NM_001428 |
| F3 | 0.68 | 0.583 | 0.795 | F3 | NM_001993 |
| FOS | 0.86 | 0.740 | 0.994 | FOS | NM_005252 |
| GBP2 | 0.78 | 0.667 | 0.920 | GBP2 | NM_004120 |
| Grb10 | 0.81 | 0.688 | 0.959 | GRB10 | NM_005311 |
| H2AFZ | 0.72 | 0.566 | 0.927 | H2AFZ | NM_002106 |
| HNRPAB | 0.55 | 0.424 | 0.712 | HNRPAB | NM_004499 |
| HOXB7 | 0.81 | 0.692 | 0.939 | HOXB7 | NM_004502 |
| IMP-1 | 1.80 | 1.280 | 2.531 | IMP-1 | NM_006546 |
| INHA | 2.09 | 1.167 | 3.760 | INHA | NM_002191 |
| ITGAV | 0.77 | 0.617 | 0.950 | ITGAV | NM_002210 |
| ITGB1 | 0.61 | 0.439 | 0.836 | ITGB1 | NM_002211 |
| ITGB4 | 0.72 | 0.579 | 0.884 | ITGB4 | NM_000213 |
| KLK10 | 0.84 | 0.765 | 0.929 | KLK10 | NM_002776 |
| KLK6 | 0.88 | 0.786 | 0.977 | KLK6 | NM_002774 |
| KRAS2 | 0.61 | 0.439 | 0.834 | KRAS | NM_004985 |
| LAMA3 | 0.73 | 0.630 | 0.842 | LAMA3 | NM_000227 |
| LAMC2 | 0.69 | 0.582 | 0.808 | LAMC2 | NM_005562 |
| LAT | 0.79 | 0.662 | 0.941 | LAT | NM_014387 |
| LEF | 1.22 | 1.039 | 1.442 | LEF1 | NM_016269 |
| MAD2L1 | 0.84 | 0.715 | 0.990 | MAD2L1 | NM_002358 |
| MADH7 | 1.39 | 1.145 | 1.688 | SMAD7 | NM_005904 |
| MCM6 | 0.75 | 0.602 | 0.931 | MCM6 | NM_005915 |
| MMP7 | 0.73 | 0.636 | 0.839 | MMP7 | NM_002423 |
| MMP9 | 1.36 | 1.181 | 1.555 | MMP9 | NM_004994 |
| MYBL2 | 1.19 | 1.020 | 1.380 | MYBL2 | NM_002466 |
| Maspin | 0.79 | 0.704 | 0.879 | SERPINB5 | NM_002639 |
| NEK2 | 0.71 | 0.545 | 0.925 | NEK2 | NM_002497 |
| NMB | 1.59 | 1.187 | 2.123 | NMB | NM_021077 |
| Nkd-1 | 1.11 | 1.017 | 1.212 | NKD1 | NM_033119 |
| ODC1 | 0.81 | 0.666 | 0.987 | ODC1 | NM_002539 |
| PCNA | 0.83 | 0.692 | 0.998 | PCNA | NM_002592 |
| PTP4A3 v2 | 1.30 | 1.108 | 1.522 | PTP4A3 | NM_032611 |
| REG4 | 0.92 | 0.863 | 0.972 | REG4 | NM_032044 |
| ROCK1 | 0.77 | 0.601 | 0.988 | ROCK1 | NM_005406 |
| RhoB | 0.66 | 0.531 | 0.819 | RHOB | NM_004040 |
| S100A2 | 0.88 | 0.792 | 0.976 | S100A2 | NM_005978 |
| S100P | 0.78 | 0.696 | 0.884 | S100P | NM_005980 |
| SAT | 0.64 | 0.502 | 0.823 | SAT | NM_002970 |
| SI | 0.76 | 0.593 | 0.985 | SI | NM_001041 |
| SIAT7B | 0.85 | 0.730 | 0.984 | ST6GALNAC2 | NM_006456 |
| SIR2 | 0.66 | 0.533 | 0.814 | SIRT1 | NM_012238 |
| SKP2 | 1.32 | 1.041 | 1.664 | SKP2 | NM_005983 |
| SLC31A1 | 0.76 | 0.612 | 0.938 | SLC31A1 | NM_001859 |
| SLPI | 0.78 | 0.679 | 0.905 | SLPI | NM_003064 |
| SNRPF | 0.73 | 0.606 | 0.868 | SNRPF | NM_003095 |
| STK15 | 0.77 | 0.645 | 0.916 | STK6 | NM_003600 |
| TCF-1 | 1.30 | 1.108 | 1.528 | TCF1 | NM_000545 |
| TGFB2 | 1.17 | 1.015 | 1.353 | TGFB2 | NM_003238 |
| TUBA1 | 0.73 | 0.590 | 0.892 | TUBA1 | NM_006000 |
| VCP | 0.63 | 0.495 | 0.809 | VCP | NM_007126 |
| VEGFC | 0.75 | 0.572 | 0.986 | VEGFC | NM_005429 |
| VEGF_altsplice2 | 1.19 | 1.009 | 1.406 | | AF214570 |
| Cdc25A | 0.28 | 0.160 | 0.488 | CDC25A | NM_001789 |
| P21 | 0.79 | 0.637 | 0.970 | CDKN1A | NM_000389 |
| rhoC | 0.61 | 0.451 | 0.815 | RHOC | NM_175744 |

The hazard ratios derived from the Cox proportional hazards regression model provided in Table 3 provide an assessment of the contribution of the interaction between gene expression measurement and treatment (surgery resection alone versus treatment with 5-FU/LV after surgical resection of tumor) on the instantaneous risk of recurrence at time t conditional on a recurrence not occurring by time t. For an individual with gene expression measurement X, the instantaneous risk of recurrence at time t, $\lambda(t|X)$ is given by the relationship $\lambda(t|X) = \lambda_o(t) \cdot \exp[\beta \cdot X + \beta 2 \cdot I(\text{Treatment}) + \beta 3 \cdot I$ (Treatment)·X] where $\lambda_o(t)$ is the baseline hazard at time t, β3 is the log hazard ratio from Table 3, and I(Treatment) is an indicator variable for treatment (0=surgical resection and 1=5-FU/LV after surgical resection of tumor). Again, the survivor function at time t is given by $S(t|X)=S_o(t)^{exp[\beta 1 \cdot X + \beta 2 \cdot I(Treatment) + \beta 3 \cdot I(Treatment) \cdot X]}$, where $=S_o(t)$ is the baseline survivor function at time t. Consequently, the risk of recurrence at time t for a patient with a gene expression measurement of X is given by 1−S(t|X). In this way, an individual patient's estimated risk of recurrence may be derived from an observed gene expression measurement.

Example 3

A Study to Identify Relationships Between Genomic Tumor Expression Profiles and the Likelihood of Recurrence in Stage II and Stage III Colon Cancer Patients Treated with Resection of the Colon The primary objective of this study was to determine whether there is a significant relationship between the expression of each of 375 test genes identified in Table 4 and clinical outcome in Stage II and Stage III colon cancer patients who receive colon resection (surgery) without chemotherapy.

Study Design

This was an observational study using tissue and outcome data from the Cleveland Clinic Foundation (CCF) surgery database in patients who were diagnosed with Stage II and Stage III colon cancer between the years of 1981 and 2000 and received colon resection surgery at CCF.

Inclusion Criteria

Patients who were diagnosed with Stage II and Stage III colon cancer and had colon resection surgery at the Cleveland Clinic Foundation (CCF) between the years of 1981 and 2000.

Exclusion Criteria

Patients identified under inclusion criteria were excluded from the present study if one or more of the following applied:
  No tumor block available from initial diagnosis in the CCF archive.
  Insufficient tumor in block as assessed by examination of hematoxylin and eosin (H&E) slide.
  Patients who were diagnosed with Stage II and Stage III signet ring type colon cancer (WHO classification).
  Insufficient RNA (<700 ng) recovered from tissue sections for RT-PCR analysis.

Of the patients initially identified under inclusion criteria, 765 patient samples were available after application of exclusion criteria and used in the gene expression study disclosed herein. The overall demographic and clinical characteristics of the number of included samples were similar to the original CCF cohort.

Gene Panel

Three-hundred seventy-five genes, including reference genes (ATP5E, CLTC, GPX1, NEDD8, PGK1, UBB), were chosen for expression analysis. These genes are listed in Table 4. For each of the 375 genes, probe and primer sequences are shown in Table A, and target amplicons used for expression analysis are shown in Table B.

Example 4

A Study to Identify Relationships Between Tumor Gene Expression Profiles and Likelihood of Recurrence in Stage II and Stage III Colon Cancer Patients Treated with Leucovorin-Modulated Fluorouracil after Resection of the Colon The primary objective of this study was to determine whether there is a significant relationship between the expression of each of 375 test genes identified in Table 4 and clinical outcome in stage II and stage III colon cancer patients who received chemotherapy with leucovorin-modulated fluorouracil after colon resection surgery.

Study Design

This study used tissue and outcome data from National Surgical Adjuvant Breast and Bowel Project (NSABP) Study C06 in Stage II and Stage III patients who received colon resection and postoperative treatment with 5-fluorouracil and leucovorin.

Inclusion Criteria

Enrollment in NSABP Study C-06: "A Clinical Trial Comparing Oral Uracil/Ftorafur (UFT) Plus Leucovorin (LV) with 5-Fluorouracil (5-FU) Plus LV in the Treatment of Patients with Stage II and III Carcinoma of the Colon" and randomization to leucovorin-modulated fluorouracil (LV+5-FU) arm of the study.

Exclusion Criteria

Patients enrolled in NSABP Study C-06 were excluded from the present study if one or more of the following applied:
  No tumor block available from initial diagnosis in the NSABP archive.
  Insufficient tumor in block as assessed by examination of hematoxylin and eosin (H&E) slide.
  Patients who were diagnosed with Stage II and Stage III signet ring type colon cancer (WHO classification).
  Insufficient RNA (<700 ng) recovered from tissue sections for RT-PCR analysis.

Of the patients enrolled in NSABP Study C-06, 508 patient samples were available after application of exclusion criteria and used in the gene expression study disclosed herein. The overall demographic and clinical characteristics of the number of included samples were similar to the original NSABP cohort.

Gene Panel

Three-hundred seventy-five genes, including reference genes (ATP5E, CLTC, GPX1, NEDD8, PGK1, UBB), were chosen for expression analysis. These genes are listed in Table 4. For each of the 375 genes, probe and primer sequences are shown in Table A, and target amplicons used for expression analysis are shown in Table B.

TABLE 4

| Name |
| --- |
| ABCB1 |
| ABCC5 |
| ABCC6 |
| ADAMTS12 |
| AKAP12 |
| AKT3 |
| ALCAM |
| AMFR |
| ANGPT2 |
| ANTXR1 |
| ANXA1 |
| ANXA2 |
| ANXA5 |
| APC |
| APG-1 |
| AREG |
| ATP5A1 |
| ATP5E |
| AURKB |
| Axin 2 |
| axin1 |
| B-Catenin |
| BAD |
| Bax |
| BCL2L11 |

TABLE 4-continued

| Name |
|---|
| BGN |
| BIK |
| BLMH |
| BRAF |
| BRCA1 |
| BRCA2 |
| BUB1 |
| c-myb (MYB official) |
| c-Src |
| C20 orf1 |
| C20ORF126 |
| C8orf4 |
| Cad17 |
| CALD1 |
| CAPG |
| CASP9 |
| CAV1 |
| CCNA2 |
| CCNB1 |
| CCNE2 |
| CCNE2 variant 1 |
| CCR7 |
| CD18 |
| CD24 |
| CD3z |
| CD44E |
| CD44s |
| CD44v6 |
| CD68 |
| CD80 |
| CDC2 |
| CDC20 |
| CDC25C |
| CDC4 |
| CDC42BPA |
| CDC6 |
| CDCA7 v2 |
| CDH1 |
| CDH11 |
| CDH3 |
| Cdx2 |
| CEBPB |
| CENPA |
| CENPF |
| CGB |
| CHFR |
| Chk1 |
| cIAP2 |
| CKS2 |
| Claudin 4 |
| CLDN1 |
| CLDN7 |
| CLIC1 |
| CLTC |
| cMet |
| cMYC |
| COL1A1 |
| COL1A2 |
| CREBBP |
| cripto (TDGF1 official) |
| CRYAB |
| CSEL1 |
| CSF1 |
| CTGF |
| CTHRC1 |
| CTSB |
| CTSL |
| CUL4A |
| CXCL12 |
| CXCR4 |
| CYP1B1 |
| CYP2C8 |
| CYP3A4 |
| CYR61 |
| DAPK1 |
| DHFR |
| DKK1 |
| DLC1 |

TABLE 4-continued

| Name |
|---|
| DPYD |
| DR4 |
| DUSP1 |
| DUT |
| E2F1 |
| EFNA1 |
| EFNB2 |
| EFP |
| EGLN3 |
| EGR1 |
| EGR3 |
| EI24 |
| EIF4E |
| EIF4EL3 |
| ELAVL1 |
| EMP1 |
| ENO1 |
| EPAS1 |
| EPHB2 |
| EphB6 |
| EREG |
| ESPL1 |
| F3 |
| FABP4 |
| FAP |
| FASN |
| FBXO5 |
| FGF18 |
| FGF2 |
| FOS |
| FOXO3A |
| FPGS |
| FST |
| FUT6 |
| FYN |
| FZD1 |
| G-Catenin |
| GADD45B |
| GBP2 |
| GCNT1 |
| GHI BRAF mut4 |
| GHI k-ras mut1 |
| GHI k-ras mut2 |
| GHI k-ras mut3 |
| GIT1 |
| GJA1 |
| GJB2 |
| GPX1 |
| Grb10 |
| GRPR |
| GSK3B |
| GSTp |
| GSTT1 |
| H2AFZ |
| HB-EGF |
| hCRA a |
| HDAC1 |
| HER2 |
| HES6 |
| HIF1A |
| HLA-G |
| HNRPAB |
| HNRPD |
| HoxA5 |
| HOXB13 |
| HOXB7 |
| HRAS |
| HSD17B2 |
| HSPA1A |
| HSPA1B |
| HSPA8 |
| HSPE1 |
| HSPG2 |
| ICAM2 |
| ID3 |
| ID4 |
| IGF1 |
| IGFBP3 |

TABLE 4-continued

| Name |
|---|
| IGFBP5 |
| IGFBP7 |
| IL6ST |
| INHBA |
| IRS1 |
| ITGA5 |
| ITGAV |
| ITGB1 |
| ITGB3 |
| ITGB4 |
| K-ras |
| KCNH2 iso a/c |
| Ki-67 |
| KIF22 |
| KIFC1 |
| KLF5 |
| KLF6 |
| KLK10 |
| KLK6 |
| KLRK1 |
| KRT8 |
| LAMA3 |
| LAMC2 |
| LAT |
| LEF |
| LGALS3 |
| LMNB1 |
| LMYC |
| LOX |
| LOXL2 |
| LRP5 |
| LRP6 |
| MAD1L1 |
| MAD2L1 |
| MADH2 |
| MADH4 |
| MADH7 |
| Maspin |
| MCM2 |
| MCM3 |
| MCM6 |
| MCP1 |
| MGAT5 |
| MMP1 |
| MMP2 |
| MMP7 |
| MMP9 |
| MRP3 |
| MSH2 |
| MSH3 |
| MUC1 |
| MUC2 |
| MYBL2 |
| MYH11 |
| MYLK |
| NAV2 |
| NCAM1 |
| NEDD8 |
| NEK2 |
| NFKBp50 |
| Nkd-1 |
| NME1 |
| NOTCH1 |
| NR4A1 |
| NRP1 |
| NRP2 |
| ODC1 |
| OPN, osteopontin |
| OSMR |
| P14ARF |
| p16-INK4 |
| p21 |
| p53R2 |
| PAI1 |
| PCNA |
| PDGFA |
| PDGFB |
| PDGFC |

TABLE 4-continued

| Name |
|---|
| PDGFD |
| PDGFRa |
| PFN2 |
| PGK1 |
| PI3K |
| PKR2 |
| PLK |
| PLK3 |
| PPM1D |
| PRDX2 |
| PRDX4 |
| PRKCA |
| PRKCB1 |
| pS2 |
| PTCH |
| PTEN |
| PTGER3 |
| PTP4A3 v2 |
| PTPRJ |
| RAB32 |
| RAD54L |
| RAF1 |
| RALBP1 |
| RANBP2 |
| RBX1 |
| RCC1 |
| REG4 |
| RhoB |
| rhoC |
| ROCK1 |
| ROCK2 |
| RPS13 |
| RRM1 |
| RRM2 |
| RUNX1 |
| S100A1 |
| S100A4 |
| S100P |
| SAT |
| SBA2 |
| SEMA4B |
| SFRP2 |
| SFRP4 |
| SGCB |
| SHC1 |
| SI |
| SIAT4A |
| SIM2 |
| SIR2 |
| SKP2 |
| SLC25A3 |
| SLC31A1 |
| SLPI |
| SMARCA3 |
| SNAI2 |
| SNRPF |
| SOD1 |
| SOD2 |
| SOS1 |
| SPARC |
| SPINT2 |
| SPRY1 |
| SPRY2 |
| ST14 |
| STAT5B |
| STC1 |
| STK15 |
| STMY3 |
| SURV |
| TAGLN |
| TCF-1 |
| TERC |
| TFF3 |
| TGFB2 |
| TGFB3 |
| TGFBI |
| TGFBR1 |
| TGFBR2 |

TABLE 4-continued

Name

THBS1
THY1
TIMP1
TIMP2
TIMP3
TK1
TLN1
TMEPAI
TMSB10
TMSB4X
TOP2A
TP
TP53BP1
TP53BP2
TRAG3
TRAIL
TS
TUBA1
TUFM
UBB
UBE2C
UBE2M
UMPS
UNC5B
Upa
UPP1
VCL
VCP
VDAC2
VEGF
VEGF_altsplice1
VEGF_altsplice2
VEGFB
VEGFC
VIM
WIF
WISP1
WNT2

Experimental Materials and Methods

The expression of 375 cancer-related test genes plus six genes designated for use as reference genes was quantitatively assessed for each patient using TaqMan® RT-PCR, which was performed in singlet with RNA input at 1 nanogram per reaction.

Data Analysis Methods

Reference Normalization

For normalization of extraneous effects, cycle threshold ($C_T$) measurements obtained by RT-PCR were normalized relative to the mean expression of a set of six reference genes. The resulting reference-normalized expression measurements typically range from 0 to 15, where a one unit increase generally reflects a 2-fold increase in RNA quantity.

Comparison of Study Cohort to Original NSABP Study Populations

The distribution of clinical and demographic variables for the current study cohort of evaluable tissue blocks was compared to the original NSABP C-04 study population. There were no clinically meaningful differences in the distributions.

Univariate Analysis

For each of the 375 genes under study, the Cox proportional hazard model was used to examine the relationship between gene expression and recurrence free interval (RFI). The likelihood ratio was used as the test of statistical significance. The method of Benjamini and Hochberg (Benjamini, Y. and Hochberg, Y. (1995). Controlling the false discovery rate: a practical and powerful approach to multiple testing. J. R. Statist. Soc. B 57, 289-300), as well as resampling and permutation based methods (Tusher V G, Tibshirani R, Chu G (2001) Significance analysis of microarrays applied to the ionizing radiation response. Proc Natl Acad Sci USA, 98:5116-5121; Storey J D, Tibshirani R (2001) Estimating false discovery rates under dependence, with applications to DNA microarrays. Stanford: Stanford University, Department of Statistics; Report No.: Technical Report 2001-28; Korn E L, Troendle J, McShane L, Simon R (2001) Controlling the number of false discoveries: Application to high-dimensional genomic data. Technical Report 003. 2001. National Cancer Institute) were applied to the resulting set of p-values to estimate false discovery rates.

Analysis of Combined Study Results (Examples 1-4)

The studies presented in Example 1 and Example 3 identified genes for which a significant association was found between gene expression and recurrence-free interval in colon cancer patients treated solely by surgical resection of tumor. The studies presented in Example 2 (only Stage III patients were analyzed in this analysis of combined study results, 171 patients) and Example 4 identified genes for which a significant association was found between gene expression and recurrence-free interval in colon cancer patients treated with 5-FU/LV (leucovorin-modulated fluorouracil) after surgical resection of tumor. In order to identify genes whose expression is associated specifically with response to 5-FU/LV, a test was performed to evaluate whether the Hazard Ratio associated with gene expression in surgery-only patients is sufficiently different from the Hazard Ratio associated with gene expression in surgery+5-FU/LV to conclude that gene expression is informative regarding response to 5-FU. The results are shown in Table 5, which show Hazard Ratios and 75% Confidence Intervals for association between normalized expression values for a particular gene and the likelihood of response to 5-FU treatment. A gene with interaction HR>1 indicates higher recurrence risk and therefore a decreased likelihood of beneficial response as gene expression increases. A gene with interaction HR<1 indicates lower recurrence risk and therefore increased likelihood of beneficial response as gene expression increases. Results are shown for all genes for which the 75% Confidence Interval for Hazard Ratio doe not include HR=1. LCL and UCL indicate the lower confidence limit and the upper confidence limit respectively.

TABLE 5

Hazard Ratios and 75% Confidence Intervals for Prediction of Treatment Response Based on Gene Expression Levels (Interaction of Treatment and Gene Expression)

| N | Gene | Hazard Ratio (HR) | HR 75% LCL | HR 75% UCL | LR P-Value* | OfficialSymbol | Accession Number |
|---|------|-------------------|------------|------------|-------------|----------------|------------------|
| 1 | ABCB1 | 1.28 | 1.054 | 1.549 | 0.147 | ABCB1 | NM_000927 |
| 2 | AMFR | 1.33 | 1.099 | 1.608 | 0.085 | AMFR | NM_001144 |
| 3 | ANXA1 | 1.16 | 1.020 | 1.314 | 0.186 | ANXA1 | NM_000700 |
| 4 | APC | 1.26 | 1.048 | 1.515 | 0.150 | APC | NM_000038 |
| 5 | AURKB | 0.75 | 0.623 | 0.913 | 0.086 | AURKB | NM_004217 |
| 6 | Axin 2 | 0.85 | 0.787 | 0.918 | 0.015 | AXIN2 | NM_004655 |

TABLE 5-continued

Hazard Ratios and 75% Confidence Intervals for Prediction of Treatment Response
Based on Gene Expression Levels (Interaction of Treatment and Gene Expression)

| N | Gene | Hazard Ratio (HR) | HR 75% LCL | HR 75% UCL | LR P-Value* | OfficialSymbol | Accession Number |
|---|---|---|---|---|---|---|---|
| 7 | B-Catenin | 1.26 | 1.052 | 1.519 | 0.141 | CTNNB1 | NM_001904 |
| 8 | BGN | 1.23 | 1.098 | 1.381 | 0.038 | BGN | NM_001711 |
| 9 | BIK | 0.73 | 0.643 | 0.831 | 0.005 | BIK | NM_001197 |
| 10 | BRAF | 0.81 | 0.674 | 0.968 | 0.173 | BRAF | NM_004333 |
| 11 | BRCA2 | 0.00 | 0.000 | — | 0.012 | BRCA2 | NM_000059 |
| 12 | BUB1 | 0.66 | 0.553 | 0.796 | 0.010 | BUB1 | NM_004336 |
| 13 | C20 orf1 | 0.76 | 0.657 | 0.889 | 0.042 | TPX2 | NM_012112 |
| 14 | C20ORF126 | 0.67 | 0.543 | 0.832 | 0.031 | PDRG1 | NM_030815 |
| 15 | CALD1 | 1.15 | 1.007 | 1.315 | 0.227 | CALD1 | NM_004342 |
| 16 | CASP9 | 0.64 | 0.420 | 0.961 | 0.203 | CASP9 | NM_001229 |
| 17 | CCNE2 variant 1 | 0.23 | 0.058 | 0.923 | 0.156 | CCNE2 | NM_057749 |
| 18 | CD44E | 1.35 | 1.106 | 1.656 | 0.085 | CD44E | X55150 |
| 19 | CD44s | 1.52 | 1.301 | 1.775 | 0.002 | CD44S | M59040 |
| 20 | CD44v6 | 1.19 | 1.019 | 1.380 | 0.196 | CD44v6 | AJ251595v6 |
| 21 | CD68 | 1.22 | 1.061 | 1.413 | 0.103 | CD68 | NM_001251 |
| 22 | CDC2 | 0.78 | 0.656 | 0.926 | 0.096 | CDC2 | NM_001786 |
| 23 | CDC4 | 0.35 | 0.187 | 0.650 | 0.041 | FBXW7 | NM_018315 |
| 24 | CDH11 | 1.34 | 1.165 | 1.540 | 0.016 | CDH11 | NM_001797 |
| 25 | CENPA | 0.16 | 0.084 | 0.287 | <.001 | CENPA | NM_001809 |
| 26 | CENPF | 0.77 | 0.658 | 0.892 | 0.045 | CENPF | NM_016343 |
| 27 | CHFR | 1.21 | 1.020 | 1.445 | 0.202 | CHFR | NM_018223 |
| 28 | CLDN1 | 1.23 | 1.102 | 1.368 | 0.029 | CLDN1 | NM_021101 |
| 29 | CLIC1 | 0.58 | 0.431 | 0.780 | 0.034 | CLIC1 | NM_001288 |
| 30 | CLTC | 1.33 | 1.056 | 1.670 | 0.153 | CLTC | NM_004859 |
| 31 | COL1A1 | 1.12 | 1.002 | 1.260 | 0.243 | COL1A1 | NM_000088 |
| 32 | COL1A2 | 1.28 | 1.138 | 1.434 | 0.015 | COL1A2 | NM_000089 |
| 33 | CREBBP | 1.35 | 1.098 | 1.672 | 0.097 | CREBBP | NM_004380 |
| 34 | CTSB | 1.27 | 1.040 | 1.542 | 0.167 | CTSB | NM_001908 |
| 35 | CTSL | 1.15 | 1.004 | 1.317 | 0.235 | CTSL | NM_001912 |
| 36 | CXCL12 | 1.12 | 1.016 | 1.237 | 0.185 | CXCL12 | NM_000609 |
| 37 | CYR61 | 0.87 | 0.778 | 0.981 | 0.180 | CYR61 | NM_001554 |
| 38 | Cdx2 | 0.80 | 0.731 | 0.866 | 0.002 | CDX2 | NM_001265 |
| 39 | Chk1 | 0.75 | 0.579 | 0.971 | 0.196 | CHEK1 | NM_001274 |
| 40 | DLC1 | 0.81 | 0.687 | 0.956 | 0.142 | DLC1 | NM_006094 |
| 41 | DUSP1 | 0.86 | 0.768 | 0.959 | 0.111 | DUSP1 | NM_004417 |
| 42 | E2F1 | 0.46 | 0.233 | 0.914 | 0.197 | E2F1 | NM_005225 |
| 43 | EFNB2 | 1.35 | 1.162 | 1.567 | 0.021 | EFNB2 | NM_004093 |
| 44 | EGR3 | 0.88 | 0.784 | 0.992 | 0.223 | EGR3 | NM_004430 |
| 45 | EI24 | 0.75 | 0.607 | 0.931 | 0.127 | EI24 | NM_004879 |
| 46 | ENO1 | 1.27 | 1.045 | 1.545 | 0.159 | ENO1 | NM_001428 |
| 47 | EPAS1 | 1.38 | 1.146 | 1.663 | 0.047 | EPAS1 | NM_001430 |
| 48 | ESPL1 | 0.70 | 0.539 | 0.920 | 0.126 | ESPL1 | NM_012291 |
| 49 | FBXO5 | 0.16 | 0.050 | 0.535 | 0.054 | FBXO5 | NM_012177 |
| 50 | FGF18 | 3.30 | 1.276 | 8.536 | 0.168 | FGF18 | NM_003862 |
| 51 | FGF2 | 0.40 | 0.238 | 0.673 | 0.032 | FGF2 | NM_002006 |
| 52 | FOS | 0.89 | 0.798 | 0.982 | 0.177 | FOS | NM_005252 |
| 53 | FOXO3A | 1.16 | 1.000 | 1.345 | 0.250 | FOXO3A | NM_001455 |
| 54 | FPGS | 1.29 | 1.040 | 1.591 | 0.174 | FPGS | NM_004957 |
| 55 | FUT6 | 0.85 | 0.750 | 0.962 | 0.132 | FUT6 | NM_000150 |
| 56 | FZD1 | 1.30 | 1.082 | 1.571 | 0.104 | FZD1 | NM_003505 |
| 57 | GJB2 | 1.31 | 1.107 | 1.561 | 0.071 | GJB2 | NM_004004 |
| 58 | GPX1 | 1.39 | 1.019 | 1.890 | 0.220 | GPX1 | NM_000581 |
| 59 | GSK3B | 0.83 | 0.695 | 0.985 | 0.213 | GSK3B | NM_002093 |
| 60 | Grb10 | 0.79 | 0.647 | 0.959 | 0.157 | GRB10 | NM_005311 |
| 61 | HES6 | 0.84 | 0.765 | 0.920 | 0.029 | HES6 | NM_018645 |
| 62 | HIF1A | 1.61 | 1.372 | 1.879 | <.001 | HIF1A | NM_001530 |
| 63 | HLA-G | 0.35 | 0.122 | 1.004 | 0.202 | HLA-G | NM_002127 |
| 64 | HNRPAB | 0.79 | 0.648 | 0.966 | 0.179 | HNRPAB | NM_004499 |
| 65 | HNRPD | 1.27 | 1.027 | 1.559 | 0.194 | HNRPD | NM_031370 |
| 66 | HOXB13 | 0.70 | 0.549 | 0.886 | 0.075 | HOXB13 | NM_006361 |
| 67 | HSD17B2 | 1.46 | 1.196 | 1.776 | 0.029 | HSD17B2 | NM_002153 |
| 68 | HSPE1 | 0.77 | 0.663 | 0.905 | 0.064 | HSPE1 | NM_002157 |
| 69 | HoxA5 | 1.27 | 1.010 | 1.592 | 0.230 | HOXA5 | NM_019102 |
| 70 | IGFBP3 | 1.23 | 1.077 | 1.394 | 0.071 | IGFBP3 | NM_000598 |
| 71 | IGFBP5 | 1.16 | 1.027 | 1.314 | 0.160 | IGFBP5 | NM_000599 |
| 72 | IGFBP7 | 1.29 | 1.108 | 1.491 | 0.052 | IGFBP7 | NM_001553 |
| 73 | IL6ST | 1.37 | 1.161 | 1.609 | 0.028 | IL6ST | NM_002184 |
| 74 | ITGA5 | 1.28 | 1.125 | 1.456 | 0.028 | ITGA5 | NM_002205 |
| 75 | KIF22 | 0.60 | 0.468 | 0.770 | 0.016 | KIF22 | NM_007317 |
| 76 | KIFC1 | 0.55 | 0.366 | 0.819 | 0.075 | KIFC1 | NM_002263 |
| 77 | KLF5 | 1.22 | 1.066 | 1.388 | 0.087 | KLF5 | NM_001730 |
| 78 | KLK10 | 1.10 | 1.017 | 1.195 | 0.168 | KLK10 | NM_002776 |
| 79 | KLRK1 | 0.53 | 0.326 | 0.847 | 0.101 | KLRK1 | NM_007360 |

TABLE 5-continued

Hazard Ratios and 75% Confidence Intervals for Prediction of Treatment Response
Based on Gene Expression Levels (Interaction of Treatment and Gene Expression)

| N | Gene | Hazard Ratio (HR) | HR 75% LCL | HR 75% UCL | LR P-Value* | OfficialSymbol | Accession Number |
|---|---|---|---|---|---|---|---|
| 80 | KRT8 | 1.21 | 1.043 | 1.399 | 0.137 | KRT8 | NM_002273 |
| 81 | Ki-67 | 0.86 | 0.738 | 0.994 | 0.233 | MKI67 | NM_002417 |
| 82 | LAT | 0.71 | 0.534 | 0.954 | 0.180 | LAT | NM_014387 |
| 83 | LEF | 1.28 | 1.110 | 1.465 | 0.045 | LEF1 | NM_016269 |
| 84 | LMYC | 0.70 | 0.550 | 0.900 | 0.096 | RLF | NM_012421 |
| 85 | LOX | 1.18 | 1.004 | 1.383 | 0.243 | LOX | NM_002317 |
| 86 | MAD2L1 | 0.65 | 0.479 | 0.882 | 0.096 | MAD2L1 | NM_002358 |
| 87 | MADH7 | 1.23 | 1.042 | 1.455 | 0.152 | SMAD7 | NM_005904 |
| 88 | MCM3 | 2.54 | 1.283 | 5.012 | 0.110 | MCM3 | NM_002388 |
| 89 | MCP1 | 1.24 | 1.089 | 1.405 | 0.055 | CCL2 | NM_002982 |
| 90 | MMP1 | 1.35 | 1.150 | 1.587 | 0.032 | MMP1 | NM_002421 |
| 91 | MMP2 | 1.20 | 1.075 | 1.344 | 0.058 | MMP2 | NM_004530 |
| 92 | MSH2 | 0.64 | 0.541 | 0.764 | 0.003 | MSH2 | NM_000251 |
| 93 | MSH3 | 0.50 | 0.317 | 0.794 | 0.080 | MSH3 | NM_002439 |
| 94 | Maspin | 1.19 | 1.073 | 1.315 | 0.052 | SERPINB5 | NM_002639 |
| 95 | NR4A1 | 0.82 | 0.750 | 0.902 | 0.015 | NR4A1 | NM_002135 |
| 96 | NRP1 | 1.83 | 1.400 | 2.379 | 0.008 | NRP1 | NM_003873 |
| 97 | PDGFA | 0.84 | 0.750 | 0.949 | 0.096 | PDGFA | NM_002607 |
| 98 | PDGFC | 1.18 | 1.023 | 1.360 | 0.183 | PDGFC | NM_016205 |
| 99 | PDGFD | 2.57 | 1.263 | 5.210 | 0.139 | PDGFD | NM_025208 |
| 100 | PDGFRa | 1.20 | 1.045 | 1.380 | 0.130 | PDGFRA | NM_006206 |
| 101 | PFN2 | 1.26 | 1.071 | 1.490 | 0.106 | PFN2 | NM_053024 |
| 102 | PKR2 | 1.59 | 1.322 | 1.912 | 0.004 | PKM2 | NM_002654 |
| 103 | PRDX2 | 0.79 | 0.656 | 0.953 | 0.148 | PRDX2 | NM_005809 |
| 104 | RAB32 | 0.75 | 0.580 | 0.962 | 0.183 | RAB32 | NM_006834 |
| 105 | RAD54L | 0.17 | 0.067 | 0.409 | 0.011 | RAD54L | NM_003579 |
| 106 | RANBP2 | 0.59 | 0.473 | 0.728 | 0.004 | RANBP2 | NM_006267 |
| 107 | RCC1 | 0.80 | 0.671 | 0.942 | 0.120 | RCC1 | NM_001269 |
| 108 | ROCK2 | 0.65 | 0.529 | 0.792 | 0.013 | ROCK2 | NM_004850 |
| 109 | RUNX1 | 1.49 | 1.257 | 1.764 | 0.007 | RUNX1 | NM_001754 |
| 110 | RhoB | 0.69 | 0.600 | 0.803 | 0.004 | RHOB | NM_004040 |
| 111 | S100P | 0.84 | 0.769 | 0.922 | 0.029 | S100P | NM_005980 |
| 112 | SAT | 0.83 | 0.693 | 0.993 | 0.232 | SAT | NM_002970 |
| 113 | SEMA4B | 1.37 | 1.199 | 1.576 | 0.007 | SEMA4B | NM_020210 |
| 114 | SIAT4A | 1.18 | 1.027 | 1.354 | 0.172 | ST3GAL1 | NM_003033 |
| 115 | SKP2 | 1.66 | 1.184 | 2.329 | 0.082 | SKP2 | NM_005983 |
| 116 | SOD1 | 0.81 | 0.668 | 0.988 | 0.221 | SOD1 | NM_000454 |
| 117 | SOS1 | 0.51 | 0.251 | 1.028 | 0.232 | SOS1 | NM_005633 |
| 118 | SPARC | 1.30 | 1.141 | 1.489 | 0.022 | SPARC | NM_003118 |
| 119 | SPRY1 | 1.20 | 1.014 | 1.414 | 0.214 | SPRY1 | AK026960 |
| 120 | STK15 | 0.74 | 0.618 | 0.882 | 0.050 | AURKA | NM_003600 |
| 121 | TCF-1 | 0.62 | 0.491 | 0.787 | 0.018 | TCF1 | NM_000545 |
| 122 | THBS1 | 1.19 | 1.049 | 1.339 | 0.110 | THBS1 | NM_003246 |
| 123 | TIMP1 | 1.34 | 1.164 | 1.533 | 0.015 | TIMP1 | NM_003254 |
| 124 | TOP2A | 0.75 | 0.635 | 0.881 | 0.042 | TOP2A | NM_001067 |
| 125 | TP53BP1 | 0.75 | 0.576 | 0.983 | 0.219 | TP53BP1 | NM_005657 |
| 126 | UBE2C | 0.77 | 0.669 | 0.889 | 0.034 | UBE2C | NM_007019 |
| 127 | UPP1 | 3.29 | 1.336 | 8.123 | 0.094 | UPP1 | NM_003364 |
| 128 | VCP | 0.70 | 0.559 | 0.867 | 0.060 | VCP | NM_007126 |
| 129 | VDAC2 | 1.38 | 1.051 | 1.812 | 0.175 | VDAC2 | NM_003375 |
| 130 | cMYC | 0.88 | 0.782 | 0.991 | 0.217 | MYC | NM_002467 |

The hazard ratios derived from the Cox proportional hazards regression model provided in Table 5 provide an assessment of the contribution of the interaction between gene expression measurement and treatment (surgery resection alone versus treatment with 5-FU/LV after surgical resection of tumor) on the instantaneous risk of recurrence at time t conditional on a recurrence not occurring by time t. For an individual with gene expression measurement X, the instantaneous risk of recurrence at time t, $\lambda(t|X)$ is given by the relationship $\lambda(t|X)=\lambda_o(t) \cdot \exp[\beta 1 \cdot X + \beta 2 \cdot I(Treatment) + \beta 3 \cdot I(Treatment) \cdot X]$ where $\lambda_o(t)$ is the baseline hazard at time t, $\beta 3$ is the log hazard ratio from Table 3, and I(Treatment) is an indicator variable for treatment (0=surgical resection and 1=5-FU/LV after surgical resection of tumor). Again, the survivor function at time t is given by $S(t|X) = S_o(t)^{\exp[\beta 1 \cdot X + \beta 2 \cdot I(Treatment) + \beta 3 \cdot I(Treatment) \cdot X]}$, where $=S_o(t)$ is the baseline survivor function at time t. Consequently, the risk of recurrence at time t for a patient with a gene expression measurement of X is given by 1−S(t|X). In this way, an individual patient's estimated risk of recurrence may be derived from an observed gene expression measurement. As an example, the hazard ratio for the TCF by treatment interaction from Table 5 is 0.62, indicating that there is a lower recurrence risk after treatment and therefore increased likelihood of beneficial response as gene expression of TCF increases. In fact, the hazard ratios for TCF, treatment and the TCF by treatment interaction are 0.91, 7.92 and 0.62, respectively. Consequently, assuming a baseline survivor function at 3 years of 0.95, the estimated risk of recurrence at 3 years after surgery resection is approximately $1 - 0.95^{\exp[ln(0.91) \cdot 5]} = 0.063$. In contrast, the estimated risk of recurrence at 3 years after surgery resection plus 5FU is $1 - 0.95^{\exp[ln(0.91) \cdot 5 + ln(7.92) + ln(0.62) \cdot 5]} = 0.047$.

Example 5

Identification of Gene Co-Expressed with Prognostic and/or Predictive Genes

A co-expression study was conducted to identify genes that exhibit expression level trends in colon cancer cells that directly correlate with those identified above that are predictive of likelihood of a beneficial response to a 5-FU therapy. A set of genes were assayed using standard methods similar to those described above. Gene expression clusters (i.e., genes that exhibited similar expression trends in samples as described above) were identified using pair-wise analysis of correlation based on Pearson correlation coefficients (optionally, Spearman correlation coefficients may be used instead or in addition). (See, e.g., Pearson K. and Lee A., Biometrika 2, 357 (1902); C. Spearman, Amer. J. Psychol 15:72-101 (1904); J. Myers, A. Well, Research Design and Statistical Analysis, p. 508 (2nd Ed., 2003).) The correlation between continuous variables is captured by the product-moment correlation coefficient. In general, a correlation coefficient >0.3 is considered to be statistically significant in a sample size of at least 20. (See, e.g., G. Norman, D. Streiner, Biostatistics: The Bare Essentials, 137-138 (3rd Ed. 2007).)

The results are shown in Table C. The column on the far left of the table shows the gene for which co-expressed genes were identified ("Variable"). The results are provided in two rows for each gene with the top row providing a conventional name for the gene (modified by an underscore and a number indicating the version number of the amplicon design, an internal reference), and bottom row indicating the correlation coefficient for co-expression of that gene with the "Variable" gene. The results are ordered from left to right according to highest to lowest correlation coefficient.

The genes in Table C that are co-expressed with the indicated variable gene can serve are referred to as "co-expressed genes", and can be assayed as a substitute for the indicated variable gene and/or in combination with such variable gene (e.g., to provide an internal control for the assay or increase statistical power) in the methods disclosed herein. Exemlary primers and probes, as well as exemplary amplicons, are provided for these genes in Tables A and B.

TABLE A

| Gene | Accession | Reagt | Sequence | SEQ ID NO |
|---|---|---|---|---|
| A-Catenin | NM_001903.1 | FPr | CGTTCCGATCCTCTATACTGCAT | SEQ ID NO: 1 |
| | | Probe | ATGCCTACAGCACCCTGATGTCGCA | SEQ ID NO: 2 |
| | | RPr | AGGTCCCTGTTGGCCTTATAGG | SEQ ID NO: 3 |
| ABCB1 | NM_000927.2 | FPr | AAACACCACTGGAGCATTGA | SEQ ID NO: 4 |
| | | Probe | CTCGCCAATGATGCTGCTCAAGTT | SEQ ID NO: 5 |
| | | RPr | CAAGCCTGGAACCTATAGCC | SEQ ID NO: 6 |
| ABCC5 | NM_005688.1 | FPr | TGCAGACTGTACCATGCTGA | SEQ ID NO: 7 |
| | | Probe | CTGCACACGGTTCTAGGCTCCG | SEQ ID NO: 8 |
| | | RPr | GGCCAGCACCATAATCCTAT | SEQ ID NO: 9 |
| ABCC6 | NM_001171.2 | FPr | GGATGAACCTCGACCTGC | SEQ ID NO: 10 |
| | | Probe | CCAGATAGCCTCGTCCGAGTGCTC | SEQ ID NO: 11 |
| | | RPr | GAGCTGCACCGTCTCCAG | SEQ ID NO: 12 |
| ACP1 | NM_004300.2 | FPr | GCTACCAAGTCCGTGCTGT | SEQ ID NO: 13 |
| | | Probe | TGATCGACAAATGTTACCCAGACACACA | SEQ ID NO: 14 |
| | | RPr | GAAAACTGCTTCTGCAATGG | SEQ ID NO: 15 |
| ADAM10 | NM_001110.1 | FPr | CCCATCAACTTGTGCCAGTA | SEQ ID NO: 16 |
| | | Probe | TGCCTACTCCACTGCACAGACCCT | SEQ ID NO: 17 |
| | | RPr | GGTGATGGTTCGACCACTG | SEQ ID NO: 18 |
| ADAM17 | NM_003183.3 | FPr | GAAGTGCCAGGAGGCGATTA | SEQ ID NO: 19 |
| | | Probe | TGCTACTTGCAAAGGCGTGTCCTACTGC | SEQ ID NO: 20 |
| | | RPr | CGGGCACTCACTGCTATTACC | SEQ ID NO: 21 |
| ADAMTS12 | NM_030955.2 | FPr | GGAGAAGGGTGGAGTGCAG | SEQ ID NO: 22 |
| | | Probe | CGCACAGTCAGAATCCATCTGGGT | SEQ ID NO: 23 |
| | | RPr | CAGGGTCAGGTCTCTGGATG | SEQ ID NO: 24 |
| ADPRT | NM_001618.2 | FPr | TTGACAACCTGCTGGACATC | SEQ ID NO: 25 |
| | | Probe | CCCTGAGCAGACTGTAGGCCACCT | SEQ ID NO: 26 |
| | | RPr | ATGGGATCCTTGCTGCTATC | SEQ ID NO: 27 |
| AGXT | NM_000030.1 | FPr | CTTTTCCCTCCAGTGGCA | SEQ ID NO: 28 |
| | | Probe | CTCCTGGAAACAGTCCACTTGGGC | SEQ ID NO: 29 |
| | | RPr | ATTTGGAAGGCACTGGGTTT | SEQ ID NO: 30 |
| AKAP12 | NM_005100.2 | FPr | TAGAGAGCCCCTGACAATCC | SEQ ID NO: 31 |
| | | Probe | TGGCTCTAGCTCCTGATGAAGCCTC | SEQ ID NO: 32 |
| | | RPr | GGTTGGTCTTGGAAAGAGGA | SEQ ID NO: 33 |
| AKT1 | NM_005163.1 | FPr | CGCTTCTATGGCGCTGAGAT | SEQ ID NO: 34 |
| | | Probe | CAGCCCTGGACTACCTGCACTCGG | SEQ ID NO: 35 |
| | | RPr | TCCCGGTACACCACGTTCTT | SEQ ID NO: 36 |
| AKT2 | NM_001626.2 | FPr | TCCTGCCACCCTTCAAACC | SEQ ID NO: 37 |
| | | Probe | CAGGTCACGTCCGAGGTCGACACA | SEQ ID NO: 38 |
| | | RPr | GGCGGTAAATTCATCATCGAA | SEQ ID NO: 39 |

TABLE A-continued

| Gene | Accession | Reagt | Sequence | SEQ ID NO |
|---|---|---|---|---|
| AKT3 | NM_005465.1 | FPr | TTGTCTCTGCCTTGGACTATCTACA | SEQ ID NO: 40 |
| | | Probe | TCACGGTACACAATCTTTCCGGA | SEQ ID NO: 41 |
| | | RPr | CCAGCATTAGATTCTCCAACTTGA | SEQ ID NO: 42 |
| AL137428 | AL137428.1 | FPr | CAAGAAGAGGCTCTACCCTGG | SEQ ID NO: 43 |
| | | Probe | ACTGGGAATTTCCAAGGCCACCTT | SEQ ID NO: 44 |
| | | RPr | AAATGAGCTCTGCGATCCTC | SEQ ID NO: 45 |
| ALCAM | NM_001627.1 | FPr | GAGGAATATGGAATCCAAGGG | SEQ ID NO: 46 |
| | | Probe | CCAGTTCCTGCCGTCTGCTCTTCT | SEQ ID NO: 47 |
| | | RPr | GTGGCGGAGATCAAGAGG | SEQ ID NO: 48 |
| ALDH1A1 | NM_000689.1 | FPr | GAAGGAGATAAGGAGGATGTTGACA | SEQ ID NO: 49 |
| | | Probe | AGTGAAGGCCGCAAGACAGGCTTTTC | SEQ ID NO: 50 |
| | | RPr | CGCCACGGAGATCCAATC | SEQ ID NO: 51 |
| ALDOA | NM_000034.2 | FPr | GCCTGTACGTGCCAGCTC | SEQ ID NO: 52 |
| | | Probe | TGCCAGAGCCTCAACTGTCTCTGC | SEQ ID NO: 53 |
| | | RPr | TCATCGGAGCTTGATCTCG | SEQ ID NO: 54 |
| AMFR | NM_001144.2 | FPr | GATGGTTCAGCTCTGCAAGGA | SEQ ID NO: 55 |
| | | Probe | CGATTTGAATATCTTTCCTTCTCGCCCACC | SEQ ID NO: 56 |
| | | RPr | TCGACCGTGGCTGCTCAT | SEQ ID NO: 57 |
| ANGPT2 | NM_001147.1 | FPr | CCGTGAAAGCTGCTCTGTAA | SEQ ID NO: 58 |
| | | Probe | AAGCTGACACAGCCCTCCCAAGTG | SEQ ID NO: 59 |
| | | RPr | TTGCAGTGGGAAGAACAGTC | SEQ ID NO: 60 |
| ANTXR1 | NM_032208.1 | FPr | CTCCAGGTGTACCTCCAACC | SEQ ID NO: 61 |
| | | Probe | AGCCTTCTCCCACAGCTGCCTACA | SEQ ID NO: 62 |
| | | RPr | GAGAAGGCTGGGAGACTCTG | SEQ ID NO: 63 |
| ANXA1 | NM_000700.1 | FPr | GCCCCTATCCTACCTTCAATCC | SEQ ID NO: 64 |
| | | Probe | TCCTCGGATGTCGCTGCCT | SEQ ID NO: 65 |
| | | RPr | CCTTTAACCATTATGGCCTTATGC | SEQ ID NO: 66 |
| ANXA2 | NM_004039.1 | FPr | CAAGACACTAAGGGCGACTACCA | SEQ ID NO: 67 |
| | | Probe | CCACCACACAGGTACAGCAGCGCT | SEQ ID NO: 68 |
| | | RPr | CGTGTCGGGCTTCAGTCAT | SEQ ID NO: 69 |
| ANXA5 | NM_001154.2 | FPr | GCTCAAGCCTGGAAGATGAC | SEQ ID NO: 70 |
| | | Probe | AGTACCCTGAAGTGTCCCCCACCA | SEQ ID NO: 71 |
| | | RPr | AGAACCACCAACATCCGCT | SEQ ID NO: 72 |
| AP-1 (JUN official) | NM_002228.2 | FPr | GACTGCAAAGATGGAAACGA | SEQ ID NO: 73 |
| | | Probe | CTATGACGATGCCCTCAACGCCTC | SEQ ID NO: 74 |
| | | RPr | TAGCCATAAGGTCCGCTCTC | SEQ ID NO: 75 |
| APC | NM_000038.1 | FPr | GGACAGCAGGAATGTGTTTC | SEQ ID NO: 76 |
| | | Probe | CATTGGCTCCCCGTGACCTGTA | SEQ ID NO: 77 |
| | | RPr | ACCCACTCGATTTGTTTCTG | SEQ ID NO: 78 |
| APEX-1 | NM_001641.2 | FPr | GATGAAGCCTTTCGCAAGTT | SEQ ID NO: 79 |
| | | Probe | CTTTCGGGAAGCCAGGCCCTT | SEQ ID NO: 80 |
| | | RPr | AGGTCTCCACACAGCACAAG | SEQ ID NO: 81 |
| APG-1 | NM_014278.2 | FPr | ACCCCGGCCTGTATATCAT | SEQ ID NO: 82 |
| | | Probe | CCAATGGCTCGAGTTCTTGATCCC | SEQ ID NO: 83 |
| | | RPr | CTATCTGGCTCTTTGCTGCAT | SEQ ID NO: 84 |
| APN (ANPEP official) | NM_001150.1 | FPr | CCACCTTGGACCAAAGTAAAGC | SEQ ID NO: 85 |
| | | Probe | CTCCCCAACACGCTGAAACCCG | SEQ ID NO: 86 |
| | | RPr | TCTCAGCGTCACCTGGTAGGA | SEQ ID NO: 87 |
| APOC1 | NM_001645.3 | FPr | GGAAACACACTGGAGGACAAG | SEQ ID NO: 88 |
| | | Probe | TCATCAGCCGCATCAAACAGAGTG | SEQ ID NO: 89 |
| | | RPr | CGCATCTTGGCAGAAAGTT | SEQ ID NO: 90 |
| AREG | NM_001657.1 | FPr | TGTGAGTGAAATGCCTTCTAGTAGTGA | SEQ ID NO: 91 |
| | | Probe | CCGTCCTCGGGAGCCGACTATGA | SEQ ID NO: 92 |
| | | RPr | TTGTGGTTCGTTATCATACTCTTCTGA | SEQ ID NO: 93 |
| ARG | NM_005158.2 | FPr | CGCAGTGCAGCTGAGTATCTG | SEQ ID NO: 94 |
| | | Probe | TCGCACCAGGAAGCTGCCATTGA | SEQ ID NO: 95 |
| | | RPr | TGCCCAGGGCTACTCTCACTT | SEQ ID NO: 96 |

TABLE A-continued

| Gene | Accession | Reagt | Sequence | SEQ ID NO |
|---|---|---|---|---|
| ARHF | NM_019034.2 | FPr | ACTGGCCCACTTAGTCCTCA | SEQ ID NO: 97 |
| | | Probe | CTCCCAACCTGCTGTCCCTCAAG | SEQ ID NO: 98 |
| | | RPr | CTGAACTCCACAGGCTGGTA | SEQ ID NO: 99 |
| ATOH1 | NM_005172.1 | FPr | GCAGCCACCTGCAACTTT | SEQ ID NO: 100 |
| | | Probe | CAGGCGAGAGAGCATCCCGTCTAC | SEQ ID NO: 101 |
| | | RPr | TCCAGGAGGGACAGCTCA | SEQ ID NO: 102 |
| ATP5A1 | NM_004046.3 | FPr | GATGCTGCCACTCAACAACT | SEQ ID NO: 103 |
| | | Probe | AGTTAGACGCACGCCACGACTCAA | SEQ ID NO: 104 |
| | | RPr | TGTCCTTGCTTCAGCAACTC | SEQ ID NO: 105 |
| ATP5E | NM_006886.2 | FPr | CCGCTTTCGCTACAGCAT | SEQ ID NO: 106 |
| | | Probe | TCCAGCCTGTCTCCAGTAGGCCAC | SEQ ID NO: 107 |
| | | RPr | TGGGAGTATCGGATGTAGCTG | SEQ ID NO: 108 |
| AURKB | NM_004217.1 | FPr | AGCTGCAGAAGAGCTGCACAT | SEQ ID NO: 109 |
| | | Probe | TGACGAGCAGCGAACAGCCACG | SEQ ID NO: 110 |
| | | RPr | GCATCTGCCAACTCCTCCAT | SEQ ID NO: 111 |
| Axin 2 | NM_004655.2 | FPr | GGCTATGTCTTTGCACCAGC | SEQ ID NO: 112 |
| | | Probe | ACCAGCGCCAACGACAGTGAGATA | SEQ ID NO: 113 |
| | | RPr | ATCCGTCAGCGCATCACT | SEQ ID NO: 114 |
| axin1 | NM_003502.2 | FPr | CCGTGTGACAGCATCGTT | SEQ ID NO: 115 |
| | | Probe | CGTACTACTTCTGCGGGGAACCCA | SEQ ID NO: 116 |
| | | RPr | CTCACCAGGGTGCGGTAG | SEQ ID NO: 117 |
| B-Catenin | NM_001904.1 | FPr | GGCTCTTGTGCGTACTGTCCTT | SEQ ID NO: 118 |
| | | Probe | AGGCTCAGTGATGTCTTCCCTGTCACCAG | SEQ ID NO: 119 |
| | | RPr | TCAGATGACGAAGAGCACAGATG | SEQ ID NO: 120 |
| BAD | NM_032989.1 | FPr | GGGTCAGGTGCCTCGAGAT | SEQ ID NO: 121 |
| | | Probe | TGGGCCCAGAGCATGTTCCAGATC | SEQ ID NO: 122 |
| | | RPr | CTGCTCACTCGGCTCAAACTC | SEQ ID NO: 123 |
| BAG1 | NM_004323.2 | FPr | CGTTGTCAGCACTTGGAATACAA | SEQ ID NO: 124 |
| | | Probe | CCCAATTAACATGACCCGGCAACCAT | SEQ ID NO: 125 |
| | | RPr | GTTCAACCTCTTCCTGTGGACTGT | SEQ ID NO: 126 |
| BAG2 | NM_004282.2 | FPr | CTAGGGGCAAAAAGCATGA | SEQ ID NO: 127 |
| | | Probe | TTCCATGCCAGACAGGAAAAAGCA | SEQ ID NO: 128 |
| | | RPr | CTAAATGCCCAAGGTGACTG | SEQ ID NO: 129 |
| BAG3 | NM_004281.2 | FPr | GAAAGTAAGCCAGGCCCAGTT | SEQ ID NO: 130 |
| | | Probe | CAGAACTCCCTCCTGGACACATCCCAA | SEQ ID NO: 131 |
| | | RPr | ACCTCTTTGCGGATCACTTGA | SEQ ID NO: 132 |
| Bak | NM_001188.1 | FPr | CCATTCCCACCATTCTACCT | SEQ ID NO: 133 |
| | | Probe | ACACCCCAGACGTCCTGGCCT | SEQ ID NO: 134 |
| | | RPr | GGGAACATAGACCCACCAAT | SEQ ID NO: 135 |
| Bax | NM_004324.1 | FPr | CCGCCGTGGACACAGACT | SEQ ID NO: 136 |
| | | Probe | TGCCACTCGGAAAAAGACCTCTCGG | SEQ ID NO: 137 |
| | | RPr | TTGCCGTCAGAAAACATGTCA | SEQ ID NO: 138 |
| BBC3 | NM_014417.1 | FPr | CCTGGAGGGTCCTGTACAAT | SEQ ID NO: 139 |
| | | Probe | CATCATGGGACTCCTGCCCTTACC | SEQ ID NO: 140 |
| | | RPr | CTAATTGGGCTCCATCTCG | SEQ ID NO: 141 |
| BCAS1 | NM_003657.1 | FPr | CCCCGAGACAACGGAGATAA | SEQ ID NO: 142 |
| | | Probe | CTTTCCGTTGGCATCCGCAACAG | SEQ ID NO: 143 |
| | | RPr | CTCGGGTTTGGCCTCTTTC | SEQ ID NO: 144 |
| Bcl2 | NM_000633.1 | FPr | CAGATGGACCTAGTACCCACTGAGA | SEQ ID NO: 145 |
| | | Probe | TTCCACGCCGAAGGACAGCGAT | SEQ ID NO: 146 |
| | | RPr | CCTATGATTTAAGGGCATTTTTCC | SEQ ID NO: 147 |
| BCL2L10 | NM_020396.2 | FPr | GCTGGGATGGCTTTTGTCA | SEQ ID NO: 148 |
| | | Probe | TCTTCAGGACCCCCTTTCCACTGGC | SEQ ID NO: 149 |
| | | RPr | GCCTGGACCAGCTGTTTTCT | SEQ ID NO: 150 |
| BCL2L11 | NM_138621.1 | FPr | AATTACCAAGCAGCCGAAGA | SEQ ID NO: 151 |
| | | Probe | CCACCCACGAATGGTTATCTTACGACTG | SEQ ID NO: 152 |
| | | RPr | CAGGCGGACAATGTAACGTA | SEQ ID NO: 153 |

TABLE A-continued

| Gene | Accession | Reagt | Sequence | SEQ ID NO |
|---|---|---|---|---|
| BCL2L12 | NM_138639.1 | FPr | AACCCACCCCTGTCTTGG | SEQ ID NO: 154 |
| | | Probe | TCCGGGTAGCTCTCAAACTCGAGG | SEQ ID NO: 155 |
| | | RPr | CTCAGCTGACGGGAAAGG | SEQ ID NO: 156 |
| Bclx | NM_001191.1 | FPr | CTTTTGTGGAACTCTATGGGAACA | SEQ ID NO: 157 |
| | | Probe | TTCGGCTCTCGGCTGCTGCA | SEQ ID NO: 158 |
| | | RPr | CAGCGGTTGAAGCGTTCCT | SEQ ID NO: 159 |
| BCRP | NM_004827.1 | FPr | TGTACTGGCGAAGAATATTTGGTAAA | SEQ ID NO: 160 |
| | | Probe | CAGGGCATCGATCTCTCACCCTGG | SEQ ID NO: 161 |
| | | RPr | GCCACGTGATTCTTCCACAA | SEQ ID NO: 162 |
| BFGF | NM_007083.1 | FPr | CCAGGAAGAATGCTTAAGATGTGA | SEQ ID NO: 163 |
| | | Probe | TTCGCCAGGTCATTGAGATCCATCCA | SEQ ID NO: 164 |
| | | RPr | TGGTGATGGGAGTTGTATTTTCAG | SEQ ID NO: 165 |
| BGN | NM_001711.3 | FPr | GAGCTCCGCAAGGATGAC | SEQ ID NO: 166 |
| | | Probe | CAAGGGTCTCCAGCACCTCTACGC | SEQ ID NO: 167 |
| | | RPr | CTTGTTGTTCACCAGGACGA | SEQ ID NO: 168 |
| BID | NM_001196.2 | FPr | GGACTGTGAGGTCAACAACG | SEQ ID NO: 169 |
| | | Probe | TGTGATGCACTCATCCCTGAGGCT | SEQ ID NO: 170 |
| | | RPr | GGAAGCCAAACACCAGTAGG | SEQ ID NO: 171 |
| BIK | NM_001197.3 | FPr | ATTCCTATGGCTCTGCAATTGTC | SEQ ID NO: 172 |
| | | Probe | CCGGTTAACTGTGGCCTGTGCCC | SEQ ID NO: 173 |
| | | RPr | GGCAGGAGTGAATGGCTCTTC | SEQ ID NO: 174 |
| BIN1 | NM_004305.1 | FPr | CCTGCAAAAGGGAACAAGAG | SEQ ID NO: 175 |
| | | Probe | CTTCGCCTCCAGATGGCTCCC | SEQ ID NO: 176 |
| | | RPr | CGTGGTTGACTCTGATCTCG | SEQ ID NO: 177 |
| BLMH | NM_000386.2 | FPr | GGTTGCTGCCTCCATCAAAG | SEQ ID NO: 178 |
| | | Probe | ACATCACAGCCAAACCACACAGCCTCT | SEQ ID NO: 179 |
| | | RPr | CCAGCTTGCTATTGAAGTGTTTTC | SEQ ID NO: 180 |
| BMP2 | NM_001200.1 | FPr | ATGTGGACGCTCTTTCAATG | SEQ ID NO: 181 |
| | | Probe | ACCGCAGTCCGTCTAAGAAGCACG | SEQ ID NO: 182 |
| | | RPr | ACCATGGTCGACCTTTAGGA | SEQ ID NO: 183 |
| BMP4 | NM_001202.2 | FPr | GGGCTAGCCATTGAGGTG | SEQ ID NO: 184 |
| | | Probe | CTCACCTCCATCAGACTCGGACCC | SEQ ID NO: 185 |
| | | RPr | GCTAATCCTGACATGCTGGC | SEQ ID NO: 186 |
| BMP7 | NM_001719.1 | FPr | TCGTGGAACATGACAAGGAATT | SEQ ID NO: 187 |
| | | Probe | TTCCACCCACGCTACCACCATCG | SEQ ID NO: 188 |
| | | RPr | TGGAAAGATCAAACCGGAACTC | SEQ ID NO: 189 |
| BMPR1A | NM_004329.2 | FPr | TTGGTTCAGCGAACTATTGC | SEQ ID NO: 190 |
| | | Probe | CAAACAGATTCAGATGGTCCGGCA | SEQ ID NO: 191 |
| | | RPr | TCTCCATATCGGCCTTTACC | SEQ ID NO: 192 |
| BRAF | NM_004333.1 | FPr | CCTTCCGACCAGCAGATGAA | SEQ ID NO: 193 |
| | | Probe | CAATTTGGGCAACGAGACCGATCCT | SEQ ID NO: 194 |
| | | RPr | TTTATATGCACATTGGGAGCTGAT | SEQ ID NO: 195 |
| BRCA1 | NM_007295.1 | FPr | TCAGGGGGCTAGAAATCTGT | SEQ ID NO: 196 |
| | | Probe | CTATGGGCCCTTCACCAACATGC | SEQ ID NO: 197 |
| | | RPr | CCATTCCAGTTGATCTGTGG | SEQ ID NO: 198 |
| BRCA2 | NM_000059.1 | FPr | AGTTCGTGCTTTGCAAGATG | SEQ ID NO: 199 |
| | | Probe | CATTCTTCACTGCTTCATAAAGCTCTGCA | SEQ ID NO: 200 |
| | | RPr | AAGGTAAGCTGGGTCTGCTG | SEQ ID NO: 201 |
| BRK | NM_005975.1 | FPr | GTGCAGGAAAGGTTCACAAA | SEQ ID NO: 202 |
| | | Probe | AGTGTCTGCGTCCAATACACGCGT | SEQ ID NO: 203 |
| | | RPr | GCACACACGATGGAGTAAGG | SEQ ID NO: 204 |
| BTF3 | NM_001207.2 | FPr | CAGTGATCCACTTTAACAACCCTAAAG | SEQ ID NO: 205 |
| | | Probe | TCAGGCATCTCTGGCAGCGAACAC | SEQ ID NO: 206 |
| | | RPr | AGCATGGCCTGTAATGGTGAA | SEQ ID NO: 207 |
| BTRC | NM_033637.2 | FPr | GTTGGGACACAGTTGGTCTG | SEQ ID NO: 208 |
| | | Probe | CAGTCGGCCCAGGACGGTCTACT | SEQ ID NO: 209 |
| | | RPr | TGAAGCAGTCAGTTGTGCTG | SEQ ID NO: 210 |

TABLE A-continued

| Gene | Accession | Reagt | Sequence | SEQ ID NO |
|---|---|---|---|---|
| BUB1 | NM_004336.1 | FPr | CCGAGGTTAATCCAGCACGTA | SEQ ID NO: 211 |
| | | Probe | TGCTGGGAGCCTACACTTGGCCC | SEQ ID NO: 212 |
| | | RPr | AAGACATGGCGCTCTCAGTTC | SEQ ID NO: 213 |
| BUB1B | NM_001211.3 | FPr | TCAACAGAAGGCTGAACCACTAGA | SEQ ID NO: 214 |
| | | Probe | TACAGTCCCAGCACCGACAATTCC | SEQ ID NO: 215 |
| | | RPr | CAACAGAGTTTGCCGAGACACT | SEQ ID NO: 216 |
| BUB3 | NM_004725.1 | FPr | CTGAAGCAGATGGTTCATCATT | SEQ ID NO: 217 |
| | | Probe | CCTCGCTTTGTTTAACAGCCCAGG | SEQ ID NO: 218 |
| | | RPr | GCTGATTCCCAAGAGTCTAACC | SEQ ID NO: 219 |
| c-abl | NM_005157.2 | FPr | CCATCTCGCTGAGATACGAA | SEQ ID NO: 220 |
| | | Probe | GGGAGGGTGTACCATTACAGGATCAACA | SEQ ID NO: 221 |
| | | RPr | AGACGTAGAGCTTGCCATCA | SEQ ID NO: 222 |
| c-kit | NM_000222.1 | FPr | GAGGCAACTGCTTATGGCTTAATTA | SEQ ID NO: 223 |
| | | Probe | TTACAGCGACAGTCATGGCCGCAT | SEQ ID NO: 224 |
| | | RPr | GGCACTCGGCTTGAGCAT | SEQ ID NO: 225 |
| c-myb (MYB official) | NM_005375.1 | FPr | AACTCAGACTTGGAAATGCCTTCT | SEQ ID NO: 226 |
| | | Probe | AACTTCCACCCCCCTCATTGGTCACA | SEQ ID NO: 227 |
| | | RPr | CTGGTCTCTATGAAATGGTGTTGTAAC | SEQ ID NO: 228 |
| c-Src | NM_005417.3 | FPr | TGAGGAGTGGTATTTTGGCAAGA | SEQ ID NO: 229 |
| | | Probe | AACCGCTCTGACTCCCGTCTGGTG | SEQ ID NO: 230 |
| | | RPr | CTCTCGGGTTCTCTGCATTGA | SEQ ID NO: 231 |
| C20 orf1 | NM_012112.2 | FPr | TCAGCTGTGAGCTGCGGATA | SEQ ID NO: 232 |
| | | Probe | CAGGTCCCATTGCCGGGCG | SEQ ID NO: 233 |
| | | RPr | ACGGTCCTAGGTTTGAGGTTAAGA | SEQ ID NO: 234 |
| C20ORF126 | NM_030815.2 | FPr | CCAGCACTGCTCGTTACTGT | SEQ ID NO: 235 |
| | | Probe | TGGGACCTCAGACCACTGAAGGC | SEQ ID NO: 236 |
| | | RPr | TTGACTTCACGGCAGTTCATA | SEQ ID NO: 237 |
| C8orf4 | NM_020130.2 | FPr | CTACGAGTCAGCCCATCCAT | SEQ ID NO: 238 |
| | | Probe | CATGGCTACCACTTCGACACAGCC | SEQ ID NO: 239 |
| | | RPr | TGCCCACGGCTTTCTTAC | SEQ ID NO: 240 |
| CA9 | NM_001216.1 | FPr | ATCCTAGCCCTGGTTTTGG | SEQ ID NO: 241 |
| | | Probe | TTTGCTGTCACCAGCGTCGC | SEQ ID NO: 242 |
| | | RPr | CTGCCTTCTCATCTGCACAA | SEQ ID NO: 243 |
| Cad17 | NM_004063.2 | FPr | GAAGGCCAAGAACCGAGTCA | SEQ ID NO: 244 |
| | | Probe | TTATATTCCAGTTTAAGGCCAATCCTC | SEQ ID NO: 245 |
| | | RPr | TCCCCAGTTAGTTCAAAAGTCACA | SEQ ID NO: 246 |
| CALD1 | NM_004342.4 | FPr | CACTAAGGTTTGAGACAGTTCCAGAA | SEQ ID NO: 247 |
| | | Probe | AACCCAAGCTCAAGACGCAGGACGAG | SEQ ID NO: 248 |
| | | RPr | GCGAATTAGCCCTCTACAACTGA | SEQ ID NO: 249 |
| CAPG | NM_001747.1 | FPr | GATTGTCACTGATGGGGAGG | SEQ ID NO: 250 |
| | | Probe | AGGACCTGGATCATCTCAGCAGGC | SEQ ID NO: 251 |
| | | RPr | CCTTCAGAGCAGGCTTGG | SEQ ID NO: 252 |
| CAPN1 | NM_005186.2 | FPr | CAAGAAGCTGTACGAGCTCATCA | SEQ ID NO: 253 |
| | | Probe | CCGCTACTCGGAGCCCGACCTG | SEQ ID NO: 254 |
| | | RPr | GCAGCAAACGAAATTGTCAAAG | SEQ ID NO: 255 |
| CASP8 | NM_033357.1 | FPr | CCTCGGGGATACTGTCTGAT | SEQ ID NO: 256 |
| | | Probe | CAACAATCACAATTTTGCAAAAGCACG | SEQ ID NO: 257 |
| | | RPr | GAAGTTTGGGCACTTTCTCC | SEQ ID NO: 258 |
| CASP9 | NM_001229.2 | FPr | TGAATGCCGTGGATTGCA | SEQ ID NO: 259 |
| | | Probe | CACTAGCCCTGGACCAGCCACTGCT | SEQ ID NO: 260 |
| | | RPr | ACAGGGATCATGGGACACAAG | SEQ ID NO: 261 |
| CAT | NM_001752.1 | FPr | ATCCATTCGATCTCACCAAGGT | SEQ ID NO: 262 |
| | | Probe | TGGCCTCACAAGGACTACCCTCTCATCC | SEQ ID NO: 263 |
| | | RPr | TCCGGTTTAAGACCAGTTTACCA | SEQ ID NO: 264 |
| CAV1 | NM_001753.3 | FPr | GTGGCTCAACATTGTGTTCC | SEQ ID NO: 265 |
| | | Probe | ATTTCAGCTGATCAGTGGGCCTCC | SEQ ID NO: 266 |
| | | RPr | CAATGGCCTCCATTTTACAG | SEQ ID NO: 267 |

TABLE A-continued

| Gene | Accession | Reagt | Sequence | SEQ ID NO |
|---|---|---|---|---|
| CBL | NM_005188.1 | FPr | TCATTCACAAACCTGGCAGT | SEQ ID NO: 268 |
| | | Probe | TTCCGGCTGAGCTGTACTCGTCTG | SEQ ID NO: 269 |
| | | RPr | CATACCCAATAGCCCACTGA | SEQ ID NO: 270 |
| CCL20 | NM_004591.1 | FPr | CCATGTGCTGTACCAAGAGTTTG | SEQ ID NO: 271 |
| | | Probe | CAGCACTGACATCAAAGCAGCCAGGA | SEQ ID NO: 272 |
| | | RPr | CGCCGCAGAGGTGGAGTA | SEQ ID NO: 273 |
| CCL3 | NM_002983.1 | FPr | AGCAGACAGTGGTCAGTCCTT | SEQ ID NO: 274 |
| | | Probe | CTCTGCTGACACTCGAGCCCACAT | SEQ ID NO: 275 |
| | | RPr | CTGCATGATTCTGAGCAGGT | SEQ ID NO: 276 |
| CCNA2 | NM_001237.2 | FPr | CCATACCTCAAGTATTTGCCATCAG | SEQ ID NO: 277 |
| | | Probe | ATTGCTGGAGCTGCCTTTCATTTAGCACT | SEQ ID NO: 278 |
| | | RPr | AGCTTTGTCCCGTGACTGTGTA | SEQ ID NO: 279 |
| CCNB1 | NM_031966.1 | FPr | TTCAGGTTGTTGCAGGAGAC | SEQ ID NO: 280 |
| | | Probe | TGTCTCCATTATTGATCGGTTCATGCA | SEQ ID NO: 281 |
| | | RPr | CATCTTCTTGGGCACACAAT | SEQ ID NO: 282 |
| CCNB2 | NM_004701.2 | FPr | AGGCTTCTGCAGGAGACTCTGT | SEQ ID NO: 283 |
| | | Probe | TCGATCCATAATGCCAACGCACATG | SEQ ID NO: 284 |
| | | RPr | GGGAAACTGGCTGAACCTGTAA | SEQ ID NO: 285 |
| CCND1 | NM_001758.1 | FPr | GCATGTTCGTGGCCTCTAAGA | SEQ ID NO: 286 |
| | | Probe | AAGGAGACCATCCCCCTGACGGC | SEQ ID NO: 287 |
| | | RPr | CGGTGTAGATGCACAGCTTCTC | SEQ ID NO: 288 |
| CCND3 | NM_001760.2 | FPr | CCTCTGTGCTACAGATTATACCTTTGC | SEQ ID NO: 289 |
| | | Probe | TACCCGCCATCCATGATCGCCA | SEQ ID NO: 290 |
| | | RPr | CACTGCAGCCCCAATGCT | SEQ ID NO: 291 |
| CCNE1 | NM_001238.1 | FPr | AAAGAAGATGATGACCGGGTTTAC | SEQ ID NO: 292 |
| | | Probe | CAAACTCAACGTGCAAGCCTCGGA | SEQ ID NO: 293 |
| | | RPr | GAGCCTCTGGATGGTGCAAT | SEQ ID NO: 294 |
| CCNE2 | NM_057749.1 | FPr | GGTCACCAAGAAACATCAGTATGAA | SEQ ID NO: 295 |
| | | Probe | CCCAGATAATACAGGTGGCCAACAATTCCT | SEQ ID NO: 296 |
| | | RPr | TTCAATGATAATGCAAGGACTGATC | SEQ ID NO: 297 |
| CCNE2 variant 1 | NM_057749var1 | FPr | ATGCTGTGGCTCCTTCCTAACT | SEQ ID NO: 298 |
| | | Probe | TACCAAGCAACCTACATGTCAAGAAAGCCC | SEQ ID NO: 299 |
| | | RPr | ACCCAAATTGTGATATACAAAAGGTT | SEQ ID NO: 300 |
| CCR7 | NM_001838.2 | FPr | GGATGACATGCACTCAGCTC | SEQ ID NO: 301 |
| | | Probe | CTCCCATCCCAGTGGAGCCAA | SEQ ID NO: 302 |
| | | RPr | CCTGACATTTCCCTTGTCCT | SEQ ID NO: 303 |
| CD105 | NM_000118.1 | FPr | GCAGGTGTCAGCAAGTATGATCAG | SEQ ID NO: 304 |
| | | Probe | CGACAGGATATTGACCACCGCCTCATT | SEQ ID NO: 305 |
| | | RPr | TTTTTCCGCTGTGGTGATGA | SEQ ID NO: 306 |
| CD134 (TNFRSF4 official) | NM_003327.1 | FPr | GCCCAGTGCGGAGAACAG | SEQ ID NO: 307 |
| | | Probe | CCAGCTTGATTCTCGTCTCTGCACTTAAGC | SEQ ID NO: 308 |
| | | RPr | AATCACACGCACCTGGAGAAC | SEQ ID NO: 309 |
| CD18 | NM_000211.1 | FPr | CGTCAGGACCCACCATGTCT | SEQ ID NO: 310 |
| | | Probe | CGCGGCCGAGACATGGCTTG | SEQ ID NO: 311 |
| | | RPr | GGTTAATTGGTGACATCCTCAAGA | SEQ ID NO: 312 |
| CD24 | NM_013230.1 | FPr | TCCAACTAATGCCACCACCAA | SEQ ID NO: 313 |
| | | Probe | CTGTTGACTGCAGGGCACCACCA | SEQ ID NO: 314 |
| | | RPr | GAGAGAGTGAGACCACGAAGAGACT | SEQ ID NO: 315 |
| CD28 | NM_006139.1 | FPr | TGTGAAAGGGAAACACCTTTG | SEQ ID NO: 316 |
| | | Probe | CCAAGTCCCCTATTTCCCGGACCT | SEQ ID NO: 317 |
| | | RPr | AGCACCCAAAAGGGCTTAG | SEQ ID NO: 318 |
| CD31 | NM_000442.1 | FPr | TGTATTTCAAGACCTCTGTGCACTT | SEQ ID NO: 319 |
| | | Probe | TTTATGAACCTGCCCTGCTCCCACA | SEQ ID NO: 320 |
| | | RPr | TTAGCCTGAGGAATTGCTGTGTT | SEQ ID NO: 321 |
| CD34 | NM_001773.1 | FPr | CCACTGCACACACCTCAGA | SEQ ID NO: 322 |
| | | Probe | CTGTTCTTGGGGCCCTACACCTTG | SEQ ID NO: 323 |
| | | RPr | CAGGAGTTTACCTGCCCCT | SEQ ID NO: 324 |

TABLE A-continued

| Gene | Accession | Reagt | Sequence | SEQ ID NO |
|---|---|---|---|---|
| CD3z | NM_000734.1 | FPr | AGATGAAGTGGAAGGCGCTT | SEQ ID NO: 325 |
| | | Probe | CACCGCGGCCATCCTGCA | SEQ ID NO: 326 |
| | | RPr | TGCCTCTGTAATCGGCAACTG | SEQ ID NO: 327 |
| CD44E | X55150 | FPr | ATCACCGACAGCACAGACA | SEQ ID NO: 328 |
| | | Probe | CCCTGCTACCAATATGGACTCCAGTCA | SEQ ID NO: 329 |
| | | RPr | ACCTGTGTTTGGATTTGCAG | SEQ ID NO: 330 |
| CD44s | M59040.1 | FPr | GACGAAGACAGTCCCTGGAT | SEQ ID NO: 331 |
| | | Probe | CACCGACAGCACAGACAGAATCCC | SEQ ID NO: 332 |
| | | RPr | ACTGGGGTGGAATGTGTCTT | SEQ ID NO: 333 |
| CD44v3 | AJ251595v3 | FPr | CACACAAAACAGAACCAGGACT | SEQ ID NO: 334 |
| | | Probe | ACCCAGTGGAACCCAAGCCATTC | SEQ ID NO: 335 |
| | | RPr | CTGAAGTAGCACTTCCGGATT | SEQ ID NO: 336 |
| CD44v6 | AJ251595v6 | FPr | CTCATACCAGCCATCCAATG | SEQ ID NO: 337 |
| | | Probe | CACCAAGCCCAGAGGACAGTTCCT | SEQ ID NO: 338 |
| | | RPr | TTGGGTTGAAGAAATCAGTCC | SEQ ID NO: 339 |
| CD68 | NM_001251.1 | FPr | TGGTTCCCAGCCCTGTGT | SEQ ID NO: 340 |
| | | Probe | CTCCAAGCCCAGATTCAGATTCGAGTCA | SEQ ID NO: 341 |
| | | RPr | CTCCTCCACCCTGGGTTGT | SEQ ID NO: 342 |
| CD80 | NM_005191.2 | FPr | TTCAGTTGCTTTGCAGGAAG | SEQ ID NO: 343 |
| | | Probe | TTCTGTGCCCACCATATTCCTCTAGACA | SEQ ID NO: 344 |
| | | RPr | TTGATCAAGGTCACCAGAGC | SEQ ID NO: 345 |
| CD82 | NM_002231.2 | FPr | GTGCAGGCTCAGGTGAAGTG | SEQ ID NO: 346 |
| | | Probe | TCAGCTTCTACAACTGGACAGACAACGCTG | SEQ ID NO: 347 |
| | | RPr | GACCTCAGGGCGATTCATGA | SEQ ID NO: 348 |
| CD8A | NM_171827.1 | FPr | AGGGTGAGGTGCTTGAGTCT | SEQ ID NO: 349 |
| | | Probe | CCAACGGCAAGGGAACAAGTACTTCT | SEQ ID NO: 350 |
| | | RPr | GGGCACAGTATCCCAGGTA | SEQ ID NO: 351 |
| CD9 | NM_001769.1 | FPr | GGGCGTGGAACAGTTTATCT | SEQ ID NO: 352 |
| | | Probe | AGACATCTGCCCCAAGAAGGACGT | SEQ ID NO: 353 |
| | | RPr | CACGGTGAAGGTTTCGAGT | SEQ ID NO: 354 |
| CDC2 | NM_001786.2 | FPr | GAGAGCGACGCGGTTGTT | SEQ ID NO: 355 |
| | | Probe | TAGCTGCCGCTGCGGCCG | SEQ ID NO: 356 |
| | | RPr | GTATGGTAGATCCCGGCTTATTATTC | SEQ ID NO: 357 |
| CDC20 | NM_001255.1 | FPr | TGGATTGGAGTTCTGGGAATG | SEQ ID NO: 358 |
| | | Probe | ACTGGCCGTGGCACTGGACAACA | SEQ ID NO: 359 |
| | | RPr | GCTTGCACTCCACAGGTACACA | SEQ ID NO: 360 |
| cdc25A | NM_001789.1 | FPr | TCTTGCTGGCTACGCCTCTT | SEQ ID NO: 361 |
| | | Probe | TGTCCCTGTTAGACGTCCTCCGTCCATA | SEQ ID NO: 362 |
| | | RPr | CTGCATTGTGGCACAGTTCTG | SEQ ID NO: 363 |
| CDC25B | NM_021874.1 | FPr | AAACGAGCAGTTTGCCATCAG | SEQ ID NO: 364 |
| | | Probe | CCTCACCGGCATAGACTGGAAGCG | SEQ ID NO: 365 |
| | | RPr | GTTGGTGATGTTCCGAAGCA | SEQ ID NO: 366 |
| CDC25C | NM_001790.2 | FPr | GGTGAGCAGAAGTGGCCTAT | SEQ ID NO: 367 |
| | | Probe | CTCCCCGTCGATGCCAGAGAACT | SEQ ID NO: 368 |
| | | RPr | CTTCAGTCTTGGCCTGTTCA | SEQ ID NO: 369 |
| CDC4 | NM_018315.2 | FPr | GCAGTCCGCTGTGTTCAA | SEQ ID NO: 370 |
| | | Probe | TGCTCCACTAACAACCCTCCTGCC | SEQ ID NO: 371 |
| | | RPr | GGATCCCACACCTTTACCATAA | SEQ ID NO: 372 |
| CDC42 | NM_001791.2 | FPr | TCCAGAGACTGCTGAAAA | SEQ ID NO: 373 |
| | | Probe | CCCGTGACCTGAAGGCTGTCAAG | SEQ ID NO: 374 |
| | | RPr | TGTGTAAGTGCAGAACAC | SEQ ID NO: 375 |
| CDC42BPA | NM_003607.2 | FPr | GAGCTGAAAGACGCACACTG | SEQ ID NO: 376 |
| | | Probe | AATTCCTGCATGGCCAGTTTCCTC | SEQ ID NO: 377 |
| | | RPr | GCCGCTCATTGATCTCCA | SEQ ID NO: 378 |
| CDC6 | NM_001254.2 | FPr | GCAACACTCCCCATTTACCTC | SEQ ID NO: 379 |
| | | Probe | TTGTTCTCCACCAAAGCAAGGCAA | SEQ ID NO: 380 |
| | | RPr | TGAGGGGGACCATTCTCTTT | SEQ ID NO: 381 |

TABLE A-continued

| Gene | Accession | Reagt | Sequence | SEQ ID NO |
|---|---|---|---|---|
| CDCA7 v2 | NM_145810.1 | FPr | AAGACCGTGGATGGCTACAT | SEQ ID NO: 382 |
| | | Probe | ATGAAGATGACCTGCCCAGAAGCC | SEQ ID NO: 383 |
| | | RPr | AGGGTCACGGATGATCTGG | SEQ ID NO: 384 |
| CDH1 | NM_004360.2 | FPr | TGAGTGTCCCCCGGTATCTTC | SEQ ID NO: 385 |
| | | Probe | TGCCAATCCCGATGAAATTGGAAATTT | SEQ ID NO: 386 |
| | | RPr | CAGCCGCTTTCAGATTTTCAT | SEQ ID NO: 387 |
| CDH11 | NM_001797.2 | FPr | GTCGGCAGAAGCAGGACT | SEQ ID NO: 388 |
| | | Probe | CCTTCTGCCCATAGTGATCAGCGA | SEQ ID NO: 389 |
| | | RPr | CTACTCATGGGCGGGATG | SEQ ID NO: 390 |
| CDH3 | NM_001793.3 | FPr | ACCCATGTACCGTCCTCG | SEQ ID NO: 391 |
| | | Probe | CCAACCCAGATGAAATCGGCAACT | SEQ ID NO: 392 |
| | | RPr | CCGCCTTCAGGTTCTCAAT | SEQ ID NO: 393 |
| CDK2 | NM_001798.2 | FPr | AATGCTGCACTACGACCCTA | SEQ ID NO: 394 |
| | | Probe | CCTTGGCCGAAATCCGCTTGT | SEQ ID NO: 395 |
| | | RPr | TTGGTCACATCCTGGAAGAA | SEQ ID NO: 396 |
| CDX1 | NM_001804.1 | FPr | AGCAACACCAGCCTCCTG | SEQ ID NO: 397 |
| | | Probe | CACCTCCTCTCCAATGCCTGTGAA | SEQ ID NO: 398 |
| | | RPr | GGGCTATGGCAGAAACTCCT | SEQ ID NO: 399 |
| Cdx2 | NM_001265.2 | FPr | GGGCAGGCAAGGTTTACA | SEQ ID NO: 400 |
| | | Probe | ATCTTAGCTGCCTTTGGCTTCCGC | SEQ ID NO: 401 |
| | | RPr | GTCTTTGGTCAGTCCAGCTTTC | SEQ ID NO: 402 |
| CEACAM1 | NM_001712.2 | FPr | ACTTGCCTGTTCAGAGCACTCA | SEQ ID NO: 403 |
| | | Probe | TCCTTCCCACCCCAGTCCTGTC | SEQ ID NO: 404 |
| | | RPr | TGGCAAATCCGAATTAGAGTGA | SEQ ID NO: 405 |
| CEACAM6 | NM_002483.2 | FPr | CACAGCCTCACTTCTAACCTTCTG | SEQ ID NO: 406 |
| | | Probe | ACCCACCCACCACTGCCAAGCTC | SEQ ID NO: 407 |
| | | RPr | TTGAATGGCGTGGATTCAATAG | SEQ ID NO: 408 |
| CEBPB | NM_005194.2 | FPr | GCAACCCACGTGTAACTGTC | SEQ ID NO: 409 |
| | | Probe | CCGGGCCCTGAGTAATCGCTTAA | SEQ ID NO: 410 |
| | | RPr | ACAAGCCCGTAGGAACATCT | SEQ ID NO: 411 |
| CEGP1 | NM_020974.1 | FPr | TGACAATCAGCACACCTGCAT | SEQ ID NO: 412 |
| | | Probe | CAGGCCCTCTTCCGAGCGGT | SEQ ID NO: 413 |
| | | RPr | TGTGACTACAGCCGTGATCCTTA | SEQ ID NO: 414 |
| CENPA | NM_001809.2 | FPr | TAAATTCACTCGTGGTGTGGA | SEQ ID NO: 415 |
| | | Probe | CTTCAATTGGCAAGCCCAGGC | SEQ ID NO: 416 |
| | | RPr | GCCTCTTGTAGGGCCAATAG | SEQ ID NO: 417 |
| CENPE | NM_001813.1 | FPr | GGATGCTGGTGACCTCTTCT | SEQ ID NO: 418 |
| | | Probe | TCCCTCACGTTGCAACAGGAATTAA | SEQ ID NO: 419 |
| | | RPr | GCCAAGGCACCAAGTAACTC | SEQ ID NO: 420 |
| CENPF | NM_016343.2 | FPr | CTCCCGTCAACAGCGTTC | SEQ ID NO: 421 |
| | | Probe | ACACTGGACCAGGAGTGCATCCAG | SEQ ID NO: 422 |
| | | RPr | GGGTGAGTCTGGCCTTCA | SEQ ID NO: 423 |
| CES2 | NM_003869.4 | FPr | ACTTTGCGAGAAATGGGAAC | SEQ ID NO: 424 |
| | | Probe | AGTGTGGCAGACCCTCGCCATT | SEQ ID NO: 425 |
| | | RPr | CAGGTATTGCTCCTCCTGGT | SEQ ID NO: 426 |
| CGA (CHGA official) | NM_001275.2 | FPr | CTGAAGGAGCTCCAAGACCT | SEQ ID NO: 427 |
| | | Probe | TGCTGATGTGCCCTCTCCTTGG | SEQ ID NO: 428 |
| | | RPr | CAAAACCGCTGTGTTTCTTC | SEQ ID NO: 429 |
| CGB | NM_000737.2 | FPr | CCACCATAGGCAGAGGCA | SEQ ID NO: 430 |
| | | Probe | ACACCCTACTCCCTGTGCCTCCAG | SEQ ID NO: 431 |
| | | RPr | AGTCGTCGAGTGCTAGGGAC | SEQ ID NO: 432 |
| CHAF1B | NM_005441.1 | FPr | GAGGCCAGTGGTGGAAACAG | SEQ ID NO: 433 |
| | | Probe | AGCTGATGAGTCTGCCCTACCGCTG | SEQ ID NO: 434 |
| | | RPr | TCCGAGGCCACAGCAAAC | SEQ ID NO: 435 |
| CHD2 | NM_001271.1 | FPr | CTCTGTGCGAGGCTGTCA | SEQ ID NO: 436 |
| | | Probe | ACCCATCTCGGGATCCCTGATACC | SEQ ID NO: 437 |
| | | RPr | GGTAAGGACTGTGGGCTGG | SEQ ID NO: 438 |

TABLE A-continued

| Gene | Accession | Reagt | Sequence | SEQ ID NO |
|---|---|---|---|---|
| CHFR | NM_018223.1 | FPr | AAGGAAGTGGTCCCTCTGTG | SEQ ID NO: 439 |
| | | Probe | TGAAGTCTCCAGCTTTGCCTCAGC | SEQ ID NO: 440 |
| | | RPr | GACGCAGTCTTTCTGTCTGG | SEQ ID NO: 441 |
| Chk1 | NM_001274.1 | FPr | GATAAATTGGTACAAGGGATCAGCTT | SEQ ID NO: 442 |
| | | Probe | CCAGCCCACATGTCCTGATCATATGC | SEQ ID NO: 443 |
| | | RPr | GGGTGCCAAGTAACTGACTATTCA | SEQ ID NO: 444 |
| Chk2 | NM_007194.1 | FPr | ATGTGGAACCCCCACCTACTT | SEQ ID NO: 445 |
| | | Probe | AGTCCCAACAGAAACAAGAACTTCAGGCG | SEQ ID NO: 446 |
| | | RPr | CAGTCCACAGCACGGTTATACC | SEQ ID NO: 447 |
| CIAP1 | NM_001166.2 | FPr | TGCCTGTGGTGGGAAGCT | SEQ ID NO: 448 |
| | | Probe | TGACATAGCATCATCCTTTGGTTCCCAGTT | SEQ ID NO: 449 |
| | | RPr | GGAAAATGCCTCCGGTGTT | SEQ ID NO: 450 |
| cIAP2 | NM_001165.2 | FPr | GGATATTTCCGTGGCTCTTATTCA | SEQ ID NO: 451 |
| | | Probe | TCTCCATCAAATCCTGTAAACTCCAGAGCA | SEQ ID NO: 452 |
| | | RPr | CTTCTCATCAAGGCAGAAAAATCTT | SEQ ID NO: 453 |
| CKS1B | NM_001826.1 | FPr | GGTCCCTAAAACCCATCTGA | SEQ ID NO: 454 |
| | | Probe | TGAACGCCAAGATTCCTCCATTCA | SEQ ID NO: 455 |
| | | RPr | TAATGGACCCATCCCTGACT | SEQ ID NO: 456 |
| CKS2 | NM_001827.1 | FPr | GGCTGGACGTGGTTTTGTCT | SEQ ID NO: 457 |
| | | Probe | CTGCGCCCGCTCTTCGCG | SEQ ID NO: 458 |
| | | RPr | CGCTGCAGAAAATGAAACGA | SEQ ID NO: 459 |
| Claudin 4 | NM_001305.2 | FPr | GGCTGCTTTGCTGCAACTG | SEQ ID NO: 460 |
| | | Probe | CGCACAGACAAGCCTTACTCCGCC | SEQ ID NO: 461 |
| | | RPr | CAGAGCGGGCAGCAGAATA | SEQ ID NO: 462 |
| CLDN1 | NM_021101.3 | FPr | TCTGGGAGGTGCCCTACTT | SEQ ID NO: 463 |
| | | Probe | TGTTCCTGTCCCCGAAAAACAACC | SEQ ID NO: 464 |
| | | RPr | TGGATAGGGCCTTGGTGTT | SEQ ID NO: 465 |
| CLDN7 | NM_001307.3 | FPr | GGTCTGCCCTAGTCATCCTG | SEQ ID NO: 466 |
| | | Probe | TGCACTGCTCTCCTGTTCCTGTCC | SEQ ID NO: 467 |
| | | RPr | GTACCCAGCCTTGCTCTCAT | SEQ ID NO: 468 |
| CLIC1 | NM_001288.3 | FPr | CGGTACTTGAGCAATGCCTA | SEQ ID NO: 469 |
| | | Probe | CGGGAAGAATTCGCTTCCACCTG | SEQ ID NO: 470 |
| | | RPr | TCGATCTCCTCATCATCTGG | SEQ ID NO: 471 |
| CLTC | NM_004859.1 | FPr | ACCGTATGGACAGCCACAG | SEQ ID NO: 472 |
| | | Probe | TCTCACATGCTGTACCCAAAGCCA | SEQ ID NO: 473 |
| | | RPr | TGACTACAGGATCAGCGCTTC | SEQ ID NO: 474 |
| CLU | NM_001831.1 | FPr | CCCCAGGATACCTACCACTACCT | SEQ ID NO: 475 |
| | | Probe | CCCTTCAGCCTGCCCCACCG | SEQ ID NO: 476 |
| | | RPr | TGCGGGACTTGGGAAAGA | SEQ ID NO: 477 |
| cMet | NM_000245.1 | FPr | GACATTTCCAGTCCTGCAGTCA | SEQ ID NO: 478 |
| | | Probe | TGCCTCTCTGCCCCACCCTTTGT | SEQ ID NO: 479 |
| | | RPr | CTCCGATCGCACACATTTGT | SEQ ID NO: 480 |
| cMYC | NM_002467.1 | FPr | TCCCTCCACTCGGAAGGACTA | SEQ ID NO: 481 |
| | | Probe | TCTGACACTGTCCAACTTGACCCTCTT | SEQ ID NO: 482 |
| | | RPr | CGGTTGTTGCTGATCTGTCTCA | SEQ ID NO: 483 |
| CNN | NM_001299.2 | FPr | TCCACCCTCCTGGCTTTG | SEQ ID NO: 484 |
| | | Probe | TCCTTTCGTCTTCGCCATGCTGG | SEQ ID NO: 485 |
| | | RPr | TCACTCCCACGTTCACCTTGT | SEQ ID NO: 486 |
| COL1A1 | NM_000088.2 | FPr | GTGGCCATCCAGCTGACC | SEQ ID NO: 487 |
| | | Probe | TCCTGCGCCTGATGTCCACCG | SEQ ID NO: 488 |
| | | RPr | CAGTGGTAGGTGATGTTCTGGGA | SEQ ID NO: 489 |
| COL1A2 | NM_000089.2 | FPr | CAGCCAAGAACTGGTATAGGAGCT | SEQ ID NO: 490 |
| | | Probe | TCTCCTAGCCAGACGTGTTTCTTGTCCTTG | SEQ ID NO: 491 |
| | | RPr | AAACTGGCTGCCAGCATTG | SEQ ID NO: 492 |
| COPS3 | NM_003653.2 | FPr | ATGCCCAGTGTTCCTGACTT | SEQ ID NO: 493 |
| | | Probe | CGAAACGCTATTCTCACAGGTTCAGC | SEQ ID NO: 494 |
| | | RPr | CTCCCCATTACAAGTGCTGA | SEQ ID NO: 495 |

TABLE A-continued

| Gene | Accession | Reagt | Sequence | SEQ ID NO |
|---|---|---|---|---|
| COX2 | NM_000963.1 | FPr | TCTGCAGAGTTGGAAGCACTCTA | SEQ ID NO: 496 |
|  |  | Probe | CAGGATACAGCTCCACAGCATCGATGTC | SEQ ID NO: 497 |
|  |  | RPr | GCCGAGGCTTTTCTACCAGAA | SEQ ID NO: 498 |
| COX3 | MITO_COX3 | FPr | TCGAGTCTCCCTTCACCATT | SEQ ID NO: 499 |
|  |  | Probe | CGACGGCATCTACGGCTCAACAT | SEQ ID NO: 500 |
|  |  | RPr | GACGTGAAGTCCGTGGAAG | SEQ ID NO: 501 |
| CP | NM_000096.1 | FPr | CGTGAGTACACAGATGCCTCC | SEQ ID NO: 502 |
|  |  | Probe | TCTTCAGGGCCTCTCTCCTTTCGA | SEQ ID NO: 503 |
|  |  | RPr | CCAGGATGCCAAGATGCT | SEQ ID NO: 504 |
| CRBP | NM_002899.2 | FPr | TGGTCTGCAAGCAAGTATTCAAG | SEQ ID NO: 505 |
|  |  | Probe | TCTGCTTGGGCCTCACTGCACCT | SEQ ID NO: 506 |
|  |  | RPr | GCTGATTGGTTGGGACAAGGT | SEQ ID NO: 507 |
| CREBBP | NM_004380.1 | FPr | TGGGAAGCAGCTGTGTACCAT | SEQ ID NO: 508 |
|  |  | Probe | CCTCGCGATGCTGCCTACTACAGCTATC | SEQ ID NO: 509 |
|  |  | RPr | GAAACACTTCTCACAGAAATGATACCTATT | SEQ ID NO: 510 |
| CRIP2 | NM_001312.1 | FPr | GTGCTACGCCACCCTGTT | SEQ ID NO: 511 |
|  |  | Probe | CCGATGTTCACGCCTTTGGGTC | SEQ ID NO: 512 |
|  |  | RPr | CAGGGGCTTCTCGTAGATGT | SEQ ID NO: 513 |
| cripto (TDGF1 official) | NM_003212.1 | FPr | GGGTCTGTGCCCCATGAC | SEQ ID NO: 514 |
|  |  | Probe | CCTGGCTGCCCAAGAAGTGTTCCCT | SEQ ID NO: 515 |
|  |  | RPr | TGACCGTGCCAGCATTTACA | SEQ ID NO: 516 |
| CRK(a) | NM_016823.2 | FPr | CTCCCTAACCTCCAGAATGG | SEQ ID NO: 517 |
|  |  | Probe | ACTCGCTTCTGGATAACCCTGGCA | SEQ ID NO: 518 |
|  |  | RPr | TGTCTTGTCGTAGGCATTGG | SEQ ID NO: 519 |
| CRMP1 | NM_001313.1 | FPr | AAGGTTTTTGGATTGCAAGG | SEQ ID NO: 520 |
|  |  | Probe | ACCGTCATACATGCCCCTGGAAAC | SEQ ID NO: 521 |
|  |  | RPr | GGGTGTAGCTGGTACCTCGT | SEQ ID NO: 522 |
| CRYAB | NM_001885.1 | FPr | GATGTGATTGAGGTGCATGG | SEQ ID NO: 523 |
|  |  | Probe | TGTTCATCCTGGCGCTCTTCATGT | SEQ ID NO: 524 |
|  |  | RPr | GAACTCCCTGGAGATGAAACC | SEQ ID NO: 525 |
| CSEL1 | NM_001316.2 | FPr | TTACGCAGCTCATGCTCTTG | SEQ ID NO: 526 |
|  |  | Probe | ACGGCTCTTTACTATGCGAGGGCC | SEQ ID NO: 527 |
|  |  | RPr | GCAGCTGTAAAGAGAGTGGCAT | SEQ ID NO: 528 |
| CSF1 | NM_000757.3 | FPr | TGCAGCGGCTGATTGACA | SEQ ID NO: 529 |
|  |  | Probe | TCAGATGGAGACCTCGTGCCAAATTACA | SEQ ID NO: 530 |
|  |  | RPr | CAACTGTTCCTGGTCTACAAACTCA | SEQ ID NO: 531 |
| CSK (SRC) | NM_004383.1 | FPr | CCTGAACATGAAGGAGCTGA | SEQ ID NO: 532 |
|  |  | Probe | TCCCGATGGTCTGCAGCAGCT | SEQ ID NO: 533 |
|  |  | RPr | CATCACGTCTCCGAACTCC | SEQ ID NO: 534 |
| CTAG1B | NM_001327.1 | FPr | GCTCTCCATCAGCTCCTGTC | SEQ ID NO: 535 |
|  |  | Probe | CCACATCAACAGGGAAAGCTGCTG | SEQ ID NO: 536 |
|  |  | RPr | AACACGGGCAGAAAGCACT | SEQ ID NO: 537 |
| CTGF | NM_001901.1 | FPr | GAGTTCAAGTGCCCTGACG | SEQ ID NO: 538 |
|  |  | Probe | AACATCATGTTCTTCTTCATGACCTCGC | SEQ ID NO: 539 |
|  |  | RPr | AGTTGTAATGGCAGGCACAG | SEQ ID NO: 540 |
| CTHRC1 | NM_138455.2 | FPr | GCTCACTTCGGCTAAAATGC | SEQ ID NO: 541 |
|  |  | Probe | ACCAACGCTGACAGCATGCATTTC | SEQ ID NO: 542 |
|  |  | RPr | TCAGCTCCATTGAATGTGAAA | SEQ ID NO: 543 |
| CTLA4 | NM_005214.2 | FPr | CACTGAGGTCCGGGTGACA | SEQ ID NO: 544 |
|  |  | Probe | CACCTGGCTGTCAGCCTGCCG | SEQ ID NO: 545 |
|  |  | RPr | GTAGGTTGCCGCACAGACTTC | SEQ ID NO: 546 |
| CTNNBIP1 | NM_020248.2 | FPr | GTTTTCCAGGTCGGAGACG | SEQ ID NO: 547 |
|  |  | Probe | CTTTGCAGCTACTGCCTCCGGTCT | SEQ ID NO: 548 |
|  |  | RPr | AGCATCCAGGGTGTTCCA | SEQ ID NO: 549 |
| CTSB | NM_001908.1 | FPr | GGCCGAGATCTACAAAAACG | SEQ ID NO: 550 |
|  |  | Probe | CCCCGTGGAGGGAGCTTTCTC | SEQ ID NO: 551 |
|  |  | RPr | GCAGGAAGTCCGAATACACA | SEQ ID NO: 552 |

TABLE A-continued

| Gene | Accession | Reagt | Sequence | SEQ ID NO |
|---|---|---|---|---|
| CTSD | NM_001909.1 | FPr | GTACATGATCCCCTGTGAGAAGGT | SEQ ID NO: 553 |
| | | Probe | ACCCTGCCCGCGATCACACTGA | SEQ ID NO: 554 |
| | | RPr | GGGACAGCTTGTAGCCTTTGC | SEQ ID NO: 555 |
| CTSH | NM_004390.1 | FPr | GCAAGTTCCAACCTGGAAAG | SEQ ID NO: 556 |
| | | Probe | TGGCTACATCCTTGACAAAGCCGA | SEQ ID NO: 557 |
| | | RPr | CATCGCTTCCTCGTCATAGA | SEQ ID NO: 558 |
| CTSL | NM_001912.1 | FPr | GGGAGGCTTATCTCACTGAGTGA | SEQ ID NO: 559 |
| | | Probe | TTGAGGCCCAGAGCAGTCTACCAGATTCT | SEQ ID NO: 560 |
| | | RPr | CCATTGCAGCCTTCATTGC | SEQ ID NO: 561 |
| CTSL2 | NM_001333.2 | FPr | TGTCTCACTGAGCGAGCAGAA | SEQ ID NO: 562 |
| | | Probe | CTTGAGGACGCGAACAGTCCACCA | SEQ ID NO: 563 |
| | | RPr | ACCATTGCAGCCCTGATTG | SEQ ID NO: 564 |
| CUL1 | NM_003592.2 | FPr | ATGCCCTGGTAATGTCTGCAT | SEQ ID NO: 565 |
| | | Probe | CAGCCACAAAGCCAGCGTCATTGT | SEQ ID NO: 566 |
| | | RPr | GCGACCACAAGCCTTATCAAG | SEQ ID NO: 567 |
| CUL4A | NM_003589.1 | FPr | AAGCATCTTCCTGTTCTTGGA | SEQ ID NO: 568 |
| | | Probe | TATGTGCTGCAGAACTCCACGCTG | SEQ ID NO: 569 |
| | | RPr | AATCCCATATCCCAGATGGA | SEQ ID NO: 570 |
| CXCL12 | NM_000609.3 | FPr | GAGCTACAGATGCCCATGC | SEQ ID NO: 571 |
| | | Probe | TTCTTCGAAAGCCATGTTGCCAGA | SEQ ID NO: 572 |
| | | RPr | TTTGAGATGCTTGACGTTGG | SEQ ID NO: 573 |
| CXCR4 | NM_003467.1 | FPr | TGACCGCTTCTACCCCAATG | SEQ ID NO: 574 |
| | | Probe | CTGAAACTGGAACACAACCACCCACAAG | SEQ ID NO: 575 |
| | | RPr | AGGATAAGGCCAACCATGATGT | SEQ ID NO: 576 |
| CYBA | NM_000101.1 | FPr | GGTGCCTACTCCATTGTGG | SEQ ID NO: 577 |
| | | Probe | TACTCCAGCAGGCACACAAACACG | SEQ ID NO: 578 |
| | | RPr | GTGGAGCCCTTCTTCCTCTT | SEQ ID NO: 579 |
| CYP1B1 | NM_000104.2 | FPr | CCAGCTTTGTGCCTGTCACTAT | SEQ ID NO: 580 |
| | | Probe | CTCATGCCACCACTGCCAACACCTC | SEQ ID NO: 581 |
| | | RPr | GGGAATGTGGTAGCCCAAGA | SEQ ID NO: 582 |
| CYP2C8 | NM_000770.2 | FPr | CCGTGTTCAAGAGGAAGCTC | SEQ ID NO: 583 |
| | | Probe | TTTTCTCAACTCCTCCACAAGGCA | SEQ ID NO: 584 |
| | | RPr | AGTGGGATCACAGGGTGAAG | SEQ ID NO: 585 |
| CYP3A4 | NM_017460.3 | FPr | AGAACAAGGACAACATAGATCCTTACATAT | SEQ ID NO: 586 |
| | | Probe | CACACCCTTTGGAAGTGGACCCAGAA | SEQ ID NO: 587 |
| | | RPr | GCAAACCTCATGCCAATGC | SEQ ID NO: 588 |
| CYR61 | NM_001554.3 | FPr | TGCTCATTCTTGAGGAGCAT | SEQ ID NO: 589 |
| | | Probe | CAGCACCCTTGGCAGTTTCGAAAT | SEQ ID NO: 590 |
| | | RPr | GTGGCTGCATTAGTGTCCAT | SEQ ID NO: 591 |
| DAPK1 | NM_004938.1 | FPr | CGCTGACATCATGAATGTTCCT | SEQ ID NO: 592 |
| | | Probe | TCATATCCAAACTCGCCTCCAGCCG | SEQ ID NO: 593 |
| | | RPr | TCTCTTTCAGCAACGATGTGTCTT | SEQ ID NO: 594 |
| DCC | NM_005215.1 | FPr | AAATGTCCTCCTCGACTGCT | SEQ ID NO: 595 |
| | | Probe | ATCACTGGAACTCCTCGGTCGGAC | SEQ ID NO: 596 |
| | | RPr | TGAATGCCATCTTTCTTCCA | SEQ ID NO: 597 |
| DCC_exons 18-23 | X76132_18-23 | FPr | GGTCACCGTTGGTGTCATCA | SEQ ID NO: 598 |
| | | Probe | CAGCCACGATGACCACTACCAGCACT | SEQ ID NO: 599 |
| | | RPr | GAGCGTCGGGTGCAAATC | SEQ ID NO: 600 |
| DCC_exons 6-7 | X76132_6-7 | FPr | ATGGAGATGTGGTCATTCCTAGTG | SEQ ID NO: 601 |
| | | Probe | TGCTTCCTCCCACTATCTGAAAATAA | SEQ ID NO: 602 |
| | | RPr | CACCACCCCAAGTATCCGTAAG | SEQ ID NO: 603 |
| DCK | NM_000788.1 | FPr | GCCGCCACAAGACTAAGGAAT | SEQ ID NO: 604 |
| | | Probe | AGCTGCCCGTCTTTCTCAGCCAG | SEQ ID NO: 605 |
| | | RPr | CGATGTTCCCTTCGATGGAG | SEQ ID NO: 606 |
| DDB1 | NM_001923.2 | FPr | TGCGGATCATCCGGAATG | SEQ ID NO: 607 |
| | | Probe | AATTGGAATCCACGAGCATGCCAGC | SEQ ID NO: 608 |
| | | RPr | TCCTTTGATGCCTGGTAAGTCA | SEQ ID NO: 609 |

TABLE A-continued

| Gene | Accession | Reagt | Sequence | SEQ ID NO |
|---|---|---|---|---|
| DET1 | NM_017996.2 | FPr | CTTGTGGAGATCACCCAATCAG | SEQ ID NO: 610 |
| | | Probe | CTATGCCCGGGACTCGGGCCT | SEQ ID NO: 611 |
| | | RPr | CCCGCCTGGATCTCAAACT | SEQ ID NO: 612 |
| DHFR | NM_000791.2 | FPr | TTGCTATAACTAAGTGCTTCTCCAAGA | SEQ ID NO: 613 |
| | | Probe | CCCAACTGAGTCCCCAGCACCT | SEQ ID NO: 614 |
| | | RPr | GTGGAATGGCAGCTCACTGTAG | SEQ ID NO: 615 |
| DHPS | NM_013407.1 | FPr | GGGAGAACGGGATCAATAGGAT | SEQ ID NO: 616 |
| | | Probe | CTCATTGGGCACCAGCAGGTTTCC | SEQ ID NO: 617 |
| | | RPr | GCATCAGCCAGTCCTCAAACT | SEQ ID NO: 618 |
| DIABLO | NM_019887.1 | FPr | CACAATGGCGGCTCTGAAG | SEQ ID NO: 619 |
| | | Probe | AAGTTACGCTGCGCGACAGCCAA | SEQ ID NO: 620 |
| | | RPr | ACACAAACACTGTCTGTACCTGAAGA | SEQ ID NO: 621 |
| DIAPH1 | NM_005219.2 | FPr | CAAGCAGTCAAGGAGAACCA | SEQ ID NO: 622 |
| | | Probe | TTCTTCTGTCTCCCGCCGCTTC | SEQ ID NO: 623 |
| | | RPr | AGTTTTGCTCGCCTCATCTT | SEQ ID NO: 624 |
| DICER1 | NM_177438.1 | FPr | TCCAATTCCAGCATCACTGT | SEQ ID NO: 625 |
| | | Probe | AGAAAAGCTGTTTGTCTCCCCAGCA | SEQ ID NO: 626 |
| | | RPr | GGCAGTGAAGGCGATAAAGT | SEQ ID NO: 627 |
| DKK1 | NM_012242.1 | FPr | TGACAACTACCAGCCGTACC | SEQ ID NO: 628 |
| | | Probe | AGTGCCGCACTCCTCGTCCTCT | SEQ ID NO: 629 |
| | | RPr | GGGACTAGCGCAGTACTCATC | SEQ ID NO: 630 |
| DLC1 | NM_006094.3 | FPr | GATTCAGACGAGGATGAGCC | SEQ ID NO: 631 |
| | | Probe | AAAGTCCATTTGCCACTGATGGCA | SEQ ID NO: 632 |
| | | RPr | CACCTCTTGCTGTCCCTTTG | SEQ ID NO: 633 |
| DPYD | NM_000110.2 | FPr | AGGACGCAAGGAGGGTTTG | SEQ ID NO: 634 |
| | | Probe | CAGTGCCTACAGTCTCGAGTCTGCCAGTG | SEQ ID NO: 635 |
| | | RPr | GATGTCCGCCGAGTCCTTACT | SEQ ID NO: 636 |
| DR4 | NM_003844.1 | FPr | TGCACAGAGGGTGTGGGTTAC | SEQ ID NO: 637 |
| | | Probe | CAATGCTTCCAACAATTTGTTTGCTTGCC | SEQ ID NO: 638 |
| | | RPr | TCTTCATCTGATTTACAAGCTGTACATG | SEQ ID NO: 639 |
| DR5 | NM_003842.2 | FPr | CTCTGAGACAGTGCTTCGATGACT | SEQ ID NO: 640 |
| | | Probe | CAGACTTGGTGCCCTTTGACTCC | SEQ ID NO: 641 |
| | | RPr | CCATGAGGCCCAACTTCCT | SEQ ID NO: 642 |
| DRG1 | NM_004147.3 | FPr | CCTGGATCTCCCAGGTATCA | SEQ ID NO: 643 |
| | | Probe | ACCTTTCCCATCCTTGGCACCTTC | SEQ ID NO: 644 |
| | | RPr | TGCAATGACTTGACGACCTC | SEQ ID NO: 645 |
| DSP | NM_004415.1 | FPr | TGGCACTACTGCATGATTGACA | SEQ ID NO: 646 |
| | | Probe | CAGGGCCATGACAATCGCCAA | SEQ ID NO: 647 |
| | | RPr | CCTGCCGCATTGTTTTCAG | SEQ ID NO: 648 |
| DTYMK | NM_012145.1 | FPr | AAATCGCTGGGAACAAGTG | SEQ ID NO: 649 |
| | | Probe | CGCCCTGGCTCAACTTTTCCTTAA | SEQ ID NO: 650 |
| | | RPr | AATGCGTATCTGTCCACGAC | SEQ ID NO: 651 |
| DUSP1 | NM_004417.2 | FPr | AGACATCAGCTCCTGGTTCA | SEQ ID NO: 652 |
| | | Probe | CGAGGCCATTGACTTCATAGACTCCA | SEQ ID NO: 653 |
| | | RPr | GACAAACACCCTTCCTCCAG | SEQ ID NO: 654 |
| DUSP2 | NM_004418.2 | FPr | TATCCCTGTGGAGGACAACC | SEQ ID NO: 655 |
| | | Probe | CCTCCTGGAACCAGGCACTGATCT | SEQ ID NO: 656 |
| | | RPr | CACCCAGTCAATGAAGCCTA | SEQ ID NO: 657 |
| DUT | NM_001948.2 | FPr | ACACATGGAGTGCTTCTGGA | SEQ ID NO: 658 |
| | | Probe | ATCAGCCCACTTGACCACCCAGTT | SEQ ID NO: 659 |
| | | RPr | CTCTTGCCTGTGCTTCCAC | SEQ ID NO: 660 |
| DYRK1B | NM_004714.1 | FPr | AGCATGACACGGAGATGAAG | SEQ ID NO: 661 |
| | | Probe | CACCTGAAGCGGCACTTCATGTTC | SEQ ID NO: 662 |
| | | RPr | AATACCAGGCACAGGTGGTT | SEQ ID NO: 663 |
| E2F1 | NM_005225.1 | FPr | ACTCCCTCTACCCTTGAGCA | SEQ ID NO: 664 |
| | | Probe | CAGAAGAACAGCTCAGGGACCCCT | SEQ ID NO: 665 |
| | | RPr | CAGGCCTCAGTTCCTTCAGT | SEQ ID NO: 666 |

TABLE A-continued

| Gene | Accession | Reagt | Sequence | SEQ ID NO |
|---|---|---|---|---|
| EDN1 endothelin | NM_001955.1 | FPr | TGCCACCTGGACATCATTTG | SEQ ID NO: 667 |
| | | Probe | CACTCCCGAGCACGTTGTTCCGT | SEQ ID NO: 668 |
| | | RPr | TGGACCTAGGGCTTCCAAGTC | SEQ ID NO: 669 |
| EFNA1 | NM_004428.2 | FPr | TACATCTCCAAACCCATCCA | SEQ ID NO: 670 |
| | | Probe | CAACCTCAAGCAGCGGTCTTCATG | SEQ ID NO: 671 |
| | | RPr | TTGCCACTGACAGTCACCTT | SEQ ID NO: 672 |
| EFNA3 | NM_004952.3 | FPr | ACTACATCTCCACGCCCACT | SEQ ID NO: 673 |
| | | Probe | CCTCAGACACTTCCAGTGCAGGTTG | SEQ ID NO: 674 |
| | | RPr | CAGCAGACGAACACCTTCAT | SEQ ID NO: 675 |
| EFNB1 | NM_004429.3 | FPr | GGAGCCCGTATCCTGGAG | SEQ ID NO: 676 |
| | | Probe | CCCTCAACCCCAAGTTCCTGAGTG | SEQ ID NO: 677 |
| | | RPr | GGATAGATCACCAAGCCCTTC | SEQ ID NO: 678 |
| EFNB2 | NM_004093.2 | FPr | TGACATTATCATCCCGCTAAGGA | SEQ ID NO: 679 |
| | | Probe | CGGACAGCGTCTTCTGCCCTCACT | SEQ ID NO: 680 |
| | | RPr | GTAGTCCCCGCTGACCTTCTC | SEQ ID NO: 681 |
| EFP | NM_005082.2 | FPr | TTGAACAGAGCCTGACCAAG | SEQ ID NO: 682 |
| | | Probe | TGATGCTTTCTCCAGAAACTCGAACTCA | SEQ ID NO: 683 |
| | | RPr | TGTTGAGATTCCTCGCAGTT | SEQ ID NO: 684 |
| EGFR | NM_005228.1 | FPr | TGTCGATGGACTTCCAGAAC | SEQ ID NO: 685 |
| | | Probe | CACCTGGGCAGCTGCCAA | SEQ ID NO: 686 |
| | | RPr | ATTGGGACAGCTTGGATCA | SEQ ID NO: 687 |
| EGLN1 | NM_022051.1 | FPr | TCAATGGCCGGACGAAAG | SEQ ID NO: 688 |
| | | Probe | CATTGCCCGGATAACAAGCAACCATG | SEQ ID NO: 689 |
| | | RPr | TTTGGATTATCAACATGACGTACATAAC | SEQ ID NO: 690 |
| EGLN3 | NM_022073.2 | FPr | GCTGGTCCTCTACTGCGG | SEQ ID NO: 691 |
| | | Probe | CCGGCTGGGCAAATACTACGTCAA | SEQ ID NO: 692 |
| | | RPr | CCACCATTGCCTTAGACCTC | SEQ ID NO: 693 |
| EGR1 | NM_001964.2 | FPr | GTCCCCGCTGCAGATCTCT | SEQ ID NO: 694 |
| | | Probe | CGGATCCTTTCCTCACTCGCCCA | SEQ ID NO: 695 |
| | | RPr | CTCCAGCTTAGGGTAGTTGTCCAT | SEQ ID NO: 696 |
| EGR3 | NM_004430.2 | FPr | CCATGTGGATGAATGAGGTG | SEQ ID NO: 697 |
| | | Probe | ACCCAGTCTCACCTTCTCCCCACC | SEQ ID NO: 698 |
| | | RPr | TGCCTGAGAAGAGGTGAGGT | SEQ ID NO: 699 |
| EI24 | NM_004879.2 | FPr | AAAGTGGTGAATGCCATTTG | SEQ ID NO: 700 |
| | | Probe | CCTCAAATGCCAGGTCAGCTATATCCTG | SEQ ID NO: 701 |
| | | RPr | GTGAGGCTTCCTCCCTGATA | SEQ ID NO: 702 |
| EIF4E | NM_001968.1 | FPr | GATCTAAGATGGCGACTGTCGAA | SEQ ID NO: 703 |
| | | Probe | ACCACCCCTACTCCTAATCCCCCGACT | SEQ ID NO: 704 |
| | | RPr | TTAGATTCCGTTTTCTCCTCTTCTG | SEQ ID NO: 705 |
| EIF4EL3 | NM_004846.1 | FPr | AAGCCGCGGTTGAATGTG | SEQ ID NO: 706 |
| | | Probe | TGACCCTCTCCCTCTCTGGATGGCA | SEQ ID NO: 707 |
| | | RPr | TGACGCCAGCTTCAATGATG | SEQ ID NO: 708 |
| ELAVL1 | NM_001419.2 | FPr | GACAGGAGGCCTCTATCCTG | SEQ ID NO: 709 |
| | | Probe | CACCCCACCCTCCACCTCAATC | SEQ ID NO: 710 |
| | | RPr | GTGAGGTAGGTCTGGGGAAG | SEQ ID NO: 711 |
| EMP1 | NM_001423.1 | FPr | GCTAGTACTTTGATGCTCCCTTGAT | SEQ ID NO: 712 |
| | | Probe | CCAGAGAGCCTCCCTGCAGCCA | SEQ ID NO: 713 |
| | | RPr | GAACAGCTGGAGGCCAAGTC | SEQ ID NO: 714 |
| EMR3 | NM_032571.2 | FPr | TGGCCTACCTCTTCACCATC | SEQ ID NO: 715 |
| | | Probe | TCAACAGCCTCCAAGGCTTCTTCA | SEQ ID NO: 716 |
| | | RPr | TGAGGAGGCAGTAGACCAAGA | SEQ ID NO: 717 |
| EMS1 | NM_005231.2 | FPr | GGCAGTGTCACTGAGTCCTTGA | SEQ ID NO: 718 |
| | | Probe | ATCCTCCCCTGCCCCGCG | SEQ ID NO: 719 |
| | | RPr | TGCACTGTGCGTCCCAAT | SEQ ID NO: 720 |
| ENO1 | NM_001428.2 | FPr | CAAGGCCGTGAACGAGAAGT | SEQ ID NO: 721 |
| | | Probe | CTGCAACTGCCTCCTGCTCAAAGTCA | SEQ ID NO: 722 |
| | | RPr | CGGTCACGGAGCCAATCT | SEQ ID NO: 723 |

TABLE A-continued

| Gene | Accession | Reagt | Sequence | SEQ ID NO |
| --- | --- | --- | --- | --- |
| EP300 | NM_001429.1 | FPr | AGCCCCAGCAACTACAGTCT | SEQ ID NO: 724 |
| | | Probe | CACTGACATCATGGCTGGCCTTG | SEQ ID NO: 725 |
| | | RPr | TGTTCAAAGGTTGACCATGC | SEQ ID NO: 726 |
| EPAS1 | NM_001430.3 | FPr | AAGCCTTGGAGGGTTTCATTG | SEQ ID NO: 727 |
| | | Probe | TGTCGCCATCTTGGGTCACCACG | SEQ ID NO: 728 |
| | | RPr | TGCTGATGTTTTCTGACAGAAAGAT | SEQ ID NO: 729 |
| EpCAM | NM_002354.1 | FPr | GGGCCCTCCAGAACAATGAT | SEQ ID NO: 730 |
| | | Probe | CCGCTCTCATCGCAGTCAGGATCAT | SEQ ID NO: 731 |
| | | RPr | TGCACTGCTTGGCCTTAAAGA | SEQ ID NO: 732 |
| EPHA2 | NM_004431.2 | FPr | CGCCTGTTCACCAAGATTGAC | SEQ ID NO: 733 |
| | | Probe | TGCGCCCGATGAGATCACCG | SEQ ID NO: 734 |
| | | RPr | GTGGCGTGCCTCGAAGTC | SEQ ID NO: 735 |
| EPHB2 | NM_004442.4 | FPr | CAACCAGGCAGCTCCATC | SEQ ID NO: 736 |
| | | Probe | CACCTGATGCATGATGGACACTGC | SEQ ID NO: 737 |
| | | RPr | GTAATGCTGTCCACGGTGC | SEQ ID NO: 738 |
| EPHB4 | NM_004444.3 | FPr | TGAACGGGGTATCCTCCTTA | SEQ ID NO: 739 |
| | | Probe | CGTCCCATTTGAGCCTGTCAATGT | SEQ ID NO: 740 |
| | | RPr | AGGTACCTCTCGGTCAGTGG | SEQ ID NO: 741 |
| EphB6 | NM_004445.1 | FPr | ACTGGTCCTCCATCGGCT | SEQ ID NO: 742 |
| | | Probe | CCTTGCACCTCAAACCAAAGCTCC | SEQ ID NO: 743 |
| | | RPr | CCAGTGTAGCATGAGTGCTGA | SEQ ID NO: 744 |
| EPM2A | NM_005670.2 | FPr | ACTGTGGCACTTAGGGGAGA | SEQ ID NO: 745 |
| | | Probe | CTGCCTCTGCCCAAAGCAAATGTC | SEQ ID NO: 746 |
| | | RPr | AGTGGAAATGTGTCCTGGCT | SEQ ID NO: 747 |
| ErbB3 | NM_001982.1 | FPr | CGGTTATGTCATGCCAGATACAC | SEQ ID NO: 748 |
| | | Probe | CCTCAAAGGTACTCCCTCCTCCCGG | SEQ ID NO: 749 |
| | | RPr | GAACTGAGACCCACTGAAGAAAGG | SEQ ID NO: 750 |
| ERCC1 | NM_001983.1 | FPr | GTCCAGGTGGATGTGAAAGA | SEQ ID NO: 751 |
| | | Probe | CAGCAGGCCCTCAAGGAGCTG | SEQ ID NO: 752 |
| | | RPr | CGGCCAGGATACACATCTTA | SEQ ID NO: 753 |
| ERCC2 | NM_000400.2 | FPr | TGGCCTTCTTCACCAGCTA | SEQ ID NO: 754 |
| | | Probe | AGGCCACGGTGCTCTCCATGTACT | SEQ ID NO: 755 |
| | | RPr | CAAGGATCCCCTGCTCATAC | SEQ ID NO: 756 |
| EREG | NM_001432.1 | FPr | ATAACAAAGTGTAGCTCTGACATGAATG | SEQ ID NO: 757 |
| | | Probe | TTGTTTGCATGGACAGTGCATCTATCTGGT | SEQ ID NO: 758 |
| | | RPr | CACACCTGCAGTAGTTTTGACTCA | SEQ ID NO: 759 |
| ERK1 | Z11696.1 | FPr | ACGGATCACAGTGGAGGAAG | SEQ ID NO: 760 |
| | | Probe | CGCTGGCTCACCCCTACCTG | SEQ ID NO: 761 |
| | | RPr | CTCATCCGTCGGGTCATAGT | SEQ ID NO: 762 |
| ERK2 | NM_002745.1 | FPr | AGTTCTTGACCCCTGGTCCT | SEQ ID NO: 763 |
| | | Probe | TCTCCAGCCCGTCTTGGCTT | SEQ ID NO: 764 |
| | | RPr | AAACGGCTCAAAGGAGTCAA | SEQ ID NO: 765 |
| ESPL1 | NM_012291.1 | FPr | ACCCCCAGACCGGATCAG | SEQ ID NO: 766 |
| | | Probe | CTGGCCCTCATGTCCCCTTCACG | SEQ ID NO: 767 |
| | | RPr | TGTAGGGCAGACTTCCTCAAACA | SEQ ID NO: 768 |
| EstR1 | NM_000125.1 | FPr | CGTGGTGCCCCTCTATGAC | SEQ ID NO: 769 |
| | | Probe | CTGGAGATGCTGGACGCCC | SEQ ID NO: 770 |
| | | RPr | GGCTAGTGGGCGCATGTAG | SEQ ID NO: 771 |
| ETV4 | NM_001986.1 | FPr | TCCAGTGCCTATGACCCC | SEQ ID NO: 772 |
| | | Probe | CAGACAAATCGCCATCAAGTCCCC | SEQ ID NO: 773 |
| | | RPr | ACTGTCCAAGGGCACCAG | SEQ ID NO: 774 |
| F3 | NM_001993.2 | FPr | GTGAAGGATGTGAAGCAGACGTA | SEQ ID NO: 775 |
| | | Probe | TGGCACGGGTCTTCTCCTACC | SEQ ID NO: 776 |
| | | RPr | AACCGGTGCTCTCCACATTC | SEQ ID NO: 777 |
| FABP4 | NM_001442.1 | FPr | GCTTTGCCACCAGGAAAGT | SEQ ID NO: 778 |
| | | Probe | CTGGCATGGCCAAACCTAACATGA | SEQ ID NO: 779 |
| | | RPr | CATCCCCATTCACACTGATG | SEQ ID NO: 780 |

TABLE A-continued

| Gene | Accession | Reagt | Sequence | SEQ ID NO |
|---|---|---|---|---|
| FAP | NM_004460.2 | FPr | CTGACCAGAACCACGGCT | SEQ ID NO: 781 |
| | | Probe | CGGCCTGTCCACGAACCACTTATA | SEQ ID NO: 782 |
| | | RPr | GGAAGTGGGTCATGTGGG | SEQ ID NO: 783 |
| fas | NM_000043.1 | FPr | GGATTGCTCAACAACCATGCT | SEQ ID NO: 784 |
| | | Probe | TCTGGACCCTCCTACCTCTGGTTCTTACGT | SEQ ID NO: 785 |
| | | RPr | GGCATTAACACTTTTGGACGATAA | SEQ ID NO: 786 |
| fasl | NM_000639.1 | FPr | GCACTTTGGGATTCTTTCCATTAT | SEQ ID NO: 787 |
| | | Probe | ACAACATTCTCGGTGCCTGTAACAAAGAA | SEQ ID NO: 788 |
| | | RPr | GCATGTAAGAAGACCCTCACTGAA | SEQ ID NO: 789 |
| FASN | NM_004104.4 | FPr | GCCTCTTCCTGTTCGACG | SEQ ID NO: 790 |
| | | Probe | TCGCCCACCTACGTACTGGCCTAC | SEQ ID NO: 791 |
| | | RPr | GCTTTGCCCGGTAGCTCT | SEQ ID NO: 792 |
| FBXO5 | NM_012177.2 | FPr | GGCTATTCCTCATTTTCTCTACAAAGTG | SEQ ID NO: 793 |
| | | Probe | CCTCCAGGAGGCTACCTTCTTCATGTTCAC | SEQ ID NO: 794 |
| | | RPr | GGATTGTAGACTGTCACCGAAATTC | SEQ ID NO: 795 |
| FBXW7 | NM_033632.1 | FPr | CCCCAGTTTCAACGAGACTT | SEQ ID NO: 796 |
| | | Probe | TCATTGCTCCCTAAAGAGTTGGCACTC | SEQ ID NO: 797 |
| | | RPr | GTTCCAGGAATGAAAGCACA | SEQ ID NO: 798 |
| FDXR | NM_004110.2 | FPr | GAGATGATTCAGTTACCGGGAG | SEQ ID NO: 799 |
| | | Probe | AATCCACAGGATCCAAAATGGGCC | SEQ ID NO: 800 |
| | | RPr | ATCTTGTCCTGGAGACCCAA | SEQ ID NO: 801 |
| FES | NM_002005.2 | FPr | CTCTGCAGGCCTAGGTGC | SEQ ID NO: 802 |
| | | Probe | CTCCTCAGCGGCTCCAGCTCATAT | SEQ ID NO: 803 |
| | | RPr | CCAGGACTGTGAAGAGCTGTC | SEQ ID NO: 804 |
| FGF18 | NM_003862.1 | FPr | CGGTAGTCAAGTCCGGATCAA | SEQ ID NO: 805 |
| | | Probe | CAAGGAGACGGAATTCTACCTGTGC | SEQ ID NO: 806 |
| | | RPr | GCTTGCCTTTGCGGTTCA | SEQ ID NO: 807 |
| FGF2 | NM_002006.2 | FPr | AGATGCAGGAGAGAGGAAGC | SEQ ID NO: 808 |
| | | Probe | CCTGCAGACTGCTTTTTGCCCAAT | SEQ ID NO: 809 |
| | | RPr | GTTTTGCAGCCTTACCCAAT | SEQ ID NO: 810 |
| FGFR1 | NM_023109.1 | FPr | CACGGGACATTCACCACATC | SEQ ID NO: 811 |
| | | Probe | ATAAAAAGACAACCAACGGCCGACTGC | SEQ ID NO: 812 |
| | | RPr | GGGTGCCATCCACTTCACA | SEQ ID NO: 813 |
| FGFR2 isoform 1 | NM_000141.2 | FPr | GAGGGACTGTTGGCATGCA | SEQ ID NO: 814 |
| | | Probe | TCCCAGAGACCAACGTTCAAGCAGTTG | SEQ ID NO: 815 |
| | | RPr | GAGTGAGAATTCGATCCAAGTCTTC | SEQ ID NO: 816 |
| FHIT | NM_002012.1 | FPr | CCAGTGGAGCGCTTCCAT | SEQ ID NO: 817 |
| | | Probe | TCGGCCACTTCATCAGGACGCAG | SEQ ID NO: 818 |
| | | RPr | CTCTCTGGGTCGTCTGAAACAA | SEQ ID NO: 819 |
| FIGF | NM_004469.2 | FPr | GGTTCCAGCTTTCTGTAGCTGT | SEQ ID NO: 820 |
| | | Probe | ATTGGTGGCCACACCACCTCCTTA | SEQ ID NO: 821 |
| | | RPr | GCCGCAGGTTCTAGTTGCT | SEQ ID NO: 822 |
| FLJ12455 | NM_022078.1 | FPr | CCACCAGCATGAAGTTTCG | SEQ ID NO: 823 |
| | | Probe | ACCCCTCACAAAGGCCATGTCTGT | SEQ ID NO: 824 |
| | | RPr | GGCTGTCTGAAGCACAACTG | SEQ ID NO: 825 |
| FLJ20712 | AK000719.1 | FPr | GCCACACAAACATGCTCCT | SEQ ID NO: 826 |
| | | Probe | ATGTCTTTCCCAGCAGCTCTGCCT | SEQ ID NO: 827 |
| | | RPr | GCCACAGGAAACTTCCGA | SEQ ID NO: 828 |
| FLT1 | NM_002019.1 | FPr | GGCTCCCGAATCTATCTTTG | SEQ ID NO: 829 |
| | | Probe | CTACAGCACCAAGAGCGACGTGTG | SEQ ID NO: 830 |
| | | RPr | TCCCACAGCAATACTCCGTA | SEQ ID NO: 831 |
| FLT4 | NM_002020.1 | FPr | ACCAAGAAGCTGAGGACCTG | SEQ ID NO: 832 |
| | | Probe | AGCCCGCTGACCATGGAAGATCT | SEQ ID NO: 833 |
| | | RPr | CCTGGAAGCTGTAGCAGACA | SEQ ID NO: 834 |
| FOS | NM_005252.2 | FPr | CGAGCCCTTTGATGACTTCCT | SEQ ID NO: 835 |
| | | Probe | TCCCAGCATCATCCAGGCCCAG | SEQ ID NO: 836 |
| | | RPr | GGAGCGGGCTGTCTCAGA | SEQ ID NO: 837 |

TABLE A-continued

| Gene | Accession | Reagt | Sequence | SEQ ID NO |
|---|---|---|---|---|
| FOXO3A | NM_001455.1 | FPr | TGAAGTCCAGGACGATGATG | SEQ ID NO: 838 |
| | | Probe | CTCTACAGCAGCTCAGCCAGCCTG | SEQ ID NO: 839 |
| | | RPr | ACGGCTTGCTTACTGAAGGT | SEQ ID NO: 840 |
| FPGS | NM_004957.3 | FPr | CAGCCCTGCCAGTTTGAC | SEQ ID NO: 841 |
| | | Probe | ATGCCGTCTTCTGCCCTAACCTGA | SEQ ID NO: 842 |
| | | RPr | GTTGCCTGTGGATGACACC | SEQ ID NO: 843 |
| FRP1 | NM_003012.2 | FPr | TTGGTACCTGTGGGTTAGCA | SEQ ID NO: 844 |
| | | Probe | TCCCCAGGGTAGAATTCAATCAGAGC | SEQ ID NO: 845 |
| | | RPr | CACATCCAAATGCAAACTGG | SEQ ID NO: 846 |
| FST | NM_006350.2 | FPr | GTAAGTCGGATGAGCCTGTCTGT | SEQ ID NO: 847 |
| | | Probe | CCAGTGACAATGCCACTTATGCCAGC | SEQ ID NO: 848 |
| | | RPr | CAGCTTCCTTCATGGCACACT | SEQ ID NO: 849 |
| Furin | NM_002569.1 | FPr | AAGTCCTCGATACGCACTATAGCA | SEQ ID NO: 850 |
| | | Probe | CCCGGATGGTCTCCACGTCAT | SEQ ID NO: 851 |
| | | RPr | CTGGCATGTGGCACATGAG | SEQ ID NO: 852 |
| FUS | NM_004960.1 | FPr | GGATAATTCAGACAACAACACCATCT | SEQ ID NO: 853 |
| | | Probe | TCAATTGTAACATTCTCACCCAGGCCTTG | SEQ ID NO: 854 |
| | | RPr | TGAAGTAATCAGCCACAGACTCAAT | SEQ ID NO: 855 |
| FUT1 | NM_000148.1 | FPr | CCGTGCTCATTGCTAACCA | SEQ ID NO: 856 |
| | | Probe | TCTGTCCCTGAACTCCCAGAACCA | SEQ ID NO: 857 |
| | | RPr | CTGCCCAAAGCCAGATGTA | SEQ ID NO: 858 |
| FUT3 | NM_000149.1 | FPr | CAGTTCGGTCCAACAGAGAA | SEQ ID NO: 859 |
| | | Probe | AGCAGGCAACCACCATGTCATTTG | SEQ ID NO: 860 |
| | | RPr | TGCGAATTATATCCCGATGA | SEQ ID NO: 861 |
| FUT6 | NM_000150.1 | FPr | CGTGTGTCTCAAGACGATCC | SEQ ID NO: 862 |
| | | Probe | TGTGTACCCTAATGGGTCCCGCTT | SEQ ID NO: 863 |
| | | RPr | GGTCCCTGTGCTGTCTGG | SEQ ID NO: 864 |
| FXYD5 | NM_014164.4 | FPr | AGAGCACCAAAGCAGCTCAT | SEQ ID NO: 865 |
| | | Probe | CACTGATGACACCACGACGCTCTC | SEQ ID NO: 866 |
| | | RPr | GTGCTTGGGGATGGTCTCT | SEQ ID NO: 867 |
| FYN | NM_002037.3 | FPr | GAAGCGCAGATCATGAAGAA | SEQ ID NO: 868 |
| | | Probe | CTGAAGCACGACAAGCTGGTCCAG | SEQ ID NO: 869 |
| | | RPr | CTCCTCAGACACCACTGCAT | SEQ ID NO: 870 |
| FZD1 | NM_003505.1 | FPr | GGTGCACCAGTTCTACCCTC | SEQ ID NO: 871 |
| | | Probe | ACTTGAGCTCAGCGGAACACTGCA | SEQ ID NO: 872 |
| | | RPr | GCGTACATGGAGCACAGGA | SEQ ID NO: 873 |
| FZD2 | NM_001466.2 | FPr | TGGATCCTCACCTGGTCG | SEQ ID NO: 874 |
| | | Probe | TGCGCTTCCACCTTCTTCACTGTC | SEQ ID NO: 875 |
| | | RPr | GCGCTGCATGTCTACCAA | SEQ ID NO: 876 |
| FZD6 | NM_003506.2 | FPr | AATGAGAGAGGTGAAAGCGG | SEQ ID NO: 877 |
| | | Probe | CGGAGCTAGCACCCCCAGGTTAAG | SEQ ID NO: 878 |
| | | RPr | AGGTTCACCACAGTCCTGTTC | SEQ ID NO: 879 |
| G-Catenin | NM_002230.1 | FPr | TCAGCAGCAAGGGCATCAT | SEQ ID NO: 880 |
| | | Probe | CGCCCGCAGGCCTCATCCT | SEQ ID NO: 881 |
| | | RPr | GGTGGTTTTCTTGAGCGTGTACT | SEQ ID NO: 882 |
| G1P2 | NM_005101.1 | FPr | CAACGAATTCCAGGTGTCC | SEQ ID NO: 883 |
| | | Probe | CTGAGCAGCTCCATGTCGGTGTC | SEQ ID NO: 884 |
| | | RPr | GATCTGCGCCTTCAGCTC | SEQ ID NO: 885 |
| GADD45 | NM_001924.2 | FPr | GTGCTGGTGACGAATCCA | SEQ ID NO: 886 |
| | | Probe | TTCATCTCAATGGAAGGATCCTGCC | SEQ ID NO: 887 |
| | | RPr | CCCGGCAAAAACAAATAAGT | SEQ ID NO: 888 |
| GADD45B | NM_015675.1 | FPr | ACCCTGACAAGACCACACT | SEQ ID NO: 889 |
| | | Probe | AACTTCAGCCCCAGCTCCCAAGTC | SEQ ID NO: 890 |
| | | RPr | TGGGAGTTCATGGGTACAGA | SEQ ID NO: 891 |
| GADD45G | NM_006705.2 | FPr | CGCGCTGCAGATCCATTT | SEQ ID NO: 892 |
| | | Probe | CGCTGATCCAGGCTTTCTGCTGC | SEQ ID NO: 893 |
| | | RPr | CGCACTATGTCGATGTCGTTCT | SEQ ID NO: 894 |

TABLE A-continued

| Gene | Accession | Reagt | Sequence | SEQ ID NO |
|---|---|---|---|---|
| GAGE4 | NM_001474.1 | FPr | GGAACAGGGTCACCCACAGA | SEQ ID NO: 895 |
| | | Probe | TCAGGACCATCTTCACACTCACACCCA | SEQ ID NO: 896 |
| | | RPr | GATTTGGCGGGTCCATCTC | SEQ ID NO: 897 |
| GBP1 | NM_002053.1 | FPr | TTGGGAAATATTTGGGCATT | SEQ ID NO: 898 |
| | | Probe | TTGGGACATTGTAGACTTGGCCAGAC | SEQ ID NO: 899 |
| | | RPr | AGAAGCTAGGGTGGTTGTCC | SEQ ID NO: 900 |
| GBP2 | NM_004120.2 | FPr | GCATGGGAACCATCAACCA | SEQ ID NO: 901 |
| | | Probe | CCATGGACCAACTTCACTATGTGACAGAGC | SEQ ID NO: 902 |
| | | RPr | TGAGGAGTTTGCCTTGATTCG | SEQ ID NO: 903 |
| GCLC | NM_001498.1 | FPr | CTGTTGCAGGAAGGCATTGA | SEQ ID NO: 904 |
| | | Probe | CATCTCCTGGCCCAGCATGTT | SEQ ID NO: 905 |
| | | RPr | GTCAGTGGGTCTCTAATAAAGAGATGAG | SEQ ID NO: 906 |
| GCLM | NM_002061.1 | FPr | TGTAGAATCAAACTCTTCATCATCAACTAG | SEQ ID NO: 907 |
| | | Probe | TGCAGTTGACATGGCCTGTTCAGTCC | SEQ ID NO: 908 |
| | | RPr | CACAGAATCCAGCTGTGCAACT | SEQ ID NO: 909 |
| GCNT1 | NM_001490.3 | FPr | TGGTGCTTGGAGCATAGAAG | SEQ ID NO: 910 |
| | | Probe | TGCCCTTCACAAAGGAAATCCCTG | SEQ ID NO: 911 |
| | | RPr | GCAACGTCCTCAGCATTTC | SEQ ID NO: 912 |
| GDF15 | NM_004864.1 | FPr | CGCTCCAGACCTATGATGACT | SEQ ID NO: 913 |
| | | Probe | TGTTAGCCAAAGACTGCCACTGCA | SEQ ID NO: 914 |
| | | RPr | ACAGTGGAAGGACCAGGACT | SEQ ID NO: 915 |
| GIT1 | NM_014030.2 | FPr | GTGTATGACGAGGTGGATCG | SEQ ID NO: 916 |
| | | Probe | AGCCAGCCACACTGCATCATTTTC | SEQ ID NO: 917 |
| | | RPr | ACCAGAGTGCTGTGGTTTTG | SEQ ID NO: 918 |
| GJA1 | NM_000165.2 | FPr | GTTCACTGGGGGTGTATGG | SEQ ID NO: 919 |
| | | Probe | ATCCCCTCCCTCTCCACCCATCTA | SEQ ID NO: 920 |
| | | RPr | AAATACCAACATGCACCTCTCTT | SEQ ID NO: 921 |
| GJB2 | NM_004004.3 | FPr | TGTCATGTACGACGGCTTCT | SEQ ID NO: 922 |
| | | Probe | AGGCGTTGCACTTCACCAGCC | SEQ ID NO: 923 |
| | | RPr | AGTCCACAGTGTTGGGACAA | SEQ ID NO: 924 |
| GPX1 | NM_000581.2 | FPr | GCTTATGACCGACCCCAA | SEQ ID NO: 925 |
| | | Probe | CTCATCACCTGGTCTCCGGTGTGT | SEQ ID NO: 926 |
| | | RPr | AAAGTTCCAGGCAACATCGT | SEQ ID NO: 927 |
| GPX2 | NM_002083.1 | FPr | CACACAGATCTCCTACTCCATCCA | SEQ ID NO: 928 |
| | | Probe | CATGCTGCATCCTAAGGCTCCTCAGG | SEQ ID NO: 929 |
| | | RPr | GGTCCAGCAGTGTCTCCTGAA | SEQ ID NO: 930 |
| Grb10 | NM_005311.2 | FPr | CTTCGCCTTTGCTGATTGC | SEQ ID NO: 931 |
| | | Probe | CTCCAAACGCCTGCCTGACGACTG | SEQ ID NO: 932 |
| | | RPr | CCATAACGCACATGCTCCAA | SEQ ID NO: 933 |
| GRB14 | NM_004490.1 | FPr | TCCCACTGAAGCCCTTTCAG | SEQ ID NO: 934 |
| | | Probe | CCTCCAAGCGAGTCCTTCTTCAACCG | SEQ ID NO: 935 |
| | | RPr | AGTGCCCAGGCGTAAACATC | SEQ ID NO: 936 |
| GRB2 | NM_002086.2 | FPr | GTCCATCAGTGCATGACGTT | SEQ ID NO: 937 |
| | | Probe | AGGCCACGTATAGTCCTAGCTGACGC | SEQ ID NO: 938 |
| | | RPr | AGCCCACTTGGTTTCTTGTT | SEQ ID NO: 939 |
| GRB7 | NM_005310.1 | FPr | CCATCTGCATCCATCTTGTT | SEQ ID NO: 940 |
| | | Probe | CTCCCCACCCTTGAGAAGTGCCT | SEQ ID NO: 941 |
| | | RPr | GGCCACCAGGGTATTATCTG | SEQ ID NO: 942 |
| GRIK1 | NM_000830.2 | FPr | GTTGGGTGCATCTCTCGG | SEQ ID NO: 943 |
| | | Probe | AATTCATGCCGAGATACAGCCGCT | SEQ ID NO: 944 |
| | | RPr | CGTGCTCCATCTTCCTAGCTT | SEQ ID NO: 945 |
| GRO1 | NM_001511.1 | FPr | CGAAAAGATGCTGAACAGTGACA | SEQ ID NO: 946 |
| | | Probe | CTTCCTCCTCCCTTCTGGTCAGTTGGAT | SEQ ID NO: 947 |
| | | RPr | TCAGGAACAGCCACCAGTGA | SEQ ID NO: 948 |
| GRP | NM_002091.1 | FPr | CTGGGTCTCATAGAAGCAAAGGA | SEQ ID NO: 949 |
| | | Probe | AGAAACCACCAGCCACCTCAACCCA | SEQ ID NO: 950 |
| | | RPr | CCACGAAGGCTGCTGATTG | SEQ ID NO: 951 |

TABLE A-continued

| Gene | Accession | Reagt | Sequence | SEQ ID NO |
|---|---|---|---|---|
| GRPR | NM_005314.1 | FPr | ATGCTGCTGGCCATTCCA | SEQ ID NO: 952 |
| | | Probe | CCGTGTTTTCTGACCTCCATCCCTTCC | SEQ ID NO: 953 |
| | | RPr | AGGTCTGGTTGGTGCTTTCCT | SEQ ID NO: 954 |
| GSK3B | NM_002093.2 | FPr | GACAAGGACGGCAGCAAG | SEQ ID NO: 955 |
| | | Probe | CCAGGAGTTGCCACCACTGTTGTC | SEQ ID NO: 956 |
| | | RPr | TTGTGGCCTGTCTGGACC | SEQ ID NO: 957 |
| GSTA3 | NM_000847.3 | FPr | TCTCCAACTTCCCTCTGCTG | SEQ ID NO: 958 |
| | | Probe | AGGCCCTGAAAACCAGAATCAGCA | SEQ ID NO: 959 |
| | | RPr | ACTTCTTCACCGTGGGCA | SEQ ID NO: 960 |
| GSTM1 | NM_000561.1 | FPr | AAGCTATGAGGAAAAGAAGTACACGAT | SEQ ID NO: 961 |
| | | Probe | TCAGCCACTGGCTTCTGTCATAATCAGGAG | SEQ ID NO: 962 |
| | | RPr | GGCCCAGCTTGAATTTTTCA | SEQ ID NO: 963 |
| GSTM3 | NM_000849.3 | FPr | CAATGCCATCTTGCGCTACAT | SEQ ID NO: 964 |
| | | Probe | CTCGCAAGCACAACATGTGTGGTGAGA | SEQ ID NO: 965 |
| | | RPr | GTCCACTCGAATCTTTTCTTCTTCA | SEQ ID NO: 966 |
| GSTp | NM_000852.2 | FPr | GAGACCCTGCTGTCCCAGAA | SEQ ID NO: 967 |
| | | Probe | TCCCACAATGAAGGTCTTGCCTCCCT | SEQ ID NO: 968 |
| | | RPr | GGTTGTAGTCAGCGAAGGAGATC | SEQ ID NO: 969 |
| GSTT1 | NM_000853.1 | FPr | CACCATCCCCACCCTGTCT | SEQ ID NO: 970 |
| | | Probe | CACAGCCGCCTGAAAGCCACAAT | SEQ ID NO: 971 |
| | | RPr | GGCCTCAGTGTGCATCATTCT | SEQ ID NO: 972 |
| H2AFZ | NM_002106.2 | FPr | CCGGAAAGGCCAAGACAA | SEQ ID NO: 973 |
| | | Probe | CCCGCTCGCAGAGAGCCGG | SEQ ID NO: 974 |
| | | RPr | AATACGGCCCACTGGGAACT | SEQ ID NO: 975 |
| HB-EGF | NM_001945.1 | FPr | GACTCCTTCGTCCCCAGTTG | SEQ ID NO: 976 |
| | | Probe | TTGGGCCTCCCATAATTGCTTTGCC | SEQ ID NO: 977 |
| | | RPr | TGGCACTTGAAGGCTCTGGTA | SEQ ID NO: 978 |
| hCRA a | U78556.1 | FPr | TGACACCCTTACCTTCCTGAGAA | SEQ ID NO: 979 |
| | | Probe | TCTGCTTTCCGCGCTCCCAGG | SEQ ID NO: 980 |
| | | RPr | AAAAACACGAGTCAAAATAGAAGTCACT | SEQ ID NO: 981 |
| HDAC1 | NM_004964.2 | FPr | CAAGTACCACAGCGATGACTACATTAA | SEQ ID NO: 982 |
| | | Probe | TTCTTGCGCTCCATCCGTCCAGA | SEQ ID NO: 983 |
| | | RPr | GCTTGCTGTACTCCGACATGTT | SEQ ID NO: 984 |
| HDAC2 | NM_001527.1 | FPr | GGTGGCTACACAATCCGTAA | SEQ ID NO: 985 |
| | | Probe | TGCAGTCTCATATGTCCAACATCGAGC | SEQ ID NO: 986 |
| | | RPr | TGGGAATCTCACAATCAAGG | SEQ ID NO: 987 |
| HDGF | NM_004494.1 | FPr | TCCTAGGCATTCTGGACCTC | SEQ ID NO: 988 |
| | | Probe | CATTCCTACCCCTGATCCCAACCC | SEQ ID NO: 989 |
| | | RPr | GCTGTTGATGCTCCATCCTT | SEQ ID NO: 990 |
| hENT1 | NM_004955.1 | FPr | AGCCGTGACTGTTGAGGTC | SEQ ID NO: 991 |
| | | Probe | AAGTCCAGCATCGCAGGCAGC | SEQ ID NO: 992 |
| | | RPr | AAGTAACGTTCCCAGGTGCT | SEQ ID NO: 993 |
| Hepsin | NM_002151.1 | FPr | AGGCTGCTGGAGGTCATCTC | SEQ ID NO: 994 |
| | | Probe | CCAGAGGCCGTTTCTTGGCCG | SEQ ID NO: 995 |
| | | RPr | CTTCCTGCGGCCACAGTCT | SEQ ID NO: 996 |
| HER2 | NM_004448.1 | FPr | CGGTGTGAGAAGTGCAGCAA | SEQ ID NO: 997 |
| | | Probe | CCAGACCATAGCACACTCGGGCAC | SEQ ID NO: 998 |
| | | RPr | CCTCTCGCAAGTGCTCCAT | SEQ ID NO: 999 |
| Herstatin | AF177761.2 | FPr | CACCCTGTCCTATCCTTCCT | SEQ ID NO: 1000 |
| | | Probe | CCCTCTTGGGACCTAGTCTCTGCCT | SEQ ID NO: 1001 |
| | | RPr | GGCCAGGGGTAGAGAGTAGA | SEQ ID NO: 1002 |
| HES6 | NM_018645.3 | FPr | TTAGGGACCCTGCAGCTCT | SEQ ID NO: 1003 |
| | | Probe | TAGCTCCCTCCCTCCACCCACTC | SEQ ID NO: 1004 |
| | | RPr | CTACAAAATTCTTCCTCCTGCC | SEQ ID NO: 1005 |
| HGF | M29145.1 | FPr | CCGAAATCCAGATGATGATG | SEQ ID NO: 1006 |
| | | Probe | CTCATGGACCCTGGTGCTACACG | SEQ ID NO: 1007 |
| | | RPr | CCCAAGGAATGAGTGGATTT | SEQ ID NO: 1008 |

TABLE A-continued

| Gene | Accession | Reagt | Sequence | SEQ ID NO |
|---|---|---|---|---|
| HIF1A | NM_001530.1 | FPr | TGAACATAAAGTCTGCAACATGGA | SEQ ID NO: 1009 |
| | | Probe | TTGCACTGCACAGGCCACATTCAC | SEQ ID NO: 1010 |
| | | RPr | TGAGGTTGGTTACTGTTGGTATCATATA | SEQ ID NO: 1011 |
| HK1 | NM_000188.1 | FPr | TACGCACAGAGGCAAGCA | SEQ ID NO: 1012 |
| | | Probe | TAAGAGTCCGGGATCCCCAGCCTA | SEQ ID NO: 1013 |
| | | RPr | GAGAGAAGTGCTGGAGAGGC | SEQ ID NO: 1014 |
| HLA-DPB1 | NM_002121.4 | FPr | TCCATGATGGTTCTGCAGGTT | SEQ ID NO: 1015 |
| | | Probe | CCCCGGACAGTGGCTCTGACG | SEQ ID NO: 1016 |
| | | RPr | TGAGCAGCACCATCAGTAACG | SEQ ID NO: 1017 |
| HLA-DRA | NM_019111.3 | FPr | GACGATTTGCCAGCTTTGAG | SEQ ID NO: 1018 |
| | | Probe | TCAAGGTGCATTGGCCAACATAGC | SEQ ID NO: 1019 |
| | | RPr | TCCAGGTTGGCTTTGTCC | SEQ ID NO: 1020 |
| HLA-DRB1 | NM_002124.1 | FPr | GCTTTCTCAGGACCTGGTTG | SEQ ID NO: 1021 |
| | | Probe | CATTTTCTGCAGTTGCCGAACCAG | SEQ ID NO: 1022 |
| | | RPr | AGGAAGCCACAAGGGAGG | SEQ ID NO: 1023 |
| HLA-G | NM_002127.2 | FPr | CCTGCGCGGCTACTACAAC | SEQ ID NO: 1024 |
| | | Probe | CGAGGCCAGTTCTCACACCCTCCAG | SEQ ID NO: 1025 |
| | | RPr | CAGGTCGCAGCCAATCATC | SEQ ID NO: 1026 |
| HMGB1 | NM_002128.3 | FPr | TGGCCTGTCCATTGGTGAT | SEQ ID NO: 1027 |
| | | Probe | TTCCACATCTCTCCCAGTTTCTTCGCAA | SEQ ID NO: 1028 |
| | | RPr | GCTTGTCATCTGCAGCAGTGTT | SEQ ID NO: 1029 |
| hMLH | NM_000249.2 | FPr | CTACTTCCAGCAACCCCAGA | SEQ ID NO: 1030 |
| | | Probe | TCCACATCAGAATCTTCCCG | SEQ ID NO: 1031 |
| | | RPr | CTTTCGGGAATCATCTTCCA | SEQ ID NO: 1032 |
| HNRPAB | NM_004499.2 | FPr | CAAGGGAGCGACCAACTGA | SEQ ID NO: 1033 |
| | | Probe | CTCCATATCCAAACAAAGCATGTGTGCG | SEQ ID NO: 1034 |
| | | RPr | GTTTGCCAAGTTAAATTTGGTACATAAT | SEQ ID NO: 1035 |
| HNRPD | NM_031370.2 | FPr | GCCAGTAAGAACGAGGAGGA | SEQ ID NO: 1036 |
| | | Probe | AAGGCCATTCAAACTCCTCCCCAC | SEQ ID NO: 1037 |
| | | RPr | CGTCGCTGCTTCAGAGTGT | SEQ ID NO: 1038 |
| HoxA1 | NM_005522.3 | FPr | AGTGACAGATGGACAATGCAAGA | SEQ ID NO: 1039 |
| | | Probe | TGAACTCCTTCCTGGAATACCCCA | SEQ ID NO: 1040 |
| | | RPr | CCGAGTCGCCACTGCTAAGT | SEQ ID NO: 1041 |
| HoxA5 | NM_019102.2 | FPr | TCCCTTGTGTTCCTTCTGTGAA | SEQ ID NO: 1042 |
| | | Probe | AGCCCTGTTCTCGTTGCCCTAATTCATC | SEQ ID NO: 1043 |
| | | RPr | GGCAATAAACAGGCTCATGATTAA | SEQ ID NO: 1044 |
| HOXB13 | NM_006361.2 | FPr | CGTGCCTTATGGTTACTTTGG | SEQ ID NO: 1045 |
| | | Probe | ACACTCGGCAGGAGTAGTACCCGC | SEQ ID NO: 1046 |
| | | RPr | CACAGGGTTTCAGCGAGC | SEQ ID NO: 1047 |
| HOXB7 | NM_004502.2 | FPr | CAGCCTCAAGTTCGGTTTTC | SEQ ID NO: 1048 |
| | | Probe | ACCGGAGCCTTCCCAGAACAAACT | SEQ ID NO: 1049 |
| | | RPr | GTTGGAAGCAAACGCACA | SEQ ID NO: 1050 |
| HRAS | NM_005343.2 | FPr | GGACGAATACGACCCCACT | SEQ ID NO: 1051 |
| | | Probe | ACCACCTGCTTCCGGTAGGAATCC | SEQ ID NO: 1052 |
| | | RPr | GCACGTCTCCCCATCAAT | SEQ ID NO: 1053 |
| HSBP1 | NM_001537.1 | FPr | GGAGATGGCCGAGACTGAC | SEQ ID NO: 1054 |
| | | Probe | CAAGACCGTGCAGGACCTCACCT | SEQ ID NO: 1055 |
| | | RPr | CTGCAGGAGTGTCTGCACC | SEQ ID NO: 1056 |
| HSD17B1 | NM_000413.1 | FPr | CTGGACCGCACGGACATC | SEQ ID NO: 1057 |
| | | Probe | ACCGCTTCTACCAATACCTCGCCCA | SEQ ID NO: 1058 |
| | | RPr | CGCCTCGCGAAAGACTTG | SEQ ID NO: 1059 |
| HSD17B2 | NM_002153.1 | FPr | GCTTTCCAAGTGGGGAATTA | SEQ ID NO: 1060 |
| | | Probe | AGTTGCTTCCATCCAACCTGGAGG | SEQ ID NO: 1061 |
| | | RPr | TGCCTGCGATATTTGTTAGG | SEQ ID NO: 1062 |
| HSPA1A | NM_005345.4 | FPr | CTGCTGCGACAGTCCACTA | SEQ ID NO: 1063 |
| | | Probe | AGAGTGACTCCCGTTGTCCCAAGG | SEQ ID NO: 1064 |
| | | RPr | CAGGTTCGCTCTGGGAAG | SEQ ID NO: 1065 |

TABLE A-continued

| Gene | Accession | Reagt | Sequence | SEQ ID NO |
|---|---|---|---|---|
| HSPA1B | NM_005346.3 | FPr | GGTCCGCTTCGTCTTTCGA | SEQ ID NO: 1066 |
| | | Probe | TGACTCCCGCGGTCCCAAGG | SEQ ID NO: 1067 |
| | | RPr | GCACAGGTTCGCTCTGGAA | SEQ ID NO: 1068 |
| HSPA4 | NM_002154.3 | FPr | TTCAGTGTGTCCAGTGCATC | SEQ ID NO: 1069 |
| | | Probe | CATTTTCCTCAGACTTGTGAACCTCCACT | SEQ ID NO: 1070 |
| | | RPr | ATCTGTTTCCATTGGCTCCT | SEQ ID NO: 1071 |
| HSPA5 | NM_005347.2 | FPr | GGCTAGTAGAACTGGATCCCAACA | SEQ ID NO: 1072 |
| | | Probe | TAATTAGACCTAGGCCTCAGCTGCACTGCC | SEQ ID NO: 1073 |
| | | RPr | GGTCTGCCCAAATGCTTTTC | SEQ ID NO: 1074 |
| HSPA8 | NM_006597.3 | FPr | CCTCCCTCTGGTGGTGCTT | SEQ ID NO: 1075 |
| | | Probe | CTCAGGGCCCACCATTGAAGAGGTTG | SEQ ID NO: 1076 |
| | | RPr | GCTACATCTACACTTGGTTGGCTTAA | SEQ ID NO: 1077 |
| HSPB1 | NM_001540.2 | FPr | CCGACTGGAGGAGCATAAA | SEQ ID NO: 1078 |
| | | Probe | CGCACTTTTCTGAGCAGACGTCCA | SEQ ID NO: 1079 |
| | | RPr | ATGCTGGCTGACTCTGCTC | SEQ ID NO: 1080 |
| HSPCA | NM_005348.2 | FPr | CAAAAGGCAGAGGCTGATAA | SEQ ID NO: 1081 |
| | | Probe | TGACCAGATCCTTCACAGACTTGTCGT | SEQ ID NO: 1082 |
| | | RPr | AGCGCAGTTTCATAAAGCAA | SEQ ID NO: 1083 |
| HSPE1 | NM_002157.1 | FPr | GCAAGCAACAGTAGTCGCTG | SEQ ID NO: 1084 |
| | | Probe | TCTCCACCCTTTCCTTTAGAACCCG | SEQ ID NO: 1085 |
| | | RPr | CCAACTTTCACGCTAACTGGT | SEQ ID NO: 1086 |
| HSPG2 | NM_005529.2 | FPr | GAGTACGTGTGCCGAGTGTT | SEQ ID NO: 1087 |
| | | Probe | CAGCTCCGTGCCTCTAGAGGCCT | SEQ ID NO: 1088 |
| | | RPr | CTCAATGGTGACCAGGACA | SEQ ID NO: 1089 |
| ICAM1 | NM_000201.1 | FPr | GCAGACAGTGACCATCTACAGCTT | SEQ ID NO: 1090 |
| | | Probe | CCGGCGCCCAACGTGATTCT | SEQ ID NO: 1091 |
| | | RPr | CTTCTGAGACCTCTGGCTTCGT | SEQ ID NO: 1092 |
| ICAM2 | NM_000873.2 | FPr | GGTCATCCTGACACTGCAAC | SEQ ID NO: 1093 |
| | | Probe | TTGCCCACAGCCACCAAAGTG | SEQ ID NO: 1094 |
| | | RPr | TGCACTCAATGGTGAAGGAC | SEQ ID NO: 1095 |
| ID1 | NM_002165.1 | FPr | AGAACCGCAAGGTGAGCAA | SEQ ID NO: 1096 |
| | | Probe | TGGAGATTCTCCAGCACGTCATCGAC | SEQ ID NO: 1097 |
| | | RPr | TCCAACTGAAGGTCCCTGATG | SEQ ID NO: 1098 |
| ID2 | NM_002166.1 | FPr | AACGACTGCTACTCCAAGCTCAA | SEQ ID NO: 1099 |
| | | Probe | TGCCCAGCATCCCCCAGAACAA | SEQ ID NO: 1100 |
| | | RPr | GGATTTCCATCTTGCTCACCTT | SEQ ID NO: 1101 |
| ID3 | NM_002167.2 | FPr | CTTCACCAAATCCCTTCCTG | SEQ ID NO: 1102 |
| | | Probe | TCACAGTCCTTCGCTCCTGAGCAC | SEQ ID NO: 1103 |
| | | RPr | CTCTGGCTCTTCAGGCTACA | SEQ ID NO: 1104 |
| ID4 | NM_001546.2 | FPr | TGGCCTGGCTCTTAATTTG | SEQ ID NO: 1105 |
| | | Probe | CTTTTGTTTTGCCCAGTATAGACTCGGAAG | SEQ ID NO: 1106 |
| | | RPr | TGCAATCATGCAAGACCAC | SEQ ID NO: 1107 |
| IFIT1 | NM_001548.1 | FPr | TGACAACCAAGCAAATGTGA | SEQ ID NO: 1108 |
| | | Probe | AAGTTGCCCCAGGTCACCAGACTC | SEQ ID NO: 1109 |
| | | RPr | CAGTCTGCCCATGTGGTAAT | SEQ ID NO: 1110 |
| IGF1 | NM_000618.1 | FPr | TCCGGAGCTGTGATCTAAGGA | SEQ ID NO: 1111 |
| | | Probe | TGTATTGCGCACCCCTCAAGCCTG | SEQ ID NO: 1112 |
| | | RPr | CGGACAGAGCGAGCTGACTT | SEQ ID NO: 1113 |
| IGF1R | NM_000875.2 | FPr | GCATGGTAGCCGAAGATTTCA | SEQ ID NO: 1114 |
| | | Probe | CGCGTCATACCAAAATCTCCGATTTGA | SEQ ID NO: 1115 |
| | | RPr | TTTCCGGTAATAGTCTGTCTCATAGATATC | SEQ ID NO: 1116 |
| IGF2 | NM_000612.2 | FPr | CCGTGCTTCCGGACAACTT | SEQ ID NO: 1117 |
| | | Probe | TACCCCGTGGGCAAGTTCTTCCAA | SEQ ID NO: 1118 |
| | | RPr | TGGACTGCTTCCAGGTGTCA | SEQ ID NO: 1119 |
| IGFBP2 | NM_000597.1 | FPr | GTGGACAGCACCATGAACA | SEQ ID NO: 1120 |
| | | Probe | CTTCCGGCCAGCACTGCCTC | SEQ ID NO: 1121 |
| | | RPr | CCTTCATACCCGACTTGAGG | SEQ ID NO: 1122 |

TABLE A-continued

| Gene | Accession | Reagt | Sequence | SEQ ID NO |
|---|---|---|---|---|
| IGFBP3 | NM_000598.1 | FPr | ACGCACCGGGTGTCTGA | SEQ ID NO: 1123 |
| | | Probe | CCCAAGTTCCACCCCTCCATTCA | SEQ ID NO: 1124 |
| | | RPr | TGCCCTTTCTTGATGATGATTATC | SEQ ID NO: 1125 |
| IGFBP5 | NM_000599.1 | FPr | TGGACAAGTACGGGATGAAGCT | SEQ ID NO: 1126 |
| | | Probe | CCCGTCAACGTACTCCATGCCTGG | SEQ ID NO: 1127 |
| | | RPr | CGAAGGTGTGGCACTGAAAGT | SEQ ID NO: 1128 |
| IGFBP6 | NM_002178.1 | FPr | TGAACCGCAGAGACCAACAG | SEQ ID NO: 1129 |
| | | Probe | ATCCAGGCACCTCTACCACGCCCTC | SEQ ID NO: 1130 |
| | | RPr | GTCTTGGACACCCGCAGAAT | SEQ ID NO: 1131 |
| IGFBP7 | NM_001553 | FPr | GGGTCACTATGGAGTTCAAAGGA | SEQ ID NO: 1132 |
| | | Probe | CCCGGTCACCAGGCAGGAGTTCT | SEQ ID NO: 1133 |
| | | RPr | GGGTCTGAATGGCCAGGTT | SEQ ID NO: 1134 |
| IHH | NM_002181.1 | FPr | AAGGACGAGGAGAACACAGG | SEQ ID NO: 1135 |
| | | Probe | ATGACCCAGCGCTGCAAGGAC | SEQ ID NO: 1136 |
| | | RPr | AGATAGCCAGCGAGTTCAGG | SEQ ID NO: 1137 |
| IL-8 | NM_000584.2 | FPr | AAGGAACCATCTCACTGTGTGTAAAC | SEQ ID NO: 1138 |
| | | Probe | TGACTTCCAAGCTGGCCGTGGC | SEQ ID NO: 1139 |
| | | RPr | ATCAGGAAGGCTGCCAAGAG | SEQ ID NO: 1140 |
| IL10 | NM_000572.1 | FPr | GGCGCTGTCATCGATTTCTT | SEQ ID NO: 1141 |
| | | Probe | CTGCTCCACGGCCTTGCTCTTG | SEQ ID NO: 1142 |
| | | RPr | TGGAGCTTATTAAAGGCATTCTTCA | SEQ ID NO: 1143 |
| IL1B | NM_000576.2 | FPr | AGCTGAGGAAGATGCTGGTT | SEQ ID NO: 1144 |
| | | Probe | TGCCCACAGACCTTCCAGGAGAAT | SEQ ID NO: 1145 |
| | | RPr | GGAAAGAAGGTGCTCAGGTC | SEQ ID NO: 1146 |
| IL6 | NM_000600.1 | FPr | CCTGAACCTTCCAAAGATGG | SEQ ID NO: 1147 |
| | | Probe | CCAGATTGGAAGCATCCATCTTTTTCA | SEQ ID NO: 1148 |
| | | RPr | ACCAGGCAAGTCTCCTCATT | SEQ ID NO: 1149 |
| IL6ST | NM_002184.2 | FPr | GGCCTAATGTTCCAGATCCT | SEQ ID NO: 1150 |
| | | Probe | CATATTGCCCAGTGGTCACCTCACA | SEQ ID NO: 1151 |
| | | RPr | AAAATTGTGCCTTGGAGGAG | SEQ ID NO: 1152 |
| ILT-2 | NM_006669.1 | FPr | AGCCATCACTCTCAGTGCAG | SEQ ID NO: 1153 |
| | | Probe | CAGGTCCTATCGTGGCCCTGA | SEQ ID NO: 1154 |
| | | RPr | ACTGCAGAGTCAGGGTCTCC | SEQ ID NO: 1155 |
| IMP-1 | NM_006546.2 | FPr | GAAAGTGTTTGCGGAGCAC | SEQ ID NO: 1156 |
| | | Probe | CTCCTACAGCGGCCAGTTCTTGGT | SEQ ID NO: 1157 |
| | | RPr | GAAGGCGTAGCCGGATTT | SEQ ID NO: 1158 |
| IMP2 | NM_006548.3 | FPr | CAATCTGATCCCAGGGTTGAA | SEQ ID NO: 1159 |
| | | Probe | CTCAGCGCACTTGGCATCTTTTCAACA | SEQ ID NO: 1160 |
| | | RPr | GGCCCTGCTGGTGGAGATA | SEQ ID NO: 1161 |
| ING1L | NM_001564.1 | FPr | TGTTTCCAAGATCCTGCTGA | SEQ ID NO: 1162 |
| | | Probe | CCATCTTTGCTTTATCTGAGGCTCGTTC | SEQ ID NO: 1163 |
| | | RPr | TCTTTCTGGTTGGCTGGAAT | SEQ ID NO: 1164 |
| ING5 | NM_032329.4 | FPr | CCTACAGCAAGTGCAAGGAA | SEQ ID NO: 1165 |
| | | Probe | CCAGCTGCACTTTGTCGTCACTGT | SEQ ID NO: 1166 |
| | | RPr | CATCTCGTAGGTCTGCATGG | SEQ ID NO: 1167 |
| INHA | NM_002191.2 | FPr | CCTCCCAGTTTCATCTTCCACTA | SEQ ID NO: 1168 |
| | | Probe | ATGTGCAGCCCACAACCACCATGA | SEQ ID NO: 1169 |
| | | RPr | AGGGACTGGAAGGGACAGGTT | SEQ ID NO: 1170 |
| INHBA | NM_002192.1 | FPr | GTGCCCGAGCCATATAGCA | SEQ ID NO: 1171 |
| | | Probe | ACGTCCGGGTCCTCACTGTCCTTCC | SEQ ID NO: 1172 |
| | | RPr | CGGTAGTGGTTGATGACTGTTGA | SEQ ID NO: 1173 |
| INHBB | NM_002193.1 | FPr | AGCCTCCAGGATACCAGCAA | SEQ ID NO: 1174 |
| | | Probe | AGCTAAGCTGCCATTTGTCACCG | SEQ ID NO: 1175 |
| | | RPr | TCTCCGACTGACAGGCATTTG | SEQ ID NO: 1176 |
| IRS1 | NM_005544.1 | FPr | CCACAGCTCACCTTCTGTCA | SEQ ID NO: 1177 |
| | | Probe | TCCATCCCAGCTCCAGCCAG | SEQ ID NO: 1178 |
| | | RPr | CCTCAGTGCCAGTCTCTTCC | SEQ ID NO: 1179 |

TABLE A-continued

| Gene | Accession | Reagt | Sequence | SEQ ID NO |
|---|---|---|---|---|
| ITGA3 | NM_002204.1 | FPr | CCATGATCCTCACTCTGCTG | SEQ ID NO: 1180 |
| | | Probe | CACTCCAGACCTCGCTTAGCATGG | SEQ ID NO: 1181 |
| | | RPr | GAAGCTTTGTAGCCGGTGAT | SEQ ID NO: 1182 |
| ITGA4 | NM_000885.2 | FPr | CAACGCTTCAGTGATCAATCC | SEQ ID NO: 1183 |
| | | Probe | CGATCCTGCATCTGTAAATCGCCC | SEQ ID NO: 1184 |
| | | RPr | GTCTGGCCGGGATTCTTT | SEQ ID NO: 1185 |
| ITGA5 | NM_002205.1 | FPr | AGGCCAGCCCTACATTATCA | SEQ ID NO: 1186 |
| | | Probe | TCTGAGCCTTGTCCTCTATCCGGC | SEQ ID NO: 1187 |
| | | RPr | GTCTTCTCCACAGTCCAGCA | SEQ ID NO: 1188 |
| ITGA6 | NM_000210.1 | FPr | CAGTGACAAACAGCCCTTCC | SEQ ID NO: 1189 |
| | | Probe | TCGCCATCTTTTGTGGGATTCCTT | SEQ ID NO: 1190 |
| | | RPr | GTTTAGCCTCATGGGCGTC | SEQ ID NO: 1191 |
| ITGA7 | NM_002206.1 | FPr | GATATGATTGGTCGCTGCTTTG | SEQ ID NO: 1192 |
| | | Probe | CAGCCAGGACCTGGCCATCCG | SEQ ID NO: 1193 |
| | | RPr | AGAACTTCCATTCCCCACCAT | SEQ ID NO: 1194 |
| ITGAV | NM_002210.2 | FPr | ACTCGGACTGCACAAGCTATT | SEQ ID NO: 1195 |
| | | Probe | CCGACAGCCACAGAATAACCCAAA | SEQ ID NO: 1196 |
| | | RPr | TGCCATCACCATTGAAATCT | SEQ ID NO: 1197 |
| ITGB1 | NM_002211.2 | FPr | TCAGAATTGGATTTGGCTCA | SEQ ID NO: 1198 |
| | | Probe | TGCTAATGTAAGGCATCACAGTCTTTTCCA | SEQ ID NO: 1199 |
| | | RPr | CCTGAGCTTAGCTGGTGTTG | SEQ ID NO: 1200 |
| ITGB3 | NM_000212.1 | FPr | ACCGGGAGCCCTACATGAC | SEQ ID NO: 1201 |
| | | Probe | AAATACCTGCAACCGTTACTGCCGTGAC | SEQ ID NO: 1202 |
| | | RPr | CCTTAAGCTCTTTCACTGACTCAATCT | SEQ ID NO: 1203 |
| ITGB4 | NM_000213.2 | FPr | CAAGGTGCCCTCAGTGGA | SEQ ID NO: 1204 |
| | | Probe | CACCAACCTGTACCCGTATTGCGA | SEQ ID NO: 1205 |
| | | RPr | GCGCACACCTTCATCTCAT | SEQ ID NO: 1206 |
| ITGB5 | NM_002213.3 | FPr | TCGTGAAAGATGACCAGGAG | SEQ ID NO: 1207 |
| | | Probe | TGCTATGTTTCTACAAAACCGCCAAGG | SEQ ID NO: 1208 |
| | | RPr | GGTGAACATCATGACGCAGT | SEQ ID NO: 1209 |
| K-ras | NM_033360.2 | FPr | GTCAAAATGGGGAGGGACTA | SEQ ID NO: 1210 |
| | | Probe | TGTATCTTGTTGAGCTATCCAAACTGCCC | SEQ ID NO: 1211 |
| | | RPr | CAGGACCACCACAGAGTGAG | SEQ ID NO: 1212 |
| KCNH2 iso a/b | NM_000238.2 | FPr | GAGCGCAAAGTGGAAATCG | SEQ ID NO: 1213 |
| | | Probe | TAGGAAGCAGCTCCCATCTTTCCGGTA | SEQ ID NO: 1214 |
| | | RPr | TCTTCACGGGCACCACATC | SEQ ID NO: 1215 |
| KCNH2 iso a/c | NM_172057.1 | FPr | TCCTGCTGCTGGTCATCTAC | SEQ ID NO: 1216 |
| | | Probe | TGTCTTCACACCCTACTCGGCTGC | SEQ ID NO: 1217 |
| | | RPr | CCTTCTTCCGTCTCCTTCAG | SEQ ID NO: 1218 |
| KCNK4 | NM_016611.2 | FPr | CCTATCAGCCGCTGGTGT | SEQ ID NO: 1219 |
| | | Probe | ATCCTGCTCGGCCTGGCTTACTTC | SEQ ID NO: 1220 |
| | | RPr | TGGTGGTGAGCACTGAGG | SEQ ID NO: 1221 |
| KDR | NM_002253.1 | FPr | GAGGACGAAGGCCTCTACAC | SEQ ID NO: 1222 |
| | | Probe | CAGGCATGCAGTGTTCTTGGCTGT | SEQ ID NO: 1223 |
| | | RPr | AAAAATGCCTCCACTTTTGC | SEQ ID NO: 1224 |
| Ki-67 | NM_002417.1 | FPr | CGGACTTTGGGTGCGACTT | SEQ ID NO: 1225 |
| | | Probe | CCACTTGTCGAACCACCGCTCGT | SEQ ID NO: 1226 |
| | | RPr | TTACAACTCTTCCACTGGGACGAT | SEQ ID NO: 1227 |
| KIAA0125 | NM_014792.2 | FPr | GTGTCCTGGTCCATGTGGT | SEQ ID NO: 1228 |
| | | Probe | CACGTGTCTCCACCTCCAAGGAGA | SEQ ID NO: 1229 |
| | | RPr | GGGAGGTGCACACTGAGG | SEQ ID NO: 1230 |
| KIF22 | NM_007317.1 | FPr | CTAAGGCACTTGCTGGAAGG | SEQ ID NO: 1231 |
| | | Probe | TCCATAGGCAAGCACACTGGCATT | SEQ ID NO: 1232 |
| | | RPr | TCTTCCCAGCTCCTGTGG | SEQ ID NO: 1233 |
| KIF2C | NM_006845.2 | FPr | AATTCCTGCTCCAAAAGAAAGTCTT | SEQ ID NO: 1234 |
| | | Probe | AAGCCGCTCCACTCGCATGTCC | SEQ ID NO: 1235 |
| | | RPr | CGTGATGCGAAGCTCTGAGA | SEQ ID NO: 1236 |

TABLE A-continued

| Gene | Accession | Reagt | Sequence | SEQ ID NO |
|---|---|---|---|---|
| KIFC1 | XM_371813.1 | FPr | CCACAGGGTTGAAGAACCAG | SEQ ID NO: 1237 |
| | | Probe | AGCCAGTTCCTGCTGTTCCTGTCC | SEQ ID NO: 1238 |
| | | RPr | CACCTGATGTGCCAGACTTC | SEQ ID NO: 1239 |
| Kitlng | NM_000899.1 | FPr | GTCCCCGGGATGGATGTT | SEQ ID NO: 1240 |
| | | Probe | CATCTCGCTTATCCAACAATGACTTGGCA | SEQ ID NO: 1241 |
| | | RPr | GATCAGTCAAGCTGTCTGACAATTG | SEQ ID NO: 1242 |
| KLF5 | NM_001730.3 | FPr | GTGCAACCGCAGCTTCTC | SEQ ID NO: 1243 |
| | | Probe | CTCTGACCACCTGGCCCTGCATAT | SEQ ID NO: 1244 |
| | | RPr | CGGGCAGTGCTCAGTTCT | SEQ ID NO: 1245 |
| KLF6 | NM_001300.4 | FPr | CACGAGACCGGCTACTTCTC | SEQ ID NO: 1246 |
| | | Probe | AGTACTCCTCCAGAGACGGCAGCG | SEQ ID NO: 1247 |
| | | RPr | GCTCTAGGCAGGTCTGTTGC | SEQ ID NO: 1248 |
| KLK10 | NM_002776.1 | FPr | GCCCAGAGGCTCCATCGT | SEQ ID NO: 1249 |
| | | Probe | CCTCTTCCTCCCCAGTCGGCTGA | SEQ ID NO: 1250 |
| | | RPr | CAGAGGTTTGAACAGTGCAGACA | SEQ ID NO: 1251 |
| KLK6 | NM_002774.2 | FPr | GACGTGAGGGTCCTGATTCT | SEQ ID NO: 1252 |
| | | Probe | TTACCCCAGCTCCATCCTTGCATC | SEQ ID NO: 1253 |
| | | RPr | TCCTCACTCATCACGTCCTC | SEQ ID NO: 1254 |
| KLRK1 | NM_007360.1 | FPr | TGAGAGCCAGGCTTCTTGTA | SEQ ID NO: 1255 |
| | | Probe | TGTCTCAAAATGCCAGCCTTCTGAA | SEQ ID NO: 1256 |
| | | RPr | ATCCTGGTCCTCTTTGCTGT | SEQ ID NO: 1257 |
| KNTC2 | NM_006101.1 | FPr | ATGTGCCAGTGAGCTTGAGT | SEQ ID NO: 1258 |
| | | Probe | CCTTGGAGAAACACAAGCACCTGC | SEQ ID NO: 1259 |
| | | RPr | TGAGCCCCTGGTTAACAGTA | SEQ ID NO: 1260 |
| KRAS2 | NM_004985.3 | FPr | GAGACCAAGGTTGCAAGGC | SEQ ID NO: 1261 |
| | | Probe | AAGCTCAAAGGTTCACACAGGGCC | SEQ ID NO: 1262 |
| | | RPr | CAGTCCATGCTGTGAAACTCTC | SEQ ID NO: 1263 |
| KRT19 | NM_002276.1 | FPr | TGAGCGGCAGAATCAGGAGTA | SEQ ID NO: 1264 |
| | | Probe | CTCATGGACATCAAGTCGCGGCTG | SEQ ID NO: 1265 |
| | | RPr | TGCGGTAGGTGGCAATCTC | SEQ ID NO: 1266 |
| KRT8 | NM_002273.1 | FPr | GGATGAAGCTTACATGAACAAGGTAGA | SEQ ID NO: 1267 |
| | | Probe | CGTCGGTCAGCCCTTCCAGGC | SEQ ID NO: 1268 |
| | | RPr | CATATAGCTGCCTGAGGAAGTTGAT | SEQ ID NO: 1269 |
| LAMA3 | NM_000227.2 | FPr | CAGATGAGGCACATGGAGAC | SEQ ID NO: 1270 |
| | | Probe | CTGATTCCTCAGGTCCTTGGCCTG | SEQ ID NO: 1271 |
| | | RPr | TTGAAATGGCAGAACGGTAG | SEQ ID NO: 1272 |
| LAMB3 | NM_000228.1 | FPr | ACTGACCAAGCCTGAGACCT | SEQ ID NO: 1273 |
| | | Probe | CCACTCGCCATACTGGGTGCAGT | SEQ ID NO: 1274 |
| | | RPr | GTCACACTTGCAGCATTTCA | SEQ ID NO: 1275 |
| LAMC2 | NM_005562.1 | FPr | ACTCAAGCGGAAATTGAAGCA | SEQ ID NO: 1276 |
| | | Probe | AGGTCTTATCAGCACAGTCTCCGCCTCC | SEQ ID NO: 1277 |
| | | RPr | ACTCCCTGAAGCCGAGACACT | SEQ ID NO: 1278 |
| LAT | NM_014387.2 | FPr | GTGAACGTTCCGGAGAGC | SEQ ID NO: 1279 |
| | | Probe | ATCCAGAGACGCTTCTGCGCTCTC | SEQ ID NO: 1280 |
| | | RPr | ACATTCACATACTCCCGGCT | SEQ ID NO: 1281 |
| LCN2 | NM_005564.2 | FPr | CGCTGGGCAACATTAAGAG | SEQ ID NO: 1282 |
| | | Probe | TCACCACTCGGACGAGGTAACTCG | SEQ ID NO: 1283 |
| | | RPr | AGCATGCTGGTTGTAGTTGGT | SEQ ID NO: 1284 |
| LDLRAP1 | NM_015627.1 | FPr | CAGTGCCTCTCGCCTGTC | SEQ ID NO: 1285 |
| | | Probe | ACTGGGACAAGCCTGACAGCAGC | SEQ ID NO: 1286 |
| | | RPr | TGAAGAGGTCATCCTGCTCTG | SEQ ID NO: 1287 |
| LEF | NM_016269.2 | FPr | GATGACGGAAAGCATCCAG | SEQ ID NO: 1288 |
| | | Probe | TGGAGGCCTCTACAACAAGGGACC | SEQ ID NO: 1289 |
| | | RPr | CCCGGAATAACTCGAGTAGGA | SEQ ID NO: 1290 |
| LGALS3 | NM_002306.1 | FPr | AGCGGAAAATGGCAGACAAT | SEQ ID NO: 1291 |
| | | Probe | ACCCAGATAACGCATCATGGAGCGA | SEQ ID NO: 1292 |
| | | RPr | CTTGAGGGTTTGGGTTTCCA | SEQ ID NO: 1293 |

TABLE A-continued

| Gene | Accession | Reagt | Sequence | SEQ ID NO |
|---|---|---|---|---|
| LGMN | NM_001008530.1 | FPr | TTGGTGCCGTTCCTATAGATG | SEQ ID NO: 1294 |
| | | Probe | CAGTGCTTGCCTCCATCTTCAGGA | SEQ ID NO: 1295 |
| | | RPr | GAACCTGCCACGATCACC | SEQ ID NO: 1296 |
| LILRB3 | NM_006864.1 | FPr | CACCTGGTCTGGGAAGATACC | SEQ ID NO: 1297 |
| | | Probe | ACCGAGACCCCAATCAAAACCTCC | SEQ ID NO: 1298 |
| | | RPr | AAGAGCAGCAGGACGAAGG | SEQ ID NO: 1299 |
| LMNB1 | NM_005573.1 | FPr | TGCAAACGCTGGTGTCACA | SEQ ID NO: 1300 |
| | | Probe | CAGCCCCCAACTGACCTCATC | SEQ ID NO: 1301 |
| | | RPr | CCCCACGAGTTCTGGTTCTTC | SEQ ID NO: 1302 |
| LMYC | NM_012421.1 | FPr | CCCATCCAGAACACTGATTG | SEQ ID NO: 1303 |
| | | Probe | TGACCTCCATCCCTTTCACTTGAATG | SEQ ID NO: 1304 |
| | | RPr | CTGCTTTCTATGCACCCTTTC | SEQ ID NO: 1305 |
| LOX | NM_002317.3 | FPr | CCAATGGGAGAACAACGG | SEQ ID NO: 1306 |
| | | Probe | CAGGCTCAGCAAGCTGAACACCTG | SEQ ID NO: 1307 |
| | | RPr | CGCTGAGGCTGGTACTGTG | SEQ ID NO: 1308 |
| LOXL2 | NM_002318.1 | FPr | TCAGCGGGCTCTTAAACAA | SEQ ID NO: 1309 |
| | | Probe | CAGCTGTCCCCGCAGTAAAGAAGC | SEQ ID NO: 1310 |
| | | RPr | AAGACAGGAGTTGACCACGC | SEQ ID NO: 1311 |
| LRP5 | NM_002335.1 | FPr | CGACTATGACCCACTGGACA | SEQ ID NO: 1312 |
| | | Probe | CGCCCATCCACCCAGTAGATGAAC | SEQ ID NO: 1313 |
| | | RPr | CTTGGCTCGCTTGATGTTC | SEQ ID NO: 1314 |
| LRP6 | NM_002336.1 | FPr | GGATGTAGCCATCTCTGCCT | SEQ ID NO: 1315 |
| | | Probe | ATAGACCTCAGGGCCTTCGCTGTG | SEQ ID NO: 1316 |
| | | RPr | AGTTCAAAGCCAATAGGGCA | SEQ ID NO: 1317 |
| LY6D | NM_003695.2 | FPr | AATGCTGATGACTTGGAGCAG | SEQ ID NO: 1318 |
| | | Probe | CACAGACCCCACAGAGGATGAAGC | SEQ ID NO: 1319 |
| | | RPr | CTGCATCCTCTGTGGGGT | SEQ ID NO: 1320 |
| MAD | NM_002357.1 | FPr | TGGTTCTGATTAGGTAACGTATTGGA | SEQ ID NO: 1321 |
| | | Probe | CTGCCCACAACTCCCTTGCACGTAA | SEQ ID NO: 1322 |
| | | RPr | GGTCAAGGTGGGACACTGAAG | SEQ ID NO: 1323 |
| MAD1L1 | NM_003550.1 | FPr | AGAAGCTGTCCCTGCAAGAG | SEQ ID NO: 1324 |
| | | Probe | CATGTTCTTCACAATCGCTGCATCC | SEQ ID NO: 1325 |
| | | RPr | AGCCGTACCAGCTCAGACTT | SEQ ID NO: 1326 |
| MAD2L1 | NM_002358.2 | FPr | CCGGGAGCAGGGAATCAC | SEQ ID NO: 1327 |
| | | Probe | CGGCCACGATTTCGGCGCT | SEQ ID NO: 1328 |
| | | RPr | ATGCTGTTGATGCCGAATGA | SEQ ID NO: 1329 |
| MADH2 | NM_005901.2 | FPr | GCTGCCTTTGGTAAGAACATGTC | SEQ ID NO: 1330 |
| | | Probe | TCCATCTTGCCATTCACGCCGC | SEQ ID NO: 1331 |
| | | RPr | ATCCCAGCAGTCTCTTCACAACT | SEQ ID NO: 1332 |
| MADH4 | NM_005359.3 | FPr | GGACATTACTGGCCTGTTCACA | SEQ ID NO: 1333 |
| | | Probe | TGCATTCCAGCCTCCCATTTCCA | SEQ ID NO: 1334 |
| | | RPr | ACCAATACTCAGGAGCAGGATGA | SEQ ID NO: 1335 |
| MADH7 | NM_005904.1 | FPr | TCCATCAAGGCTTTCGACTA | SEQ ID NO: 1336 |
| | | Probe | CTGCAGGCTGTACGCCTTCTCG | SEQ ID NO: 1337 |
| | | RPr | CTGCTGCATAAACTCGTGGT | SEQ ID NO: 1338 |
| MAP2 | NM_031846.1 | FPr | CGGACCACCAGGTCAGAG | SEQ ID NO: 1339 |
| | | Probe | CCACTCTTCCCTGCTCTGCGAATT | SEQ ID NO: 1340 |
| | | RPr | CAGGGGTAGTGGGTGTTGAG | SEQ ID NO: 1341 |
| MAP2K1 | NM_002755.2 | FPr | GCCTTTCTTACCCAGAAGCAGAA | SEQ ID NO: 1342 |
| | | Probe | TCTCAAAGTCGTCATCCTTCAGTTCTCCCA | SEQ ID NO: 1343 |
| | | RPr | CAGCCCCCAGCTCACTGAT | SEQ ID NO: 1344 |
| MAP3K1 | XM_042066.8 | FPr | GGTTGGCATCAAAAGGAACT | SEQ ID NO: 1345 |
| | | Probe | AATTGTCCCTGAAACTCTCCTGCACC | SEQ ID NO: 1346 |
| | | RPr | TGCCATAAATGCAATTGTCC | SEQ ID NO: 1347 |
| MAPK14 | NM_139012.1 | FPr | TGAGTGGAAAAGCCTGACTATG | SEQ ID NO: 1348 |
| | | Probe | TGAAGTCATCAGCTTTGTGCCACCACC | SEQ ID NO: 1349 |
| | | RPr | GGACTCCATCTCTTCTTGGTCAA | SEQ ID NO: 1350 |

TABLE A-continued

| Gene | Accession | Reagt | Sequence | SEQ ID NO |
|---|---|---|---|---|
| Maspin | NM_002639.1 | FPr | CAGATGGCCACTTTGAGAACATT | SEQ ID NO: 1351 |
| | | Probe | AGCTGACAACAGTGTGAACGACCAGCC | SEQ ID NO: 1352 |
| | | RPr | GGCAGCATTAACCACAAGGATT | SEQ ID NO: 1353 |
| MAX | NM_002382.3 | FPr | CAAACGGGCTCATCATAATGC | SEQ ID NO: 1354 |
| | | Probe | TGATGTGGTCCCTACGTTTTCGTTCCA | SEQ ID NO: 1355 |
| | | RPr | TCCCGCAAACTGTGAAAGCT | SEQ ID NO: 1356 |
| MCM2 | NM_004526.1 | FPr | GACTTTTGCCCGCTACCTTTC | SEQ ID NO: 1357 |
| | | Probe | ACAGCTCATTGTTGTCACGCCGGA | SEQ ID NO: 1358 |
| | | RPr | GCCACTAACTGCTTCAGTATGAAGAG | SEQ ID NO: 1359 |
| MCM3 | NM_002388.2 | FPr | GGAGAACAATCCCCTTGAGA | SEQ ID NO: 1360 |
| | | Probe | TGGCCTTTCTGTCTACAAGGATCACCA | SEQ ID NO: 1361 |
| | | RPr | ATCTCCTGGATGGTGATGGT | SEQ ID NO: 1362 |
| MCM6 | NM_005915.2 | FPr | TGATGGTCCTATGTGTCACATTCA | SEQ ID NO: 1363 |
| | | Probe | CAGGTTTCATACCAACACAGGCTTCAGCAC | SEQ ID NO: 1364 |
| | | RPr | TGGGACAGGAAACACACCAA | SEQ ID NO: 1365 |
| MCP1 | NM_002982.1 | FPr | CGCTCAGCCAGATGCAATC | SEQ ID NO: 1366 |
| | | Probe | TGCCCCAGTCACCTGCTGTTA | SEQ ID NO: 1367 |
| | | RPr | GCACTGAGATCTTCCTATTGGTGAA | SEQ ID NO: 1368 |
| MDK | NM_002391.2 | FPr | GGAGCCGACTGCAAGTACA | SEQ ID NO: 1369 |
| | | Probe | ATCACACGCACCCCAGTTCTCAAA | SEQ ID NO: 1370 |
| | | RPr | GACTTTGGTGCCTGTGCC | SEQ ID NO: 1371 |
| MDM2 | NM_002392.1 | FPr | CTACAGGGACGCCATCGAA | SEQ ID NO: 1372 |
| | | Probe | CTTACACCAGCATCAAGATCGG | SEQ ID NO: 1373 |
| | | RPr | ATCCAACCAATCACCTGAATGTT | SEQ ID NO: 1374 |
| MGAT5 | NM_002410.2 | FPr | GGAGTCGAAGGTGGACAATC | SEQ ID NO: 1375 |
| | | Probe | AATGGCACCGGAACAAACTCAACC | SEQ ID NO: 1376 |
| | | RPr | TGGGAACAGCTGTAGTGGAGT | SEQ ID NO: 1377 |
| MGMT | NM_002412.1 | FPr | GTGAAATGAAACGCACCACA | SEQ ID NO: 1378 |
| | | Probe | CAGCCCTTTGGGGAAGCTGG | SEQ ID NO: 1379 |
| | | RPr | GACCCTGCTCACAACCAGAC | SEQ ID NO: 1380 |
| mGST1 | NM_020300.2 | FPr | ACGGATCTACCACACCATTGC | SEQ ID NO: 1381 |
| | | Probe | TTTGACACCCCTTCCCCAGCCA | SEQ ID NO: 1382 |
| | | RPr | TCCATATCCAACAAAAAAACTCAAAG | SEQ ID NO: 1383 |
| MMP1 | NM_002421.2 | FPr | GGGAGATCATCGGGACAACTC | SEQ ID NO: 1384 |
| | | Probe | AGCAAGATTTCCTCCAGGTCCATCAAAAGG | SEQ ID NO: 1385 |
| | | RPr | GGGCCTGGTTGAAAAGCAT | SEQ ID NO: 1386 |
| MMP12 | NM_002426.1 | FPr | CCAACGCTTGCCAAATCCT | SEQ ID NO: 1387 |
| | | Probe | AACCAGCTCTCTGTGACCCCAATT | SEQ ID NO: 1388 |
| | | RPr | ACGGTAGTGACAGCATCAAAACTC | SEQ ID NO: 1389 |
| MMP2 | NM_004530.1 | FPr | CCATGATGGAGAGGCAGACA | SEQ ID NO: 1390 |
| | | Probe | CTGGGAGCATGGCGATGGATACCC | SEQ ID NO: 1391 |
| | | RPr | GGAGTCCGTCCTTACCGTCAA | SEQ ID NO: 1392 |
| MMP7 | NM_002423.2 | FPr | GGATGGTAGCAGTCTAGGGATTAACT | SEQ ID NO: 1393 |
| | | Probe | CCTGTATGCTGCAACTCATGAACTTGGC | SEQ ID NO: 1394 |
| | | RPr | GGAATGTCCCATACCCAAAGAA | SEQ ID NO: 1395 |
| MMP9 | NM_004994.1 | FPr | GAGAACCAATCTCACCGACA | SEQ ID NO: 1396 |
| | | Probe | ACAGGTATTCCTCTGCCAGCTGCC | SEQ ID NO: 1397 |
| | | RPr | CACCCGAGTGTAACCATAGC | SEQ ID NO: 1398 |
| MRP1 | NM_004996.2 | FPr | TCATGGTGCCCGTCAATG | SEQ ID NO: 1399 |
| | | Probe | ACCTGATACGTCTTGGTCTTCATCGCCAT | SEQ ID NO: 1400 |
| | | RPr | CGATTGTCTTTGCTCTTCATGTG | SEQ ID NO: 1401 |
| MRP2 | NM_000392.1 | FPr | AGGGGATGACTTGGACACAT | SEQ ID NO: 1402 |
| | | Probe | CTGCCATTCGACATGACTGCAATTT | SEQ ID NO: 1403 |
| | | RPr | AAAACTGCATGGCTTTGTCA | SEQ ID NO: 1404 |
| MRP3 | NM_003786.2 | FPr | TCATCCTGGCGATCTACTTCCT | SEQ ID NO: 1405 |
| | | Probe | TCTGTCCTGGCTGGAGTCGCTTTCAT | SEQ ID NO: 1406 |
| | | RPr | CCGTTGAGTGGAATCAGCAA | SEQ ID NO: 1407 |

TABLE A-continued

| Gene | Accession | Reagt | Sequence | SEQ ID NO |
|---|---|---|---|---|
| MRP4 | NM_005845.1 | FPr | AGCGCCTGGAATCTACAACT | SEQ ID NO: 1408 |
| | | Probe | CGGAGTCCAGTGTTTTCCCACTTG | SEQ ID NO: 1409 |
| | | RPr | AGAGCCCCTGGAGAGAAGAT | SEQ ID NO: 1410 |
| MRPL40 | NM_003776.2 | FPr | ACTTGCAGGCTGCTATCCTT | SEQ ID NO: 1411 |
| | | Probe | TTCCTACTCTCAGGGGCAGCATGTT | SEQ ID NO: 1412 |
| | | RPr | AGCAGACTTGAACCCTGGTC | SEQ ID NO: 1413 |
| MSH2 | NM_000251.1 | FPr | GATGCAGAATTGAGGCAGAC | SEQ ID NO: 1414 |
| | | Probe | CAAGAAGATTTACTTCGTCGATTCCCAGA | SEQ ID NO: 1415 |
| | | RPr | TCTTGGCAAGTCGGTTAAGA | SEQ ID NO: 1416 |
| MSH3 | NM_002439.1 | FPr | TGATTACCATCATGGCTCAGA | SEQ ID NO: 1417 |
| | | Probe | TCCCAATTGTCGCTTCTTCTGCAG | SEQ ID NO: 1418 |
| | | RPr | CTTGTGAAAATGCCATCCAC | SEQ ID NO: 1419 |
| MSH6 | NM_000179.1 | FPr | TCTATTGGGGGATTGGTAGG | SEQ ID NO: 1420 |
| | | Probe | CCGTTACCAGCTGGAAATTCCTGAGA | SEQ ID NO: 1421 |
| | | RPr | CAAATTGCGAGTGGTGAAAT | SEQ ID NO: 1422 |
| MT3 | NM_005954.1 | FPr | GTGTGAGAAGTGTGCCAAGG | SEQ ID NO: 1423 |
| | | Probe | CTCTCCGCCTTTGCACACAGT | SEQ ID NO: 1424 |
| | | RPr | CTGCACTTCTCTGCTTCTGC | SEQ ID NO: 1425 |
| MTA1 | NM_004689.2 | FPr | CCGCCCTCACCTGAAGAGA | SEQ ID NO: 1426 |
| | | Probe | CCCAGTGTCCGCCAAGGAGCG | SEQ ID NO: 1427 |
| | | RPr | GGAATAAGTTAGCCGCGCTTCT | SEQ ID NO: 1428 |
| MUC1 | NM_002456.1 | FPr | GGCCAGGATCTGTGGTGGTA | SEQ ID NO: 1429 |
| | | Probe | CTCTGGCCTTCCGAGAAGGTACC | SEQ ID NO: 1430 |
| | | RPr | CTCCACGTCGTGGACATTGA | SEQ ID NO: 1431 |
| MUC2 | NM_002457.1 | FPr | CTATGAGCCATGTGGGAACC | SEQ ID NO: 1432 |
| | | Probe | AGCTTCGAGACCTGCAGGACCATC | SEQ ID NO: 1433 |
| | | RPr | ATGTTGGAGTGGATGCCG | SEQ ID NO: 1434 |
| MUC5B | XM_039877.11 | FPr | TGCCCTTGCACTGTCCTAA | SEQ ID NO: 1435 |
| | | Probe | TCAGCCATCCTGCACACCTACACC | SEQ ID NO: 1436 |
| | | RPr | CAGCCACACTCATCCACG | SEQ ID NO: 1437 |
| MUTYH | NM_012222.1 | FPr | GTACGACCAAGAGAAACGGG | SEQ ID NO: 1438 |
| | | Probe | TCTGCCCGTCTTCTCCATGGTAGG | SEQ ID NO: 1439 |
| | | RPr | CCTGTCCAGGTCCATCTCA | SEQ ID NO: 1440 |
| MVP | NM_017458.1 | FPr | ACGAGAACGAGGGCATCTATGT | SEQ ID NO: 1441 |
| | | Probe | CGCACCTTTCCGGTCTTGACATCCT | SEQ ID NO: 1442 |
| | | RPr | GCATGTAGGTGCTTCCAATCAC | SEQ ID NO: 1443 |
| MX1 | NM_002462.2 | FPr | GAAGGAATGGGAATCAGTCATGA | SEQ ID NO: 1444 |
| | | Probe | TCACCCTGGAGATCAGCTCCCGA | SEQ ID NO: 1445 |
| | | RPr | GTCTATTAGAGTCAGATCCGGGACAT | SEQ ID NO: 1446 |
| MXD4 | NM_006454.2 | FPr | AGAAACTGGAGGAGCAGGAC | SEQ ID NO: 1447 |
| | | Probe | TGCAGCTGCTCCTTGATGCTCAGT | SEQ ID NO: 1448 |
| | | RPr | CTTCAGGAAACGATGCTCCT | SEQ ID NO: 1449 |
| MYBL2 | NM_002466.1 | FPr | GCCGAGATCGCCAAGATG | SEQ ID NO: 1450 |
| | | Probe | CAGCATTGTCTGTCCTCCCTGGCA | SEQ ID NO: 1451 |
| | | RPr | CTTTTGATGGTAGAGTTCCAGTGATTC | SEQ ID NO: 1452 |
| MYH11 | NM_002474.1 | FPr | CGGTACTTCTCAGGGCTAATATATACG | SEQ ID NO: 1453 |
| | | Probe | CTCTTCTGCGTGGTGGTCAACCCCTA | SEQ ID NO: 1454 |
| | | RPr | CCGAGTAGATGGGCAGGTGTT | SEQ ID NO: 1455 |
| MYLK | NM_053025.1 | FPr | TGACGGAGCGTGAGTGCAT | SEQ ID NO: 1456 |
| | | Probe | CCCTCCGAGATCTGCCGCATGTACT | SEQ ID NO: 1457 |
| | | RPr | ATGCCCTGCTTGTGGATGTAC | SEQ ID NO: 1458 |
| NAT2 | NM_000015.1 | FPr | TAACTGACATTCTTGAGCACCAGAT | SEQ ID NO: 1459 |
| | | Probe | CGGGCTGTTCCCTTTGAGAACCTTAACA | SEQ ID NO: 1460 |
| | | RPr | ATGGCTTGCCCACAATGC | SEQ ID NO: 1461 |
| NAV2 | NM_182964.3 | FPr | CTCTCCCAGCACAGCTTGA | SEQ ID NO: 1462 |
| | | Probe | CCTCACTGAGTCAACCAGCCTGGA | SEQ ID NO: 1463 |
| | | RPr | CACCAGTGTCATCCAGCAAC | SEQ ID NO: 1464 |

TABLE A-continued

| Gene | Accession | Reagt | Sequence | SEQ ID NO |
|---|---|---|---|---|
| NCAM1 | NM_000615.1 | FPr | TAGTTCCCAGCTGACCATCA | SEQ ID NO: 1465 |
|  |  | Probe | CTCAGCCTCGTCGTTCTTATCCACC | SEQ ID NO: 1466 |
|  |  | RPr | CAGCCTTGTTCTCAGCAATG | SEQ ID NO: 1467 |
| NDE1 | NM_017668.1 | FPr | CTACTGCGGAAAGTCGGG | SEQ ID NO: 1468 |
|  |  | Probe | CTGGAGTCCAAACTCGCTTCCTGC | SEQ ID NO: 1469 |
|  |  | RPr | GGACTGATCGTACACGAGGTT | SEQ ID NO: 1470 |
| NDRG1 | NM_006096.2 | FPr | AGGGCAACATTCCACAGC | SEQ ID NO: 1471 |
|  |  | Probe | CTGCAAGGACACTCATCACAGCCA | SEQ ID NO: 1472 |
|  |  | RPr | CAGTGCTCCTACTCCGGC | SEQ ID NO: 1473 |
| NDUFS3 | NM_004551.1 | FPr | TATCCATCCTGATGGCGTC | SEQ ID NO: 1474 |
|  |  | Probe | CCCAGTGCTGACTTTCCTCAGGGA | SEQ ID NO: 1475 |
|  |  | RPr | TTGAACTGTGCATTGGTGTG | SEQ ID NO: 1476 |
| NEDD8 | NM_006156.1 | FPr | TGCTGGCTACTGGGTGTTAGT | SEQ ID NO: 1477 |
|  |  | Probe | TGCAGTCCTGTGTGCTTCCCTCTC | SEQ ID NO: 1478 |
|  |  | RPr | GACAACCAGGGACACAGTCA | SEQ ID NO: 1479 |
| NEK2 | NM_002497.1 | FPr | GTGAGGCAGCGCGACTCT | SEQ ID NO: 1480 |
|  |  | Probe | TGCCTTCCCGGGCTGAGGACT | SEQ ID NO: 1481 |
|  |  | RPr | TGCCAATGGTGTACAACACTTCA | SEQ ID NO: 1482 |
| NF2 | NM_000268.2 | FPr | ACTCCAGAGCTGACCTCCAC | SEQ ID NO: 1483 |
|  |  | Probe | CTACAATGACTTCCCAGGCTGGGC | SEQ ID NO: 1484 |
|  |  | RPr | TCAGGGCTTCAGTGTCTCAC | SEQ ID NO: 1485 |
| NFKBp50 | NM_003998.1 | FPr | CAGACCAAGGAGATGGACCT | SEQ ID NO: 1486 |
|  |  | Probe | AAGCTGTAAACATGAGCCGCACCA | SEQ ID NO: 1487 |
|  |  | RPr | AGCTGCCAGTGCTATCCG | SEQ ID NO: 1488 |
| NFKBp65 | NM_021975.1 | FPr | CTGCCGGGATGGCTTCTAT | SEQ ID NO: 1489 |
|  |  | Probe | CTGAGCTCTGCCCGGACCGCT | SEQ ID NO: 1490 |
|  |  | RPr | CCAGGTTCTGGAAACTGTGGAT | SEQ ID NO: 1491 |
| NISCH | NM_007184.1 | FPr | CCAAGGAATCATGTTCGTTCAG | SEQ ID NO: 1492 |
|  |  | Probe | TGGCCAGCAGCCTCTCGTCCAC | SEQ ID NO: 1493 |
|  |  | RPr | TGGTGCTCGGGAGTCAGACT | SEQ ID NO: 1494 |
| Nkd-1 | NM_033119.3 | FPr | GAGAGAGTGAGCGAACCCTG | SEQ ID NO: 1495 |
|  |  | Probe | CCAGGCTCCAAGAAGCAGCTGAAG | SEQ ID NO: 1496 |
|  |  | RPr | CGTCGCACTGGAGCTCTT | SEQ ID NO: 1497 |
| NMB | NM_021077.1 | FPr | GGCTGCTGGTACAAATACTGC | SEQ ID NO: 1498 |
|  |  | Probe | TGTCTGCCCCTATTATTGGTGTCATTTCT | SEQ ID NO: 1499 |
|  |  | RPr | CAATCTAAGCCACGCTGTTG | SEQ ID NO: 1500 |
| NMBR | NM_002511.1 | FPr | TGATCCATCTCTAGGCCACA | SEQ ID NO: 1501 |
|  |  | Probe | TTGTCACCTTAGTTGCCCGGGTTC | SEQ ID NO: 1502 |
|  |  | RPr | GAGCAAATGGGTTGACACAA | SEQ ID NO: 1503 |
| NME1 | NM_000269.1 | FPr | CCAACCCTGCAGACTCCAA | SEQ ID NO: 1504 |
|  |  | Probe | CCTGGGACCATCCGTGGAGACTTCT | SEQ ID NO: 1505 |
|  |  | RPr | ATGTATAATGTTCCTGCCAACTTGTATG | SEQ ID NO: 1506 |
| NOS3 | NM_000603.2 | FPr | ATCTCCGCCTCGCTCATG | SEQ ID NO: 1507 |
|  |  | Probe | TTCACTCGCTTCGCCATCACCG | SEQ ID NO: 1508 |
|  |  | RPr | TCGGAGCCATACAGGATTGTC | SEQ ID NO: 1509 |
| NOTCH1 | NM_017617.2 | FPr | CGGGTCCACCAGTTTGAATG | SEQ ID NO: 1510 |
|  |  | Probe | CCGCTCTGCAGCCGGGACA | SEQ ID NO: 1511 |
|  |  | RPr | GTTGTATTGGTTCGGCACCAT | SEQ ID NO: 1512 |
| NOTCH2 | NM_024408.2 | FPr | CACTTCCCTGCTGGGATTAT | SEQ ID NO: 1513 |
|  |  | Probe | CCGTGTTGCACAGCTCATCACACT | SEQ ID NO: 1514 |
|  |  | RPr | AGTTGTCAAACAGGCACTCG | SEQ ID NO: 1515 |
| NPM1 | NM_002520.2 | FPr | AATGTTGTCCAGGTTCTATTGC | SEQ ID NO: 1516 |
|  |  | Probe | AACAGGCATTTTGGACAACACATTCTTG | SEQ ID NO: 1517 |
|  |  | RPr | CAAGCAAAGGGTGGAGTTC | SEQ ID NO: 1518 |
| NR4A1 | NM_002135.2 | FPr | CACAGCTTGCTTGTCGATGTC | SEQ ID NO: 1519 |
|  |  | Probe | CCTTCGCCTGCCTCTCTGCCC | SEQ ID NO: 1520 |
|  |  | RPr | ATGCCGGTCGGTGATGAG | SEQ ID NO: 1521 |

TABLE A-continued

| Gene | Accession | Reagt | Sequence | SEQ ID NO |
|---|---|---|---|---|
| NRG1 | NM_013957.1 | FPr | CGAGACTCTCCTCATAGTGAAAGGTAT | SEQ ID NO: 1522 |
| | | Probe | ATGACCACCCCGGCTCGTATGTCA | SEQ ID NO: 1523 |
| | | RPr | CTTGGCGTGTGGAAATCTACAG | SEQ ID NO: 1524 |
| NRP1 | NM_003873.1 | FPr | CAGCTCTCTCCACGCGATTC | SEQ ID NO: 1525 |
| | | Probe | CAGGATCTACCCCGAGAGAGCCACTCAT | SEQ ID NO: 1526 |
| | | RPr | CCCAGCAGCTCCATTCTGA | SEQ ID NO: 1527 |
| NRP2 | NM_003872.1 | FPr | CTACAGCCTAAACGGCAAGG | SEQ ID NO: 1528 |
| | | Probe | AGGACCCCAGGACCCAGCAG | SEQ ID NO: 1529 |
| | | RPr | GTTCCCTTCGAACAGCTTTG | SEQ ID NO: 1530 |
| NTN1 | NM_004822.1 | FPr | AGAAGGACTATGCCGTCCAG | SEQ ID NO: 1531 |
| | | Probe | ATCCACATCCTGAAGGCGGACAAG | SEQ ID NO: 1532 |
| | | RPr | CCGTGAACTTCCACCAGTC | SEQ ID NO: 1533 |
| NUFIP1 | NM_012345.1 | FPr | GCTTCCACATCGTGGTATTG | SEQ ID NO: 1534 |
| | | Probe | CTTCTGATAGGTTTCCTCGGCATCAGA | SEQ ID NO: 1535 |
| | | RPr | AACTGCAGGGTTGAAGGACT | SEQ ID NO: 1536 |
| ODC1 | NM_002539.1 | FPr | AGAGATCACCGGCGTAATCAA | SEQ ID NO: 1537 |
| | | Probe | CCAGCGTTGGACAAATACTTTCCGTCA | SEQ ID NO: 1538 |
| | | RPr | CGGGCTCAGCTATGATTCTCA | SEQ ID NO: 1539 |
| OPN, osteopontin | NM_000582.1 | FPr | CAACCGAAGTTTTCACTCCAGTT | SEQ ID NO: 1540 |
| | | Probe | TCCCCACAGTAGACACATATGATGGCCG | SEQ ID NO: 1541 |
| | | RPr | CCTCAGTCCATAAACCACACTATCA | SEQ ID NO: 1542 |
| ORC1L | NM_004153.2 | FPr | TCCTTGACCATACCGGAGG | SEQ ID NO: 1543 |
| | | Probe | TGCATGTACATCTCCGGTGTCCCT | SEQ ID NO: 1544 |
| | | RPr | CAGTGGCAGTCTTCCCTGTC | SEQ ID NO: 1545 |
| OSM | NM_020530.3 | FPr | GTTTCTGAAGGGGAGGTCAC | SEQ ID NO: 1546 |
| | | Probe | CTGAGCTGGCCTCCTATGCCTCAT | SEQ ID NO: 1547 |
| | | RPr | AGGTGTCTGGTTTGGGACA | SEQ ID NO: 1548 |
| OSMR | NM_003999.1 | FPr | GCTCATCATGGTCATGTGCT | SEQ ID NO: 1549 |
| | | Probe | CAGGTCTCCTTGATCCACTGACTTTTCA | SEQ ID NO: 1550 |
| | | RPr | TGTAAGGGTCAGGGATGTCA | SEQ ID NO: 1551 |
| P14ARF | S78535.1 | FPr | CCCTCGTGCTGATGCTACT | SEQ ID NO: 1552 |
| | | Probe | CTGCCCTAGACGCTGGCTCCTC | SEQ ID NO: 1553 |
| | | RPr | CATCATGACCTGGTCTTCTAGG | SEQ ID NO: 1554 |
| p16-INK4 | L27211.1 | FPr | GCGGAAGGTCCCTCAGACA | SEQ ID NO: 1555 |
| | | Probe | CTCAGAGCCTCTCTGGTTCTTTCAATCGG | SEQ ID NO: 1556 |
| | | RPr | TGATGATCTAAGTTTCCCGAGGTT | SEQ ID NO: 1557 |
| p21 | NM_000389.1 | FPr | TGGAGACTCTCAGGGTCGAAA | SEQ ID NO: 1558 |
| | | Probe | CGGCGGCAGACCAGCATGAC | SEQ ID NO: 1559 |
| | | RPr | GGCGTTTGGAGTGGTAGAAATC | SEQ ID NO: 1560 |
| p27 | NM_004064.1 | FPr | CGGTGGACCACGAAGAGTTAA | SEQ ID NO: 1561 |
| | | Probe | CCGGGACTTGGAGAAGCACTGCA | SEQ ID NO: 1562 |
| | | RPr | GGCTCGCCTCTTCCATGTC | SEQ ID NO: 1563 |
| P53 | NM_000546.2 | FPr | CTTTGAACCCTTGCTTGCAA | SEQ ID NO: 1564 |
| | | Probe | AAGTCCTGGGTGCTTCTGACGCACA | SEQ ID NO: 1565 |
| | | RPr | CCCGGGACAAAGCAAATG | SEQ ID NO: 1566 |
| p53R2 | AB036063.1 | FPr | CCCAGCTAGTGTTCCTCAGA | SEQ ID NO: 1567 |
| | | Probe | TCGGCCAGCTTTTTCCAATCTTTG | SEQ ID NO: 1568 |
| | | RPr | CCGTAAGCCCTTCCTCTATG | SEQ ID NO: 1569 |
| PADI4 | NM_012387.1 | FPr | AGCAGTGGCTTGCTTTCTTC | SEQ ID NO: 1570 |
| | | Probe | CCTGTGATGTCCCAGTTTCCCACTC | SEQ ID NO: 1571 |
| | | RPr | TGCTAGGACCATGTTGGGAT | SEQ ID NO: 1572 |
| PAI1 | NM_000602.1 | FPr | CCGCAACGTGGTTTTCTCA | SEQ ID NO: 1573 |
| | | Probe | CTCGGTGTTGGCCATGCTCCAG | SEQ ID NO: 1574 |
| | | RPr | TGCTGGGTTTCTCCTCCTGTT | SEQ ID NO: 1575 |
| Pak1 | NM_002576.3 | FPr | GAGCTGTGGGTTGTTATGGA | SEQ ID NO: 1576 |
| | | Probe | ACATCTGTCAAGGAGCCTCCAGCC | SEQ ID NO: 1577 |
| | | RPr | CCATGCAAGTTTCTGTCACC | SEQ ID NO: 1578 |

TABLE A-continued

| Gene | Accession | Reagt | Sequence | SEQ ID NO |
|---|---|---|---|---|
| PARC | NM_015089.1 | FPr | GGAGCTGACCTGCTTCCTAC | SEQ ID NO: 1579 |
| | | Probe | TCCTTATGCATCGAGGCCAGGC | SEQ ID NO: 1580 |
| | | RPr | AGCAGAGCACCACAGCATAG | SEQ ID NO: 1581 |
| PCAF | NM_003884.3 | FPr | AGGTGGCTGTGTTACTGCAA | SEQ ID NO: 1582 |
| | | Probe | TGCCACAGTTCTGCGACAGTCTACC | SEQ ID NO: 1583 |
| | | RPr | CACCTGTGTGGTTTCGTACC | SEQ ID NO: 1584 |
| PCNA | NM_002592.1 | FPr | GAAGGTGTTGGAGGCACTCAAG | SEQ ID NO: 1585 |
| | | Probe | ATCCCAGCAGGCCTCGTTGATGAG | SEQ ID NO: 1586 |
| | | RPr | GGTTTACACCGCTGGAGCTAA | SEQ ID NO: 1587 |
| PDGFA | NM_002607.2 | FPr | TTGTTGGTGTGCCCTGGTG | SEQ ID NO: 1588 |
| | | Probe | TGGTGGCGGTCACTCCCTCTGC | SEQ ID NO: 1589 |
| | | RPr | TGGGTTCTGTCCAAACACTGG | SEQ ID NO: 1590 |
| PDGFB | NM_002608.1 | FPr | ACTGAAGGAGACCCTTGGAG | SEQ ID NO: 1591 |
| | | Probe | TCTCCTGCCGATGCCCCTAGG | SEQ ID NO: 1592 |
| | | RPr | TAAATAACCCTGCCCACACA | SEQ ID NO: 1593 |
| PDGFC | NM_016205.1 | FPr | AGTTACTAAAAAATACCACGAGGTCCTT | SEQ ID NO: 1594 |
| | | Probe | CCCTGACACCGGTCTTTGGTCTCAACT | SEQ ID NO: 1595 |
| | | RPr | GTCGGTGAGTGATTTGTGCAA | SEQ ID NO: 1596 |
| PDGFD | NM_025208.2 | FPr | TATCGAGGCAGGTCATACCA | SEQ ID NO: 1597 |
| | | Probe | TCCAGGTCAACTTTTGACTTCCGGT | SEQ ID NO: 1598 |
| | | RPr | TAACGCTTGGCATCATCATT | SEQ ID NO: 1599 |
| PDGFRa | NM_006206.2 | FPr | GGGAGTTTCCAAGAGATGGA | SEQ ID NO: 1600 |
| | | Probe | CCCAAGACCCGACCAAGCACTAG | SEQ ID NO: 1601 |
| | | RPr | CTTCAACCACCTTCCCAAAC | SEQ ID NO: 1602 |
| PDGFRb | NM_002609.2 | FPr | CCAGCTCTCCTTCCAGCTAC | SEQ ID NO: 1603 |
| | | Probe | ATCAATGTCCCTGTCCGAGTGCTG | SEQ ID NO: 1604 |
| | | RPr | GGGTGGCTCTCACTTAGCTC | SEQ ID NO: 1605 |
| PFN1 | NM_005022.2 | FPr | GGAAAACGTTCGTCAACATC | SEQ ID NO: 1606 |
| | | Probe | CAACCAGGACACCCACCTCAGCT | SEQ ID NO: 1607 |
| | | RPr | AAAACTTGACCGGTCTTTGC | SEQ ID NO: 1608 |
| PFN2 | NM_053024.1 | FPr | TCTATACGTCGATGGTGACTGC | SEQ ID NO: 1609 |
| | | Probe | CTCCCCACCTTGACTCTTTGTCCG | SEQ ID NO: 1610 |
| | | RPr | GCCGACAGCCACATTGTAT | SEQ ID NO: 1611 |
| PGK1 | NM_000291.1 | FPr | AGAGCCAGTTGCTGTAGAACTCAA | SEQ ID NO: 1612 |
| | | Probe | TCTCTGCTGGGCAAGGATGTTCTGTTC | SEQ ID NO: 1613 |
| | | RPr | CTGGGCCTACACAGTCCTTCA | SEQ ID NO: 1614 |
| PI3K | NM_002646.2 | FPr | TGCTACCTGGACAGCCCG | SEQ ID NO: 1615 |
| | | Probe | TCCTCCTGAAACGAGCTGTGTCTGACTT | SEQ ID NO: 1616 |
| | | RPr | AGGCCGTCCTTCAGTAACCA | SEQ ID NO: 1617 |
| PI3KC2A | NM_002645.1 | FPr | ATACCAATCACCGCACAAACC | SEQ ID NO: 1618 |
| | | Probe | TGCGCTGTGACTGGACTTAACAAATAGCCT | SEQ ID NO: 1619 |
| | | RPr | CACACTAGCATTTTCTCCGCATA | SEQ ID NO: 1620 |
| PIK3CA | NM_006218.1 | FPr | GTGATTGAAGAGCATGCCAA | SEQ ID NO: 1621 |
| | | Probe | TCCTGCTTCTCGGGATACAGACCA | SEQ ID NO: 1622 |
| | | RPr | GTCCTGCGTGGGAATAGC | SEQ ID NO: 1623 |
| PIM1 | NM_002648.2 | FPr | CTGCTCAAGGACACCGTCTA | SEQ ID NO: 1624 |
| | | Probe | TACACTCGGGTCCCATCGAAGTCC | SEQ ID NO: 1625 |
| | | RPr | GGATCCACTCTGGAGGGC | SEQ ID NO: 1626 |
| Pin1 | NM_006221.1 | FPr | GATCAACGGCTACATCCAGA | SEQ ID NO: 1627 |
| | | Probe | TCAAAGTCCTCCTCTCCCGACTTGA | SEQ ID NO: 1628 |
| | | RPr | TGAACTGTGAGGCCAGAGAC | SEQ ID NO: 1629 |
| PKD1 | NM_000296.2 | FPr | CAGCACCAGCGATTACGAC | SEQ ID NO: 1630 |
| | | Probe | AGCCATTGTGAGGACTCTCCCAGC | SEQ ID NO: 1631 |
| | | RPr | CTGAATAGGCCCACGTCC | SEQ ID NO: 1632 |
| PKR2 | NM_002654.3 | FPr | CCGCCTGGACATTGATTCAC | SEQ ID NO: 1633 |
| | | Probe | ACCCATCACAGCCCGGAACACTG | SEQ ID NO: 1634 |
| | | RPr | CTGGGCCAATGGTACAGATGA | SEQ ID NO: 1635 |

TABLE A-continued

| Gene | Accession | Reagt | Sequence | SEQ ID NO |
|---|---|---|---|---|
| PLA2G2A | NM_000300.2 | FPr | GCATCCCTCACCCATCCTA | SEQ ID NO: 1636 |
| | | Probe | AGGCCAGGCAGGAGCCCTTCTATA | SEQ ID NO: 1637 |
| | | RPr | GCTGGAAATCTGCTGGATGT | SEQ ID NO: 1638 |
| PLAUR | NM_002659.1 | FPr | CCCATGGATGCTCCTCTGAA | SEQ ID NO: 1639 |
| | | Probe | CATTGACTGCCGAGGCCCATG | SEQ ID NO: 1640 |
| | | RPr | CCGGTGGCTACCAGACATTG | SEQ ID NO: 1641 |
| PLK | NM_005030.2 | FPr | AATGAATACAGTATTCCCAAGCACAT | SEQ ID NO: 1642 |
| | | Probe | AACCCCGTGGCCGCCTCC | SEQ ID NO: 1643 |
| | | RPr | TGTCTGAAGCATCTTCTGGATGA | SEQ ID NO: 1644 |
| PLK3 | NM_004073.2 | FPr | TGAAGGAGACGTACCGCTG | SEQ ID NO: 1645 |
| | | Probe | CAAGCAGGTTCACTACACGCTGCC | SEQ ID NO: 1646 |
| | | RPr | CAGGCAGTGAGAGGCTGG | SEQ ID NO: 1647 |
| PLOD2 | NM_000935.2 | FPr | CAGGGAGGTGGTTGCAAAT | SEQ ID NO: 1648 |
| | | Probe | TCCAGCCTTTTCGTGGTGACTCAA | SEQ ID NO: 1649 |
| | | RPr | TCTCCCAGGATGCATGAAG | SEQ ID NO: 1650 |
| PMS1 | NM_000534.2 | FPr | CTTACGGTTTTCGTGGAGAAG | SEQ ID NO: 1651 |
| | | Probe | CCTCAGCTATACAACAAATTGACCCCAAG | SEQ ID NO: 1652 |
| | | RPr | AGCAGCCGTTCTTGTTGTAA | SEQ ID NO: 1653 |
| PMS2 | NM_000535.2 | FPr | GATGTGGACTGCCATTCAAA | SEQ ID NO: 1654 |
| | | Probe | TCGAAATTTACATCCGGTATCTTCCTGG | SEQ ID NO: 1655 |
| | | RPr | TGCGAGATTAGTTGGCTGAG | SEQ ID NO: 1656 |
| PPARG | NM_005037.3 | FPr | TGACTTTATGGAGCCCAAGTT | SEQ ID NO: 1657 |
| | | Probe | TTCCAGTGCATTGAACTTCACAGCA | SEQ ID NO: 1658 |
| | | RPr | GCCAAGTCGCTGTCATCTAA | SEQ ID NO: 1659 |
| PPID | NM_005038.1 | FPr | TCCTCATTTGGATGGGAAAC | SEQ ID NO: 1660 |
| | | Probe | TTCCTTTAATTACTTGGCCAAACACCACA | SEQ ID NO: 1661 |
| | | RPr | CCAATATCCTTGCCACTCCTA | SEQ ID NO: 1662 |
| PPM1D | NM_003620.1 | FPr | GCCATCCGCAAAGGCTTT | SEQ ID NO: 1663 |
| | | Probe | TCGCTTGTCACCTTGCCATGTGG | SEQ ID NO: 1664 |
| | | RPr | GGCCATTCCGCCAGTTTC | SEQ ID NO: 1665 |
| PPP2R4 | NM_178001.1 | FPr | GGCTCAGAGCATAAGGCTTC | SEQ ID NO: 1666 |
| | | Probe | TTGGTCACTTCTCCCAACTTGGGC | SEQ ID NO: 1667 |
| | | RPr | ACGGGAACTCAGAAAACTGG | SEQ ID NO: 1668 |
| PR | NM_000926.2 | FPr | GCATCAGGCTGTCATTATGG | SEQ ID NO: 1669 |
| | | Probe | TGTCCTTACCTGTGGGAGCTGTAAGGTC | SEQ ID NO: 1670 |
| | | RPr | AGTAGTTGTGCTGCCCTTCC | SEQ ID NO: 1671 |
| PRDX2 | NM_005809.4 | FPr | GGTGTCCTTCGCCAGATCAC | SEQ ID NO: 1672 |
| | | Probe | TTAATGATTTGCCTGTGGGACGCTCC | SEQ ID NO: 1673 |
| | | RPr | CAGCCGCAGAGCCTCATC | SEQ ID NO: 1674 |
| PRDX3 | NM_006793.2 | FPr | TGACCCCAATGGAGTCATCA | SEQ ID NO: 1675 |
| | | Probe | CATTTGAGCGTCAACGATCTCCCAGTG | SEQ ID NO: 1676 |
| | | RPr | CCAAGCGGAGGGTTTCTTC | SEQ ID NO: 1677 |
| PRDX4 | NM_006406.1 | FPr | TTACCCATTTGGCCTGGATTAA | SEQ ID NO: 1678 |
| | | Probe | CCAAGTCCTCCTTGTCTTCGAGGGGT | SEQ ID NO: 1679 |
| | | RPr | CTGAAAGAAGTGGAATCCTTATTGG | SEQ ID NO: 1680 |
| PRDX6 | NM_004905.2 | FPr | CTGTGAGCCAGAGGATGTCA | SEQ ID NO: 1681 |
| | | Probe | CTGCCAATTGTGTTTCCTGCAGC | SEQ ID NO: 1682 |
| | | RPr | TGTGATGACACCAGGATGTG | SEQ ID NO: 1683 |
| PRKCA | NM_002737.1 | FPr | CAAGCAATGCGTCATCAATGT | SEQ ID NO: 1684 |
| | | Probe | CAGCCTCTGCGGAATGGATCACACT | SEQ ID NO: 1685 |
| | | RPr | GTAAATCCGCCCCCTCTTCT | SEQ ID NO: 1686 |
| PRKCB1 | NM_002738.5 | FPr | GACCCAGCTCCACTCCTG | SEQ ID NO: 1687 |
| | | Probe | CCAGACCATGGACCGCCTGTACTT | SEQ ID NO: 1688 |
| | | RPr | CCCATTCACGTACTCCATCA | SEQ ID NO: 1689 |
| PRKCD | NM_006254.1 | FPr | CTGACACTTGCCGCAGAGAA | SEQ ID NO: 1690 |
| | | Probe | CCCTTTCTCACCCACCTCATCTGCAC | SEQ ID NO: 1691 |
| | | RPr | AGGTGGTCCTTGGTCTGGAA | SEQ ID NO: 1692 |

TABLE A-continued

| Gene | Accession | Reagt | Sequence | SEQ ID NO |
|---|---|---|---|---|
| PRKR | NM_002759.1 | FPr | GCGATACATGAGCCCAGAACA | SEQ ID NO: 1693 |
| | | Probe | AGGTCCACTTCCTTTCCATAGTCTTGCGA | SEQ ID NO: 1694 |
| | | RPr | TCAGCAAGAATTAGCCCCAAAG | SEQ ID NO: 1695 |
| pS2 | NM_003225.1 | FPr | GCCCTCCCAGTGTGCAAAT | SEQ ID NO: 1696 |
| | | Probe | TGCTGTTTCGACGACACCGTTCG | SEQ ID NO: 1697 |
| | | RPr | CGTCGATGGTATTAGGATAGAAGCA | SEQ ID NO: 1698 |
| PTCH | NM_000264.2 | FPr | CCACGACAAAGCCGACTAC | SEQ ID NO: 1699 |
| | | Probe | CCTGAAACAAGGCTGAGAATCCCG | SEQ ID NO: 1700 |
| | | RPr | TACTCGATGGGCTCTGCTG | SEQ ID NO: 1701 |
| PTEN | NM_000314.1 | FPr | TGGCTAAGTGAAGATGACAATCATG | SEQ ID NO: 1702 |
| | | Probe | CCTTTCCAGCTTTACAGTGAATTGCTGCA | SEQ ID NO: 1703 |
| | | RPr | TGCACATATCATTACACCAGTTCGT | SEQ ID NO: 1704 |
| PTGER3 | NM_000957.2 | FPr | TAACTGGGGCAACCTTTTCT | SEQ ID NO: 1705 |
| | | Probe | CCTTTGCCTTCCTGGGGCTCTT | SEQ ID NO: 1706 |
| | | RPr | TTGCAGGAAAAGGTGACTGT | SEQ ID NO: 1707 |
| PTHLH | NM_002820.1 | FPr | AGTGACTGGGAGTGGGCTAGAA | SEQ ID NO: 1708 |
| | | Probe | TGACACCTCCACAACGTCGCTGGA | SEQ ID NO: 1709 |
| | | RPr | AAGCCTGTTACCGTGAATCGA | SEQ ID NO: 1710 |
| PTHR1 | NM_000316.1 | FPr | CGAGGTACAAGCTGAGATCAAGAA | SEQ ID NO: 1711 |
| | | Probe | CCAGTGCCAGTGTCCAGCGGCT | SEQ ID NO: 1712 |
| | | RPr | GCGTGCCTTTCGCTTGAA | SEQ ID NO: 1713 |
| PTK2 | NM_005607.3 | FPr | GACCGGTCGAATGATAAGGT | SEQ ID NO: 1714 |
| | | Probe | ACCAGGCCCGTCACATTCTCGTAC | SEQ ID NO: 1715 |
| | | RPr | CTGGACATCTCGATGACAGC | SEQ ID NO: 1716 |
| PTK2B | NM_004103.3 | FPr | CAAGCCCAGCCGACCTAAG | SEQ ID NO: 1717 |
| | | Probe | CTCCGCAAACCAACCTCCTGGCT | SEQ ID NO: 1718 |
| | | RPr | GAACCTGGAACTGCAGCTTTG | SEQ ID NO: 1719 |
| PTP4A3 | NM_007079.2 | FPr | CCTGTTCTCGGCACCTTAAA | SEQ ID NO: 1720 |
| | | Probe | ACCTGACTGCCCCGGGGTCTAATA | SEQ ID NO: 1721 |
| | | RPr | TATTGCCTTCGGGTGTCC | SEQ ID NO: 1722 |
| PTP4A3 v2 | NM_032611.1 | FPr | AATATTTGTGCGGGGTATGG | SEQ ID NO: 1723 |
| | | Probe | CCAAGAGAAACGAGATTTAAAAACCCACC | SEQ ID NO: 1724 |
| | | RPr | AACGAGATCCCTGTGCTTGT | SEQ ID NO: 1725 |
| PTPD1 | NM_007039.2 | FPr | CGCTTGCCTAACTCATACTTTCC | SEQ ID NO: 1726 |
| | | Probe | TCCACGCAGCGTGGCACTG | SEQ ID NO: 1727 |
| | | RPr | CCATTCAGACTGCGCCACTT | SEQ ID NO: 1728 |
| PTPN1 | NM_002827.2 | FPr | AATGAGGAAGTTTCGGATGG | SEQ ID NO: 1729 |
| | | Probe | CTGATCCAGACAGCCGACCAGCT | SEQ ID NO: 1730 |
| | | RPr | CTTCGATCACAGCCAGGTAG | SEQ ID NO: 1731 |
| PTPRF | NM_002840.2 | FPr | TGTTTTAGCTGAGGGACGTG | SEQ ID NO: 1732 |
| | | Probe | CCGACGTCCCCAAACCTAGCTAGG | SEQ ID NO: 1733 |
| | | RPr | TACCAACCCTGGAATGTTGA | SEQ ID NO: 1734 |
| PTPRJ | NM_002843.2 | FPr | AACTTCCGGTACCTCGTTCGT | SEQ ID NO: 1735 |
| | | Probe | ACTACATGAAGCAGAGTCCTCCCGAATCG | SEQ ID NO: 1736 |
| | | RPr | AGCACTGCAATGCACCAGAA | SEQ ID NO: 1737 |
| PTPRO | NM_030667.1 | FPr | CATGGCCTGATCATGGTGT | SEQ ID NO: 1738 |
| | | Probe | CCCACAGCAAATGCTGCAGAAAGT | SEQ ID NO: 1739 |
| | | RPr | CCATGTGTACAAACTGCAGGA | SEQ ID NO: 1740 |
| PTTG1 | NM_004219.2 | FPr | GGCTACTCTGATCTATGTTGATAAGGAA | SEQ ID NO: 1741 |
| | | Probe | CACACGGGTGCCTGGTTCTCCA | SEQ ID NO: 1742 |
| | | RPr | GCTTCAGCCCATCCTTAGCA | SEQ ID NO: 1743 |
| RAB32 | NM_006834.2 | FPr | CCTGCAGCTGTGGGACAT | SEQ ID NO: 1744 |
| | | Probe | CGATTTGGCAACATGACCCGAGTA | SEQ ID NO: 1745 |
| | | RPr | AGCACCAACAGCTTCCTTG | SEQ ID NO: 1746 |
| RAB6C | NM_032144.1 | FPr | GCGACAGCTCCTCTAGTTCCA | SEQ ID NO: 1747 |
| | | Probe | TTCCCGAAGTCTCCGCCCG | SEQ ID NO: 1748 |
| | | RPr | GGAACACCAGCTTGAATTCCT | SEQ ID NO: 1749 |

TABLE A-continued

| Gene | Accession | Reagt | Sequence | SEQ ID NO |
|---|---|---|---|---|
| RAC1 | NM_006908.3 | FPr | TGTTGTAAATGTCTCAGCCCC | SEQ ID NO: 1750 |
| | | Probe | CGTTCTTGGTCCTGTCCCTTGGA | SEQ ID NO: 1751 |
| | | RPr | TTGAGCAAAGCGTACAAAGG | SEQ ID NO: 1752 |
| RAD51C | NM_058216.1 | FPr | GAACTTCTTGAGCAGGAGCATACC | SEQ ID NO: 1753 |
| | | Probe | AGGGCTTCATAATCACCTTCTGTTC | SEQ ID NO: 1754 |
| | | RPr | TCCACCCCAAGAATATCATCTAGT | SEQ ID NO: 1755 |
| RAD54L | NM_003579.2 | FPr | AGCTAGCCTCAGTGACACACATG | SEQ ID NO: 1756 |
| | | Probe | ACACAACGTCGGCAGTGCAACCTG | SEQ ID NO: 1757 |
| | | RPr | CCGGATCTGACGGCTGTT | SEQ ID NO: 1758 |
| RAF1 | NM_002880.1 | FPr | CGTCGTATGCGAGAGTCTGT | SEQ ID NO: 1759 |
| | | Probe | TCCAGGATGCCTGTTAGTTCTCAGCA | SEQ ID NO: 1760 |
| | | RPr | TGAAGGCGTGAGGTGTAGAA | SEQ ID NO: 1761 |
| RALBP1 | NM_006788.2 | FPr | GGTGTCAGATATAAATGTGCAAATGC | SEQ ID NO: 1762 |
| | | Probe | TGCTGTCCTGTCGGTCTCAGTACGTTCA | SEQ ID NO: 1763 |
| | | RPr | TTCGATATTGCCAGCAGCTATAAA | SEQ ID NO: 1764 |
| RANBP2 | NM_006267.3 | FPr | TCCTTCAGCTTTCACACTGG | SEQ ID NO: 1765 |
| | | Probe | TCCAGAAGAGTCATGCAACTTCATTTCTG | SEQ ID NO: 1766 |
| | | RPr | AAATCCTGTTCCCACCTGAC | SEQ ID NO: 1767 |
| ranBP7 | NM_006391.1 | FPr | AACATGATTATCCAAGCCGC | SEQ ID NO: 1768 |
| | | Probe | AAGCCAATTTTGTCCACAATGGCA | SEQ ID NO: 1769 |
| | | RPr | GCCAACAAGCACTGTTATCG | SEQ ID NO: 1770 |
| RANBP9 | NM_005493.2 | FPr | CAAGTCAGTTGAGACGCCAGTT | SEQ ID NO: 1771 |
| | | Probe | TTCTATGGCGGCCTGACTTCCTCCA | SEQ ID NO: 1772 |
| | | RPr | TGCAGCTCTCGTCCAAAGTG | SEQ ID NO: 1773 |
| RAP1GDS1 | NM_021159.3 | FPr | TGTGGATGCTGGATTGATTT | SEQ ID NO: 1774 |
| | | Probe | CCACTGGTGCAGCTGCTAAATAGCA | SEQ ID NO: 1775 |
| | | RPr | AAGCAGCACTTCCTGGTCTT | SEQ ID NO: 1776 |
| RARA | NM_000964.1 | FPr | AGTCTGTGAGAAACGACCGAAAC | SEQ ID NO: 1777 |
| | | Probe | TCGGGCTTGGGCACCTCCTTCTT | SEQ ID NO: 1778 |
| | | RPr | CGGCGTCAGCGTGTAGCT | SEQ ID NO: 1779 |
| RARB | NM_016152.2 | FPr | TGCCTGGACATCCTGATTCT | SEQ ID NO: 1780 |
| | | Probe | TGCACCAGGTATACCCCAGAACAAGA | SEQ ID NO: 1781 |
| | | RPr | AAGGCCGTCTGAGAAAGTCA | SEQ ID NO: 1782 |
| RASSF1 | NM_007182.3 | FPr | AGTGGGAGACACCTGACCTT | SEQ ID NO: 1783 |
| | | Probe | TTGATCTTCTGCTCAATCTCAGCTTGAGA | SEQ ID NO: 1784 |
| | | RPr | TGATCTGGGCATTGTACTCC | SEQ ID NO: 1785 |
| RBM5 | NM_005778.1 | FPr | CGAGAGGGAGAGCAAGACCAT | SEQ ID NO: 1786 |
| | | Probe | CTGCGCGGCCTTCCCATCA | SEQ ID NO: 1787 |
| | | RPr | TCTCGAATATCGCTCTCTGTGATG | SEQ ID NO: 1788 |
| RBX1 | NM_014248.2 | FPr | GGAACCACATTATGGATCTTTGC | SEQ ID NO: 1789 |
| | | Probe | TAGAATGTCAAGCTAACCAGGCGTCCGC | SEQ ID NO: 1790 |
| | | RPr | CATGCGACAGTACACTCTTCTGAA | SEQ ID NO: 1791 |
| RCC1 | NM_001269.2 | FPr | GGGCTGGGTGAGAATGTG | SEQ ID NO: 1792 |
| | | Probe | ATACCAGGGCCGGCTTCTTCCTCT | SEQ ID NO: 1793 |
| | | RPr | CACAACATCCTCCGGAATG | SEQ ID NO: 1794 |
| REG4 | NM_032044.2 | FPr | TGCTAACTCCTGCACAGCC | SEQ ID NO: 1795 |
| | | Probe | TCCTCTTCCTTTCTGCTAGCCTGGC | SEQ ID NO: 1796 |
| | | RPr | TGCTAGGTTTCCCCTCTGAA | SEQ ID NO: 1797 |
| RFC | NM_003056.1 | FPr | TCAAGACCATCATCACTTTCATTGT | SEQ ID NO: 1798 |
| | | Probe | CCTCCCGGTCCGCAAGCAGTT | SEQ ID NO: 1799 |
| | | RPr | GGATCAGGAAGTACACGGAGTATAACT | SEQ ID NO: 1800 |
| RhoB | NM_004040.2 | FPr | AAGCATGAACAGGACTTGACC | SEQ ID NO: 1801 |
| | | Probe | CTTTCCAACCCCTGGGGAAGACAT | SEQ ID NO: 1802 |
| | | RPr | CCTCCCCAAGTCAGTTGC | SEQ ID NO: 1803 |
| rhoC | NM_175744.1 | FPr | CCCGTTCGGTCTGAGGAA | SEQ ID NO: 1804 |
| | | Probe | TCCGGTTCGCCATGTCCCG | SEQ ID NO: 1805 |
| | | RPr | GAGCACTCAAGGTAGCCAAAGG | SEQ ID NO: 1806 |

TABLE A-continued

| Gene | Accession | Reagt | Sequence | SEQ ID NO |
|---|---|---|---|---|
| RIZ1 | NM_012231.1 | FPr | CCAGACGAGCGATTAGAAGC | SEQ ID NO: 1807 |
| | | Probe | TGTGAGGTGAATGATTTGGGGGA | SEQ ID NO: 1808 |
| | | RPr | TCCTCCTCTTCCTCCTCCTC | SEQ ID NO: 1809 |
| RNF11 | NM_014372.3 | FPr | ACCCTGGAAGAGATGGATCA | SEQ ID NO: 1810 |
| | | Probe | CCATCATACAGATCACACACTCCCGG | SEQ ID NO: 1811 |
| | | RPr | ATTGGGTCCCCATAAACAAA | SEQ ID NO: 1812 |
| ROCK1 | NM_005406.1 | FPr | TGTGCACATAGGAATGAGCTTC | SEQ ID NO: 1813 |
| | | Probe | TCACTCTCTTTGCTGGCCAACTGC | SEQ ID NO: 1814 |
| | | RPr | GTTTAGCACGCAATTGCTCA | SEQ ID NO: 1815 |
| ROCK2 | NM_004850.3 | FPr | GATCCGAGACCCTCGCTC | SEQ ID NO: 1816 |
| | | Probe | CCCATCAACGTGGAGAGCTTGCT | SEQ ID NO: 1817 |
| | | RPr | AGGACCAAGGAATTTAAGCCA | SEQ ID NO: 1818 |
| RPLPO | NM_001002.2 | FPr | CCATTCTATCATCAACGGGTACAA | SEQ ID NO: 1819 |
| | | Probe | TCTCCACAGACAAGGCCAGGACTCG | SEQ ID NO: 1820 |
| | | RPr | TCAGCAAGTGGGAAGGTGTAATC | SEQ ID NO: 1821 |
| RPS13 | NM_001017.2 | FPr | CAGTCGGCTTTACCCTATCG | SEQ ID NO: 1822 |
| | | Probe | CAACTTCAACCAAGTGGGGACGCT | SEQ ID NO: 1823 |
| | | RPr | TCTGCTCCTTCACGTCGTC | SEQ ID NO: 1824 |
| RRM1 | NM_001033.1 | FPr | GGGCTACTGGCAGCTACATT | SEQ ID NO: 1825 |
| | | Probe | CATTGGAATTGCCATTAGTCCCAGC | SEQ ID NO: 1826 |
| | | RPr | CTCTCAGCATCGGTACAAGG | SEQ ID NO: 1827 |
| RRM2 | NM_001034.1 | FPr | CAGCGGGATTAAACAGTCCT | SEQ ID NO: 1828 |
| | | Probe | CCAGCACAGCCAGTTAAAAGATGCA | SEQ ID NO: 1829 |
| | | RPr | ATCGCGTTGAAGCAGTGAG | SEQ ID NO: 1830 |
| RTN4 | NM_007008.1 | FPr | GACTGGAGTGGTGTTTGGTG | SEQ ID NO: 1831 |
| | | Probe | CCAGCCTATTCCTGCTGCTTTCATTG | SEQ ID NO: 1832 |
| | | RPr | CTGTTACGCTCACAATGCTG | SEQ ID NO: 1833 |
| RUNX1 | NM_001754.2 | FPr | AACAGAGACATTGCCAACCA | SEQ ID NO: 1834 |
| | | Probe | TTGGATCTGCTTGCTGTCCAAACC | SEQ ID NO: 1835 |
| | | RPr | GTGATTTGCCCAGGAAGTTT | SEQ ID NO: 1836 |
| RXRA | NM_002957.3 | FPr | GCTCTGTTGTGTCCTGTTGC | SEQ ID NO: 1837 |
| | | Probe | TCAGTCACAGGAAGGCCAGAGCC | SEQ ID NO: 1838 |
| | | RPr | GTACGGAGAAGCCACTTCACA | SEQ ID NO: 1839 |
| S100A1 | NM_006271.1 | FPr | TGGACAAGGTGATGAAGGAG | SEQ ID NO: 1840 |
| | | Probe | CCTCCCCGTCTCCATTCTCGTCTA | SEQ ID NO: 1841 |
| | | RPr | AGCACCACATACTCCTGGAA | SEQ ID NO: 1842 |
| S100A2 | NM_005978.2 | FPr | TGGCTGTGCTGGTCACTACCT | SEQ ID NO: 1843 |
| | | Probe | CACAAGTACTCCTGCCAAGAGGGCGAC | SEQ ID NO: 1844 |
| | | RPr | TCCCCCTTACTCAGCTTGAACT | SEQ ID NO: 1845 |
| S100A4 | NM_002961.2 | FPr | GACTGCTGTCATGGCGTG | SEQ ID NO: 1846 |
| | | Probe | ATCACATCCAGGGCCTTCTCCAGA | SEQ ID NO: 1847 |
| | | RPr | CGAGTACTTGTGGAAGGTGGAC | SEQ ID NO: 1848 |
| S100A8 | NM_002964.3 | FPr | ACTCCCTGATAAAGGGGAATTT | SEQ ID NO: 1849 |
| | | Probe | CATGCCGTCTACAGGGATGACCTG | SEQ ID NO: 1850 |
| | | RPr | TGAGGACACTCGGTCTCTAGC | SEQ ID NO: 1851 |
| S100A9 | NM_002965.2 | FPr | CTTTGGGACAGAGTGCAAGA | SEQ ID NO: 1852 |
| | | Probe | CGATGACTTGCAAAATGTCGCAGC | SEQ ID NO: 1853 |
| | | RPr | TGGTCTCTATGTTGCGTTCC | SEQ ID NO: 1854 |
| S100P | NM_005980.2 | FPr | AGACAAGGATGCCGTGGATAA | SEQ ID NO: 1855 |
| | | Probe | TTGCTCAAGGACCTGGACGCCAA | SEQ ID NO: 1856 |
| | | RPr | GAAGTCCACCTGGGCATCTC | SEQ ID NO: 1857 |
| SAT | NM_002970.1 | FPr | CCTTTTACCACTGCCTGGTT | SEQ ID NO: 1858 |
| | | Probe | TCCAGTGCTCTTTCGGCACTTCTG | SEQ ID NO: 1859 |
| | | RPr | ACAATGCTGTGTCCTTCCG | SEQ ID NO: 1860 |
| SBA2 | NM_018639.3 | FPr | GGACTCAACGATGGGCAG | SEQ ID NO: 1861 |
| | | Probe | CCCTGTCTGCACCTCCCAGATCTT | SEQ ID NO: 1862 |
| | | RPr | CGGAAAGATTCAAAAGCAGG | SEQ ID NO: 1863 |

TABLE A-continued

| Gene | Accession | Reagt | Sequence | SEQ ID NO |
|---|---|---|---|---|
| SDC1 | NM_002997.1 | FPr | GAAATTGACGAGGGGTGTCT | SEQ ID NO: 1864 |
| | | Probe | CTCTGAGCGCCTCCATCCAAGG | SEQ ID NO: 1865 |
| | | RPr | AGGAGCTAACGGAGAACCTG | SEQ ID NO: 1866 |
| SEMA3B | NM_004636.1 | FPr | GCTCCAGGATGTGTTTCTGTTG | SEQ ID NO: 1867 |
| | | Probe | TCGCGGGACCACCGGACC | SEQ ID NO: 1868 |
| | | RPr | ACGTGGAGAAGACGGCATAGA | SEQ ID NO: 1869 |
| SEMA3F | NM_004186.1 | FPr | CGCGAGCCCCTCATTATACA | SEQ ID NO: 1870 |
| | | Probe | CTCCCCACAGCGCATCGAGGAA | SEQ ID NO: 1871 |
| | | RPr | CACTCGCCGTTGACATCCT | SEQ ID NO: 1872 |
| SEMA4B | NM_020210.1 | FPr | TTCCAGCCCAACACAGTGAA | SEQ ID NO: 1873 |
| | | Probe | ACTTTGGCCTGCCCGCTCCTCT | SEQ ID NO: 1874 |
| | | RPr | GAGTCGGGTCGCCAGGTT | SEQ ID NO: 1875 |
| SFRP2 | NM_003013.2 | FPr | CAAGCTGAACGGTGTGTCC | SEQ ID NO: 1876 |
| | | Probe | CAGCACCGATTTCTTCAGGTCCCT | SEQ ID NO: 1877 |
| | | RPr | TGCAAGCTGTCTTTGAGCC | SEQ ID NO: 1878 |
| SFRP4 | NM_003014.2 | FPr | TACAGGATGAGGCTGGGC | SEQ ID NO: 1879 |
| | | Probe | CCTGGGACAGCCTATGTAAGGCCA | SEQ ID NO: 1880 |
| | | RPr | GTTGTTAGGGCAAGGGGC | SEQ ID NO: 1881 |
| SGCB | NM_000232.1 | FPr | CAGTGGAGACCAGTTGGGTAGTG | SEQ ID NO: 1882 |
| | | Probe | CACACATGCAGAGCTTGTAGCGTACCCA | SEQ ID NO: 1883 |
| | | RPr | CCTTGAAGAGCGTCCCATCA | SEQ ID NO: 1884 |
| SHC1 | NM_003029.3 | FPr | CCAACACCTTCTTGGCTTCT | SEQ ID NO: 1885 |
| | | Probe | CCTGTGTTCTTGCTGAGCACCCTC | SEQ ID NO: 1886 |
| | | RPr | CTGTTATCCCAACCCAAACC | SEQ ID NO: 1887 |
| SHH | NM_000193.2 | FPr | GTCCAAGGCACATATCCACTG | SEQ ID NO: 1888 |
| | | Probe | CACCGAGTTCTCTGCTTTCACCGA | SEQ ID NO: 1889 |
| | | RPr | GAAGCAGCCTCCCGATTT | SEQ ID NO: 1890 |
| SI | NM_001041.1 | FPr | AACGGACTCCCTCAATTTGT | SEQ ID NO: 1891 |
| | | Probe | TGTCCATGGTCATGCAAATCTTGC | SEQ ID NO: 1892 |
| | | RPr | GAAATTGCAGGGTCCAAGAT | SEQ ID NO: 1893 |
| Siah-1 | NM_003031.2 | FPr | TTGGCATTGGAACTACATTCA | SEQ ID NO: 1894 |
| | | Probe | TCCGCGGTATCCTCGGATTAGTTC | SEQ ID NO: 1895 |
| | | RPr | GGTATGGAGAAGGGGGTCC | SEQ ID NO: 1896 |
| SIAT4A | NM_003033.2 | FPr | AACCACAGTTGGAGGAGGAC | SEQ ID NO: 1897 |
| | | Probe | CAGAGACAGTTTCCCTCCCCGCT | SEQ ID NO: 1898 |
| | | RPr | CGAAGGAAGGGTGTTGGTAT | SEQ ID NO: 1899 |
| SIAT7B | NM_006456.1 | FPr | TCCAGCCCAAATCCTCCT | SEQ ID NO: 1900 |
| | | Probe | TGGCACATCCTACCCCAGATGCTA | SEQ ID NO: 1901 |
| | | RPr | GGTGTCCTGGAGTCCTTGAA | SEQ ID NO: 1902 |
| SIM2 | NM_005069.2 | FPr | GATGGTAGGAAGGGATGTGC | SEQ ID NO: 1903 |
| | | Probe | CGCCTCTCCACGCACTCAGCTAT | SEQ ID NO: 1904 |
| | | RPr | CACAAGGAGCTGTGAATGAGG | SEQ ID NO: 1905 |
| SIN3A | NM_015477.1 | FPr | CCAGAGTCATGCTCATCCAG | SEQ ID NO: 1906 |
| | | Probe | CTGTCCCTGCACTGGTGCAACTG | SEQ ID NO: 1907 |
| | | RPr | CCACCTTCAGCCTCTGAAAT | SEQ ID NO: 1908 |
| SIR2 | NM_012238.3 | FPr | AGCTGGGGTGTCTGTTTCAT | SEQ ID NO: 1909 |
| | | Probe | CCTGACTTCAGGTCAAGGGATGG | SEQ ID NO: 1910 |
| | | RPr | ACAGCAAGGCGAGCATAAAT | SEQ ID NO: 1911 |
| SKP1A | NM_006930.2 | FPr | CCATTGCCTTTGCTTTGTTCAT | SEQ ID NO: 1912 |
| | | Probe | TCCCATGGTTTTTATTCTGCCCTGCTG | SEQ ID NO: 1913 |
| | | RPr | TTCCGGATTTCCTTTCTTTGC | SEQ ID NO: 1914 |
| SKP2 | NM_005983.2 | FPr | AGTTGCAGAATCTAAGCCTGGAA | SEQ ID NO: 1915 |
| | | Probe | CCTGCGGCTTTCGGATCCCA | SEQ ID NO: 1916 |
| | | RPr | TGAGTTTTTTGCGAGAGTATTGACA | SEQ ID NO: 1917 |
| SLC25A3 | NM_213611.1 | FPr | TCTGCCAGTGCTGAATTCTT | SEQ ID NO: 1918 |
| | | Probe | TGCTGACATTGCCCTGGCTCCTAT | SEQ ID NO: 1919 |
| | | RPr | TTCGAACCTTAGCAGCTTCC | SEQ ID NO: 1920 |

TABLE A-continued

| Gene | Accession | Reagt | Sequence | SEQ ID NO |
|---|---|---|---|---|
| SLC2A1 | NM_006516.1 | FPr | GCCTGAGTCTCCTGTGCC | SEQ ID NO: 1921 |
| | | Probe | ACATCCCAGGCTTCACCCTGAATG | SEQ ID NO: 1922 |
| | | RPr | AGTCTCCACCCTCAGGCAT | SEQ ID NO: 1923 |
| SLC31A1 | NM_001859.2 | FPr | CCGTTCGAAGAGTCGTGAG | SEQ ID NO: 1924 |
| | | Probe | TCTCCGAATCTTAACCCGTCACCC | SEQ ID NO: 1925 |
| | | RPr | AGTCCAGCCACTAGCACCTC | SEQ ID NO: 1926 |
| SLC5A8 | NM_145913.2 | FPr | CCTGCTTTCAACCACATTGA | SEQ ID NO: 1927 |
| | | Probe | TCCCATTGCTCTTGCCACTCTGAT | SEQ ID NO: 1928 |
| | | RPr | AGAGCAGCTTCACAAACGAG | SEQ ID NO: 1929 |
| SLC7A5 | NM_003486.4 | FPr | GCGCAGAGGCCAGTTAAA | SEQ ID NO: 1930 |
| | | Probe | AGATCACCTCCTCGAACCCACTCC | SEQ ID NO: 1931 |
| | | RPr | AGCTGAGCTGTGGGTTGC | SEQ ID NO: 1932 |
| SLPI | NM_003064.2 | FPr | ATGGCCAATGTTTGATGCT | SEQ ID NO: 1933 |
| | | Probe | TGGCCATCCATCTCACAGAAATTGG | SEQ ID NO: 1934 |
| | | RPr | ACACTTCAAGTCACGCTTGC | SEQ ID NO: 1935 |
| SMARCA3 | NM_003071.2 | FPr | AGGGACTGTCCTGGCACAT | SEQ ID NO: 1936 |
| | | Probe | AGCAAAAGACCCAGGACATCTGCA | SEQ ID NO: 1937 |
| | | RPr | CAACAAATTTGCCGCAGTC | SEQ ID NO: 1938 |
| SNAI1 | NM_005985.2 | FPr | CCCAATCGGAAGCCTAACTA | SEQ ID NO: 1939 |
| | | Probe | TCTGGATTAGAGTCCTGCAGCTCGC | SEQ ID NO: 1940 |
| | | RPr | GTAGGGCTGCTGGAAGGTAA | SEQ ID NO: 1941 |
| SNAI2 | NM_003068.3 | FPr | GGCTGGCCAAACATAAGCA | SEQ ID NO: 1942 |
| | | Probe | CTGCACTGCGATGCCCAGTCTAGAAAATC | SEQ ID NO: 1943 |
| | | RPr | TCCTTGTCACAGTATTTACAGCTGAA | SEQ ID NO: 1944 |
| SNRPF | NM_003095.1 | FPr | GGCTGGTCGGCAGAGAGTAG | SEQ ID NO: 1945 |
| | | Probe | AAACTCATGTAAACCACGGCCGAATGTTG | SEQ ID NO: 1946 |
| | | RPr | TGAGGAAAGGTTTGGGATTGA | SEQ ID NO: 1947 |
| SOD1 | NM_000454.3 | FPr | TGAAGAGAGGCATGTTGGAG | SEQ ID NO: 1948 |
| | | Probe | TTTGTCAGCAGTCACATTGCCCAA | SEQ ID NO: 1949 |
| | | RPr | AATAGACACATCGGCCACAC | SEQ ID NO: 1950 |
| SOD2 | NM_000636.1 | FPr | GCTTGTCCAAATCAGGATCCA | SEQ ID NO: 1951 |
| | | Probe | AACAACAGGCCTTATTCCACTGCTGGG | SEQ ID NO: 1952 |
| | | RPr | AGCGTGCTCCCACACATCA | SEQ ID NO: 1953 |
| SOS1 | NM_005633.2 | FPr | TCTGCACCAAATTCTCCAAG | SEQ ID NO: 1954 |
| | | Probe | AACACCGTTAACACCTCCGCCTG | SEQ ID NO: 1955 |
| | | RPr | GTGGTACTGGAAGCACCAGA | SEQ ID NO: 1956 |
| SOX17 | NM_022454.2 | FPr | TCGTGTGCAAGCCTGAGA | SEQ ID NO: 1957 |
| | | Probe | CTCCCCTACCAGGGGCATGACTC | SEQ ID NO: 1958 |
| | | RPr | CTGTCGGGGAGATTCACAC | SEQ ID NO: 1959 |
| SPARC | NM_003118.1 | FPr | TCTTCCCTGTACACTGGCAGTTC | SEQ ID NO: 1960 |
| | | Probe | TGGACCAGCACCCCATTGACGG | SEQ ID NO: 1961 |
| | | RPr | AGCTCGGTGTGGGAGAGGTA | SEQ ID NO: 1962 |
| SPINT2 | NM_021102.1 | FPr | AGGAATGCAGCGGATTCCT | SEQ ID NO: 1963 |
| | | Probe | CCCAAGTGCTCCCAGAAGGCAGG | SEQ ID NO: 1964 |
| | | RPr | TCGCTGGAGTGGTCTTCAGA | SEQ ID NO: 1965 |
| SPRY1 | AK026960.1 | FPr | CAGACCAGTCCCTGGTCATAGG | SEQ ID NO: 1966 |
| | | Probe | CTGGGTCCGGATTGCCCTTTCAG | SEQ ID NO: 1967 |
| | | RPr | CCTTCAAGTCATCCACAATCAGTT | SEQ ID NO: 1968 |
| SPRY2 | NM_005842.1 | FPr | TGTGGCAAGTGCAAATGTAA | SEQ ID NO: 1969 |
| | | Probe | CAGAGGCCTTGGGTAGGTGCACTC | SEQ ID NO: 1970 |
| | | RPr | GTCGCAGATCCAGTCTGATG | SEQ ID NO: 1971 |
| SR-A1 | NM_021228.1 | FPr | AGATGGAAGAAGCCAACCTG | SEQ ID NO: 1972 |
| | | Probe | CTGGATCAGCTCCTGGGCCTTC | SEQ ID NO: 1973 |
| | | RPr | CTGTGGCTGAGGATCTGGT | SEQ ID NO: 1974 |
| ST14 | NM_021978.2 | FPr | TGACTGCACATGGAACATTG | SEQ ID NO: 1975 |
| | | Probe | AGGTGCCCAACAACCAGCATGT | SEQ ID NO: 1976 |
| | | RPr | AAGAATTTGAAGCGCACCTT | SEQ ID NO: 1977 |

TABLE A-continued

| Gene | Accession | Reagt | Sequence | SEQ ID NO |
|---|---|---|---|---|
| STAT1 | NM_007315.1 | FPr | GGGCTCAGCTTTCAGAAGTG | SEQ ID NO: 1978 |
| | | Probe | TGGCAGTTTTCTTCTGTCACCAAAA | SEQ ID NO: 1979 |
| | | RPr | ACATGTTCAGCTGGTCCACA | SEQ ID NO: 1980 |
| STAT3 | NM_003150.1 | FPr | TCACATGCCACTTTGGTGTT | SEQ ID NO: 1981 |
| | | Probe | TCCTGGGAGAGATTGACCAGCA | SEQ ID NO: 1982 |
| | | RPr | CTTGCAGGAAGCGGCTATAC | SEQ ID NO: 1983 |
| STAT5A | NM_003152.1 | FPr | GAGGCGCTCAACATGAAATTC | SEQ ID NO: 1984 |
| | | Probe | CGGTTGCTCTGCACTTCGGCCT | SEQ ID NO: 1985 |
| | | RPr | GCCAGGAACACGAGGTTCTC | SEQ ID NO: 1986 |
| STAT5B | NM_012448.1 | FPr | CCAGTGGTGGTGATCGTTCA | SEQ ID NO: 1987 |
| | | Probe | CAGCCAGGACAACAATGCGACGG | SEQ ID NO: 1988 |
| | | RPr | GCAAAAGCATTGTCCCAGAGA | SEQ ID NO: 1989 |
| STC1 | NM_003155.1 | FPr | CTCCGAGGTGAGGAGGACT | SEQ ID NO: 1990 |
| | | Probe | CACATCAAACGCACATCCCATGAG | SEQ ID NO: 1991 |
| | | RPr | ACCTCTCCCTGGTTATGCAC | SEQ ID NO: 1992 |
| STK11 | NM_000455.3 | FPr | GGACTCGGAGACGCTGTG | SEQ ID NO: 1993 |
| | | Probe | TTCTTGAGGATCTTGACGGCCCTC | SEQ ID NO: 1994 |
| | | RPr | GGGATCCTTCGCAACTTCTT | SEQ ID NO: 1995 |
| STK15 | NM_003600.1 | FPr | CATCTTCCAGGAGGACCACT | SEQ ID NO: 1996 |
| | | Probe | CTCTGTGGCACCCTGGACTACCTG | SEQ ID NO: 1997 |
| | | RPr | TCCGACCTTCAATCATTTCA | SEQ ID NO: 1998 |
| STMN1 | NM_005563.2 | FPr | AATACCCAACGCACAAATGA | SEQ ID NO: 1999 |
| | | Probe | CACGTTCTCTGCCCCGTTTCTTG | SEQ ID NO: 2000 |
| | | RPr | GGAGACAATGCAAACCACAC | SEQ ID NO: 2001 |
| STMY3 | NM_005940.2 | FPr | CCTGGAGGCTGCAACATACC | SEQ ID NO: 2002 |
| | | Probe | ATCCTCCTGAAGCCCTTTTCGCAGC | SEQ ID NO: 2003 |
| | | RPr | TACAATGGCTTTGGAGGATAGCA | SEQ ID NO: 2004 |
| STS | NM_000351.2 | FPr | GAAGATCCCTTTCCTCCTACTGTTC | SEQ ID NO: 2005 |
| | | Probe | CTTCGTGGCTCTCGGCTTCCCA | SEQ ID NO: 2006 |
| | | RPr | GGATGATGTTCGGCCTTGAT | SEQ ID NO: 2007 |
| SURV | NM_001168.1 | FPr | TGTTTTGATTCCCGGGCTTA | SEQ ID NO: 2008 |
| | | Probe | TGCCTTCTTCCTCCCTCACTTCTCACCT | SEQ ID NO: 2009 |
| | | RPr | CAAAGCTGTCAGCTCTAGCAAAG | SEQ ID NO: 2010 |
| TAGLN | NM_003186.2 | FPr | GATGGAGCAGGTGGCTCAGT | SEQ ID NO: 2011 |
| | | Probe | CCCAGAGTCCTCAGCCGCCTTCAG | SEQ ID NO: 2012 |
| | | RPr | AGTCTGGAACATGTCAGTCTTGATG | SEQ ID NO: 2013 |
| TBP | NM_003194.1 | FPr | GCCCGAAACGCCGAATATA | SEQ ID NO: 2014 |
| | | Probe | TACCGCAGCAAACCGCTTGGG | SEQ ID NO: 2015 |
| | | RPr | CGTGGCTCTCTTATCCTCATGAT | SEQ ID NO: 2016 |
| TCF-1 | NM_000545.3 | FPr | GAGGTCCTGAGCACTGCC | SEQ ID NO: 2017 |
| | | Probe | CTGGGTTCACAGGCTCCTTTGTCC | SEQ ID NO: 2018 |
| | | RPr | GATGTGGGACCATGCTTGT | SEQ ID NO: 2019 |
| TCF-7 | NM_003202.2 | FPr | GCAGCTGCAGTCAACAGTTC | SEQ ID NO: 2020 |
| | | Probe | AAGTCATGGCCCAAATCCAGTGTG | SEQ ID NO: 2021 |
| | | RPr | CTGTGAATGGGGAGGGGT | SEQ ID NO: 2022 |
| TCF7L1 | NM_031283.1 | FPr | CCGGGACACTTTCCAGAAG | SEQ ID NO: 2023 |
| | | Probe | TCTCACTTCGGCGAAATAGTCCCG | SEQ ID NO: 2024 |
| | | RPr | AGAACGCGCTGTCCTGAG | SEQ ID NO: 2025 |
| TCF7L2 | NM_030756.1 | FPr | CCAATCACGACAGGAGGATT | SEQ ID NO: 2026 |
| | | Probe | AGACACCCCTACCCCACAGCTCTG | SEQ ID NO: 2027 |
| | | RPr | TGGACACGGAAGCATTGAC | SEQ ID NO: 2028 |
| TCFL4 | NM_170607.2 | FPr | CTGACTGCTCTGCTTAAAGGTGAA | SEQ ID NO: 2029 |
| | | Probe | TAGCAGGAACAACAACAAAAGCCAACCAA | SEQ ID NO: 2030 |
| | | RPr | ATGTCTTGCACTGGCTACCTTGT | SEQ ID NO: 2031 |
| TEK | NM_000459.1 | FPr | ACTTCGGTGCTACTTAACAACTTACATC | SEQ ID NO: 2032 |
| | | Probe | AGCTCGGACCACGTACTGCTCCCTG | SEQ ID NO: 2033 |
| | | RPr | CCTGGGCCTTGGTGTTGAC | SEQ ID NO: 2034 |

TABLE A-continued

| Gene | Accession | Reagt | Sequence | SEQ ID NO |
|---|---|---|---|---|
| TERC | U86046.1 | FPr | AAGAGGAACGGAGCGAGTC | SEQ ID NO: 2035 |
| | | Probe | CACGTCCCACAGCTCAGGGAATC | SEQ ID NO: 2036 |
| | | RPr | ATGTGTGAGCCGAGTCCTG | SEQ ID NO: 2037 |
| TERT | NM_003219.1 | FPr | GACATGGAGAACAAGCTGTTTGC | SEQ ID NO: 2038 |
| | | Probe | ACCAAACGCAGGAGCAGCCCG | SEQ ID NO: 2039 |
| | | RPr | GAGGTGTCACCAACAAGAAATCAT | SEQ ID NO: 2040 |
| TFF3 | NM_003226.1 | FPr | AGGCACTGTTCATCTCAGTTTTTCT | SEQ ID NO: 2041 |
| | | Probe | CAGAAAGCTTGCCGGGAGCAAAGG | SEQ ID NO: 2042 |
| | | RPr | CATCAGGCTCCAGATATGAACTTTC | SEQ ID NO: 2043 |
| TGFA | NM_003236.1 | FPr | GGTGTGCCACAGACCTTCCT | SEQ ID NO: 2044 |
| | | Probe | TTGGCCTGTAATCACCTGTGCAGCCTT | SEQ ID NO: 2045 |
| | | RPr | ACGGAGTTCTTGACAGAGTTTTGA | SEQ ID NO: 2046 |
| TGFB2 | NM_003238.1 | FPr | ACCAGTCCCCCAGAAGACTA | SEQ ID NO: 2047 |
| | | Probe | TCCTGAGCCCGAGGAAGTCCC | SEQ ID NO: 2048 |
| | | RPr | CCTGGTGCTGTTGTAGATGG | SEQ ID NO: 2049 |
| TGFB3 | NM_003239.1 | FPr | GGATCGAGCTCTTCCAGATCCT | SEQ ID NO: 2050 |
| | | Probe | CGGCCAGATGAGCACATTGCC | SEQ ID NO: 2051 |
| | | RPr | GCCACCGATATAGCGCTGTT | SEQ ID NO: 2052 |
| TGFBI | NM_000358.1 | FPr | GCTACGAGTGCTGTCCTGG | SEQ ID NO: 2053 |
| | | Probe | CCTTCTCCCCAGGGACCTTTTCAT | SEQ ID NO: 2054 |
| | | RPr | AGTGGTAGGGCTGCTGGAC | SEQ ID NO: 2055 |
| TGFBR1 | NM_004612.1 | FPr | GTCATCACCTGGCCTTGG | SEQ ID NO: 2056 |
| | | Probe | AGCAATGACAGCTGCCAGTTCCAC | SEQ ID NO: 2057 |
| | | RPr | GCAGACGAAGCACACTGGT | SEQ ID NO: 2058 |
| TGFBR2 | NM_003242.2 | FPr | AACACCAATGGGTTCCATCT | SEQ ID NO: 2059 |
| | | Probe | TTCTGGGCTCCTGATTGCTCAAGC | SEQ ID NO: 2060 |
| | | RPr | CCTCTTCATCAGGCCAAACT | SEQ ID NO: 2061 |
| THBS1 | NM_003246.1 | FPr | CATCCGCAAAGTGACTGAAGAG | SEQ ID NO: 2062 |
| | | Probe | CCAATGAGCTGAGGCGGCCTCC | SEQ ID NO: 2063 |
| | | RPr | GTACTGAACTCCGTTGTGATAGCATAG | SEQ ID NO: 2064 |
| THY1 | NM_006288.2 | FPr | GGACAAGACCCTCTCAGGCT | SEQ ID NO: 2065 |
| | | Probe | CAAGCTCCCAAGAGCTTCCAGAGC | SEQ ID NO: 2066 |
| | | RPr | TTGGAGGCTGTGGGTCAG | SEQ ID NO: 2067 |
| TIMP1 | NM_003254.1 | FPr | TCCCTGCGGTCCCAGATAG | SEQ ID NO: 2068 |
| | | Probe | ATCCTGCCCGGAGTGGAACTGAAGC | SEQ ID NO: 2069 |
| | | RPr | GTGGGAACAGGGTGGACACT | SEQ ID NO: 2070 |
| TIMP2 | NM_003255.2 | FPr | TCACCCTCTGTGACTTCATCGT | SEQ ID NO: 2071 |
| | | Probe | CCCTGGGACACCCTGAGCACCA | SEQ ID NO: 2072 |
| | | RPr | TGTGGTTCAGGCTCTTCTTCTG | SEQ ID NO: 2073 |
| TIMP3 | NM_000362.2 | FPr | CTACCTGCCTTGCTTTGTGA | SEQ ID NO: 2074 |
| | | Probe | CCAAGAACGAGTGTCTCTGGACCG | SEQ ID NO: 2075 |
| | | RPr | ACCGAAATTGGAGAGCATGT | SEQ ID NO: 2076 |
| TJP1 | NM_003257.1 | FPr | ACTTTGCTGGGACAAAGGTC | SEQ ID NO: 2077 |
| | | Probe | CTCGGGCCTGCCCACTTCTTC | SEQ ID NO: 2078 |
| | | RPr | CACATGGACTCCTCAGCATC | SEQ ID NO: 2079 |
| TK1 | NM_003258.1 | FPr | GCCGGGAAGACCGTAATTGT | SEQ ID NO: 2080 |
| | | Probe | CAAATGGCTTCCTCTGGAAGGTCCCA | SEQ ID NO: 2081 |
| | | RPr | CAGCGGCACCAGGTTCAG | SEQ ID NO: 2082 |
| TLN1 | NM_006289.2 | FPr | AAGCAGAAGGGAGAGCGTAAGA | SEQ ID NO: 2083 |
| | | Probe | CTTCCAGGCACACAAGAATTGTGGGC | SEQ ID NO: 2084 |
| | | RPr | CCTTGGCCTCAATCTCACTCA | SEQ ID NO: 2085 |
| TMEPAI | NM_020182.3 | FPr | CAGAAGGATGCCTGTGGC | SEQ ID NO: 2086 |
| | | Probe | ATTCCGTTGCCTGACACTGTGCTC | SEQ ID NO: 2087 |
| | | RPr | GTAGACCTGCGGCTCTGG | SEQ ID NO: 2088 |
| TMSB10 | NM_021103.2 | FPr | GAAATCGCCAGCTTCGATAA | SEQ ID NO: 2089 |
| | | Probe | CGTCTCCGTTTTCTTCAGCTTGGC | SEQ ID NO: 2090 |
| | | RPr | GTCGGCAGGGTGTTCTTTT | SEQ ID NO: 2091 |

TABLE A-continued

| Gene | Accession | Reagt | Sequence | SEQ ID NO |
|---|---|---|---|---|
| TMSB4X | NM_021109.2 | FPr | CACATCAAAGAACTACTGACAACGAA | SEQ ID NO: 2092 |
| | | Probe | CCGCGCCTGCCTTTCCCA | SEQ ID NO: 2093 |
| | | RPr | CCTGCCAGCCAGATAGATAGACA | SEQ ID NO: 2094 |
| TNC | NM_002160.1 | FPr | AGCTCGGAACCTCACCGT | SEQ ID NO: 2095 |
| | | Probe | CAGCCTTCGGGCTGTGGACATAC | SEQ ID NO: 2096 |
| | | RPr | GTAGCAGCCTTGAGGCCC | SEQ ID NO: 2097 |
| TNF | NM_000594.1 | FPr | GGAGAAGGGTGACCGACTCA | SEQ ID NO: 2098 |
| | | Probe | CGCTGAGATCAATCGGCCCGACTA | SEQ ID NO: 2099 |
| | | RPr | TGCCCAGACTCGGCAAAG | SEQ ID NO: 2100 |
| TNFRSF5 | NM_001250.3 | FPr | TCTCACCTCGCTATGGTTCGT | SEQ ID NO: 2101 |
| | | Probe | TGCCTCTGCAGTGCGTCCTCTGG | SEQ ID NO: 2102 |
| | | RPr | GATGGACAGCGGTCAGCAA | SEQ ID NO: 2103 |
| TNFRSF6B | NM_003823.2 | FPr | CCTCAGCACCAGGGTACCA | SEQ ID NO: 2104 |
| | | Probe | TGACGGCACGCTCACACTCCTCAG | SEQ ID NO: 2105 |
| | | RPr | TGTCCTGGAAAGCCACAAAGT | SEQ ID NO: 2106 |
| TNFSF4 | NM_003326.2 | FPr | CTTCATCTTCCCTCTACCCAGA | SEQ ID NO: 2107 |
| | | Probe | CAGGGGTTGGACCCTTTCCATCTT | SEQ ID NO: 2108 |
| | | RPr | GCTGCATTTCCCACATTCTC | SEQ ID NO: 2109 |
| TOP2A | NM_001067.1 | FPr | AATCCAAGGGGGAGAGTGAT | SEQ ID NO: 2110 |
| | | Probe | CATATGGACTTTGACTCAGCTGTGGC | SEQ ID NO: 2111 |
| | | RPr | GTACAGATTTTGCCCGAGGA | SEQ ID NO: 2112 |
| TOP2B | NM_001068.1 | FPr | TGTGGACATCTTCCCCTCAGA | SEQ ID NO: 2113 |
| | | Probe | TTCCCTACTGAGCCACCTTCTCTG | SEQ ID NO: 2114 |
| | | RPr | CTAGCCCGACCGGTTCGT | SEQ ID NO: 2115 |
| TP | NM_001953.2 | FPr | CTATATGCAGCCAGAGATGTGACA | SEQ ID NO: 2116 |
| | | Probe | ACAGCCTGCCACTCATACAGCC | SEQ ID NO: 2117 |
| | | RPr | CCACGAGTTTCTTACTGAGAATGG | SEQ ID NO: 2118 |
| TP53BP1 | NM_005657.1 | FPr | TGCTGTTGCTGAGTCTGTTG | SEQ ID NO: 2119 |
| | | Probe | CCAGTCCCCAGAAGACCATGTCTG | SEQ ID NO: 2120 |
| | | RPr | CTTGCCTGGCTTCACAGATA | SEQ ID NO: 2121 |
| TP53BP2 | NM_005426.1 | FPr | GGGCCAAATATTCAGAAGC | SEQ ID NO: 2122 |
| | | Probe | CCACCATAGCGGCCATGGAG | SEQ ID NO: 2123 |
| | | RPr | GGATGGGTATGATGGGACAG | SEQ ID NO: 2124 |
| TP53I3 | NM_004881.2 | FPr | GCGGACTTAATGCAGAGACA | SEQ ID NO: 2125 |
| | | Probe | CAGTATGACCCACCTCCAGGAGCC | SEQ ID NO: 2126 |
| | | RPr | TCAAGTCCCAAAATGTTGCT | SEQ ID NO: 2127 |
| TRAG3 | NM_004909.1 | FPr | GACGCTGGTCTGGTGAAGATG | SEQ ID NO: 2128 |
| | | Probe | CCAGGAAACCACGAGCCTCCAGC | SEQ ID NO: 2129 |
| | | RPr | TGGGTGGTTGTTGGACAATG | SEQ ID NO: 2130 |
| TRAIL | NM_003810.1 | FPr | CTTCACAGTGCTCCTGCAGTCT | SEQ ID NO: 2131 |
| | | Probe | AAGTACACGTAAGTTACAGCCACACA | SEQ ID NO: 2132 |
| | | RPr | CATCTGCTTCAGCTCGTTGGT | SEQ ID NO: 2133 |
| TS | NM_001071.1 | FPr | GCCTCGGTGTGCCTTTCA | SEQ ID NO: 2134 |
| | | Probe | CATCGCCAGCTACGCCCTGCTC | SEQ ID NO: 2135 |
| | | RPr | CGTGATGTGCGCAATCATG | SEQ ID NO: 2136 |
| TST | NM_003312.4 | FPr | GGAGCCGGATGCAGTAGGA | SEQ ID NO: 2137 |
| | | Probe | ACCACGGATATGGCCCGAGTCCA | SEQ ID NO: 2138 |
| | | RPr | AAGTCCATGAAAGGCATGTTGA | SEQ ID NO: 2139 |
| TUBA1 | NM_006000.1 | FPr | TGTCACCCCGACTCAACGT | SEQ ID NO: 2140 |
| | | Probe | AGACGCACCGCCCGGACTCAC | SEQ ID NO: 2141 |
| | | RPr | ACGTGGACTGAGATGCATTCAC | SEQ ID NO: 2142 |
| TUBB | NM_001069.1 | FPr | CGAGGACGAGGCTTAAAAAC | SEQ ID NO: 2143 |
| | | Probe | TCTCAGATCAATCGTGCATCCTTAGTGAA | SEQ ID NO: 2144 |
| | | RPr | ACCATGCTTGAGGACAACAG | SEQ ID NO: 2145 |
| TUFM | NM_003321.3 | FPr | GTATCACCATCAATGCGGC | SEQ ID NO: 2146 |
| | | Probe | CATGTGGAGTATAGCACTGCCGCC | SEQ ID NO: 2147 |
| | | RPr | CAGTCTGTGTGGGCGTAGTG | SEQ ID NO: 2148 |

TABLE A-continued

| Gene | Accession | Reagt | Sequence | SEQ ID NO |
|---|---|---|---|---|
| TULP3 | NM_003324.2 | FPr | TGTGTATAGTCCTGCCCCTCAA | SEQ ID NO: 2149 |
| | | Probe | CCGGATTATCCGACATCTTACTGTGA | SEQ ID NO: 2150 |
| | | RPr | CCCGATCCATTCCCCTTTTA | SEQ ID NO: 2151 |
| tusc4 | NM_006545.4 | FPr | GGAGGAGCTAAATGCCTCAG | SEQ ID NO: 2152 |
| | | Probe | ACTCATCAATGGGCAGAGTGCACC | SEQ ID NO: 2153 |
| | | RPr | CCTTCAAGTGGATGGTGTTG | SEQ ID NO: 2154 |
| UBB | NM_018955.1 | FPr | GAGTCGACCCTGCACCTG | SEQ ID NO: 2155 |
| | | Probe | AATTAACAGCCACCCCTCAGGCG | SEQ ID NO: 2156 |
| | | RPr | GCGAATGCCATGACTGAA | SEQ ID NO: 2157 |
| UBC | NM_021009.2 | FPr | ACGCACCCTGTCTGACTACA | SEQ ID NO: 2158 |
| | | Probe | CATCCAGAAAGAGTCCACCCTGCA | SEQ ID NO: 2159 |
| | | RPr | ACCTCTAAGACGGAGCACCA | SEQ ID NO: 2160 |
| UBE2C | NM_007019.2 | FPr | TGTCTGGCGATAAAGGGATT | SEQ ID NO: 2161 |
| | | Probe | TCTGCCTTCCCTGAATCAGACAACC | SEQ ID NO: 2162 |
| | | RPr | ATGGTCCCTACCCATTGAA | SEQ ID NO: 2163 |
| UBE2M | NM_003969.1 | FPr | CTCCATAATTTATGGCCTGCAGTA | SEQ ID NO: 2164 |
| | | Probe | TCTTCTTGGAGCCCAACCCCGAG | SEQ ID NO: 2165 |
| | | RPr | TGCGGCCTCCTTGTTCAG | SEQ ID NO: 2166 |
| UBL1 | NM_003352.3 | FPr | GTGAAGCCACCGTCATCATG | SEQ ID NO: 2167 |
| | | Probe | CTGACCAGGAGGCAAAACCTTCAACTGA | SEQ ID NO: 2168 |
| | | RPr | CCTTCCTTCTTATCCCCCAAGT | SEQ ID NO: 2169 |
| UCP2 | NM_003355.2 | FPr | ACCATGCTCCAGAAGGAGG | SEQ ID NO: 2170 |
| | | Probe | CCCCGAGCCTTCTACAAAGGGTTC | SEQ ID NO: 2171 |
| | | RPr | AACCCAAGCGGAGAAAGG | SEQ ID NO: 2172 |
| UGT1A1 | NM_000463.2 | FPr | CCATGCAGCCTGGAATTTG | SEQ ID NO: 2173 |
| | | Probe | CTACCCAGTGCCCCAACCCATTCTC | SEQ ID NO: 2174 |
| | | RPr | GAGAGGCCTGGGCACGTA | SEQ ID NO: 2175 |
| UMPS | NM_000373.1 | FPr | TGCGGAAATGAGCTCCAC | SEQ ID NO: 2176 |
| | | Probe | CCCTGGCCACTGGGGACTACACTA | SEQ ID NO: 2177 |
| | | RPr | CCTCAGCCATTCTAACCGC | SEQ ID NO: 2178 |
| UNC5A | XM_030300.7 | FPr | GACAGCTGATCCAGGAGCC | SEQ ID NO: 2179 |
| | | Probe | CGGGTCCTGCACTTCAAGGACAGT | SEQ ID NO: 2180 |
| | | RPr | ATGGATAGGCGCAGGTTG | SEQ ID NO: 2181 |
| UNC5B | NM_170744.2 | FPr | AGAACGGAGGCCGTGACT | SEQ ID NO: 2182 |
| | | Probe | CGGGACGCTGCTCGACTCTAAGAA | SEQ ID NO: 2183 |
| | | RPr | CATGCACAGCCCATCTGT | SEQ ID NO: 2184 |
| UNC5C | NM_003728.2 | FPr | CTGAACACAGTGGAGCTGGT | SEQ ID NO: 2185 |
| | | Probe | ACCTGCCGCACACAGAGTTTGC | SEQ ID NO: 2186 |
| | | RPr | CTGGAAGATCTGCCCCTTCTC | SEQ ID NO: 2187 |
| upa | NM_002658.1 | FPr | GTGGATGTGCCCTGAAGGA | SEQ ID NO: 2188 |
| | | Probe | AAGCCAGGCGTCTACACGAGAGTCTCAC | SEQ ID NO: 2189 |
| | | RPr | CTGCGGATCCAGGGTAAGAA | SEQ ID NO: 2190 |
| UPP1 | NM_003364.2 | FPr | ACGGGTCCTGCCTCAGTT | SEQ ID NO: 2191 |
| | | Probe | TCAGCTTTCTCTGCATTGGCTCCC | SEQ ID NO: 2192 |
| | | RPr | CGGGGCAATCATTGTGAC | SEQ ID NO: 2193 |
| VCAM1 | NM_001078.2 | FPr | TGGCTTCAGGAGCTGAATACC | SEQ ID NO: 2194 |
| | | Probe | CAGGCACACACAGGTGGGACACAAAT | SEQ ID NO: 2195 |
| | | RPr | TGCTGTCGTGATGAGAAAATAGTG | SEQ ID NO: 2196 |
| VCL | NM_003373.2 | FPr | GATACCACAACTCCCATCAAGCT | SEQ ID NO: 2197 |
| | | Probe | AGTGGCAGCCACGGCGCC | SEQ ID NO: 2198 |
| | | RPr | TCCCTGTTAGGCGCATCAG | SEQ ID NO: 2199 |
| VCP | NM_007126.2 | FPr | GGCTTTGGCAGCTTCAGAT | SEQ ID NO: 2200 |
| | | Probe | AGCTCCACCCTGGTTCCTGAAG | SEQ ID NO: 2201 |
| | | RPr | CTCCACTGCCCTGACTGG | SEQ ID NO: 2202 |
| VDAC1 | NM_003374.1 | FPr | GCTGCGACATGGATTTCGA | SEQ ID NO: 2203 |
| | | Probe | TTGCTGGGCCTTCCATCCGG | SEQ ID NO: 2204 |
| | | RPr | CCAGCCCTCGTAACCTAGCA | SEQ ID NO: 2205 |

TABLE A-continued

| Gene | Accession | Reagt | Sequence | SEQ ID NO |
|---|---|---|---|---|
| VDAC2 | NM_003375.2 | FPr | ACCCACGGACAGACTTGC | SEQ ID NO: 2206 |
|  |  | Probe | CGCGTCCAATGTGTATTCCTCCAT | SEQ ID NO: 2207 |
|  |  | RPr | AGCTTTGCCAAGGTCAGC | SEQ ID NO: 2208 |
| VDR | NM_000376.1 | FPr | GCCCTGGATTTCAGAAAGAG | SEQ ID NO: 2209 |
|  |  | Probe | CAAGTCTGGATCTGGGACCCTTTCC | SEQ ID NO: 2210 |
|  |  | RPr | AGTTACAAGCCAGGGAAGGA | SEQ ID NO: 2211 |
| VEGF | NM_003376.3 | FPr | CTGCTGTCTTGGGTGCATTG | SEQ ID NO: 2212 |
|  |  | Probe | TTGCCTTGCTGCTCTACCTCCACCA | SEQ ID NO: 2213 |
|  |  | RPr | GCAGCCTGGGACCACTTG | SEQ ID NO: 2214 |
| VEGF_altsplice1 | AF486837.1 | FPr | TGTGAATGCAGACCAAAGAAAGA | SEQ ID NO: 2215 |
|  |  | Probe | AGAGCAAGACAAGAAAATCCCTGTGGGC | SEQ ID NO: 2216 |
|  |  | RPr | GCTTTCTCCGCTCTGAGCAA | SEQ ID NO: 2217 |
| VEGF_altsplice2 | AF214570.1 | FPr | AGCTTCCTACAGCACAACAAAT | SEQ ID NO: 2218 |
|  |  | Probe | TGTCTTGCTCTATCTTTCTTTGGTCTGCA | SEQ ID NO: 2219 |
|  |  | RPr | CTCGGCTTGTCACATTTTTC | SEQ ID NO: 2220 |
| VEGFB | NM_003377.2 | FPr | TGACGATGGCCTGGAGTGT | SEQ ID NO: 2221 |
|  |  | Probe | CTGGGCAGCACCAAGTCCGGA | SEQ ID NO: 2222 |
|  |  | RPr | GGTACCGGATCATGAGGATCTG | SEQ ID NO: 2223 |
| VEGFC | NM_005429.2 | FPr | CCTCAGCAAGACGTTATTTGAAATT | SEQ ID NO: 2224 |
|  |  | Probe | CCTCTCTCTCAAGGCCCCAAACCAGT | SEQ ID NO: 2225 |
|  |  | RPr | AAGTGTGATTGGCAAAACTGATTG | SEQ ID NO: 2226 |
| VIM | NM_003380.1 | FPr | TGCCCTTAAAGGAACCAATGA | SEQ ID NO: 2227 |
|  |  | Probe | ATTTCACGCATCTGGCGTTCCA | SEQ ID NO: 2228 |
|  |  | RPr | GCTTCAACGGCAAAGTTCTCTT | SEQ ID NO: 2229 |
| WIF | NM_007191.2 | FPr | TACAAGCTGAGTGCCCAGG | SEQ ID NO: 2230 |
|  |  | Probe | TACAAAAGCCTCCATTTCGGCACC | SEQ ID NO: 2231 |
|  |  | RPr | CACTCGCAGATGCGTCTTT | SEQ ID NO: 2232 |
| WISP1 | NM_003882.2 | FPr | AGAGGCATCCATGAACTTCACA | SEQ ID NO: 2233 |
|  |  | Probe | CGGGCTGCATCAGCACACGC | SEQ ID NO: 2234 |
|  |  | RPr | CAAACTCCACAGTACTGGGTTGA | SEQ ID NO: 2235 |
| Wnt-3a | NM_033131.2 | FPr | ACAAAGCTACCAGGGAGTCG | SEQ ID NO: 2236 |
|  |  | Probe | TTTGTCCACGCCATTGCCTCAG | SEQ ID NO: 2237 |
|  |  | RPr | TGAGCGTGTCACTGCAAAG | SEQ ID NO: 2238 |
| Wnt-5a | NM_003392.2 | FPr | GTATCAGGACCACATGCAGTACATC | SEQ ID NO: 2239 |
|  |  | Probe | TTGATGCCTGTCTTCGCGCCTTCT | SEQ ID NO: 2240 |
|  |  | RPr | TGTCGGAATTGATACTGGCATT | SEQ ID NO: 2241 |
| Wnt-5b | NM_032642.2 | FPr | TGTCTTCAGGGTCTTGTCCA | SEQ ID NO: 2242 |
|  |  | Probe | TTCCGTAAGAGGCCTGGTGCTCTC | SEQ ID NO: 2243 |
|  |  | RPr | GTGCACGTGGATGAAAGAGT | SEQ ID NO: 2244 |
| WNT2 | NM_003391.1 | FPr | CGGTGGAATCTGGCTCTG | SEQ ID NO: 2245 |
|  |  | Probe | CTCCCTCTGCTCTTGACCTGGCTC | SEQ ID NO: 2246 |
|  |  | RPr | CCATGAAGAGTTGACCTCGG | SEQ ID NO: 2247 |
| WWOX | NM_016373.1 | FPr | ATCGCAGCTGGTGGGTGTA | SEQ ID NO: 2248 |
|  |  | Probe | CTGCTGTTTACCTTGGCGAGGCCTTT | SEQ ID NO: 2249 |
|  |  | RPr | AGCTCCCTGTTGCATGGACTT | SEQ ID NO: 2250 |
| XPA | NM_000380.2 | FPr | GGGTAGAGGGAAAAGGGTTC | SEQ ID NO: 2251 |
|  |  | Probe | CAAAGGCTGAACTGGATTCTTAACCAAGA | SEQ ID NO: 2252 |
|  |  | RPr | TGCACCACCATTGCTATTATT | SEQ ID NO: 2253 |
| XPC | NM_004628.2 | FPr | GATACATCGTCTGCGAGGAA | SEQ ID NO: 2254 |
|  |  | Probe | TTCAAAGACGTGCTCCTGACTGCC | SEQ ID NO: 2255 |
|  |  | RPr | CTTTCAATGACTGCCTGCTC | SEQ ID NO: 2256 |
| XRCC1 | NM_006297.1 | FPr | GGAGATGAAGCCCCCAAG | SEQ ID NO: 2257 |
|  |  | Probe | AGAAGCAACCCCAGACCAAAACCA | SEQ ID NO: 2258 |
|  |  | RPr | GTCCAGCTGCCTGAGTGG | SEQ ID NO: 2259 |
| YB-1 | NM_004559.1 | FPr | AGACTGTGGAGTTTGATGTTGTTGA | SEQ ID NO: 2260 |
|  |  | Probe | TTGCTGCCTCCGCACCCTTTTCT | SEQ ID NO: 2261 |
|  |  | RPr | GGAACACCACCAGGACCTGTAA | SEQ ID NO: 2262 |

TABLE A-continued

| Gene | Accession | Reagt | Sequence | SEQ ID NO |
|---|---|---|---|---|
| YWHAH | NM_003405.2 | FPr | CATGGCCTCCGCTATGAA | SEQ ID NO: 2263 |
| | | Probe | AGGTTCATTCAGCTCTGTCACCGC | SEQ ID NO: 2264 |
| | | RPr | GGAGATTTCGATCTTCATTGGA | SEQ ID NO: 2265 |
| zbtb7 | NM_015898.2 | FPr | CTGCGTTCACACCCCAGT | SEQ ID NO: 2266 |
| | | Probe | TCTCTCCAGAACAGCTCGCCCTGT | SEQ ID NO: 2267 |
| | | RPr | CTCAGCCACGACAGATGGT | SEQ ID NO: 2268 |
| ZG16 | NM_152338.1 | FPr | TGCTGAGCCTCCTCTCCTT | SEQ ID NO: 2269 |
| | | Probe | TACTCCTCATCACAGTGCCCTGC | SEQ ID NO: 2270 |
| | | RPr | GGATGGGGGTTAGTGATAAGG | SEQ ID NO: 2271 |

TABLE B

| Gene | Locus Link | Sequence | SEQ ID NO |
|---|---|---|---|
| A-Catenin | NM_001903.1 | CGTTCCGATCCTCTATACTGCATCCCAGGCATGCCTACAGCACCCTGATGTCGCAGCCTATAAGGCCAACAGGGACCT | SEQ ID NO: 1 |
| ABCB1 | NM_000927.2 | AAACACCACTGGAGCATTGACTACCAGGCTCGCCAATGATGCTGCTCAAGTTAAAGGGGCTATAGGTTCCAGGCTTG | SEQ ID NO: 2 |
| ABCC5 | NM_005688.1 | TGCAGACTGTACCATGCTGACCATTGCCCATCGCCTGCACACGGTTCTAGGCTCCGATAGGATTATGGTGCTGGCC | SEQ ID NO: 3 |
| ABCC6 | NM_001171.2 | GGATGAACCTCGACCTGCTGCAGGAGCACTCGGACGAGGCTATCTGGGCAGCCCTGGAGACGGTGCAGCTC | SEQ ID NO: 4 |
| ACP1 | NM_004300.2 | GCTACCAAGTCCGTGCTGTTTGTGTGTCTGGGTAACATTTGTCGATCACCCATTGCAGAAGCAGTTTTC | SEQ ID NO: 5 |
| ADAM10 | NM_001110.1 | CCCATCAACTTGTGCCAGTACAGGGTCTGTGCAGTGGAGTAGGCACTTCAGTGGTCGAACCATCACC | SEQ ID NO: 6 |
| ADAM17 | NM_003183.3 | GAAGTGCCAGGAGGCGATTAATGCTACTTGCAAAGGCGTGTCCTACTGCACAGGTAATAGCAGTGAGTGCCCG | SEQ ID NO: 7 |
| ADAMTS12 | NM_030955.2 | GGAGAAGGGTGGAGTGCAGCACCCAGATGGATTCTGACTGTGCGGCCATCCAGAGACCTGACCCTG | SEQ ID NO: 8 |
| ADPRT | NM_001618.2 | TTGACAACCTGCTGGACATCGAGGTGGCCTACAGTCTGCTCAGGGGAGGGTCTGATGATAGCAGCAAGGATCCCAT | SEQ ID NO: 9 |
| AGXT | NM_000030.1 | CTTTTCCCTCCAGTGGCACCTCCTGGAAACAGTCCACTTGGGCGCAAAACCCAGTGCCTTCCAAAT | SEQ ID NO: 10 |
| AKAP12 | NM_005100.2 | TAGAGAGCCCCTGACAATCCTGAGGCTTCATCAGGAGCTAGAGCCATTTAACATTTCCTCTTTCCAAGACCAACC | SEQ ID NO: 11 |
| AKT1 | NM_005163.1 | CGCTTCTATGGCGCTGAGATTGTGTCAGCCCTGGACTACCTGCACTCGGAGAAGAACGTGGTGTACCGGGA | SEQ ID NO: 12 |
| AKT2 | NM_001626.2 | TCCTGCCACCCTTCAAACCTCAGGTCACGTCCGAGGTCGACACAAGGTACTTCGATGATGAATTTACCGCC | SEQ ID NO: 13 |
| AKT3 | NM_005465.1 | TTGTCTCTGCCTTGGACTATCTACATTCCGGAAAGATTGTGTACCGTGATCTCAAGTTGGAGAATCTAATGCTGG | SEQ ID NO: 14 |
| AL137428 | AL137428.1 | CAAGAAGAGGCTCTACCCTGGGACTGGGAATTTCCAAGGCCACCTTTGAGGATCGCAGAGCTCATTT | SEQ ID NO: 15 |
| ALCAM | NM_001627.1 | GAGGAATATGGAATCCAAGGGGCCAGTTCCTGCCGTCTGCTCTTCTGCCTCTTGATCTCCGCCAC | SEQ ID NO: 16 |
| ALDH1A1 | NM_000689.1 | GAAGGAGATAAGGAGGATGTTGACAAGGCAGTGAAGGCCGCAAGACAGGCTTTTCAGATTGGATCTCCGTGGCG | SEQ ID NO: 17 |
| ALDOA | NM_000034.2 | GCCTGTACGTGCCAGCTCCCCGACTGCCAGAGCCTCAACTGTCTCTGCTTCGAGATCAAGCTCCGATGA | SEQ ID NO: 18 |
| AMFR | NM_001144.2 | GATGGTTCAGCTCTGCAAGGATCGATTTGAATATCTTTCCTTCTCGCCCACCACGCCGATGAGCAGCCACGGTCGA | SEQ ID NO: 19 |
| ANGPT2 | NM_001147.1 | CCGTGAAAGCTGCTCTGTAAAAGCTGACACAGCCCTCCCAAGTGAGCAGGACTGTTCTTCCCACTGCAA | SEQ ID NO: 20 |

TABLE B-continued

| Gene | Locus Link | Sequence | SEQ ID NO |
|---|---|---|---|
| ANTXR1 | NM_032208.1 | CTCCAGGTGTACCTCCAACCCTAGCCTTCTCCCACAGCTGCCTACAACAGAGTCTC CCAGCCTTCTC | SEQ ID NO: 21 |
| ANXA1 | NM_000700.1 | GCCCCTATCCTACCTTCAATCCATCCTCGGATGTCGCTGCCTTGCATAAGGCCATA ATGGTTAAAGG | SEQ ID NO: 22 |
| ANXA2 | NM_004039.1 | CAAGACACTAAGGGCGACTACCAGAAAGCGCTGCTGTACCTGTGTGGTGGAGATGA CTGAAGCCCGACACG | SEQ ID NO: 23 |
| ANXA5 | NM_001154.2 | GCTCAAGCCTGGAAGATGACGTGGTGGGGGACACTTCAGGGTACTACCAGCGGATG TTGGTGGTTCT | SEQ ID NO: 24 |
| AP-1 (JUN official) | NM_002228.2 | GACTGCAAAGATGGAAACGACCTTCTATGACGATGCCCTCAACGCCTCGTTCCTCC CGTCCGAGAGCGGACCTTATGGCTA | SEQ ID NO: 25 |
| APC | NM_000038.1 | GGACAGCAGGAATGTGTTTCTCCATACAGGTCACGGGGAGCCAATGGTTCAGAAAC AAATCGAGTGGGT | SEQ ID NO: 26 |
| APEX-1 | NM_001641.2 | GATGAAGCCTTTCGCAAGTTCCTGAAGGGCCTGGCTTCCCGAAAGCCCCTTGTGCT GTGTGGAGACCT | SEQ ID NO: 27 |
| APG-1 | NM_014278.2 | ACCCCGGCCTGTATATCATTGGGATCAAGAACTCGAGCCATTGGAAATGCAGCAAA GAGCCAGATAG | SEQ ID NO: 28 |
| APN (ANPEP official) | NM_001150.1 | CCACCTTGGACCAAAGTAAAGCGTGGAATCGTTACCGCCTCCCCAACACGCTGAAA CCCGATTCCTACCAGGTGACGCTGAGA | SEQ ID NO: 29 |
| APOC1 | NM_001645.3 | GGAAACACACTGGAGGACAAGGCTCGGGAACTCATCAGCCGCATCAAACAGAGTGA ACTTTCTGCCAAGATGCG | SEQ ID NO: 30 |
| AREG | NM_001657.1 | TGTGAGTGAAATGCCTTCTAGTAGTGAACCGTCCTCGGGAGCCGACTATGACTACT CAGAAGAGTATGATAACGAACCACAA | SEQ ID NO: 31 |
| ARG | NM_005158.2 | CGCAGTGCAGCTGAGTATCTGCTCAGCAGTCTAATCAATGGCAGCTTCCTGGTGCG AGAAAGTGAGAGTAGCCCTGGGCA | SEQ ID NO: 32 |
| ARHF | NM_019034.2 | ACTGGCCCACTTAGTCCTCAAGCTCCCAACCTGCTGTCCCTCAAGCCCCGCTTCTA CCAGCCTGTGGAGTTCAG | SEQ ID NO: 33 |
| ATOH1 | NM_005172.1 | GCAGCCACCTGCAACTTTGCAGGCGAGAGAGCATCCCGTCTACCCGCCTGAGCTGT CCCTCCTGGA | SEQ ID NO: 34 |
| ATP5A1 | NM_004046.3 | GATGCTGCCACTCAACAACTTTTGAGTCGTGGCGTGCGTCTAACTGAGTTGCTGAA GCAAGGACA | SEQ ID NO: 35 |
| ATP5E | NM_006886.2 | CCGCTTTCGCTACAGCATGGTGGCCTACTGGAGACAGGCTGGACTCAGCTACATCC GATACTCCCA | SEQ ID NO: 36 |
| AURKB | NM_004217.1 | AGCTGCAGAAGAGCTGCACATTTGACGAGCAGCGAACAGCCACGATCATGGAGGAG TTGGCAGATGC | SEQ ID NO: 37 |
| Axin 2 | NM_004655.2 | GGCTATGTCTTTGCACCAGCCACCAGCGCCAACGACAGTGAGATATCCAGTGATGC GCTGACGGAT | SEQ ID NO: 38 |
| axin1 | NM_003502.2 | CCGTGTGACAGCATCGTTGTGGCGTACTACTTCTGCGGGGAACCCATCCCCTACCG CACCCTGGTGAG | SEQ ID NO: 39 |
| B-Catenin | NM_001904.1 | GGCTCTTGTGCGTACTGTCCTTCGGGCTGGTGACAGGGAAGACATCACTGAGCCTG CCATCTGTGCTCTTCGTCATCTGA | SEQ ID NO: 40 |
| BAD | NM_032989.1 | GGGTCAGGTGCCTCGAGATCGGGCTTGGGCCCAGAGCATGTTCCAGATCCCAGAGT TTGAGCCGAGTGAGCAG | SEQ ID NO: 41 |
| BAG1 | NM_004323.2 | CGTTGTCAGCACTTGGAATACAAGATGGTTGCCGGGTCATGTTAATTGGGAAAAAG AACAGTCCACAGGAAGAGGTTGAAC | SEQ ID NO: 42 |
| BAG2 | NM_004282.2 | CTAGGGGCAAAAAGCATGACTGCTTTTTCCTGTCTGGCATGGAATCACGCAGTCAC CTTGGGCATTTAG | SEQ ID NO: 43 |
| BAG3 | NM_004281.2 | GAAAGTAAGCCAGGCCCAGTTGGACCAGAACTCCCTCCTGGACACATCCCAATTCA AGTGATCCGCAAAGAGGT | SEQ ID NO: 44 |
| Bak | NM_001188.1 | CCATTCCCACCATTCTACCTGAGGCAGGACGTCTGGGGTGTGGGATTGGTGGGT CTATGTTCCC | SEQ ID NO: 45 |

TABLE B-continued

| Gene | Locus Link | Sequence | SEQ ID NO |
| --- | --- | --- | --- |
| Bax | NM_004324.1 | CCGCCGTGGACACAGACTCCCCCCGAGAGGTCTTTTTCCGAGTGGCAGCTGACATG TTTTCTGACGGCAA | SEQ ID NO: 46 |
| BBC3 | NM_014417.1 | CCTGGAGGGTCCTGTACAATCTCATCATGGGACTCCTGCCCTTACCCAGGGGCCAC AGAGCCCCCGAGATGGAGCCCAATTAG | SEQ ID NO: 47 |
| BCAS1 | NM_003657.1 | CCCCGAGACAACGGAGATAAGTGCTGTTGCGGATGCCAACGGAAAGAATCTTGGGA AAGAGGCCAAACCCGAG | SEQ ID NO: 48 |
| Bcl2 | NM_000633.1 | CAGATGGACCTAGTACCCACTGAGATTTCCACGCCGAAGGACAGCGATGGGAAAAA TGCCCTTAAATCATAGG | SEQ ID NO: 49 |
| BCL2L10 | NM_020396.2 | GCTGGGATGGCTTTTGTCACTTCTTCAGGACCCCCTTTCCACTGGCTTTTTGGAGA AAACAGCTGGTCCAGGC | SEQ ID NO: 50 |
| BCL2L11 | NM_138621.1 | AATTACCAAGCAGCCGAAGACCACCCACGAATGGTTATCTTACGACTGTTACGTTA CATTGTCCGCCTG | SEQ ID NO: 51 |
| BCL2L12 | NM_138639.1 | AACCCACCCCTGTCTTGGAGCTCCGGGTAGCTCTCAAACTCGAGGCTGCGCACCCC CTTTCCCGTCAGCTGAG | SEQ ID NO: 52 |
| Bclx | NM_001191.1 | CTTTTGTGGAACTCTATGGGAACAATGCAGCAGCCGAGAGCCGAAAGGGCCAGGAA CGCTTCAACCGCTG | SEQ ID NO: 53 |
| BCRP | NM_004827.1 | TGTACTGGCGAAGAATATTTGGTAAAGCAGGGCATCGATCTCTCACCCTGGGGCTT GTGGAAGAATCACGTGGC | SEQ ID NO: 54 |
| BFGF | NM_007083.1 | CCAGGAAGAATGCTTAAGATGTGAGTGGATGGATCTCAATGACCTGGCGAAGACTG AAAATACAACTCCCATCACCA | SEQ ID NO: 55 |
| BGN | NM_001711.3 | GAGCTCCGCAAGGATGACTTCAAGGGTCTCCAGCACCTCTACGCCCTCGTCCTGGT GAACAACAAG | SEQ ID NO: 56 |
| BID | NM_001196.2 | GGACTGTGAGGTCAACAACGGTTCCAGCCTCAGGGATGAGTGCATCACAAACCTAC TGGTGTTTGGCTTCC | SEQ ID NO: 57 |
| BIK | NM_001197.3 | ATTCCTATGGCTCTGCAATTGTCACCGGTTAACTGTGGCCTGTGCCCAGGAAGAGC CATTCACTCCTGCC | SEQ ID NO: 58 |
| BIN1 | NM_004305.1 | CCTGCAAAAGGGAACAAGAGCCCTTCGCCTCCAGATGGCTCCCCTGCCGCCACCCC CGAGATCAGAGTCAACCACG | SEQ ID NO: 59 |
| BLMH | NM_000386.2 | GGTTGCTGCCTCCATCAAAGATGGAGAGGCTGTGTGGTTTGGCTGTGATGTTGGAA AACACTTCAATAGCAAGCTGG | SEQ ID NO: 60 |
| BMP2 | NM_001200.1 | ATGTGGACGCTCTTTCAATGGACGTGTCCCCGCGTGCTTCTTAGACGGACTGCGGT CTCCTAAAGGTCGACCATGGT | SEQ ID NO: 61 |
| BMP4 | NM_001202.2 | GGGCTAGCCATTGAGGTGACTCACCTCCATCAGACTCGGACCCACCAGGGCCAGCA TGTCAGGATTAGC | SEQ ID NO: 62 |
| BMP7 | NM_001719.1 | TCGTGGAACATGACAAGGAATTCTTCCACCCACGCTACCACCATCGAGAGTTCCGG TTTGATCTTTCCA | SEQ ID NO: 63 |
| BMPR1A | NM_004329.2 | TTGGTTCAGCGAACTATTGCCAAACAGATTCAGATGGTCCGGCAAGTTGGTAAAGG CCGATATGGAGA | SEQ ID NO: 64 |
| BRAF | NM_004333.1 | CCTTCCGACCAGCAGATGAAGATCATCGAAATCAATTTGGGCAACGAGACCGATCC TCATCAGCTCCCAATGTGCATATAAA | SEQ ID NO: 65 |
| BRCA1 | NM_007295.1 | TCAGGGGCTAGAAATCTGTTGCTATGGGCCCTTCACCAACATGCCCACAGATCAA CTGGAATGG | SEQ ID NO: 66 |
| BRCA2 | NM_000059.1 | AGTTCGTGCTTTGCAAGATGGTGCAGAGCTTTATGAAGCAGTGAAGAATGCAGCAG ACCCAGCTTACCTT | SEQ ID NO: 67 |
| BRK | NM_005975.1 | GTGCAGGAAAGGTTCACAAATGTGGAGTGTCTGCGTCCAATACACGCGTGTGCTCC TCTCCTTACTCCATCGTGTGTGC | SEQ ID NO: 68 |
| BTF3 | NM_001207.2 | CAGTGATCCACTTTAACAACCCTAAAGTTCAGGCATCTCTGGCAGCGAACACTTTC ACCATTACAGGCCATGCT | SEQ ID NO: 69 |
| BTRC | NM_033637.2 | GTTGGGACACAGTTGGTCTGCAGTCGGCCCAGGACGGTCTACTCAGCACAACTGAC TGCTTCA | SEQ ID NO: 70 |
| BUB1 | NM_004336.1 | CCGAGGTTAATCCAGCACGTATGGGGCAAGTGTAGGCTCCCAGCAGGAACTGAGA GCGCCATGTCTT | SEQ ID NO: 71 |

TABLE B-continued

| Gene | Locus Link | Sequence | SEQ ID NO |
|---|---|---|---|
| BUB1B | NM_001211.3 | TCAACAGAAGGCTGAACCACTAGAAAGACTACAGTCCCAGCACCGACAATTCCAAG CTCGAGTGTCTCGGCAAACTCTGTTG | SEQ ID NO: 72 |
| BUB3 | NM_004725.1 | CTGAAGCAGATGGTTCATCATTTCCTGGGCTGTTAAACAAAGCGAGGTTAAGGTTA GACTCTTGGGAATCAGC | SEQ ID NO: 73 |
| c-abl | NM_005157.2 | CCATCTCGCTGAGATACGAAGGGAGGGTGTACCATTACAGGATCAACACTGCTTCT GATGGCAAGCTCTACGTCT | SEQ ID NO: 74 |
| c-kit | NM_000222.1 | GAGGCAACTGCTTATGGCTTAATTAAGTCAGATGCGGCCATGACTGTCGCTGTAAA GATGCTCAAGCCGAGTGCC | SEQ ID NO: 75 |
| c-myb (MYB official) | NM_005375.1 | AACTCAGACTTGGAAATGCCTTCTTTAACTTCCACCCCCCTCATTGGTCACAAATT GACTGTTACAACACCATTTCATAGAGACCAG | SEQ ID NO: 76 |
| c-Src | NM_005417.3 | TGAGGAGTGGTATTTTGGCAAGATCACCAGACGGGAGTCAGAGCGGTTACTGCTCA ATGCAGAGAACCCGAGAG | SEQ ID NO: 77 |
| C20 orf1 | NM_012112.2 | TCAGCTGTGAGCTGCGGATACCGCCCGGCAATGGGACCTGCTCTTAACCTCAAACC TAGGACCGT | SEQ ID NO: 78 |
| C20ORF126 | NM_030815.2 | CCAGCACTGCTCGTTACTGTCTGCCTTCAGTGGTCTGAGGTCCCAGTATGAACTGC CGTGAAGTCAA | SEQ ID NO: 79 |
| C8orf4 | NM_020130.2 | CTACGAGTCAGCCCATCCATCCATGGCTACCACTTCGACACAGCCTCTCGTAAGAA AGCCGTGGGCA | SEQ ID NO: 80 |
| CA9 | NM_001216.1 | ATCCTAGCCCTGGTTTTTGGCCTCCTTTTTGCTGTCACCAGCGTCGCGTTCCTTGT GCAGATGAGAAGGCAG | SEQ ID NO: 81 |
| Cad17 | NM_004063.2 | GAAGGCCAAGAACCGAGTCAAATTATATTCCAGTTTAAGGCCAATCCTCCTGCTGT GACTTTTGAACTAACTGGGGA | SEQ ID NO: 82 |
| CALD1 | NM_004342.4 | CACTAAGGTTTGAGACAGTTCCAGAAAGAACCCAAGCTCAAGACGCAGGACGAGCT CAGTTGTAGAGGGCTAATTCGC | SEQ ID NO: 83 |
| CAPG | NM_001747.1 | GATTGTCACTGATGGGGAGGAGCCTGCTGAGATGATCCAGGTCCTGGGCCCCAAGC CTGCTCTGAAGG | SEQ ID NO: 84 |
| CAPN1 | NM_005186.2 | CAAGAAGCTGTACGAGCTCATCATCACCCGCTACTCGGAGCCCGACCTGGCGGTCG ACTTTGACAATTTCGTTTGCTGC | SEQ ID NO: 85 |
| CASP8 | NM_033357.1 | CCTCGGGGATACTGTCTGATCATCAACAATCACAATTTTGCAAAAGCACGGGAGAA AGTGCCCAAACTTC | SEQ ID NO: 86 |
| CASP9 | NM_001229.2 | TGAATGCCGTGGATTGCACGTGGCCTCTTGAGCAGTGGCTGGTCCAGGGCTAGTGA CTTGTGTCCCATGATCCCTGT | SEQ ID NO: 87 |
| CAT | NM_001752.1 | ATCCATTCGATCTCACCAAGGTTTGGCCTCACAAGGACTACCCTCTCATCCCAGTT GGTAAACTGGTCTTAAACCGGA | SEQ ID NO: 88 |
| CAV1 | NM_001753.3 | GTGGCTAACATTGTGTTCCCATTTCAGCTGATCAGTGGGCCTCCAAGGAGGGGCT GTAAAATGGAGGCCATTG | SEQ ID NO: 89 |
| CBL | NM_005188.1 | TCATTCACAAACCTGGCAGTTATATCTTCCGGCTGAGCTGTACTCGTCTGGGTCAG TGGGCTATTGGGTATG | SEQ ID NO: 90 |
| CCL20 | NM_004591.1 | CCATGTGCTGTACCAAGAGTTTGCTCCTGGCTGCTTTGATGTCAGTGCTGCTACTC CACCTCTGCGGCG | SEQ ID NO: 91 |
| CCL3 | NM_002983.1 | AGCAGACAGTGGTCAGTCCTTTCTTGGCTCTGCTGACACTCGAGCCCACATTCCGT CACCTGCTCAGAATCATGCAG | SEQ ID NO: 92 |
| CCNA2 | NM_001237.2 | CCATACCTCAAGTATTTGCCATCAGTTATTGCTGGAGCTGCCTTTCATTTAGCACT CTACACAGTCACGGGACAAAGCT | SEQ ID NO: 93 |
| CCNB1 | NM_031966.1 | TTCAGGTTGTTCAGGAGACCATGTACATGACTGTCTCCATTATTGATCGGTTCAT GCAGAATAATTGTGTGCCCAAGAAGATG | SEQ ID NO: 94 |
| CCNB2 | NM_004701.2 | AGGCTTCTGCAGGAGACTCTGTACATGTGCGTTGGCATTATGGATCGATTTTACA GGTTCAGCCAGTTTCCC | SEQ ID NO: 95 |
| CCND1 | NM_001758.1 | GCATGTTCGTGGCCTCTAAGATGAAGGAGACCATCCCCCTGACGGCCGAGAAGCTG TGCATCTACACCG | SEQ ID NO: 96 |
| CCND3 | NM_001760.2 | CCTCTGTGCTACAGATTATACCTTTGCCATGTACCCGCCATCCATGATCGCCACGG GCAGCATTGGGGCTGCAGTG | SEQ ID NO: 97 |

TABLE B-continued

| Gene | Locus Link | Sequence | SEQ ID NO |
|---|---|---|---|
| CCNE1 | NM_001238.1 | AAAGAAGATGATGACCGGGTTTACCCAAACTCAACGTGCAAGCCTCGGATTATTGC ACCATCCAGAGGCTC | SEQ ID NO: 98 |
| CCNE2 | NM_057749.1 | ATGCTGTGGCTCCTTCCTAACTGGGGCTTTCTTGACATGTAGGTTGCTTGGTAATA ACCTTTTTGTATATCACAATTTGGGT | SEQ ID NO: 99 |
| CCNE2 variant 1 | NM_057749var1 | GGTCACCAAGAAACATCAGTATGAAATTAGGAATTGTTGGCCACCTGTATTATCTG GGGGGATCAGTCCTTGCATTATCATTGAA | SEQ ID NO: 100 |
| CCR7 | NM_001838.2 | GGATGACATGCACTCAGCTCTTGGCTCCACTGGGATGGGAGGAGAGGACAAGGGAA ATGTCAGG | SEQ ID NO: 101 |
| CD105 | NM_000118.1 | GCAGGTGTCAGCAAGTATGATCAGCAATGAGGCGGTGGTCAATATCCTGTCGAGCT CATCACCACAGCGGAAAAA | SEQ ID NO: 102 |
| CD134 (TNFRSF4 official) | NM_003327.1 | GCCCAGTGCGGAGAACAGGTCCAGCTTGATTCTCGTCTCTGCACTTAAGCTGTTCT CCAGGTGCGTGTGATT | SEQ ID NO: 103 |
| CD18 | NM_000211.1 | CGTCAGGACCCACCATGTCTGCCCCATCACGCGGCCGAGACATGGCTTGGCCACAG CTCTTGAGGATGTCACCAATTAACC | SEQ ID NO: 104 |
| CD24 | NM_013230.1 | TCCAACTAATGCCACCACCAAGGCGGCTGGTGGTGCCCTGCAGTCAACAGCCAGTC TCTTCGTGGTCTCACTCTCTC | SEQ ID NO: 105 |
| CD28 | NM_006139.1 | TGTGAAAGGGAAACACCTTTGTCCAAGTCCCCTATTTCCCGGACCTTCTAAGCCCT TTTGGGTGCT | SEQ ID NO: 106 |
| CD31 | NM_000442.1 | TGTATTTCAAGACCTCTGTGCACTTATTTATGAACCTGCCCTGCTCCCACAGAACA CAGCAATTCCTCAGGCTAA | SEQ ID NO: 107 |
| CD34 | NM_001773.1 | CCACTGCACACACCTCAGAGGCTGTTCTTGGGGCCCTACACCTTGAGGAGGGGCAG GTAAACTCCTG | SEQ ID NO: 108 |
| CD3z | NM_000734.1 | AGATGAAGTGGAAGGCGCTTTTCACCGCGGCCATCCTGCAGGCACAGTTGCCGATT ACAGAGGCA | SEQ ID NO: 109 |
| CD44E | X55150 | ATCACCGACAGCACAGACAGAATCCCTGCTACCAATATGGACTCCAGTCATAGTAC AACGCTTCAGCCTACTGCAAATCCAAACACAGGT | SEQ ID NO: 110 |
| CD44s | M59040.1 | GACGAAGACAGTCCCTGGATCACCGACAGCACAGACAGAATCCCTGCTACCAGAGA CCAAGACACATTCCACCCCAGT | SEQ ID NO: 111 |
| CD44v3 | AJ251595v3 | CACACAAAACAGAACCAGGACTGGACCCAGTGGAACCCAAGCCATTCAAATCCGGA AGTGCTACTTCAG | SEQ ID NO: 112 |
| CD44v6 | AJ251595v6 | CTCATACCAGCCATCCAATGCAAGGAAGGACAACACCAAGCCCAGAGGACAGTTCC TGGACTGATTTCTTCAACCCAA | SEQ ID NO: 113 |
| CD68 | NM_001251.1 | TGGTTCCCAGCCCTGTGTCCACCTCCAAGCCCAGATTCAGATTCGAGTCATGTACA CAACCCAGGGTGGAGGAG | SEQ ID NO: 114 |
| CD80 | NM_005191.2 | TTCAGTTGCTTTGCAGGAAGTGTCTAGAGGAATATGGTGGGCACAGAAGTAGCTCT GGTGACCTTGATCAA | SEQ ID NO: 115 |
| CD82 | NM_002231.2 | GTGCAGGCTCAGGTGAAGTGCTGCGGCTGGGTCAGCTTCTACAACTGGACAGACAA CGCTGAGCTCATGAATCGCCCTGAGGTC | SEQ ID NO: 116 |
| CD8A | NM_171827.1 | AGGGTGAGGTGCTTGAGTCTCCAACGGCAAGGGAACAAGTACTTCTTGATACCTGG GATACTGTGCCC | SEQ ID NO: 117 |
| CD9 | NM_001769.1 | GGGCGTGGAACAGTTTATCTCAGACATCTGCCCCAAGAAGGACGTACTCGAAACCT TCACCGTG | SEQ ID NO: 118 |
| CDC2 | NM_001786.2 | GAGAGCGACGCGGTTGTTGTAGCTGCCGCTGCGGCCGCCGCGGAATAATAAGCCGG GATCTACCATAC | SEQ ID NO: 119 |
| CDC20 | NM_001255.1 | TGGATTGGAGTTCTGGGAATGTACTGGCCGTGGCACTGGACAACAGTGTGTACCTG TGGAGTGCAAGC | SEQ ID NO: 120 |
| cdc25A | NM_001789.1 | TCTTGCTGGCTACGCCTCTTCTGTCCCTGTTAGACGTCCTCCGTCCATATCAGAAC TGTGCCACAATGCAG | SEQ ID NO: 121 |
| CDC25B | NM_021874.1 | AAACGAGCAGTTTGCCATCAGACGCTTCCAGTCTATGCCGGTGAGGCTGCTGGGCC ACAGCCCCGTGCTTCGGAACATCACCAAC | SEQ ID NO: 122 |
| CDC25C | NM_001790.2 | GGTGAGCAGAAGTGGCCTATATCGCTCCCCGTCGATGCCAGAGAACTTGAACAGGC CAAGACTGAAG | SEQ ID NO: 123 |

TABLE B-continued

| Gene | Locus Link | Sequence | SEQ ID NO |
|---|---|---|---|
| CDC4 | NM_018315.2 | GCAGTCCGCTGTGTTCAATATGATGGCAGGAGGGTTGTTAGTGGAGCATATGATTT TATGGTAAAGGTGTGGGATCC | SEQ ID NO: 124 |
| CDC42 | NM_001791.2 | TCCAGAGACTGCTGAAAAGCTGGCCCGTGACCTGAAGGCTGTCAAGTATGTGGAGT GTTCTGCACTTACACA | SEQ ID NO: 125 |
| CDC42BPA | NM_003607.2 | GAGCTGAAAGACGCACACTGTCAGAGGAAACTGGCCATGCAGGAATTCATGGAGAT CAATGAGCGGC | SEQ ID NO: 126 |
| CDC6 | NM_001254.2 | GCAACACTCCCCATTTACCTCCTTGTTCTCCACCAAAGCAAGGCAAGAAAGAGAAT GGTCCCCCTCA | SEQ ID NO: 127 |
| CDCA7 v2 | NM_145810.1 | AAGACCGTGGATGGCTACATGAATGAAGATGACCTGCCCAGAAGCCGTCGCTCCAG ATCATCCGTGACCCT | SEQ ID NO: 128 |
| CDH1 | NM_004360.2 | TGAGTGTCCCCCGGTATCTTCCCCGCCCTGCCAATCCCGATGAAATTGGAAATTTT ATTGATGAAAATCTGAAAGCGGCTG | SEQ ID NO: 129 |
| CDH11 | NM_001797.2 | GTCGGCAGAAGCAGGACTTGTACCTTCTGCCCATAGTGATCAGCGATGGCGGCATC CCGCCCATGAGTAG | SEQ ID NO: 130 |
| CDH3 | NM_001793.3 | ACCCATGTACCGTCCTCGGCCAGCCAACCCAGATGAAATCGGCAACTTTATAATTG AGAACCTGAAGGCGG | SEQ ID NO: 131 |
| CDK2 | NM_001798.2 | AATGCTGCACTACGACCCTAACAAGCGGATTTCGGCCAAGGCAGCCCTGGCTCACC CTTTCTTCCAGGATGTGACCAA | SEQ ID NO: 132 |
| CDX1 | NM_001804.1 | AGCAACACCAGCCTCCTGGCCACCTCCTCTCCAATGCCTGTGAAAGAGGAGTTTCT GCCATAGCCC | SEQ ID NO: 133 |
| Cdx2 | NM_001265.2 | GGGCAGGCAAGGTTTACACTGCGGAAGCCAAAGGCAGCTAAGATAGAAAGCTGGAC TGACCAAAGAC | SEQ ID NO: 134 |
| CEACAM1 | NM_001712.2 | ACTTGCCTGTTCAGAGCACTCATTCCTTCCCACCCCCAGTCCTGTCCTATCACTCT AATTCGGATTTGCCA | SEQ ID NO: 135 |
| CEACAM6 | NM_002483.2 | CACAGCCTCACTTCTAACCTTCTGGAACCCACCCACCACTGCCAAGCTCACTATTG AATCCACGCCATTCAA | SEQ ID NO: 136 |
| CEBPB | NM_005194.2 | GCAACCCACGTGTAACTGTCAGCCGGGCCCTGAGTAATCGCTTAAAGATGTTCCTA CGGGCTTGT | SEQ ID NO: 137 |
| CEGP1 | NM_020974.1 | TGACAATCAGCACACCTGCATTCACCGCTCGGAAGAGGGCCTGAGCTGCATGAATA AGGATCACGGCTGTAGTCACA | SEQ ID NO: 138 |
| CENPA | NM_001809.2 | TAAATTCACTCGTGGTGTGGACTTCAATTGGCAAGCCCAGGCCCTATTGGCCCTAC AAGAGGC | SEQ ID NO: 139 |
| CENPE | NM_001813.1 | GGATGCTGGTGACCTCTTCTTCCCTCACGTTGCAACAGGAATTAAAGGCTAAAAGA AAACGAAGAGTTACTTGGTGCCTTGGC | SEQ ID NO: 140 |
| CENPF | NM_016343.2 | CTCCCGTCAACAGCGTTCTTTCCAAACACTGGACCAGGAGTGCATCCAGATGAAGG CCAGACTCACCC | SEQ ID NO: 141 |
| CES2 | NM_003869.4 | ACTTTGCGAGAAATGGGAACCCCAATGGCGAGGGTCTGCCACACTGGCCGCTGTTC GACCAGGAGGAGCAATACCTG | SEQ ID NO: 142 |
| CGA (CHGA official) | NM_001275.2 | CTGAAGGAGCTCCAAGACCTCGCTCTCCAAGGCGCCAAGGAGAGGGCACATCAGCA GAAGAAACACAGCGGTTTTG | SEQ ID NO: 143 |
| CGB | NM_000737.2 | CCACCATAGGCAGAGGCAGGCCTTCCTACACCCTACTCCCTGTGCCTCCAGCCTCG ACTAGTCCCTAGCACTCGACGACT | SEQ ID NO: 144 |
| CHAF1B | NM_005441.1 | GAGGCCAGTGGTGGAAACAGGTGTGGAGCTGATGAGTCTGCCCTACCGCCTGGTGT TTGCTGTGGCCTCGGA | SEQ ID NO: 145 |
| CHD2 | NM_001271.1 | CTCTGTGCGAGGCTGTCAGCCACACTAGGTATCAGGGATCCCGAGATGGGTACCAG CCCACAGTCCTTACC | SEQ ID NO: 146 |
| CHFR | NM_018223.1 | AAGGAAGTGGTCCCTCTGTGGCAAGTGATGAAGTCTCCAGCTTTGCCTCAGCTCTC CCAGACAGAAAGACTGCGTC | SEQ ID NO: 147 |
| Chk1 | NM_001274.1 | GATAAATTGGTACAAGGGATCAGCTTTTCCCAGCCCACATGTCCTGATCATATGCT TTTGAATAGTCAGTTACTTGGCACCC | SEQ ID NO: 148 |

TABLE B-continued

| Gene | Locus Link | Sequence | SEQ ID NO |
|---|---|---|---|
| Chk2 | NM_007194.1 | ATGTGGAACCCCCACCTACTTGGCGCCTGAAGTTCTTGTTTCTGTTGGGACTGCTG GGTATAACCGTGCTGTGGACTG | SEQ ID NO: 149 |
| CIAP1 | NM_001166.2 | TGCCTGTGGTGGGAAGCTCAGTAACTGGGAACCAAAGGATGATGCTATGTCAGAAC ACCGGAGGCATTTTCC | SEQ ID NO: 150 |
| cIAP2 | NM_001165.2 | GGATATTTCCGTGGCTCTTATTCAAACTCTCCATCAAATCCTGTAAACTCCAGAGC AAATCAAGATTTTTCTGCCTTGATGAGAAG | SEQ ID NO: 151 |
| CKS1B | NM_001826.1 | GGTCCCTAAAACCCATCTGATGTCTGAATCTGAATGGAGGAATCTTGGCGTTCAGC AGAGTCAGGGATGGGTCCATTA | SEQ ID NO: 152 |
| CKS2 | NM_001827.1 | GGCTGGACGTGGTTTTGTCTGCTGCGCCCGCTCTTCGCGCTCTCGTTTCATTTTCT GCAGCG | SEQ ID NO: 153 |
| Claudin 4 | NM_001305.2 | GGCTGCTTTGCTGCAACTGTCCACCCCGCACAGACAAGCCTTACTCCGCCAAGTAT TCTGCTGCCCGCTCTG | SEQ ID NO: 154 |
| CLDN1 | NM_021101.3 | TCTGGGAGGTGCCCTACTTTGCTGTTCCTGTCCCCGAAAAACAACCTCTTACCCAA CACCAAGGCCCTATCCA | SEQ ID NO: 155 |
| CLDN7 | NM_001307.3 | GGTCTGCCCTAGTCATCCTGGGAGGTGCACTGCTCTCCTGTTCCTGTCCTGGGAAT GAGAGCAAGGCTGGGTAC | SEQ ID NO: 156 |
| CLIC1 | NM_001288.3 | CGGTACTTGAGCAATGCCTACGCCCGGGAAGAATTCGCTTCCACCTGTCCAGATGA TGAGGAGATCGA | SEQ ID NO: 157 |
| CLTC | NM_004859.1 | ACCGTATGGACAGCCACAGCCTGGCTTTGGGTACAGCATGTGAGATGAAGCGCTGA TCCTGTAGTCA | SEQ ID NO: 158 |
| CLU | NM_001831.1 | CCCCAGGATACCTACCACTACCTGCCCTTCAGCCTGCCCCACCGGAGGCCTCACTT CTTCTTTCCCAAGTCCCGCA | SEQ ID NO: 159 |
| cMet | NM_000245.1 | GACATTTCCAGTCCTGCAGTCAATGCCTCTCTGCCCCACCCTTTGTTCAGTGTGGC TGGTGCCACGACAAATGTGTGCGATCGGAG | SEQ ID NO: 160 |
| cMYC | NM_002467.1 | TCCCTCCACTCGGAAGGACTATCCTGCTGCCAAGAGGGTCAAGTTGGACAGTGTCA GAGTCCTGAGACAGATCAGCAACAACCG | SEQ ID NO: 161 |
| CNN | NM_001299.2 | TCCACCCTCCTGGCTTTGGCCAGCATGGCGAAGACGAAAGGAAACAAGGTGAACGT GGGAGTGA | SEQ ID NO: 162 |
| COL1A1 | NM_000088.2 | GTGGCCATCCAGCTGACCTTCCTGCGCCTGATGTCCACCGAGGCCTCCCAGAACAT CACCTACCACTG | SEQ ID NO: 163 |
| COL1A2 | NM_000089.2 | CAGCCAAGAACTGGTATAGGAGCTCCAAGGACAAGAAACACGTCTGGCTAGGAGAA ACTATCAATGCTGGCAGCCAGTTT | SEQ ID NO: 164 |
| COPS3 | NM_003653.2 | ATGCCCAGTGTTCCTGACTTCGAAACGCTATTCTCACAGGTTCAGCTCTTCATCAG CACTTGTAATGGGGAG | SEQ ID NO: 165 |
| COX2 | NM_000963.1 | TCTGCAGAGTTGGAAGCACTCTATGGTGACATCGATGCTGTGGAGCTGTATCCTGC CCTTCTGGTAGAAAAGCCTCGGC | SEQ ID NO: 166 |
| COX3 | MITO_COX3 | TCGAGTCTCCCTTCACCATTCCGACGGCATCTACGGCTCAACATTTTTTGTAGCC ACAGGCTTCCACGGACTTCACGTC | SEQ ID NO: 167 |
| CP | NM_000096.1 | CGTGAGTACACAGATGCCTCCTTCACAAATCGAAAGGAGAGAGGCCCTGAAGAAGA GCATCTTGGCATCCTGG | SEQ ID NO: 168 |
| CRBP | NM_002899.2 | TGGTCTGCAAGCAAGTATTCAAGAAGGTGCAGTGAGGCCCAAGCAGACAACCTTGT CCCAACCAATCAGC | SEQ ID NO: 169 |
| CREBBP | NM_004380.1 | TGGGAAGCAGCTGTGTACCATTCCTCGCGATGCTGCCTACTACAGCTATCAGAATA GGTATCATTTCTGTGAGAAGTGTTTC | SEQ ID NO: 170 |
| CRIP2 | NM_001312.1 | GTGCTACGCCACCCTGTTCGGACCCAAAGGCGTGAACATCGGGGGCGCGGGCTCCT ACATCTACGAGAAGCCCCTG | SEQ ID NO: 171 |
| cripto (TDGF1 official) | NM_003212.1 | GGGTCTGTGCCCCATGACACCTGGCTGCCCAAGAAGTGTTCCCTGTGTAAATGCTG GCACGGTCA | SEQ ID NO: 172 |
| CRK(a) | NM_016823.2 | CTCCCTAACCTCCAGAATGGGCCCATATATGCCAGGGTTATCCAGAAGCGAGTCCC CAATGCCTACGACAAGACA | SEQ ID NO: 173 |

TABLE B-continued

| Gene | Locus Link | Sequence | SEQ ID NO |
|---|---|---|---|
| CRMP1 | NM_001313.1 | AAGGTTTTTGGATTGCAAGGGGTTTCCAGGGGCATGTATGACGGTCCTGTGTACGA GGTACCAGCTACACCC | SEQ ID NO: 174 |
| CRYAB | NM_001885.1 | GATGTGATTGAGGTGCATGGAAAACATGAAGAGCGCCAGGATGAACATGGTTTCAT CTCCAGGGAGTTC | SEQ ID NO: 175 |
| CSEL1 | NM_001316.2 | TTACGCAGCTCATGCTCTTGAACGGCTCTTTACTATGCGAGGGCCTAACAATGCCA CTCTCTTTACAGCTGC | SEQ ID NO: 176 |
| CSF1 | NM_000757.3 | TGCAGCGGCTGATTGACAGTCAGATGGAGACCTCGTGCCAAATTACATTTGAGTTT GTAGACCAGGAACAGTTG | SEQ ID NO: 177 |
| CSK (SRC) | NM_004383.1 | CCTGAACATGAAGGAGCTGAAGCTGCTGCAGACCATCGGGAAGGGGGAGTTCGGAG ACGTGATG | SEQ ID NO: 178 |
| CTAG1B | NM_001327.1 | GCTCTCCATCAGCTCCTGTCTCCAGCAGCTTTCCCTGTTGATGTGGATCACGCAGT GCTTTCTGCCCGTGTT | SEQ ID NO: 179 |
| CTGF | NM_001901.1 | GAGTTCAAGTGCCCTGACGGCGAGGTCATGAAGAAGAACATGATGTTCATCAAGAC CTGTGCCTGCCATTACAACT | SEQ ID NO: 180 |
| CTHRC1 | NM_138455.2 | GCTCACTTCGGCTAAAATGCAGAAATGCATGCTGTCAGCGTTGGTATTTCACATTC AATGGAGCTGA | SEQ ID NO: 181 |
| CTLA4 | NM_005214.2 | CACTGAGGTCCGGGTGACAGTGCTTCGGCAGGCTGACAGCCAGGTGACTGAAGTCT GTGCGGCAACCTAC | SEQ ID NO: 182 |
| CTNNBIP1 | NM_020248.2 | GTTTTCCAGGTCGGAGACGGAAGACCGGAGGCAGTAGCTGCAAAGCCCTTGGAACA CCCTGGATGCT | SEQ ID NO: 183 |
| CTSB | NM_001908.1 | GGCCGAGATCTACAAAAACGGCCCCGTGGAGGGAGCTTTCTCTGTGTATTCGGACT TCCTGC | SEQ ID NO: 184 |
| CTSD | NM_001909.1 | GTACATGATCCCCTGTGAGAAGGTGTCCACCCTGCCCGCGATCACACTGAAGCTGG GAGGCAAAGGCTACAAGCTGTCCC | SEQ ID NO: 185 |
| CTSH | NM_004390.1 | GCAAGTTCCAACCTGGAAAGGCCATCGGCTTTGTCAAGGATGTAGCCAACATCACA ATCTATGACGAGGAAGCGATG | SEQ ID NO: 186 |
| CTSL | NM_001912.1 | GGGAGGCTTATCTCACTGAGTGAGCAGAATCTGGTAGACTGCTCTGGGCCTCAAGG CAATGAAGGCTGCAATGG | SEQ ID NO: 187 |
| CTSL2 | NM_001333.2 | TGTCTCACTGAGCGAGCAGAATCTGGTGGACTGTTCGCGTCCTCAAGGCAATCAGG GCTGCAATGGT | SEQ ID NO: 188 |
| CUL1 | NM_003592.2 | ATGCCCTGGTAATGTCTGCATTCAACAATGACGCTGGCTTTGTGGCTGCTCTTGAT AAGGCTTGTGGTCGC | SEQ ID NO: 189 |
| CUL4A | NM_003589.1 | AAGCATCTTCCTGTTCTTGGACCGCACCTATGTGCTGCAGAACTCCACGCTGCCCT CCATCTGGGATATGGGATT | SEQ ID NO: 190 |
| CXCL12 | NM_000609.3 | GAGCTACAGATGCCCATGCCGATTCTTCGAAAGCCATGTTGCCAGAGCCAACGTCA AGCATCTCAAA | SEQ ID NO: 191 |
| CXCR4 | NM_003467.1 | TGACCGCTTCTACCCCAATGACTTGTGGGTGGTTGTGTTCCAGTTTCAGCACATCA TGGTTGGCCTTATCCT | SEQ ID NO: 192 |
| CYBA | NM_000101.1 | GGTGCCTACTCCATTGTGGCGGGCGTGTTTGTGTGCCTGCTGGAGTACCCCCGGGG GAAGAGGAAGAAGGGCTCCAC | SEQ ID NO: 193 |
| CYP1B1 | NM_000104.2 | CCAGCTTTGTGCCTGTCACTATTCCTCATGCCACCACTGCCAACACCTCTGTCTTG GGCTACCACATTCCC | SEQ ID NO: 194 |
| CYP2C8 | NM_000770.2 | CCGTGTTCAAGAGGAAGCTCACTGCCTTGTGGAGGAGTTGAGAAAAACCAAGGCTT CACCCTGTGATCCCACT | SEQ ID NO: 195 |
| CYP3A4 | NM_017460.3 | AGAACAAGGACAACATGATCCTTACATATACACACCCTTTGGAAGTGGACCCAGA AACTGCATTGGCATGAGGTTTGC | SEQ ID NO: 196 |
| CYR61 | NM_001554.3 | TGCTCATTCTTGAGGAGCATTAAGGTATTTCGAAACTGCCAAGGGTGCTGGTGCGG ATGGACACTAATGCAGCCAC | SEQ ID NO: 197 |
| DAPK1 | NM_004938.1 | CGCTGACATCATGAATGTTCCTCGACCGGCTGGAGGCGAGTTTGGATATGACAAAG ACACATCGTTGCTGAAAGAGA | SEQ ID NO: 198 |
| DCC | NM_005215.1 | AAATGTCCTCCTCGACTGCTCCGCGGAGTCCGACCGAGGAGTTCCAGTGATCAAGT GGAAGAAAGATGGCATTCA | SEQ ID NO: 199 |

TABLE B-continued

| Gene | Locus Link | Sequence | SEQ ID NO |
| --- | --- | --- | --- |
| DCC_exons18-23 | X76132_18-23 | GGTCACCGTTGGTGTCATCACAGTGCTGGTAGTGGTCATCGTGGCTGTGATTTGCA CCCGACGCTC | SEQ ID NO: 200 |
| DCC_exons6-7 | X76132_6-7 | ATGGAGATGTGGTCATTCCTAGTGATTATTTTCAGATAGTGGGAGGAAGCAACTTA CGGATACTTGGGGTGGTG | SEQ ID NO: 201 |
| DCK | NM_000788.1 | GCCGCCACAAGACTAAGGAATGGCCACCCCGCCCAAGAGAAGCTGCCCGTCTTTCT CAGCCAGCTCTGAGGGGACCCGCATCAAGAAAATCTCCATCGAAGGGAACATCG | SEQ ID NO: 202 |
| DDB1 | NM_001923.2 | TGCGGATCATCCGGAATGGAATTGGAATCCACGAGCATGCCAGCATTGACTTACCA GGCATCAAAGGA | SEQ ID NO: 203 |
| DET1 | NM_017996.2 | CTTGTGGAGATCACCCAATCAGGTTCTATGCCCGGGACTCGGGCCTGCTCAAGTTT GAGATCCAGGCGGG | SEQ ID NO: 204 |
| DHFR | NM_000791.2 | TTGCTATAACTAAGTGCTTCTCCAAGACCCCAACTGAGTCCCCAGCACCTGCTACA GTGAGCTGCCATTCCAC | SEQ ID NO: 205 |
| DHPS | NM_013407.1 | GGGAGAACGGGATCAATAGGATCGGAAACCTGCTGGTGCCCAATGAGAATTACTGC AAGTTTGAGGACTGGCTGATGC | SEQ ID NO: 206 |
| DIABLO | NM_019887.1 | CACAATGGCGGCTCTGAAGAGTTGGCTGTCGCGCAGCGTAACTTCATTCTTCAGGT ACAGACAGTGTTTGTGT | SEQ ID NO: 207 |
| DIAPH1 | NM_005219.2 | CAAGCAGTCAAGGAGAACCAGAAGCGGCGGGAGACAGAAGAAAGATGAGGCGAGC AAAACT | SEQ ID NO: 208 |
| DICER1 | NM_177438.1 | TCCAATTCCAGCATCACTGTGGAGAAAAGCTGTTTGTCTCCCCAGCATACTTTATC GCCTTCACTGCC | SEQ ID NO: 209 |
| DKK1 | NM_012242.1 | TGACAACTACCAGCCGTACCCGTGCGCAGAGGACGAGGAGTGCGGCACTGATGAGT ACTGCGCTAGTCCC | SEQ ID NO: 210 |
| DLC1 | NM_006094.3 | GATTCAGACGAGGATGAGCCTTGTGCCATCAGTGGCAAATGGACTTTCCAAAGGGA CAGCAAGAGGTG | SEQ ID NO: 211 |
| DPYD | NM_000110.2 | AGGACGCAAGGAGGGTTTGTCACTGGCAGACTCGAGACTGTAGGCACTGCCATGGC CCCTGTGCTCAGTAAGGACTCGGCGGACATC | SEQ ID NO: 212 |
| DR4 | NM_003844.1 | TGCACAGAGGGTGTGGGTTACACCAATGCTTCCAACAATTTGTTTGCTTGCCTCCC ATGTACAGCTTGTAAATCAGATGAAGA | SEQ ID NO: 213 |
| DR5 | NM_003842.2 | CTCTGAGACAGTGCTTCGATGACTTTGCAGACTTGGTGCCCTTTGACTCCTGGGAG CCGCTCATGAGGAAGTTGGGCCTCATGG | SEQ ID NO: 214 |
| DRG1 | NM_004147.3 | CCTGGATCTCCCAGGTATCATTGAAGGTGCCAAGGATGGGAAAGGTAGAGGTCGTC AAGTCATTGCA | SEQ ID NO: 215 |
| DSP | NM_004415.1 | TGGCACTACTGCATGATTGACATAGAGAAGATCAGGGCCATGACAATCGCCAAGCT GAAAACAATGCGGCAGG | SEQ ID NO: 216 |
| DTYMK | NM_012145.1 | AAATCGCTGGGAACAAGTGCCGTTAATTAAGGAAAAGTTGAGCCAGGGCGTGACCC TCGTCGTGGACAGATACGCATT | SEQ ID NO: 217 |
| DUSP1 | NM_004417.2 | AGACATCAGCTCCTGGTTCAACGAGGCCATTGACTTCATAGACTCCATCAAGAATG CTGGAGGAAGGGTGTTTGTC | SEQ ID NO: 218 |
| DUSP2 | NM_004418.2 | TATCCCTGTGGAGGACAACCAGATGGTGGAGATCAGTGCCTGGTTCCAGGAGGCCA TAGGCTTCATTGACTGGGTG | SEQ ID NO: 219 |
| DUT | NM_001948.2 | ACACATGGAGTGCTTCTGGAACTATCAGCCCACTTGACCACCCAGTTTGTGGAAGC ACAGGCAAGAG | SEQ ID NO: 220 |
| DYRK1B | NM_004714.1 | AGCATGACACGGAGATGAAGTACTATATAGTACACCTGAAGCGGCACTTCATGTTC CGGAACCACCTGTGCCTGGTATT | SEQ ID NO: 221 |
| E2F1 | NM_005225.1 | ACTCCCTCTACCCTTGAGCAAGGGCAGGGGTCCCTGAGCTGTTCTTCTGCCCCATA CTGAAGGAACTGAGGCCTG | SEQ ID NO: 222 |
| EDN1 endothelin | NM_001955.1 | TGCCACCTGGACATCATTTGGGTCAACACTCCCGAGCACGTTGTTCCGTATGGACT TGGAAGCCCTAGGTCCA | SEQ ID NO: 223 |
| EFNA1 | NM_004428.2 | TACATCTCCAAACCCATCCACCAGCATGAAGACCGCTGCTTGAGGTTGAAGGTGAC TGTCAGTGGCAA | SEQ ID NO: 224 |
| EFNA3 | NM_004952.3 | ACTACATCTCCACGCCCACTCACAACCTGCACTGGAAGTGTCTGAGGATGAAGGTC TTCGTCTGCTG | SEQ ID NO: 225 |

TABLE B-continued

| Gene | Locus Link | Sequence | SEQ ID NO |
|---|---|---|---|
| EFNB1 | NM_004429.3 | GGAGCCCGTATCCTGGAGCTCCCTCAACCCCAAGTTCCTGAGTGGGAAGGGCTTGG TGATCTATCC | SEQ ID NO: 226 |
| EFNB2 | NM_004093.2 | TGACATTATCATCCCGCTAAGGACTGCGGACAGCGTCTTCTGCCCTCACTACGAGA AGGTCAGCGGGGACTAC | SEQ ID NO: 227 |
| EFP | NM_005082.2 | TTGAACAGAGCCTGACCAAGAGGGATGAGTTCGAGTTTCTGGAGAAAGCATCAAAA CTGCGAGGAATCTCAACA | SEQ ID NO: 228 |
| EGFR | NM_005228.1 | TGTCGATGGACTTCCAGAACCACCTGGGCAGCTGCCAAAAGTGTGATCCAAGCTGT CCCAAT | SEQ ID NO: 229 |
| EGLN1 | NM_022051.1 | TCAATGGCCGGACGAAAGCCATGGTTGCTTGTTATCCGGGCAATGGAACGGGTTAT GTACGTCATGTTGATAATCCAAA | SEQ ID NO: 230 |
| EGLN3 | NM_022073.2 | GCTGGTCCTCTACTGCGGGAGCCGGCTGGGCAAATACTACGTCAAGGAGAGGTCTA AGGCAATGGTGG | SEQ ID NO: 231 |
| EGR1 | NM_001964.2 | GTCCCCGCTGCAGATCTCTGACCCGTTCGGATCCTTTCCTCACTCGCCCACCATGG ACAACTACCCTAAGCTGGAG | SEQ ID NO: 232 |
| EGR3 | NM_004430.2 | CCATGTGGATGAATGAGGTGTCTCCTTTCCATACCCAGTCTCACCTTCTCCCCACC CTACCTCACCTCTTCTCAGGCA | SEQ ID NO: 233 |
| EI24 | NM_004879.2 | AAAGTGGTGAATGCCATTTGGTTTCAGGATATAGCTGACCTGGCATTTGAGGTATC AGGGAGGAAGCCTCAC | SEQ ID NO: 234 |
| EIF4E | NM_001968.1 | GATCTAAGATGGCGACTGTCGAACCGGAAACCACCCCTACTCCTAATCCCCGACT ACAGAAGAGGAGAAAACGGAATCTAA | SEQ ID NO: 235 |
| EIF4EL3 | NM_004846.1 | AAGCCGCGGTTGAATGTGCCATGACCCTCTCCCTCTCTGGATGGCACCATCATTGA AGCTGGCGTCA | SEQ ID NO: 236 |
| ELAVL1 | NM_001419.2 | GACAGGAGGCCTCTATCCTGTCCCTCCACCCCACCCTCCACCTCAATCCCCTCCCA TCTTCCCCAGACCTACCTCAC | SEQ ID NO: 237 |
| EMP1 | NM_001423.1 | GCTAGTACTTTGATGCTCCCTTGATGGGGTCCAGAGAGCCTCCCTGCAGCCACCAG ACTTGGCCTCCAGCTGTTC | SEQ ID NO: 238 |
| EMR3 | NM_032571.2 | TGGCCTACCTCTTCACCATCATCAACAGCCTCCAAGGCTTCTTCATCTTCTTGGTC TACTGCCTCCTCA | SEQ ID NO: 239 |
| EMS1 | NM_005231.2 | GGCAGTGTCACTGAGTCCTTGAAATCCTCCCCTGCCCCGCGGGTCTCTGGATTGGG ACGCACAGTGCA | SEQ ID NO: 240 |
| ENO1 | NM_001428.2 | CAAGGCCGTGAACGAGAAGTCCTGCAACTGCCTCCTGCTCAAAGTCAACCAGATTG GCTCCGTGACCG | SEQ ID NO: 241 |
| EP300 | NM_001429.1 | AGCCCCAGCAACTACAGTCTGGGATGCCAAGGCCAGCCATGATGTCAGTGGCCCAG CATGGTCAACCTTTGAACA | SEQ ID NO: 242 |
| EPAS1 | NM_001430.3 | AAGCCTTGGAGGGTTTCATTGCCGTGGTGACCCAAGATGGCGACATGATCTTTCTG TCAGAAAACATCAGCA | SEQ ID NO: 243 |
| EpCAM | NM_002354.1 | GGGCCCTCCAGAACAATGATGGGCTTTATGATCCTGACTGCGATGAGAGCGGGCTC TTTAAGGCCAAGCAGTGCA | SEQ ID NO: 244 |
| EPHA2 | NM_004431.2 | CGCCTGTTCACCAAGATTGACACCATTGCGCCCGATGAGATCACCGTCAGCAGCGA CTTCGAGGCACGCCAC | SEQ ID NO: 245 |
| EPHB2 | NM_004442.4 | CAACCAGGCAGCTCCATCGGCAGTGTCCATCATGCATCAGGTGAGCCGCACCGTGG ACAGCATTAC | SEQ ID NO: 246 |
| EPHB4 | NM_004444.3 | TGAACGGGTATCCTCCTTAGCCACGGGGCCCGTCCCATTTGAGCCTGTCAATGTC ACCACTGACCGAGAGGTACCT | SEQ ID NO: 247 |
| EphB6 | NM_004445.1 | ACTGGTCCTCCATCGGCTCCCCAGGAGCTTTGGTTTGAGGTGCAAGGCTCAGCACT CATGCTACACTGG | SEQ ID NO: 248 |
| EPM2A | NM_005670.2 | ACTGTGGCACTTAGGGGAGATGACATTTGCTTTGGGCAGAGGCAGCTAGCCAGGAC ACATTTCCACT | SEQ ID NO: 249 |
| ErbB3 | NM_001982.1 | CGGTTATGTCATGCCAGATACACACCTCAAAGGTACTCCCTCCTCCCGGGAAGGCA CCCTTTCTTCAGTGGGTCTCAGTTC | SEQ ID NO: 250 |
| ERCC1 | NM_001983.1 | GTCCAGGTGGATGTGAAAGATCCCCAGCAGGCCCTCAAGGAGCTGGCTAAGATGTG TATCCTGGCCG | SEQ ID NO: 251 |

TABLE B-continued

| Gene | Locus Link | Sequence | SEQ ID NO |
|---|---|---|---|
| ERCC2 | NM_000400.2 | TGGCCTTCTTCACCAGCTACCAGTACATGGAGAGCACCGTGGCCTCCTGGTATGAG CAGGGGATCCTTG | SEQ ID NO: 252 |
| EREG | NM_001432.1 | ATAACAAAGTGTAGCTCTGACATGAATGGCTATTGTTTGCATGGACAGTGCATCTA TCTGGTGGACATGAGTCAAAACTACTGCAGGTGTG | SEQ ID NO: 253 |
| ERK1 | Z11696.1 | ACGGATCACAGTGGAGGAAGCGCTGGCTCACCCCTACCTGGAGCAGTACTATGACC CGACGGATGAG | SEQ ID NO: 254 |
| ERK2 | NM_002745.1 | AGTTCTTGACCCCTGGTCCTGTCTCCAGCCCGTCTTGGCTTATCCACTTTGACTCC TTTGAGCCGTTT | SEQ ID NO: 255 |
| ESPL1 | NM_012291.1 | ACCCCCAGACCGGATCAGGCAAGCTGGCCCTCATGTCCCCTTCACGGTGTTTGAGG AAGTCTGCCCTACA | SEQ ID NO: 256 |
| EstR1 | NM_000125.1 | CGTGGTGCCCCTCTATGACCTGCTGCTGGAGATGCTGGACGCCCACCGCCTACATG CGCCCACTAGCC | SEQ ID NO: 257 |
| ETV4 | NM_001986.1 | TCCAGTGCCTATGACCCCCCCAGACAAATCGCCATCAAGTCCCCTGCCCCTGGTGC CCTTGGACAGT | SEQ ID NO: 258 |
| F3 | NM_001993.2 | GTGAAGGATGTGAAGCAGACGTACTTGGCACGGGTCTTCTCCTACCCGGCAGGGAA TGTGGAGAGCACCGGTT | SEQ ID NO: 259 |
| FABP4 | NM_001442.1 | GCTTTGCCACCAGGAAAGTGGCTGGCATGGCCAAACCTAACATGATCATCAGTGTG AATGGGGATG | SEQ ID NO: 260 |
| FAP | NM_004460.2 | CTGACCAGAACCACGGCTTATCCGGCCTGTCCACGAACCACTTATACACCCACATG ACCCACTTCC | SEQ ID NO: 261 |
| fas | NM_000043.1 | GGATTGCTCAACAACCATGCTGGGCATCTGGACCCTCCTACCTCTGGTTCTTACGT CTGTTGCTAGATTATCGTCCAAAAGTGTTAATGCC | SEQ ID NO: 262 |
| fasl | NM_000639.1 | GCACTTTGGGATTCTTTCCATTATGATTCTTTGTTACAGGCACCGAGAATGTTGTA TTCAGTGAGGGTCTTCTTACATGC | SEQ ID NO: 263 |
| FASN | NM_004104.4 | GCCTCTTCCTGTTCGACGGCTCGCCCACCTACGTACTGGCCTACACCCAGAGCTAC CGGGCAAAGC | SEQ ID NO: 264 |
| FBXO5 | NM_012177.2 | GGCTATTCCTCATTTTCTCTACAAAGTGGCCTCAGTGAACATGAAGAAGGTAGCCT CCTGGAGGAGAATTTCGGTGACAGTCTACAATCC | SEQ ID NO: 265 |
| FBXW7 | NM_033632.1 | CCCCAGTTTCAACGAGACTTCATTTCATTGCTCCCTAAAGAGTTGGCACTCTATGT GCTTTCATTCCTGGAAC | SEQ ID NO: 266 |
| FDXR | NM_004110.2 | GAGATGATTCAGTTACCGGGAGCCCGGCCCATTTTGGATCCTGTGGATTTCTTGGG TCTCCAGGACAAGAT | SEQ ID NO: 267 |
| FES | NM_002005.2 | CTCTGCAGGCCTAGGTGCAGCTCCTCAGCGGCTCCAGCTCATATGCTGACAGCTCT TCACAGTCCTGG | SEQ ID NO: 268 |
| FGF18 | NM_003862.1 | CGGTAGTCAAGTCCGGATCAAGGGCAAGGAGACGGAATTCTACCTGTGCATGAACC GCAAAGGCAAGC | SEQ ID NO: 269 |
| FGF2 | NM_002006.2 | AGATGCAGGAGAGAGGAAGCCTTGCAAACCTGCAGACTGCTTTTTGCCCAATATAG ATTGGGTAAGGCTGCAAAAC | SEQ ID NO: 270 |
| FGFR1 | NM_023109.1 | CACGGGACATTCACCACATCGACTACTATAAAAAGACAACCAACGGCCGACTGCCT GTGAAGTGGATGGCACCC | SEQ ID NO: 271 |
| FGFR2 isoform 1 | NM_000141.2 | GAGGGACTGTTGGCATGCAGTGCCCTCCCAGAGACCAACGTTCAAGCAGTTGGTAG AAGCTTGGATCGAATTCTCACTC | SEQ ID NO: 272 |
| FHIT | NM_002012.1 | CCAGTGGAGCGCTTCCATGACCTGCGTCCTGATGAAGTGGCCGATTTGTTTCAGAC GACCCAGAGAG | SEQ ID NO: 273 |
| FIGF | NM_004469.2 | GGTTCCAGCTTTCTGTAGCTGTAAGCATTGGTGGCCACACCACCTCCTTACAAAGC AACTAGAACCTGCGGC | SEQ ID NO: 274 |
| FLJ12455 | NM_022078.1 | CCACCAGCATGAAGTTTCGGACAGACATGGCCTTTGTGAGGGGTTCCAGTTGTGCT TCAGACAGCC | SEQ ID NO: 275 |
| FLJ20712 | AK000719.1 | GCCACACAAACATGCTCCTGCTCCTGGCGGAGGCAGAGCTGCTGGGAAAGACATTT CGGAAGTTTCCTGTGGC | SEQ ID NO: 276 |
| FLT1 | NM_002019.1 | GGCTCCCGAATCTATCTTTGACAAAATCTACAGCACCAAGAGCGACGTGTGGTCTT ACGGAGTATTGCTGTGGGA | SEQ ID NO: 277 |

TABLE B-continued

| Gene | Locus Link | Sequence | SEQ ID NO |
|---|---|---|---|
| FLT4 | NM_002020.1 | ACCAAGAAGCTGAGGACCTGTGGCTGAGCCCGCTGACCATGGAAGATCTTGTCTGC TACAGCTTCCAGG | SEQ ID NO: 278 |
| FOS | NM_005252.2 | CGAGCCCTTTGATGACTTCCTGTTCCCAGCATCATCCAGGCCCAGTGGCTCTGAGA CAGCCCGCTCC | SEQ ID NO: 279 |
| FOXO3A | NM_001455.1 | TGAAGTCCAGGACGATGATGCGCCTCTCTCGCCCATGCTCTACAGCAGCTCAGCCA GCCTGTCACCTTCAGTAAGCAAGCCGT | SEQ ID NO: 280 |
| FPGS | NM_004957.3 | CAGCCCTGCCAGTTTGACTATGCCGTCTTCTGCCCTAACCTGACAGAGGTGTCATC CACAGGCAAC | SEQ ID NO: 281 |
| FRP1 | NM_003012.2 | TTGGTACCTGTGGGTTAGCATCAAGTTCTCCCCAGGGTAGAATTCAATCAGAGCTC CAGTTTGCATTTGGATGTG | SEQ ID NO: 282 |
| FST | NM_006350.2 | GTAAGTCGGATGAGCCTGTCTGTGCCAGTGACAATGCCACTTATGCCAGCGAGTGT GCCATGAAGGAAGCTG | SEQ ID NO: 283 |
| Furin | NM_002569.1 | AAGTCCTCGATACGCACTATAGCACCGAGAATGACGTGGAGACCATCCGGGCCAGC GTCTGCGCCCCCTGCCACGCCTCATGTGCCACATGCCAG | SEQ ID NO: 284 |
| FUS | NM_004960.1 | GGATAATTCAGACAACAACACCATCTTTGTGCAAGGCCTGGGTGAGAATGTTACAA TTGAGTCTGTGGCTGATTACTTCA | SEQ ID NO: 285 |
| FUT1 | NM_000148.1 | CCGTGCTCATTGCTAACCACTGTCTGTCCCTGAACTCCCAGAACCACTACATCTGG CTTTGGGCAG | SEQ ID NO: 286 |
| FUT3 | NM_000149.1 | CAGTTCGGTCCAACAGAGAAAGCAGGCAACCACCATGTCATTTGAAAACAGTTTCA TCGGGATATAATTCGCA | SEQ ID NO: 287 |
| FUT6 | NM_000150.1 | CGTGTGTCTCAAGACGATCCCACTGTGTACCCTAATGGGTCCCGCTTCCCAGACAG CACAGGGACC | SEQ ID NO: 288 |
| FXYD5 | NM_014164.4 | AGAGCACCAAAGCAGCTCATCCCACTGATGACACCACGACGCTCTCTGAGAGACCA TCCCCAAGCAC | SEQ ID NO: 289 |
| FYN | NM_002037.3 | GAAGCGCAGATCATGAAGAAGCTGAAGCACGACAAGCTGGTCCAGCTCTATGCAGT GGTGTCTGAGGAG | SEQ ID NO: 290 |
| FZD1 | NM_003505.1 | GGTGCACCAGTTCTACCCTCTAGTGAAAGTGCAGTGTTCCGCTGAGCTCAAGTTCT TCCTGTGCTCCATGTACGC | SEQ ID NO: 291 |
| FZD2 | NM_001466.2 | TGGATCCTCACCTGGTCGGTGCTGTGCTGCGCTTCCACCTTCTTCACTGTCACCAC GTACTTGGTAGACATGCAGCGC | SEQ ID NO: 292 |
| FZD6 | NM_003506.2 | AATGAGAGAGGTGAAAGCGGACGGAGCTAGCACCCCCAGGTTAAGAGAACAGGACT GTGGTGAACCT | SEQ ID NO: 293 |
| G-Catenin | NM_002230.1 | TCAGCAGCAAGGGCATCATGGAGGAGGATGAGGCCTGCGGGCGCCAGTACACGCTC AAGAAAACCACC | SEQ ID NO: 294 |
| G1P2 | NM_005101.1 | CAACGAATTCCAGGTGTCCCTGAGCAGCTCCATGTCGGTGTCAGAGCTGAAGGCGC AGATC | SEQ ID NO: 295 |
| GADD45 | NM_001924.2 | GTGCTGGTGACGAATCCACATTCATCTCAATGGAAGGATCCTGCCTTAAGTCAACT TATTTGTTTTGCCGGG | SEQ ID NO: 296 |
| GADD45B | NM_015675.1 | ACCCTCGACAAGACCACACTTTGGGACTTGGGAGCTGGGGCTGAAGTTGCTCTGTA CCCATGAACTCCCA | SEQ ID NO: 297 |
| GADD45G | NM_006705.2 | CGCGCTGCAGATCCATTTTACGCTGATCCAGGCTTTCTGCTGCGAGAACGACATCG ACATAGTGCG | SEQ ID NO: 298 |
| GAGE4 | NM_001474.1 | GGAACAGGGTCACCCACAGACTGGGTGTGAGTGTGAAGATGGTCCTGATGGGCAGG AGATGGACCCGCCAAATC | SEQ ID NO: 299 |
| GBP1 | NM_002053.1 | TTGGGAAATATTTGGGCATTGGTCTGGCCAAGTCTACAATGTCCCAATATCAAGGA CAACCACCCTAGCTTCT | SEQ ID NO: 300 |
| GBP2 | NM_004120.2 | GCATGGGAACCATCAACCAGCAGGCCATGGACCAACTTCACTATGTGACAGAGCTG ACAGATCGAATCAAGGCAAACTCCTCA | SEQ ID NO: 301 |
| GCLC | NM_001498.1 | CTGTTGCAGGAAGGCATTGATCATCTCCTGGCCCAGCATGTTGCTCATCTCTTTAT TAGAGACCCACTGAC | SEQ ID NO: 302 |
| GCLM | NM_002061.1 | TGTAGAATCAAACTCTTCATCATCAACTAGAAGTGCAGTTGACATGGCCTGTTCAG TCCTTGGAGTTGCACAGCTGGATTCTGTG | SEQ ID NO: 303 |

TABLE B-continued

| Gene | Locus Link | Sequence | SEQ ID NO |
|---|---|---|---|
| GCNT1 | NM_001490.3 | TGGTGCTTGGAGCATAGAAGACTGCCCTTCACAAAGGAAATCCCTGATTATTGTTT GAAATGCTGAGGACGTTGC | SEQ ID NO: 304 |
| GDF15 | NM_004864.1 | CGCTCCAGACCTATGATGACTTGTTAGCCAAAGACTGCCACTGCATATGAGCAGTC CTGGTCCTTCCACTGT | SEQ ID NO: 305 |
| GIT1 | NM_014030.2 | GTGTATGACGAGGTGGATCGAAGAGAAAATGATGCAGTGTGGCTGGCTACCCAAAA CCACAGCACTCTGGT | SEQ ID NO: 306 |
| GJA1 | NM_000165.2 | GTTCACTGGGGGTGTATGGGGTAGATGGGTGGAGAGGGAGGGGATAAGAGAGGTGC ATGTTGGTATTT | SEQ ID NO: 307 |
| GJB2 | NM_004004.3 | TGTCATGTACGACGGCTTCTCCATGCAGCGGCTGGTGAAGTGCAACGCCTGGCCTT GTCCCAACACTGTGGACT | SEQ ID NO: 308 |
| GPX1 | NM_000581.2 | GCTTATGACCGACCCCAAGCTCATCACCTGGTCTCCGGTGTGTCGCAACGATGTTG CCTGGAACTTT | SEQ ID NO: 309 |
| GPX2 | NM_002083.1 | CACACAGATCTCCTACTCCATCCAGTCCTGAGGAGCCTTAGGATGCAGCATGCCTT CAGGAGACACTGCTGGACC | SEQ ID NO: 310 |
| Grb10 | NM_005311.2 | CTTCGCCTTTGCTGATTGCCTCTCCAAACGCCTGCCTGACGACTGCCTTGGAGCAT GTGCGTTATGG | SEQ ID NO: 311 |
| GRB14 | NM_004490.1 | TCCCACTGAAGCCCTTTCAGTTGCGGTTGAAGAAGGACTCGCTTGGAGGAAAAAAG GATGTTTACGCCTGGGCACT | SEQ ID NO: 312 |
| GRB2 | NM_002086.2 | GTCCATCAGTGCATGACGTTTAAGGCCACGTATAGTCCTAGCTGACGCCAATAATA AAAACAAGAAACCAAGTGGGCT | SEQ ID NO: 313 |
| GRB7 | NM_005310.1 | CCATCTGCATCCATCTTGTTTGGGCTCCCCACCCTTGAGAAGTGCCTCAGATAATA CCCTGGTGGCC | SEQ ID NO: 314 |
| GRIK1 | NM_000830.2 | GTTGGGTGCATCTCTCGGGCGTCCGGCAGCGGCTGTATCTCGGCATGAATTAAGAA GCTAGGAAGATGGAGCACG | SEQ ID NO: 315 |
| GRO1 | NM_001511.1 | CGAAAAGATGCTGAACAGTGACAAATCCAACTGACCAGAAGGGAGGAGGAAGCTCA CTGGTGGCTGTTCCTGA | SEQ ID NO: 316 |
| GRP | NM_002091.1 | CTGGGTCTCATAGAAGCAAAGGAGAACAGAAACCACCAGCCACCTCAACCCAAGGC CTTGGGCAATCAGCAGCCTTCGTGG | SEQ ID NO: 317 |
| GRPR | NM_005314.1 | ATGCTGCTGGCCATTCCAGAGGCCGTGTTTTCTGACCTCCATCCCTTCCATGAGGA AAGCACCAACCAGACCT | SEQ ID NO: 318 |
| GSK3B | NM_002093.2 | GACAAGGACGGCAGCAAGGTGACAACAGTGGTGGCAACTCCTGGGCAGGGTCCAGA CAGGCCACAA | SEQ ID NO: 319 |
| GSTA3 | NM_000847.3 | TCTCCAACTTCCCTCTGCTGAAGGCCCTGAAAACCAGAATCAGCAACCTGCCCACG GTGAAGAAGT | SEQ ID NO: 320 |
| GSTM1 | NM_000561.1 | AAGCTATGAGGAAAAGAAGTACACGATGGGGGACGCTCCTGATTATGACAGAAGCC AGTGGCTGAATGAAAAATTCAAGCTGGGCC | SEQ ID NO: 321 |
| GSTM3 | NM_000849.3 | CAATGCCATCTTGCGCTACATCGCTCGCAAGCACAACATGTGTGGTGAGACTGAAG AAGAAAAGATTCGAGTGGAC | SEQ ID NO: 322 |
| GSTp | NM_000852.2 | GAGACCCTGCTGTCCCAGAACCAGGGAGGCAAGACCTTCATTGTGGGAGACCAGAT CTCCTTCGCTGACTACAACC | SEQ ID NO: 323 |
| GSTT1 | NM_000853.1 | CACCATCCCACCCTGTCTTCCACAGCCGCCTGAAAGCCACAATGAGAATGATGCA CACTGAGGCC | SEQ ID NO: 324 |
| H2AFZ | NM_002106.2 | CCGGAAAGGCCAAGACAAAGGCGGTTTCCCGCTCGCAGAGAGCCGGCTTGCAGTTC CCAGTGGGCCGTATT | SEQ ID NO: 325 |
| HB-EGF | NM_001945.1 | GACTCCTTCGTCCCCAGTTGCCGTCTAGGATTGGGCCTCCCATAATTGCTTTGCCA AAATACCAGAGCCTTCAAGTGCCA | SEQ ID NO: 326 |
| hCRA a | U78556.1 | TGACACCCTTACCTTCCTGAGAAATACCCCCTGGGAGCGCGGAAAGCAGAGCGGAC AGGTCAGTGACTTCTATTTTTGACTCGTGTTTTT | SEQ ID NO: 327 |
| HDAC1 | NM_004964.2 | CAAGTACCACAGCGATGACTACATTAAATTCTTGCGCTCCATCCGTCCAGATAACA TGTCGGAGTACAGCAAGC | SEQ ID NO: 328 |
| HDAC2 | NM_001527.1 | GGTGGCTACACAATCCGTAATGTTGCTCGATGTTGGACATATGAGACTGCAGTTGC CCTTGATTGTGAGATTCCCA | SEQ ID NO: 329 |

TABLE B-continued

| Gene | Locus Link | Sequence | SEQ ID NO |
|---|---|---|---|
| HDGF | NM_004494.1 | TCCTAGGCATTCTGGACCTCTGGGTTGGGATCAGGGGTAGGAATGGAAGGATGGAG CATCAACAGC | SEQ ID NO: 330 |
| hENT1 | NM_004955.1 | AGCCGTGACTGTTGAGGTCAAGTCCAGCATCGCAGGCAGCAGCACCTGGGAACGTT ACTT | SEQ ID NO: 331 |
| Hepsin | NM_002151.1 | AGGCTGCTGGAGGTCATCTCCGTGTGTGATTGCCCCAGAGGCCGTTTCTTGGCCGC CATCTGCCAAGACTGTGGCCGCAGGAAG | SEQ ID NO: 332 |
| HER2 | NM_004448.1 | CGGTGTGAGAAGTGCAGCAAGCCCTGTGCCCGAGTGTGCTATGGTCTGGGCATGGA GCACTTGCGAGAGG | SEQ ID NO: 333 |
| Herstatin | AF177761.2 | CACCCTGTCCTATCCTTCCTCAGACCCTCTTGGGACCTAGTCTCTGCCTTCTACTC TCTACCCCTGGCC | SEQ ID NO: 334 |
| HES6 | NM_018645.3 | TTAGGGACCCTGCAGCTCTGGAGTGGGTGGAGGGAGGGAGCTACGGGCAGGAGGAA GAATTTTGTAG | SEQ ID NO: 335 |
| HGF | M29145.1 | CCGAAATCCAGATGATGATGCTCATGGACCCTGGTGCTACACGGGAAATCCACTCA TTCCTTGGG | SEQ ID NO: 336 |
| HIF1A | NM_001530.1 | TGAACATAAAGTCTGCAACATGGAAGGTATTGCACTGCACAGGCCACATTCACGTA TATGATACCAACAGTAACCAACCTCA | SEQ ID NO: 337 |
| HK1 | NM_000188.1 | TACGCACAGAGGCAAGCAGCTAAGAGTCCGGGATCCCCAGCCTACTGCCTCTCCAG CACTTCTCTC | SEQ ID NO: 338 |
| HLA-DPB1 | NM_002121.4 | TCCATGATGGTTCTGCAGGTTTCTGCGGCCCCCCGGACAGTGGCTCTGACGGCGTT ACTGATGGTGCTGCTCA | SEQ ID NO: 339 |
| HLA-DRA | NM_019111.3 | GACGATTTGCCAGCTTTGAGGCTCAAGGTGCATTGGCCAACATAGCTGTGGACAAA GCCAACCTGGA | SEQ ID NO: 340 |
| HLA-DRB1 | NM_002124.1 | GCTTTCTCAGGACCTGGTTGCTACTGGTTCGGCAACTGCAGAAAATGTCCTCCCTT GTGGCTTCCT | SEQ ID NO: 341 |
| HLA-G | NM_002127.2 | CCTGCGCGGCTACTACAACCAGAGCGAGGCCAGTTCTCACACCCTCCAGTGGATGA TTGGCTGCGACCTG | SEQ ID NO: 342 |
| HMGB1 | NM_002128.3 | TGGCCTGTCCATTGGTGATGTTGCGAAGAAACTGGGAGAGATGTGGAATAACACTG CTGCAGATGACAAGC | SEQ ID NO: 343 |
| hMLH | NM_000249.2 | CTACTTCCAGCAACCCCAGAAAGAGACATCGGGAAGATTCTGATGTGGAAATGGTG GAAGATGATTCCCGAAAG | SEQ ID NO: 344 |
| HNRPAB | NM_004499.2 | CAAGGGAGCGACCAACTGATCGCACACATGCTTTGTTTGGATATGGAGTGAACACA ATTATGTACCAAATTTAACTTGGCAAAC | SEQ ID NO: 345 |
| HNRPD | NM_031370.2 | GCCAGTAAGAACGAGGAGGATGAAGGCCATTCAAACTCCTCCCCACGACACTCTGA AGCAGCGACG | SEQ ID NO: 346 |
| HoxA1 | NM_005522.3 | AGTGACAGATGGACAATGCAAGAATGAACTCCTTCCTGGAATACCCCATACTTAGC AGTGGCGACTCGG | SEQ ID NO: 347 |
| HoxA5 | NM_019102.2 | TCCCTTGTGTTCCTTCTGTGAAGAAGCCCTGTTCTCGTTGCCCTAATTCATCTTTT AATCATGAGCCTGTTTATTGCC | SEQ ID NO: 348 |
| HOXB13 | NM_006361.2 | CGTGCCTTATGGTTACTTTGGAGGCGGGTACTACTCCTGCCGAGTGTCCCGGAGCT CGCTGAAACCCTGTG | SEQ ID NO: 349 |
| HOXB7 | NM_004502.2 | CAGCCTCAAGTTCGGTTTTCGCTACCGGAGCCTTCCCAGAACAAACTTCTTGTGCG TTTGCTTCCAAC | SEQ ID NO: 350 |
| HRAS | NM_005343.2 | GGACGAATACGACCCCACTATAGAGGATTCCTACCGGAAGCAGGTGGTCATTGATG GGGAGACGTGC | SEQ ID NO: 351 |
| HSBP1 | NM_001537.1 | GGAGATGGCCGAGACTGACCCCAAGACCGTGCAGGACCTCACCTCGGTGGTGCAGA CACTCCTGCAG | SEQ ID NO: 352 |
| HSD17B1 | NM_000413.1 | CTGGACCGCACGGACATCCACACCTTCCACCGCTTCTACCAATACCTCGCCCACAG CAAGCAAGTCTTTCGCGAGGCG | SEQ ID NO: 353 |
| HSD17B2 | NM_002153.1 | GCTTTCCAAGTGGGGAATTAAAGTTGCTTCCATCCAACCTGGAGGCTTCCTAACAA ATATCGCAGGCA | SEQ ID NO: 354 |
| HSPA1A | NM_005345.4 | CTGCTGCGACAGTCCACTACCTTTTTCGAGAGTGACTCCCGTTGTCCCAAGGCTTC CCAGAGCGAACCTG | SEQ ID NO: 355 |

TABLE B-continued

| Gene | Locus Link | Sequence | SEQ ID NO |
|---|---|---|---|
| HSPA1B | NM_005346.3 | GGTCCGCTTCGTCTTTCGAGAGTGACTCCCGCGGTCCCAAGGCTTTCCAGAGCGAA CCTGTGC | SEQ ID NO: 356 |
| HSPA4 | NM_002154.3 | TTCAGTGTGTCCAGTGCATCTTTAGTGGAGGTTCACAAGTCTGAGGAAAATGAGGA GCCAATGGAAACAGAT | SEQ ID NO: 357 |
| HSPA5 | NM_005347.2 | GGCTAGTAGAACTGGATCCCAACACCAAACTCTTAATTAGACCTAGGCCTCAGCTG CACTGCCCGAAAAGCATTTGGGCAGACC | SEQ ID NO: 358 |
| HSPA8 | NM_006597.3 | CCTCCCTCTGGTGGTGCTTCCTCAGGGCCCACCATTGAAGAGGTTGATTAAGCCAA CCAAGTGTAGATGTAGC | SEQ ID NO: 359 |
| HSPB1 | NM_001540.2 | CCGACTGGAGGAGCATAAAAGCGCAGCCGAGCCCAGCGCCCCGCACTTTTCTGAGC AGACGTCCAGAGCAGAGTCAGCCAGCAT | SEQ ID NO: 360 |
| HSPCA | NM_005348.2 | CAAAAGGCAGAGGCTGATAAGAACGACAAGTCTGTGAAGGATCTGGTCATCTTGCT TTATGAAACTGCGCT | SEQ ID NO: 361 |
| HSPE1 | NM_002157.1 | GCAAGCAACAGTAGTCGCTGTTGGATCGGGTTCTAAAGGAAAGGGTGGAGAGATTC AACCAGTTAGCGTGAAAGTTGG | SEQ ID NO: 362 |
| HSPG2 | NM_005529.2 | GAGTACGTGTGCCGAGTGTTGGGCAGCTCCGTGCCTCTAGAGGCCTCTGTCCTGGT CACCATTGAG | SEQ ID NO: 363 |
| ICAM1 | NM_000201.1 | GCAGACAGTGACCATCTACAGCTTTCCGGCGCCCAACGTGATTCTGACGAAGCCAG AGGTCTCAGAAG | SEQ ID NO: 364 |
| ICAM2 | NM_000873.2 | GGTCATCCTGACACTGCAACCCACTTTGGTGGCTGTGGGCAAGTCCTTCACCATTG AGTGCA | SEQ ID NO: 365 |
| ID1 | NM_002165.1 | AGAACCGCAAGGTGAGCAAGGTGGAGATTCTCCAGCACGTCATCGACTACATCAGG GACCTTCAGTTGGA | SEQ ID NO: 366 |
| ID2 | NM_002166.1 | AACGACTGCTACTCCAAGCTCAAGGAGCTGGTGCCCAGCATCCCCCAGAACAAGAA GGTGAGCAAGATGGAAATCC | SEQ ID NO: 367 |
| ID3 | NM_002167.2 | CTTCACCAAATCCCTTCCTGGAGACTAAACCTGGTGCTCAGGAGCGAAGGACTGTG AACTTGTAGCCTGAAGAGCCAGAG | SEQ ID NO: 368 |
| ID4 | NM_001546.2 | TGGCCTGGCTCTTAATTTGCTTTTGTTTTGCCCAGTATAGACTCGGAAGTAACAGT TATAGCTAGTGGTCTTGCATGATTGCA | SEQ ID NO: 369 |
| IFIT1 | NM_001548.1 | TGACAACCAAGCAAATGTGAGGAGTCTGGTGACCTGGGCAACTTTGCCTGGATGT ATTACCACATGGGCAGACTG | SEQ ID NO: 370 |
| IGF1 | NM_000618.1 | TCCGGAGCTGTGATCTAAGGAGGCTGGAGATGTATTGCGCACCCCTCAAGCCTGCC AAGTCAGCTCGCTCTGTCCG | SEQ ID NO: 371 |
| IGF1R | NM_000875.2 | GCATGGTAGCCGAAGATTTCACAGTCAAAATCGGAGATTTTGGTATGACGCGAGAT ATCTATGAGACAGACTATTACCGGAAA | SEQ ID NO: 372 |
| IGF2 | NM_000612.2 | CCGTGCTTCCGGACAACTTCCCCAGATACCCCGTGGGCAAGTTCTTCCAATATGAC ACCTGGAAGCAGTCCA | SEQ ID NO: 373 |
| IGFBP2 | NM_000597.1 | GTGGACAGCACCATGAACATGTTGGGCGGGGAGGCAGTGCTGGCCGGAAGCCCCT CAAGTCGGGTATGAAGG | SEQ ID NO: 374 |
| IGFBP3 | NM_000598.1 | ACGCACCGGGTGTCTGATCCCAAGTTCCACCCCCTCCATTCAAAGATAATCATCAT CAAGAAAGGGCA | SEQ ID NO: 375 |
| IGFBP5 | NM_000599.1 | TGGACAAGTACGGGATGAAGCTGCCAGGCATGGAGTACGTTGACGGGGACTTTCAG TGCCACACCTTCG | SEQ ID NO: 376 |
| IGFBP6 | NM_002178.1 | TGAACCGCAGAGACCAACAGAGGAATCCAGGCACCTCTACCACGCCCTCCCAGCCC AATTCTGCGGGTGTCCAAGAC | SEQ ID NO: 377 |
| IGFBP7 | NM_001553 | GGGTCACTATGGAGTTCAAAGGACAGAACTCCTGCCTGGTGACCGGGACAACCTGG CCATTCAGACCC | SEQ ID NO: 378 |
| IHH | NM_002181.1 | AAGGACGAGGAGAACACAGGCGCCGACCGCCTCATGACCCAGCGCTGCAAGGACCG CCTGAACTCGCTGGCTATCT | SEQ ID NO: 379 |
| IL-8 | NM_000584.2 | AAGGAACCATCTCACTGTGTGTAAACATGACTTCCAAGCTGGCCGTGGCTCTCTTG GCAGCCTTCCTGAT | SEQ ID NO: 380 |
| IL10 | NM_000572.1 | GGCGCTGTCATCGATTTCTTCCCTGTGAAAACAAGAGCAAGGCCGTGGAGCAGGTG AAGAATGCCTTTAATAAGCTCCA | SEQ ID NO: 381 |

TABLE B-continued

| Gene | Locus Link | Sequence | SEQ ID NO |
|---|---|---|---|
| IL1B | NM_000576.2 | AGCTGAGGAAGATGCTGGTTCCCTGCCCACAGACCTTCCAGGAGAATGACCTGAGC ACCTTCTTTCC | SEQ ID NO: 382 |
| IL6 | NM_000600.1 | CCTGAACCTTCCAAAGATGGCTGAAAAAGATGGATGCTTCCAATCTGGATTCAATG AGGAGACTTGCCTGGT | SEQ ID NO: 383 |
| IL6ST | NM_002184.2 | GGCCTAATGTTCCAGATCCTTCAAAGAGTCATATTGCCCAGTGGTCACCTCACACT CCTCCAAGGCACAATTTT | SEQ ID NO: 384 |
| ILT-2 | NM_006669.1 | AGCCATCACTCTCAGTGCAGCCAGGTCCTATCGTGGCCCCTGAGGAGACCCTGACT CTGCAGT | SEQ ID NO: 385 |
| IMP-1 | NM_006546.2 | GAAAGTGTTTGCGGAGCACAAGATCTCCTACAGCGGCCAGTTCTTGGTCAAATCCG GCTACGCCTTC | SEQ ID NO: 386 |
| IMP2 | NM_006548.3 | CAATCTGATCCCAGGGTTGAACCTCAGCGCACTTGGCATCTTTTCAACAGGACTGT CCGTGCTATCTCCACCAGCAGGGCC | SEQ ID NO: 387 |
| ING1L | NM_001564.1 | TGTTTCCAAGATCCTGCTGAAAGTGAACGAGCCTCAGATAAAGCAAAGATGGATTC CAGCCAACCAGAAAGA | SEQ ID NO: 388 |
| ING5 | NM_032329.4 | CCTACAGCAAGTGCAAGGAATACAGTGACGACAAAGTGCAGCTGGCCATGCAGACC TACGAGATG | SEQ ID NO: 389 |
| INHA | NM_002191.2 | CCTCCCAGTTTCATCTTCCACTACTGTCATGGTGGTTGTGGGCTGCACATCCCACC AAACCTGTCCCTTCCAGTCCCT | SEQ ID NO: 390 |
| INHBA | NM_002192.1 | GTGCCCGAGCCATATAGCAGGCACGTCCGGGTCCTCACTGTCCTTCCACTCAACAG TCATCAACCACTACCG | SEQ ID NO: 391 |
| INHBB | NM_002193.1 | AGCCTCCAGGATACCAGCAAATGGATGCGGTGACAAATGGCAGCTTAGCTACAAAT GCCTGTCAGTCGGAGA | SEQ ID NO: 392 |
| IRS1 | NM_005544.1 | CCACAGCTCACCTTCTGTCAGGTGTCCATCCCAGCTCCAGCCAGCTCCCAGAGAGG AAGAGACTGGCACTGAGG | SEQ ID NO: 393 |
| ITGA3 | NM_002204.1 | CCATGATCCTCACTCTGCTGGTGGACTATACACTCCAGACCTCGCTTAGCATGGTA AATCACCGGCTACAAAGCTTC | SEQ ID NO: 394 |
| ITGA4 | NM_000885.2 | CAACGCTTCAGTGATCAATCCCGGGGCGATTTACAGATGCAGGATCGGAAAGAATC CCGGCCAGAC | SEQ ID NO: 395 |
| ITGA5 | NM_002205.1 | AGGCCAGCCCTACATTATCAGAGCAAGAGCCGGATAGAGGACAAGGCTCAGATCTT GCTGGACTGTGGAGAAGAC | SEQ ID NO: 396 |
| ITGA6 | NM_000210.1 | CAGTGACAAACAGCCCTTCCAACCCAAGGAATCCCACAAAAGATGGCGATGACGCC CATGAGGCTAAAC | SEQ ID NO: 397 |
| ITGA7 | NM_002206.1 | GATATGATTGGTCGCTGCTTTGTGCTCAGCCAGGACCTGGCCATCCGGGATGAGTT GGATGGTGGGAATGGAAGTTCT | SEQ ID NO: 398 |
| ITGAV | NM_002210.2 | ACTCGGACTGCACAAGCTATTTTTGATGACAGCTATTTGGGTTATTCTGTGGCTGT CGGAGATTTCAATGGTGATGGCA | SEQ ID NO: 399 |
| ITGB1 | NM_002211.2 | TCAGAATTGGATTTGGCTCATTTGTGGAAAAGACTGTGATGCCTTACATTAGCACA ACACCAGCTAAGCTCAGG | SEQ ID NO: 400 |
| ITGB3 | NM_000212.1 | ACCGGGAGCCCTACATGACCGAAAATACCTGCAACCGTTACTGCCGTGACGAGATT GAGTCAGTGAAAGAGCTTAAGG | SEQ ID NO: 401 |
| ITGB4 | NM_000213.2 | CAAGGTGCCCTCAGTGGAGCTCACCAACCTGTACCCGTATTGCGACTATGAGATGA AGGTGTGCGC | SEQ ID NO: 402 |
| ITGB5 | NM_002213.3 | TCGTGAAAGATGACCAGGAGGCTGTGCTATGTTTCTACAAAACCGCCAAGGACTGC GTCATGATGTTCACC | SEQ ID NO: 403 |
| K-ras | NM_033360.2 | GTCAAAATGGGGAGGGACTAGGGCAGTTTGGATAGCTCAACAAGATACAATCTCAC TCTGTGGTGGTCCTG | SEQ ID NO: 404 |
| KCNH2 iso a/b | NM_000238.2 | GAGCGCAAAGTGGAAATCGCCTTCTACCGGAAAGATGGGAGCTGCTTCCTATGTCT GGTGGATGTGGTGCCGTGAAGA | SEQ ID NO: 405 |
| KCNH2 iso a/c | NM_172057.1 | TCCTGCTGCTGGTCATCTACACCGGCTGTCTTCACACCCTACTCGGCTGCCTTCCTG CTGAAGGAGACGGAAGAAGG | SEQ ID NO: 406 |
| KCNK4 | NM_016611.2 | CCTATCAGCCGCTGGTGTGGTTCTGGATCCTGCTCGGCCTGGCTTACTTCGCCTCA GTGCTCACCACCA | SEQ ID NO: 407 |

TABLE B-continued

| Gene | Locus Link | Sequence | SEQ ID NO |
|---|---|---|---|
| KDR | NM_002253.1 | GAGGACGAAGGCCTCTACACCTGCCAGGCATGCAGTGTTCTTGGCTGTGCAAAAGT GGAGGCATTTTT | SEQ ID NO: 408 |
| Ki-67 | NM_002417.1 | CGGACTTTGGGTGCGACTTGACGAGCGGTGGTTCGACAAGTGGCCTTGCGGGCCGG ATCGTCCCAGTGGAAGAGTTGTAA | SEQ ID NO: 409 |
| KIAA0125 | NM_014792.2 | GTGTCCTGGTCCATGTGGTGCACGTGTCTCCACCTCCAAGGAGAGGCTCCTCAGTG TGCACCTCCC | SEQ ID NO: 410 |
| KIF22 | NM_007317.1 | CTAAGGCACTTGCTGGAAGGGCAGAATGCCAGTGTGCTTGCCTATGGACCCACAGG AGCTGGGAAGA | SEQ ID NO: 411 |
| KIF2C | NM_006845.2 | AATTCCTGCTCCAAAAGAAAGTCTTCGAAGCCGCTCCACTCGCATGTCCACTGTCT CAGAGCTTCGCATCACG | SEQ ID NO: 412 |
| KIFC1 | XM_371813.1 | CCACAGGGTTGAAGAACCAGAAGCCAGTTCCTGCTGTTCCTGTCCAGAAGTCTGGC ACATCAGGTG | SEQ ID NO: 413 |
| Kitlng | NM_000899.1 | GTCCCCGGGATGGATGTTTTGCCAAGTCATTGTTGGATAAGCGAGATGGTAGTACA ATTGTCAGACAGCTTGACTGATC | SEQ ID NO: 414 |
| KLF5 | NM_001730.3 | GTGCAACCGCAGCTTCTCGCGCTCTGACCACCTGGCCCTGCATATGAAGAGGCACC AGAACTGAGCACTGCCCG | SEQ ID NO: 415 |
| KLF6 | NM_001300.4 | CACGAGACCGGCTACTTCTCGGCGCTGCCGTCTCTGGAGGAGTACTGGCAACAGAC CTGCCTAGAGC | SEQ ID NO: 416 |
| KLK10 | NM_002776.1 | GCCCAGAGGCTCCATCGTCCATCCTCTTCCTCCCCAGTCGGCTGAACTCTCCCCTT GTCTGCACTGTTCAAACCTCTG | SEQ ID NO: 417 |
| KLK6 | NM_002774.2 | GACGTGAGGGTCCTGATTCTCCCTGGTTTTACCCCAGCTCCATCCTTGCATCACTG GGGAGGACGTGATGAGTGAGGA | SEQ ID NO: 418 |
| KLRK1 | NM_007360.1 | TGAGAGCCAGGCTTCTTGTATGTCTCAAAATGCCAGCCTTCTGAAAGTATACAGCA AAGAGGACCAGGAT | SEQ ID NO: 419 |
| KNTC2 | NM_006101.1 | ATGTGCCAGTGAGCTTGAGTCCTTGGAGAAACACAAGCACCTGCTAGAAAGTACTG TTAACCAGGGGCTCA | SEQ ID NO: 420 |
| KRAS2 | NM_004985.3 | GAGACCAAGGTTGCAAGGCCAGGCCCTGTGTGAACCTTTGAGCTTTCATAGAGAGT TTCACAGCATGGACTG | SEQ ID NO: 421 |
| KRT19 | NM_002276.1 | TGAGCGGCAGAATCAGGAGTACCAGCGGCTCATGGACATCAAGTCGCGGCTGGAGC AGGAGATTGCCACCTACCGCA | SEQ ID NO: 422 |
| KRT8 | NM_002273.1 | GGATGAAGCTTACATGAACAAGGTAGAGCTGGAGTCTCGCCTGGAAGGGCTGACCG ACGAGATCAACTTCCTCAGGCAGCTATATG | SEQ ID NO: 423 |
| LAMA3 | NM_000227.2 | CAGATGAGGCACATGGAGACCCAGGCCAAGGACCTGAGGAATCAGTTGCTCAACTA CCGTTCTGCCATTTCAA | SEQ ID NO: 424 |
| LAMB3 | NM_000228.1 | ACTGACCAAGCCTGAGACCTACTGCACCCAGTATGGCGAGTGGCAGATGAAATGCT GCAAGTGTGAC | SEQ ID NO: 425 |
| LAMC2 | NM_005562.1 | ACTCAAGCGGAAATTGAAGCAGATAGGTCTTATCAGCACAGTCTCCGCCTCCTGGA TTCAGTGTCTCGGCTTCAGGGAGT | SEQ ID NO: 426 |
| LAT | NM_014387.2 | GTGAACGTTCCGGAGAGCGGGGAGAGCGCAGAAGCGTCTCTGGATGGCAGCCGGG AGTATGTGAATGT | SEQ ID NO: 427 |
| LCN2 | NM_005564.2 | CGCTGGGCAACATTAAGAGTTACCCTGGATTAACGAGTTACCTCGTCCGAGTGGTGA GCACCAACTACAACCAGCATGCT | SEQ ID NO: 428 |
| LDLRAP1 | NM_015627.1 | CAGTGCCTCTCGCCTGTCGACTGGGACAAGCCTGACAGCAGCGGCACAGAGCA GGATGACCTCTTCA | SEQ ID NO: 429 |
| LEF | NM_016269.2 | GATGACGGAAAGCATCCAGATGGAGGCCTCTACAACAAGGGACCCTCCTACTC GAGTTATTCCGGG | SEQ ID NO: 430 |
| LGALS3 | NM_002306.1 | AGCGGAAAATGGCAGACAATTTTTCGCTCCATGATGCGTTATCTGGGTCTGGAAA CCCAAACCCTCAAG | SEQ ID NO: 431 |
| LGMN | NM_001008530.1 | TTGGTGCCGTTCCTATAGATGATCCTGAAGATGGAGGCAAGCACTGGGTGGTGAT CGTGGCAGGTTC | SEQ ID NO: 432 |
| LILRB3 | NM_006864.1 | CACCTGGTCTGGGAAGATACCTGGAGGTTTTGATTGGGGTCTCGGTGGCCTTCGTC CTGCTGCTCTT | SEQ ID NO: 433 |

TABLE B-continued

| Gene | Locus Link | Sequence | SEQ ID NO |
|---|---|---|---|
| LMNB1 | NM_005573.1 | TGCAAACGCTGGTGTCACAGCCAGCCCCCCAACTGACCTCATCTGGAAGAACCAG AACTCGTGGGG | SEQ ID NO: 434 |
| LMYC | NM_012421.1 | CCCATCCAGAACACTGATTGCTGTCATTCAAGTGAAAGGGATGGAGGTCAGAAA GGGTGCATAGAAAGCAG | SEQ ID NO: 435 |
| LOX | NM_002317.3 | CCAATGGAGAACAACGGGCAGGTGTTCAGCTTGCTGAGCCTGGGCTCACAGTA CCAGCCTCAGCG | SEQ ID NO: 436 |
| LOXL2 | NM_002318.1 | TCAGCGGGCTCTTAAACAACCAGCTGTCCCCGCAGTAAAGAAGCCTGCGTGGTCA ACTCCTGTCTT | SEQ ID NO: 437 |
| LRP5 | NM_002335.1 | CGACTATGACCCACTGGACAAGTTCATCTACTGGGTGGATGGGCGCCAGAACATCA AGCGAGCCAAG | SEQ ID NO: 438 |
| LRP6 | NM_002336.1 | GGATGTAGCCATCTCTGCCTCTATAGACCTCAGGGCCTTCGCTGTGCTTGCCCTATT GGCTTTGAACT | SEQ ID NO: 439 |
| LY6D | NM_003695.2 | AATGCTGATGACTTGGAGCAGGCCCCACAGACCCCACAGAGGATGAAGCCACCC CACAGAGGATGCAG | SEQ ID NO: 440 |
| MAD | NM_002357.1 | TGGTTCTGATTAGGTAACGTATTGGACCTGCCCACAACTCCCTTGCACGTAAACT TCAGTGTCCCACCTTGACC | SEQ ID NO: 441 |
| MAD1L1 | NM_003550.1 | AGAAGCTGTCCCTGCAAGAGCAGGATGCAGCGATTGTGAAGAACATGAAGTCTG AGCTGGTACGGCT | SEQ ID NO: 442 |
| MAD2L1 | NM_002358.2 | CCGGGAGCAGGGAATCACCCTGCGCGGGAGCGCCGAAATCGTGGCCGAGTTC TTCTCATTCGGCATCAACAGCAT | SEQ ID NO: 443 |
| MADH2 | NM_005901.2 | GCTGCCTTTGGTAAGAACATGTCGTCCATCTTGCCATTCACGCCGCCAGTTGTG AAGAGACTGCTGGGAT | SEQ ID NO: 444 |
| MADH4 | NM_005359.3 | GGACATTACTGGCCTGTTCACAATGAGCTTGCATTCCAGCCTCCCATTTCCAATC ATCCTGCTCCTGAGTATTGGT | SEQ ID NO: 445 |
| MADH7 | NM_005904.1 | TCCATCAAGGCTTTCGACTACGAGAAGGCGTACAGCCTGCAGCGGCCCAATGA CCACGAGTTTATGCAGCAG | SEQ ID NO: 446 |
| MAP2 | NM_031846.1 | CGGACCACCAGGTCAGAGCCAATTCGCAGAGCAGGGAAGAGTGGTACCTAACAC CCACTACCCCTG | SEQ ID NO: 447 |
| MAP2K1 | NM_002755.2 | GCCTTTCTTACCCAGAAGCAGAAGGTGGGAGAACTGAAGGATGACGACTTTGAGA AGATCAGTGAGCTGGGGGCTG | SEQ ID NO: 448 |
| MAP3K1 | XM_042066.8 | GGTTGGCATCAAAAGGAACTGGTGCAGGAGAGTTTCAGGGACAATTACTGGGAC AATTGCATTTATGGCA | SEQ ID NO: 449 |
| MAPK14 | NM_139012.1 | TGAGTGGAAAAGCCTGACCTATGATGAAGTCATCAGCTTTGTGCCACCACCCCTTG ACCAAGAAGAGATGGAGTCC | SEQ ID NO: 450 |
| Maspin | NM_002639.1 | CAGATGCCACTTTGAGAACATTTTAGCTGACAACAGTGTGAACGACCAGACCAAA ATCCTTGTGGTTAATGCTGCC | SEQ ID NO: 451 |
| MAX | NM_002382.3 | CAAACGGGCTCATCATAATGCACTGGAACGAAAACGTAGGGACCACATCAAAGA CAGCTTTCACAGTTTGCGGGA | SEQ ID NO: 452 |
| MCM2 | NM_004526.1 | GACTTTTGCCCGCTACCTTTCATTCCGGCGTGACAACAATGAGCTGTTGCTCTTCA TACTGAAGCAGTTAGTGGC | SEQ ID NO: 453 |
| MCM3 | NM_002388.2 | GGAGAACAATCCCCTTGAGACAGAATATGGCCTTTCTGTCTACAAGGATCACCAGA CCATCACCATCCAGGAGAT | SEQ ID NO: 454 |
| MCM6 | NM_005915.2 | TGATGGTCCTATGTGTCACATTCATCACAGGTTTCATACCAACACAGGCTTCAGCA CTTCCTTTGGTGTGTTTCCTGTCCCA | SEQ ID NO: 455 |
| MCP1 | NM_002982.1 | CGCTCAGCCAGATGCAATCAATGCCCCAGTCACCTGCTGTTATAACTTCACCAATA GGAAGATCTCAGTGC | SEQ ID NO: 456 |
| MDK | NM_002391.2 | GGAGCCGACTGCAAGTACAAGTTTGAGAACTGGGGTGCGTGTGATGGGGGCACAGG CACCAAAGTC | SEQ ID NO: 457 |
| MDM2 | NM_002392.1 | CTACAGGGACGCCATCGAATCCGGATCTTGATGCTGGTGTAAGTGAACATTCAGGT GATTGGTTGGAT | SEQ ID NO: 458 |
| MGAT5 | NM_002410.2 | GGAGTCGAAGGTGGACAATCTTGTTGTCAATGGCACCGGAACAAACTCAACCAACT CCACTACAGCTGTTCCCA | SEQ ID NO: 459 |

TABLE B-continued

| Gene | Locus Link | Sequence | SEQ ID NO |
|---|---|---|---|
| MGMT | NM_002412.1 | GTGAAATGAAACGCACCACACTGGACAGCCCTTTGGGGAAGCTGGAGCTGTCTGG TTGTGAGCAGGGTC | SEQ ID NO: 460 |
| mGST1 | NM_020300.2 | ACGGATCTACCACACCATTGCATATTTGACACCCCTTCCCCAGCCAAATAGAGCT TTGAGTTTTTTTGTTGGATATGGA | SEQ ID NO: 461 |
| MMP1 | NM_002421.2 | GGGAGATCATCGGGACAACTCTCCTTTTGATGGACCTGGAGGAAATCTTGCTCATGC TTTTCAACCAGGCCC | SEQ ID NO: 462 |
| MMP12 | NM_002426.1 | CCAACGCTTGCCAAATCCTGACAATTCAGAACCAGCTCTCTGTGACCCCAATTTGA GTTTTGATGCTGTCACTACCGT | SEQ ID NO: 463 |
| MMP2 | NM_004530.1 | CCATGATGGAGAGGCAGACATCATGATCAACTTTGGCCGCTGGGAGCATGGCGAT GGATACCCCTTTGACGGTAAGGACGGACTCC | SEQ ID NO: 464 |
| MMP7 | NM_002423.2 | GGATGGTAGCAGTCTAGGGATTAACTTCCTGTATGCTGCAACTCATGAACTTGGCCA TTCTTTGGGTATGGGACATTCC | SEQ ID NO: 465 |
| MMP9 | NM_004994.1 | GAGAACCAATCTCACCGACAGGCAGCTGGCAGAGGAATACCTGTACCGCTATGGTT ACACTCGGGTG | SEQ ID NO: 466 |
| MRP1 | NM_004996.2 | TCATGGTGCCCGTCAATGCTGTGATGGCGATGAAGACCAAGACGTATCAGGTGGCC CACATGAAGAGCAAAGACAATCG | SEQ ID NO: 467 |
| MRP2 | NM_000392.1 | AGGGGATGACTTGGACACATCTGCCATTCGACATGACTGCAATTTTGACAAAGCCAT GCAGTTTT | SEQ ID NO: 468 |
| MRP3 | NM_003786.2 | TCATCCTGGCGATCTACTTCCTCTGGCAGAACCTAGGTCCCTCTGTCCTGGCTGGA GTCGCTTTCATGGTCTTGCTGATTCCACTCAACGG | SEQ ID NO: 469 |
| MRP4 | NM_005845.1 | AGCGCCTGGAATCTACAACTCGGAGTCCAGTGTTTTCCCACTTGTCATCTTCTCTC CAGGGGCTCT | SEQ ID NO: 470 |
| MRPL40 | NM_003776.2 | ACTTGCAGGCTGCTATCCTTAACATGCTGCCCCTGAGAGTAGGAATGACCAGGGT TCAAGTCTGCT | SEQ ID NO: 471 |
| MSH2 | NM_000251.1 | GATGCAGAATTGAGGCAGACTTTACAAGAAGATTTACTTCGTCGATTCCCAGATCT TAACCGACTTGCCAAGA | SEQ ID NO: 472 |
| MSH3 | NM_002439.1 | TGATTACCATCATGGCTCAGATTGGCTCCTATGTTCCTGCAGAAGAAGCGACAATT GGGATTGTGGATGGCATTTTCACAAG | SEQ ID NO: 473 |
| MSH6 | NM_000179.1 | TCTATTGGGGATTGGTAGGAACCGTTACCAGCTGGAAATTCCTGAGAATTTCACC ACTCGCAATTTG | SEQ ID NO: 474 |
| MT3 | NM_005954.1 | GTGTGAGAAGTGTGCCAAGGACTGTGTGTGCAAAGGCGGAGAGGCAGCTGAGGC AGAAGCAGAGAAGTGCAG | SEQ ID NO: 475 |
| MTA1 | NM_004689.2 | CCGCCCTCACCTGAAGAGAAACGCGCTCCTTGGCGGACACTGGGGGAGGAGAGG AAGAAGCGCGGCTAACTTATTCC | SEQ ID NO: 476 |
| MUC1 | NM_002456.1 | GGCCAGGATCTGTGGTGGTACAATTGACTCTGGCCTTCCGAGAAGGTACCATCA ATGTCCACGACGTGGAG | SEQ ID NO: 477 |
| MUC2 | NM_002457.1 | CTATGAGCCATGTGGGAACCGGAGCTTCGAGACCTGCAGGACCATCAACGGCAT CCACTCCAACAT | SEQ ID NO: 478 |
| MUC5B | XM_039877.11 | TGCCCTTGCACTGTCCTAACGGCTCAGCCATCCTGCACACCTACACCCACGTGGA TGAGTGTGGCTG | SEQ ID NO: 479 |
| MUTYH | NM_012222.1 | GTACGACCAAGAGAAACGGGACCTACCATGGAGAAGACGGGCAGAAGATGAGAT GGACCTGGACAGG | SEQ ID NO: 480 |
| MVP | NM_017458.1 | ACGAGAACGAGGGCATCTATGTGCAGGATGTCAAGACCGGAAAGGTGCGCGCT GTGATTGGAAGCACCTACATGC | SEQ ID NO: 481 |
| MX1 | NM_002462.2 | GAAGGAATGGGAATCAGTCATGAGCTAATCACCCTGGAGATCAGCTCCCGAGAT GTCCCGGATCTGACTCTAATAGAC | SEQ ID NO: 482 |
| MXD4 | NM_006454.2 | AGAAACTGGAGGAGCAGGACCGCCGGGCACTGAGCATCAAGGAGCAGCTGCAG CAGGAGCATCGTTTCCTGAAG | SEQ ID NO: 483 |
| MYBL2 | NM_002466.1 | GCCGAGATCGCCAAGATGTTGCCAGGGAGGACAGACAATGCTGTGAAGAATCA CTGGAACTCTACCATCAAAAG | SEQ ID NO: 484 |
| MYH11 | NM_002474.1 | CGGTACTTCTCAGGGCTAATATATACGTACTCTGGCCTCTTCTGCGTGGTGGTCAA CCCCTATAAACACCTGCCCATCTACTCGG | SEQ ID NO: 485 |

TABLE B-continued

| Gene | Locus Link | Sequence | SEQ ID NO |
|---|---|---|---|
| MYLK | NM_053025.1 | TGACGGAGCGTGAGTGCATCAAGTACATGCGGCAGATCTCGGAGGGAGTGGAGTA CATCCACAAGCAGGGCAT | SEQ ID NO: 486 |
| NAT2 | NM_000015.1 | TAACTGACATTCTTGAGCACCAGATCCGGGCTGTTCCCTTTGAGAACCTTAACATG CATTGTGGGCAAGCCAT | SEQ ID NO: 487 |
| NAV2 | NM_182964.3 | CTCTCCCAGCACAGCTTGAACCTCACTGAGTCAACCAGCCTGGACATGTTGCTG GATGACACTGGTG | SEQ ID NO: 488 |
| NCAM1 | NM_000615.1 | TAGTTCCCAGCTGACCATCAAAAAGGTGGATAAGAACGACGAGGCTGAGTACA TCTGCATTGCTGAGAACAAGGCTG | SEQ ID NO: 489 |
| NDE1 | NM_017668.1 | CTACTGCGGAAAGTCGGGGCACTGGAGTCCAAACTCGCTTCCTGCCGGAACCTC GTGTACGATCAGTCC | SEQ ID NO: 490 |
| NDRG1 | NM_006096.2 | AGGGCAACATTCCACAGCTGCCCTGGCTGTGATGAGTGTCCTTGCAGGGGCCGG AGTAGGAGCACTG | SEQ ID NO: 491 |
| NDUFS3 | NM_004551.1 | TATCCATCCTGATGGCGTCATCCCAGTGCTGACTTTCCTCAGGGATCACACCAAT GCACAGTTCAA | SEQ ID NO: 492 |
| NEDD8 | NM_006156.1 | TGCTGGCTACTGGGTGTTAGTTTGCAGTCCTGTGTGCTTCCCTCTCTTATGACTGTG TCCCTGGTTGTC | SEQ ID NO: 493 |
| NEK2 | NM_002497.1 | GTGAGGCAGCGCGACTCTGGCGACTGGCCGGCCATGCCTTCCCGGGCTGAGGACT ATGAAGTGTTGTACACCATTGGCA | SEQ ID NO: 494 |
| NF2 | NM_000268.2 | ACTCAGAGCTGACCTCCACCGCCCAGCCTGGGAAGTCATTGTAGGGAGTGAGACA CTGAAGCCCTGA | SEQ ID NO: 495 |
| NFKBp50 | NM_003998.1 | CAGACCAAGGAGATGGACCTCAGCGTGGTGCGGCTCATGTTTACAGCTTTTCTTC CGGATAGCACTGGCAGCT | SEQ ID NO: 496 |
| NFKBp65 | NM_021975.1 | CTGCCGGGATGGCTTCTATGAGGCTGAGCTCTGCCCGGACCGCTGCATCCACAG TTTCCAGAACCTGG | SEQ ID NO: 497 |
| NISCH | NM_007184.1 | CCAAGGAATCATGTTCGTTCAGGAGGAGGCCCTGGCCAGCAGCCTCTCGTCCACTG ACAGTCTGACTCCCGAGCACCA | SEQ ID NO: 498 |
| Nkd-1 | NM_033119.3 | GAGAGAGTGAGCGAACCCTGCCCAGGCTCCAAGAAGCAGCTGAAGTTTGAAGAGC TCCAGTGCGACG | SEQ ID NO: 499 |
| NMB | NM_021077.1 | GGCTGCTGGTACAAATACTGCAGAAATGACACCAATAATAGGGGCAGACACAACA GCGTGGCTTAGATTG | SEQ ID NO: 500 |
| NMBR | NM_002511.1 | TGATCCATCTCTAGGCCACATGATTGTCACCTTAGTTGCCCGGGTTCTCAGTTTTG GCAATTCTTGTGTCAACCCATTTGCTC | SEQ ID NO: 501 |
| NME1 | NM_000269.1 | CCAACCCTGCAGACTCCAAGCCTGGGACCATCCGTGGAGACTTCTGCATACAAGTT GGCAGGAACATTATACAT | SEQ ID NO: 502 |
| NOS3 | NM_000603.2 | ATCTCCGCCTCGCTCATGGGCACGGTGATGGCGAAGCGAGTGAAGGCGACAATCC TGTATGGCTCCGA | SEQ ID NO: 503 |
| NOTCH1 | NM_017617.2 | CGGGTCCACCAGTTTGAATGGTCAATGCGAGTGGCTGTCCCGGCTGCAGAGCGGC ATGGTGCCGAACCAATACAAC | SEQ ID NO: 504 |
| NOTCH2 | NM_024408.2 | CACTTCCCTGCTGGGATTATATCAACAACCAGTGTGATGAGCTGTGCAACACGGT CGAGTGCCTGTTTGACAACT | SEQ ID NO: 505 |
| NPM1 | NM_002520.2 | AATGTTGTCCAGGTTCTATTGCCAAGAATGTGTTGTCCAAAATGCCTGTTTAGTTT TTAAAGATGGAACTCCACCCTTTGCTTG | SEQ ID NO: 506 |
| NR4A1 | NM_002135.2 | CACAGCTTGCTTGTCGATGTCCCTGCCTTCGCCTGCCTCTCTGCCCTTGTCCTCA TCACCGACCGGCAT | SEQ ID NO: 507 |
| NRG1 | NM_013957.1 | CGAGACTCTCCTCATAGTGAAAGGTATGTGTCAGCCATGACCACCCCGGCTCGTA TGTCACCTGTAGATTCCACACGCCAAG | SEQ ID NO: 508 |
| NRP1 | NM_003873.1 | CAGCTCTCTCCACGCGATTCATCAGGATCTACCCCGAGAGAGCCACTCATGGCG GACTGGGGCTCAGAATGGAGCTGCTGGG | SEQ ID NO: 509 |
| NRP2 | NM_003872.1 | CTACAGCCTAAACGGCAAGGACTGGGAATACATTCAGGACCCCAGGACCCAGCA GCCAAAGCTGTTCGAAGGGAAC | SEQ ID NO: 510 |
| NTN1 | NM_004822.1 | AGAAGGACTATGCCGTCCAGATCCACATCCTGAAGGCGGACAAGGCGGGGACTG GTGGAAGTTCACGG | SEQ ID NO: 511 |

TABLE B-continued

| Gene | Locus Link | Sequence | SEQ ID NO |
|---|---|---|---|
| NUFIP1 | NM_012345.1 | GCTTCCACATCGTGGTATTGGAGACAGTCTTCTGATAGGTTTCCTCGGCATCAGA AGTCCTTCAACCCTGCAGTT | SEQ ID NO: 512 |
| ODC1 | NM_002539.1 | AGAGATCACCGGCGTAATCAACCCAGCGTTGGACAAATACTTTCCGTCAGACTCTG GAGTGAGAATCATAGCTGAGCCCG | SEQ ID NO: 513 |
| OPN, osteopontin | NM_000582.1 | CAACCGAAGTTTTCACTCCAGTTGTCCCCACAGTAGACACATATGATGGCCGAG GTGATAGTGTGGTTTATGGACTGAGG | SEQ ID NO: 514 |
| ORC1L | NM_004153.2 | TCCTTGACCATACCGGAGGGTGCATGTACATCTCCGGTGTCCCTGGGACAGGGA AGACTGCCACTG | SEQ ID NO: 515 |
| OSM | NM_020530.3 | GTTTCTGAAGGGGAGGTCACAGCCTGAGCTGGCCTCCTATGCCTCATCATGTCCC AAACCAGACACCT | SEQ ID NO: 516 |
| OSMR | NM_003999.1 | GCTCATCATGGTCATGTGCTACTTGAAAAGTCAGTGGATCAAGGAGACCTGTTA TCCTGACATCCCTGACCCTTACA | SEQ ID NO: 517 |
| P14ARF | S78535.1 | CCCTCGTGCTGATGCTACTGAGGAGCCAGCGTCTAGGGCAGCAGCCGCTTCCTAG AAGACCAGGTCATGATG | SEQ ID NO: 518 |
| p16-INK4 | L27211.1 | GCGGAAGGTCCCTCAGACATCCCCGATTGAAAGAACCAGAGAGGCTCTGAGAAAC CTCGGGAAACTTAGATCATCA | SEQ ID NO: 519 |
| p21 | NM_000389.1 | TGGAGACTCTCAGGGTCGAAAACGGCGGCAGACCAGCATGACAGATTTCTAC CACTCCAAACGCC | SEQ ID NO: 520 |
| p27 | NM_004064.1 | CGGTGGACCACGAAGAGTTAACCCGGGACTTGGAGAAGCACTGCAGAGACAT GGAAGAGGCGAGCC | SEQ ID NO: 521 |
| P53 | NM_000546.2 | CTTTGAACCCTTGCTTGCAATAGGTGTGCGTCAGAAGCACCCAGGACTTCCATT TGCTTTGTCCCGGG | SEQ ID NO: 522 |
| p53R2 | AB036063.1 | CCCAGCTAGTGTTCCTCAGAACAAAGATTGGAAAAAGCTGGCCGAGAACCATT TATACATAGAGGAAGGGCTTACGG | SEQ ID NO: 523 |
| PADI4 | NM_012387.1 | AGCAGTGGCTTGCTTTCTTCCTGTGATGTCCCAGTTTCCCACTCTGAAGATC CCAACATGGTCCTAGCA | SEQ ID NO: 524 |
| PAI1 | NM_000602.1 | CCGCAACGTGGTTTTCTCACCCTATGGGGTGGCCTCGGTGTTGGCCATGCTCCA GCTGACAACAGGAGGAGAAACCCAGCA | SEQ ID NO: 525 |
| Pak1 | NM_002576.3 | GAGCTGTGGGTTGTTATGGAATACTTGGCTGGAGGCTCCTTGACAGATGTGGTGA CAGAAACTTGCATGG | SEQ ID NO: 526 |
| PARC | NM_015089.1 | GGAGCTGACCTGCTTCCTACATCGCCTGGCCTCGATGCATAAGGACTATGCTGT GGTGCTCTGCT | SEQ ID NO: 527 |
| PCAF | NM_003884.3 | AGGTGGCTGTGTTACTGCAACGTGCCACAGTTCTGCGACAGTCTACCTCGGTAC GAAACCACACAGGTG | SEQ ID NO: 528 |
| PCNA | NM_002592.1 | GAAGGTGTTGGAGGCACTCAAGGACCTCATCAACGAGGCCTGCTGGGATATTA GCTCCAGCGGTGTAAACC | SEQ ID NO: 529 |
| PDGFA | NM_002607.2 | TTGTTGGTGTGCCCTGGTGCCGTGGTGGCGGTCACTCCCTCTGCTGCCAGTGTT TGGACAGAACCCA | SEQ ID NO: 530 |
| PDGFB | NM_002608.1 | ACTGAAGGAGACCCTTGGAGCCTAGGGGCATCGGCAGGAGAGTGTGTGGGCAG GGTTATTTA | SEQ ID NO: 531 |
| PDGFC | NM_016205.1 | AGTTACTAAAAATACCACGAGGTCCTTCAGTTGAGACCAAAGACCGGTGTCA GGGGATTGCACAAATCACTCACCGAC | SEQ ID NO: 532 |
| PDGFD | NM_025208.2 | TATCGAGGCAGGTCATACCATGACCGGAAGTCAAAAGTTGACCTGGATAGGCTCA ATGATGATGCCAAGCGTTA | SEQ ID NO: 533 |
| PDGFRa | NM_006206.2 | GGGAGTTTCCAAGAGATGGACTAGTGCTTGGTCGGGTCTTGGGGTCTGGAGCGTTT GGGAAGGTGGTTGAAG | SEQ ID NO: 534 |
| PDGFRb | NM_002609.2 | CCAGCTCTCCTTCCAGCTACAGATCAATGTCCCTGTCCGAGTGCTGGAGCTAAGTGA GAGCCACCCC | SEQ ID NO: 535 |
| PFN1 | NM_005022.2 | GGAAAACGTTCGTCAACATCACGCCAGCTGAGGTGGGTGTCCTGGTTGGCAAAGA CCGGTCAAGTTTT | SEQ ID NO: 536 |
| PFN2 | NM_053024.1 | TCTATACGTCGATGGTGACTGCACAATGGACATCCGGACAAAGAGTCAAGGTGGG GAGCCAACATACAATGTGGCTGTCGGC | SEQ ID NO: 537 |

TABLE B-continued

| Gene | Locus Link | Sequence | SEQ ID NO |
| --- | --- | --- | --- |
| PGK1 | NM_000291.1 | AGAGCCAGTTGCTGTAGAACTCAAATCTCTGCTGGGCAAGGATGTTCTGTTCTTG AAGGACTGTGTAGGCCCAG | SEQ ID NO: 538 |
| PI3K | NM_002646.2 | TGCTACCTGGACAGCCCGTTGGTGCGCTTCCTCCTGAAACGAGCTGTGTCTGACT TGAGAGTGACTCACTACTTCTTCTGGTTACTGAAGGACGGCCT | SEQ ID NO: 539 |
| PI3KC2A | NM_002645.1 | ATACCAATCACCGCACAAACCCAGGCTATTTGTTAAGTCCAGTCACAGCGCA AAGAAACATATGCGGAGAAAATGCTAGTGTG | SEQ ID NO: 540 |
| PIK3CA | NM_006218.1 | GTGATTGAAGAGCATGCCAATTGGTCTGTATCCCGAGAAGCAGGATTTAGCTATT CCCACGCAGGAC | SEQ ID NO: 541 |
| PIM1 | NM_002648.2 | CTGCTCAAGGACACCGTCTACACGGACTTCGATGGGACCCGAGTGTATAGCCCTC CAGAGTGGATCC | SEQ ID NO: 542 |
| Pin1 | NM_006221.1 | GATCAACGGCTACATCCAGAAGATCAAGTCGGGAGAGGAGGACTTTGAGTCTCT GGCCTCACAGTTCA | SEQ ID NO: 543 |
| PKD1 | NM_000296.2 | CAGCACCAGCGATTACGACGTTGGCTGGGAGAGTCCTCACAATGGCTCGGGG ACGTGGGCCTATTCAG | SEQ ID NO: 544 |
| PKR2 | NM_002654.3 | CCGCCTGGACATTGATTCACCACCCATCACAGCCCGGAACACTGGCATCATCT GTACCATTGGCCCAG | SEQ ID NO: 545 |
| PLA2G2A | NM_000300.2 | GCATCCCTCACCCATCCTAGAGGCCAGGCAGGAGCCCTTCTATACCCACCCA GAATGAGACATCCAGCAGATTTCCAGC | SEQ ID NO: 546 |
| PLAUR | NM_002659.1 | CCCATGGATGCTCCTCTGAAGAGACTTTCCTCATTGACTGCCGAGGCCCCATGA ATCAATGTCTGGTAGCCACCGG | SEQ ID NO: 547 |
| PLK | NM_005030.2 | AATGAATACAGTATTCCCAAGCACATCAACCCCGTGGCCGCCTCCCTCATCCAG AAGATGCTTCAGACA | SEQ ID NO: 548 |
| PLK3 | NM_004073.2 | TGAAGGAGACGTACCGCTGCATCAAGCAGGTTCACTACACGCTGCCTGCCAGCCT CTCACTGCCTG | SEQ ID NO: 549 |
| PLOD2 | NM_000935.2 | CAGGGAGGTGGTTGCAAATTTCTAAGGTACAATTGCTCTATTGAGTCACCACGA AAAGGCTGGAGCTTCATGCATCCTGGGAGA | SEQ ID NO: 550 |
| PMS1 | NM_000534.2 | CTTACGGTTTTCGTGGAGAAGCCTTGGGGTCAATTTGTTGTATAGCTGAGGTTTTAA TTACAACAAGAACGGCTGCT | SEQ ID NO: 551 |
| PMS2 | NM_000535.2 | GATGTGGACTGCCATTCAAACCAGGAAGATACCGGATGTAAATTTCGAGTTTTGC CTCAGCCAACTAATCTCGCA | SEQ ID NO: 552 |
| PPARG | NM_005037.3 | TGACTTTATGGAGCCCAAGTTTGAGTTTGCTGTGAAGTTCAATGCACTGGAATT AGATGACAGCGACTTGGC | SEQ ID NO: 553 |
| PPID | NM_005038.1 | TCCTCATTTGGATGGGAAACATGTGGTGTTTGGCCAAGTAATTAAAGGAATAGGAG TGGCAAGGATATTGG | SEQ ID NO: 554 |
| PPM1D | NM_003620.1 | GCCATCCGCAAAGGCTTTCTCGCTTGTCACCTTGCCATGTGGAAGAAACTGGC GGAATGGCC | SEQ ID NO: 555 |
| PPP2R4 | NM_178001.1 | GGCTCAGAGCATAAGGCTTCAGGGCCCAAGTTGGGAGAAGTGACCAAAGTG TAGCCAGTTTTCTGAGTTCCGT | SEQ ID NO: 556 |
| PR | NM_000926.2 | GCATCAGGCTGTCATTATGGTGTCCTTACCTGTGGGAGCTGTAAGGTCTTCTTTAAG AGGGCAATGGAAGGGCAGCACAACTACT | SEQ ID NO: 557 |
| PRDX2 | NM_005809.4 | GGTGTCCTTCGCCAGATCACTGTTAATGATTTGCCTGTGGGACGCTCCGTGGAT GAGGCTCTGCGGCTG | SEQ ID NO: 558 |
| PRDX3 | NM_006793.2 | TGACCCCAATGGAGTCATCAAGCATTTGAGCGTCAACGATCTCCCAGTGGGCCGA AGCGTGGAAGAAACCCTCCGCTTGG | SEQ ID NO: 559 |
| PRDX4 | NM_006406.1 | TTACCCATTTGGCCTGGATTAATACCCCTCGAAGACAAGGAGGACTTGGGCCAAT AAGGATTCCACTTCTTTCAG | SEQ ID NO: 560 |
| PRDX6 | NM_004905.2 | CTGTGAGCCAGAGGATGTCAGCTGCCAATTGTGTTTTCCTGCAGCAATTCCATAAA CACATCCTGGTGTCATCACA | SEQ ID NO: 561 |
| PRKCA | NM_002737.1 | CAAGCAATGCGTCATCAATGTCCCCAGCCTCTGCGGAATGGATCACACTGAGAA GAGGGGGCGGATTTAC | SEQ ID NO: 562 |
| PRKCB1 | NM_002738.5 | GACCCAGCTCCACTCCTGCTTCCAGACCATGGACCGCCTGTACTTTGTGATGGAGT ACGTGAATGGG | SEQ ID NO: 563 |

TABLE B-continued

| Gene | Locus Link | Sequence | SEQ ID NO |
|---|---|---|---|
| PRKCD | NM_006254.1 | CTGACACTTGCCGCAGAGAATCCCTTTCTCACCCACCTCATCTGCACCTTCCAGACC AAGGACCACCT | SEQ ID NO: 564 |
| PRKR | NM_002759.1 | GCGATACATGAGCCCAGAACAGATTCTTCGCAAGACTATGGAAAGGAAGTGGAC CTCTACGCTTTGGGGCTAATTCTTGCTGA | SEQ ID NO: 565 |
| pS2 | NM_003225.1 | GCCCTCCCAGTGTGCAAATAAGGGCTGCTGTTTCGACGACACCGTTCGTGGGGTCC CCTGGTGCTTCTATCCTAATACCATCGACG | SEQ ID NO: 566 |
| PTCH | NM_000264.2 | CCACGACAAAGCCGACTACATGCCTGAAACAAGGCTGAGAATCCCGGCAGCAG AGCCCATCGAGTA | SEQ ID NO: 567 |
| PTEN | NM_000314.1 | TGGCTAAGTGAAGATGACAATCATGTTGCAGCAATTCACTGTAAAGCTGGAAAGG GACGAACTGGTGTAATGATATGTGCA | SEQ ID NO: 568 |
| PTGER3 | NM_000957.2 | TAACTGGGGCAACCTTTTCTTCGCCTCTGCCTTTGCCTTCCTGGGGCTCTTGGCGC TGACAGTCACCTTTTCCTGCAA | SEQ ID NO: 569 |
| PTHLH | NM_002820.1 | AGTGACTGGGAGTGGGCTAGAAGGGGACCACCTGTCTGACACCTCCACAACGTC GCTGGAGCTCGATTCACGGTAACAGGCTT | SEQ ID NO: 570 |
| PTHR1 | NM_000316.1 | CGAGGTACAAGCTGAGATCAAGAATCTTGGAGCCGCTGGACACTGGCACTGGA CTTCAAGCGAAAGGCACGC | SEQ ID NO: 571 |
| PTK2 | NM_005607.3 | GACCGGTCGAATGATAAGGTGTACGAGAATGTGACGGGCCTGGTGAAAGCTGTCA TCGAGATGTCCAG | SEQ ID NO: 572 |
| PTK2B | NM_004103.3 | CAAGCCCAGCCGACCTAAGTACAGACCCCCTCCGCAAACCAACCTCCTGGCTCCA AAGCTGCAGTTCCAGGTTC | SEQ ID NO: 573 |
| PTP4A3 | NM_007079.2 | AATATTTGTGCGGGGTATGGGGGTGGGTTTTTAAATCTCGTTTCTCTTGGACAAGCA CAGGGATCTCGTT | SEQ ID NO: 574 |
| PTP4A3 v2 | NM_032611.1 | CCTGTTCTCGGCACCTTAAATTATTAGACCCCGGGGCAGTCAGGTGCTCCGGACAC CCGAAGGCAATA | SEQ ID NO: 575 |
| PTPD1 | NM_007039.2 | CGCTTGCCTAACTCATACTTTCCCGTTGACACTTGATCCACGCAGCGTGGCACTGG GACGTAAGTGGCGCAGTCTGAATGG | SEQ ID NO: 576 |
| PTPN1 | NM_002827.2 | AATGAGGAAGTTTCGGATGGGGCTGATCCAGACAGCCGACCAGCTGCGCTTCTC CTACCTGGCTGTGATCGAAG | SEQ ID NO: 577 |
| PTPRF | NM_002840.2 | TGTTTTAGCTGAGGGACGTGGTGCCGACGTCCCCAAACCTAGCTAGGCTAAGTCAA GATCAACATTCCAGGGTTGGTA | SEQ ID NO: 578 |
| PTPRJ | NM_002843.2 | AACTTCCGGTACCTCGTTCGTGACTACATGAAGCAGAGTCCTCCCGAATCGCCGA TTCTGGTGCATTGCAGTGCT | SEQ ID NO: 579 |
| PTPRO | NM_030667.1 | CATGGCCTGATCATGGTGTGCCCACAGCAAATGCTGCAGAAAGTATCCTGCAGTTT GTACACATGG | SEQ ID NO: 580 |
| PTTG1 | NM_004219.2 | GGCTACTCTGATCTATGTTGATAAGGAAAATGGAGAACCAGGCACCCGTGTGGT TGCTAAGGATGGGCTGAAGC | SEQ ID NO: 581 |
| RAB32 | NM_006834.2 | CCTGCAGCTGTGGGACATCGCGGGGCAGGAGCGATTTGGCAACATGACCCGAGTA TACTACAAGGAAGCTGTTGGTGCT | SEQ ID NO: 582 |
| RAB6C | NM_032144.1 | GCGACAGCTCCTCTAGTTCCACCATGTCCGCGGGCGGAGACTTCGGGAATCCGCTG AGGAAATTCAAGCTGGTGTTCC | SEQ ID NO: 583 |
| RAC1 | NM_006908.3 | TGTTGTAAATGTCTCAGCCCCTCGTTCTTGGTCCTGTCCCTTGGAACCTTTGT ACGCTTTGCTCAA | SEQ ID NO: 584 |
| RAD51C | NM_058216.1 | GAACTTCTTGAGCAGGAGCATACCCAGGGCTTCATAATCACCTTCTGTTCAGCAC TAGATGATATTCTTGGGGGTGGA | SEQ ID NO: 585 |
| RAD54L | NM_003579.2 | AGCTAGCCTCAGTGACACACATGACAGGTTGCACTGCCGACGTTGTGTCAACAGCC GTCAGATCCGG | SEQ ID NO: 586 |
| RAF1 | NM_002880.1 | CGTCGTATGCGAGAGTCTGTTTCCAGGATGCCTGTTAGTTCTCAGCACAGATATTC TACACCTCACGCCTTCA | SEQ ID NO: 587 |
| RALBP1 | NM_006788.2 | GGTGTCAGATATAAATGTGCAAATGCCTTCTTGCTGTCCTGTCGGTCTCAGTACG TTCACTTTATAGCTGCTGGCAATATCGAA | SEQ ID NO: 588 |
| RANBP2 | NM_006267.3 | TCCTTCAGCTTTCACACTGGGCTCAGAAATGAAGTTGCATGACTCTTCTGGAAGTC AGGTGGGAACAGGATTT | SEQ ID NO: 589 |

TABLE B-continued

| Gene | Locus Link | Sequence | SEQ ID NO |
|---|---|---|---|
| ranBP7 | NM_006391.1 | AACATGATTATCCAAGCCGCTGGACTGCCATTGTGGACAAAATTGGCTTTTATCT TCAGTCCGATAACAGTGCTTGTTGGC | SEQ ID NO: 590 |
| RANBP9 | NM_005493.2 | CAAGTCAGTTGAGACGCCAGTTGTGTGGAGGAAGTCAGGCCGCCATAGAAAGAA TGATCCACTTTGGACGAGAGCTGCA | SEQ ID NO: 591 |
| RAP1GDS1 | NM_021159.3 | TGTGGATGCTGGATTGATTTCACCACTGGTGCAGCTGCTAAATAGCAAAGACCA GGAAGTGCTGCTT | SEQ ID NO: 592 |
| RARA | NM_000964.1 | AGTCTGTGAGAAACGACCGAAACAAGAAGAAGAAGGAGGTGCCCAAGCCCGAG TGCTCTGAGAGCTACACGCTGACGCCG | SEQ ID NO: 593 |
| RARB | NM_016152.2 | TGCCTGGACATCCTGATTCTTAGAATTTGCACCAGGTATACCCCAGAACAAGACA CCATGACTTTCTCAGACGGCCTT | SEQ ID NO: 594 |
| RASSF1 | NM_007182.3 | AGTGGGAGACACCTGACCTTTCTCAAGCTGAGATTGAGCAGAAGATCAAGGAGT ACAATGCCCAGATCA | SEQ ID NO: 595 |
| RBM5 | NM_005778.1 | CGAGAGGGAGAGCAAGACCATCATGCTGCGCGGCCTTCCCATCACCATCACAGA GAGCGATATTCGAGA | SEQ ID NO: 596 |
| RBX1 | NM_014248.2 | GGAACCACATTATGGATCTTTGCATAGAATGTCAAGCTAACCAGGCGTCCGCTA CTTCAGAAGAGTGTACTGTCGCATG | SEQ ID NO: 597 |
| RCC1 | NM_001269.2 | GGGCTGGGTGAGAATGTGATGGAGAGGAAGAAGCCGGCCCTGGTATCCATTCC GGAGGATGTTGTG | SEQ ID NO: 598 |
| REG4 | NM_032044.2 | TGCTAACTCCTGCACAGCCCCGTCCTCTTCCTTTCTGCTAGCCTGGCTAAATCT GCTCATTATTTCAGAGGGGAAACCTAGCA | SEQ ID NO: 599 |
| RFC | NM_003056.1 | TCAAGACCATCATCACTTTTCATTGTCTCGGACGTGCGGGGCCTGGGCCTCCCGGT CCGCAAGCAGTTCCAGTTATACTCCGTGTACTTCCTGATCC | SEQ ID NO: 600 |
| RhoB | NM_004040.2 | AAGCATGAACAGGACTTGACCATCTTTCCAACCCCTGGGGAAGACATTTGCAA CTGACTTGGGGAGG | SEQ ID NO: 601 |
| rhoC | NM_175744.1 | CCCGTTCGGTCTGAGGAAGGCCGGGACATGGCGAACCGGATCAGTGCCTTTGG CTACCTTGAGTGCTC | SEQ ID NO: 602 |
| RIZ1 | NM_012231.1 | CCAGACGAGCGATTAGAAGCGGCAGCTTGTGAGGTGAATGATTTGGGGAAGA GGAGGAGGAGGAAGAGGAGGA | SEQ ID NO: 603 |
| RNF11 | NM_014372.3 | ACCCTGGAAGAGATGGATCAGAAAAAAGATCCGGGAGTGTGTGATCTGTATGAT GGACTTTGTTTATGGGGACCCAAT | SEQ ID NO: 604 |
| ROCK1 | NM_005406.1 | TGTGCACATAGGAATGAGCTTCAGATGCAGTTGGCCAGCAAAGAGAGTGATAT TGAGCAATTGCGTGCTAAAC | SEQ ID NO: 605 |
| ROCK2 | NM_004850.3 | GATCCGAGACCCTCGCTCCCCCATCAACGTGGAGAGCTTGCTGGATGGCTTAAA TTCCTTGGTCCT | SEQ ID NO: 606 |
| RPLP0 | NM_001002.2 | CCATTCTATCATCAACGGGTACAAACGAGTCCTGGCCTTGTCTGTGGAGACGGA TTACACCTTCCCACTTGCTGA | SEQ ID NO: 607 |
| RPS13 | NM_001017.2 | CAGTCGGCTTTACCCTATCGACGCAGCGTCCCCACTTGGTTGAAGTTGACAT CTGACGACGTGAAGGAGCAGA | SEQ ID NO: 608 |
| RRM1 | NM_001033.1 | GGGCTACTGGCAGCTACATTGCTGGGACTAATGGCAATTCCAATGGCCTTGTAC CGATGCTGAGAG | SEQ ID NO: 609 |
| RRM2 | NM_001034.1 | CAGCGGGATTAAACAGTCCTTTAACCAGCACAGCCAGTTAAAAGATGCAGCCT CACTGCTTCAACGCAGAT | SEQ ID NO: 610 |
| RTN4 | NM_007008.1 | GACTGGAGTGGTGTTTGGTGCCAGCCTATTCCTGCTGCTTTCATTGACAGTAT TCAGCATTGTGAGCGTAACAG | SEQ ID NO: 611 |
| RUNX1 | NM_001754.2 | AACAGAGACATTGCCAACCATATTGGATCTGCTTGCTGTCCAAACCAGCAAAC TTCCTGGGCAAATCAC | SEQ ID NO: 612 |
| RXRA | NM_002957.3 | GCTCTGTTGTGTCCTGTTGCCGGCTCTGGCCTTCCTGTGACTGACTGTGAAGTGGC TTCTCCGTAC | SEQ ID NO: 613 |
| S100A1 | NM_006271.1 | TGGACAAGGTGATGAAGGAGCTAGACGAGAATGGAGACGGGGAGGTGGACTT CCAGGAGTATGTGGTGCT | SEQ ID NO: 614 |
| S100A2 | NM_005978.2 | TGGCTGTGCTGGTCACTACCTTCCACAAGTACTCCTGCCAAGAGGGCGACAAG TTCAAGCTGAGTAAGGGGA | SEQ ID NO: 615 |

TABLE B-continued

| Gene | Locus Link | Sequence | SEQ ID NO |
|---|---|---|---|
| S100A4 | NM_002961.2 | GACTGCTGTCATGGCGTGCCCTCTGGAGAAGGCCCTGGATGTGATGGTGTCCA CCTTCCACAAGTACTCG | SEQ ID NO: 616 |
| S100A8 | NM_002964.3 | ACTCCCTGATAAAGGGGAATTTCCATGCCGTCTACAGGGATGACCTGAAGAA ATTGCTAGAGACCGAGTGTCCTCA | SEQ ID NO: 617 |
| S100A9 | NM_002965.2 | CTTTGGGACAGAGTGCAAGACGATGACTTGCAAAATGTCGCAGCTGGAACG CAACATAGAGACCA | SEQ ID NO: 618 |
| S100P | NM_005980.2 | AGACAAGGATGCCGTGGATAAATTGCTCAAGGACCTGGACGCCAATGGAGAT GCCCAGGTGGACTTC | SEQ ID NO: 619 |
| SAT | NM_002970.1 | CCTTTTACCACTGCCTGGTTGCAGAAGTGCCGAAAGAGCACTGGACTCCGG AAGGACACAGCATTGT | SEQ ID NO: 620 |
| SBA2 | NM_018639.3 | GGACTCAACGATGGGCAGATCAAGATCTGGGAGGTGCAGACAGGGCTCCTGC TTTTGAATCTTTCCG | SEQ ID NO: 621 |
| SDC1 | NM_002997.1 | GAAATTGACGAGGGGTGTCTTGGGCAGAGCTGGCTCTGAGCGCCTCCATCCAA GGCCAGGTTCTCCGTTAGCTCCT | SEQ ID NO: 622 |
| SEMA3B | NM_004636.1 | GCTCCAGGATGTGTTTCTGTTGTCCTCGCGGGACCACCGGACCCCGCTGCTCT ATGCCGTCTTCTCCACGT | SEQ ID NO: 623 |
| SEMA3F | NM_004186.1 | CGCGAGCCCCTCATTATACACTGGGCAGCCTCCCCACAGCGCATCGAGGAATGC GTGCTCTCAGGCAAGGATGTCAACGGCGAGTG | SEQ ID NO: 624 |
| SEMA4B | NM_020210.1 | TTCCAGCCCAACACAGTGAACACTTTGGCCTGCCCGCTCCTCTCCAACCTGGC GACCCGACTC | SEQ ID NO: 625 |
| SFRP2 | NM_003013.2 | CAAGCTGAACGGTGTGTCCGAAAGGGACCTGAAGAAATCGGTGCTGTGGCTC AAAGACAGCTTGCA | SEQ ID NO: 626 |
| SFRP4 | NM_003014.2 | TACAGGATGAGGCTGGGCATTGCCTGGGACAGCCTATGTAAGGCCATGTGCCCC TTGCCCTAACAAC | SEQ ID NO: 627 |
| SGCB | NM_000232.1 | CAGTGGAGACCAGTTGGGTAGTGGTGACTGGGTACGCTACAAGCTCTGCATG TGTGCTGATGGGACGCTCTTCAAGG | SEQ ID NO: 628 |
| SHC1 | NM_003029.3 | CCAACACCTTCTTGGCTTCTGGGACCTGTGTTCTTGCTGAGCACCCTCTCCGG TTTGGGTTGGGATAACAG | SEQ ID NO: 629 |
| SHH | NM_000193.2 | GTCCAAGGCACATATCCACTGCTCGGTGAAAGCAGAGAACTCGGTGGCGGCCAAA TCGGGAGGCTGCTTC | SEQ ID NO: 630 |
| SI | NM_001041.1 | AACGGACTCCCTCAATTTGTGCAAGATTTGCATGACCATGGACAGAAATATGTCA TCATCTTGGACCCTGCAATTTC | SEQ ID NO: 631 |
| Siah-1 | NM_003031.2 | TTGGCATTGGAACTACATTCAATCCGCGGTATCCTCGGATTAGTTCTAGGACC CCCTTCTCCATACC | SEQ ID NO: 632 |
| SIAT4A | NM_003033.2 | AACCACAGTTGGAGGAGGACGGCAGAGACAGTTTCCCTCCCCGCTATACCAA CACCCTTCCTTCG | SEQ ID NO: 633 |
| SIAT7B | NM_006456.1 | TCCAGCCCAAATCCTCCTGGTGGCACATCCTACCCCAGATGCTAAAGTGATTC AAGGACTCCAGGACACC | SEQ ID NO: 634 |
| SIM2 | NM_005069.2 | GATGGTAGGAAGGGATGTGCCCGCCTCTCCACGCACTCAGCTATACCTCATT CACAGCTCCTTGTG | SEQ ID NO: 635 |
| SIN3A | NM_015477.1 | CCAGAGTCATGCTCATCCAGCCCCACCAGTTGCACCAGTGCAGGGACAG CAGCAATTTCAGAGGCTGAAGGTGG | SEQ ID NO: 636 |
| SIR2 | NM_012238.3 | AGCTGGGGTGTCTGTTTCATGTGGAATACCTGACTTCAGGTCAAGGGATG GTATTTATGCTCGCCTTGCTGT | SEQ ID NO: 637 |
| SKP1A | NM_006930.2 | CCATTGCCTTTGCTTTGTTCATAATTTCAGCAGGGCAGAATAAAAACCATG GGAGGCAAAGAAAGGAAATCCGGAA | SEQ ID NO: 638 |
| SKP2 | NM_005983.2 | AGTTGCAGAATCTAAGCCTGGAAGGCCTGCGGCTTTCGGATCCCATTGTCAA TACTCTCGCAAAAAACTCA | SEQ ID NO: 639 |
| SLC25A3 | NM_213611.1 | TCTGCCAGTGCTGAATTCTTTGCTGACATTGCCCTGGCTCCTATGGAAG CTGCTAAGGTTCGAA | SEQ ID NO: 640 |
| SLC2A1 | NM_006516.1 | GCCTGAGTCTCCTGTGCCCACATCCCAGGCTTCACCCTGAATGGTTCCATGC CTGAGGGTGGAGACT | SEQ ID NO: 641 |

TABLE B-continued

| Gene | Locus Link | Sequence | SEQ ID NO |
|---|---|---|---|
| SLC31A1 | NM_001859.2 | CCGTTCGAAGAGTCGTGAGGGGGTGACGGGTTAAGATTCGGAGAGAGAGGT GCTAGTGGCTGGACT | SEQ ID NO: 642 |
| SLC5A8 | NM_145913.2 | CCTGCTTTCAACCACATTGAATTGAACTCAGATCAGAGTGGCAAGAGCAA TGGGACTCGTTTGTGAAGCTGCTCT | SEQ ID NO: 643 |
| SLC7A5 | NM_003486.4 | GCGCAGAGGCCAGTTAAAGTAGATCACCTCCTCGAACCCACTCCGGTTCCCCGC AACCCACAGCTCAGCT | SEQ ID NO: 644 |
| SLPI | NM_003064.2 | ATGGCCAATGTTTGATGCTTAACCCCCCCAATTTCTGTGAGATGGATGGCCAG TGCAAGCGTGACTTGAAGTGT | SEQ ID NO: 645 |
| SMARCA3 | NM_003071.2 | AGGGACTGTCCTGGCACATTATGCAGATGTCCTGGGTCTTTTGCTTAGACTG CGGCAAATTTGTTG | SEQ ID NO: 646 |
| SNAI1 | NM_005985.2 | CCCAATCGGAAGCCTAACTACAGCGAGCTGCAGGACTCTAATCCAGAGTTTA CCTTCCAGCAGCCCTAC | SEQ ID NO: 647 |
| SNAI2 | NM_003068.3 | GGCTGGCCAAACATAAGCAGCTGCACTGCGATGCCCAGTCTAGAAAATCTTTC AGCTGTAAATACTGTGACAAGGA | SEQ ID NO: 648 |
| SNRPF | NM_003095.1 | GGCTGGTCGGCAGAGAGTAGCCTGCAACATTCGGCCGTGGTTTACATGAGT TTACCCCTCAATCCCAAACCTTTCCTCA | SEQ ID NO: 649 |
| SOD1 | NM_000454.3 | TGAAGAGAGGCATGTTGGAGACTTGGGCAATGTGACTGCTGACAAAGATGG TGTGGCCGATGTGTCTATT | SEQ ID NO: 650 |
| SOD2 | NM_000636.1 | GCTTGTCCAAATCAGGATCCACTGCAAGGAACAACAGGCCTTATTCCACTGC TGGGGATTGATGTGTGGGAGCACGCT | SEQ ID NO: 651 |
| SOS1 | NM_005633.2 | TCTGCACCAAATTCTCCAAGAACACCGTTAACACCTCCGCCTGCTTCTGGTG CTTCCAGTACCAC | SEQ ID NO: 652 |
| SOX17 | NM_022454.2 | TCGTGTGCAAGCCTGAGATGGGCCTCCCCTACCAGGGGCATGACTCC GGTGTGAATCTCCCCGACAG | SEQ ID NO: 653 |
| SPARC | NM_003118.1 | TCTTCCCTGTACACTGGCAGTTCGGCCAGCTGGACCAGCACCCCATTGACG GGTACCTCTCCCACACCGAGCT | SEQ ID NO: 654 |
| SPINT2 | NM_021102.1 | AGGAATGCAGCGGATTCCTCTGTCCCAAGTGCTCCCAGAAGGCAGGATTCTGA AGACCACTCCAGCGA | SEQ ID NO: 655 |
| SPRY1 | AK026960.1 | CAGACCAGTCCCTGGTCATAGGTCTGAAAGGGCAATCCGGACCCAGCCCAA GCAACTGATTGTGGATGACTTGAAGG | SEQ ID NO: 656 |
| SPRY2 | NM_005842.1 | TGTGGCAAGTGCAAATGTAAGGAGTGCACCTACCCAAGGCCTCTGCCATCAGA CTGGATCTGCGAC | SEQ ID NO: 657 |
| SR-A1 | NM_021228.1 | AGATGGAAGAAGCCAACCTGGCGAGCCGAGCGAAGGCCCAGGAGCTGATCC AGGCCACCAACCAGATCCTCAGCCACAG | SEQ ID NO: 658 |
| ST14 | NM_021978.2 | TGACTGCACATGGAACATTGAGGTGCCCAACAACCAGCATGTGAAGGTGCG CTTCAAATTCTT | SEQ ID NO: 659 |
| STAT1 | NM_007315.1 | GGGCTCAGCTTTCAGAAGTGCTGAGTTGGCAGTTTTCTTCTGTCACCAAA AGAGGTCTCAATGTGGACCAGCTGAACATGT | SEQ ID NO: 660 |
| STAT3 | NM_003150.1 | TCACATGCCACTTTGGTGTTTCATAATCTCCTGGGAGAGATTGACCAGCAGT ATAGCCGCTTCCTGCAAG | SEQ ID NO: 661 |
| STAT5A | NM_003152.1 | GAGGCGCTCAACATGAAATTCAAGGCCGAAGTGCAGAGCAACCGGGGCCT GACCAAGGAGAACCTCGTGTTCCTGGC | SEQ ID NO: 662 |
| STAT5B | NM_012448.1 | CCAGTGGTGGTGATCGTTCATGGCAGCCAGGACAACAATGCGACGGCCAC TGTTCTCTGGGACAATGCTTTTGC | SEQ ID NO: 663 |
| STC1 | NM_003155.1 | CTCCGAGGTGAGGAGGACTCTCCCTCCCACATCAAACGCACATCCCATGAG AGTGCATAACCAGGGAGAGGT | SEQ ID NO: 664 |
| STK11 | NM_000455.3 | GGACTCGGAGACGCTGTGCAGGAGGGCCGTCAAGATCCTCAAGAAGAAG AAGTTGCGAAGGATCCC | SEQ ID NO: 665 |
| STK15 | NM_003600.1 | CATCTTCCAGGAGGACCACTCTCTGTGGCACCCTGGACTACCTGCCCCCTG AAAATGATTGAAGGTCGGA | SEQ ID NO: 666 |
| STMN1 | NM_005563.2 | AATACCCAACGCACAAATGACCGCACGTTCTCTGCCCCGTTTCTTGCCC CAGTGTGGTTTGCATTGTCTCC | SEQ ID NO: 667 |

TABLE B-continued

| Gene | Locus Link | Sequence | SEQ ID NO |
|---|---|---|---|
| STMY3 | NM_005940.2 | CCTGGAGGCTGCAACATACCTCAATCCTGTCCCAGGCCGGATCCTCCTGAAG CCCTTTTCGCAGCACTGCTATCCTCCAAAGCCATTGTA | SEQ ID NO: 668 |
| STS | NM_000351.2 | GAAGATCCCTTTCCTCCTACTGTTCTTTCTGTGGGAAGCCGAGAGCCACGAA GCATCAAGGCCGAACATCATCC | SEQ ID NO: 669 |
| SURV | NM_001168.1 | TGTTTTGATTCCCGGGCTTACCAGGTGAGAAGTGAGGGAGGAAGAAGGCA GTGTCCCTTTTGCTAGAGCTGACAGCTTTG | SEQ ID NO: 670 |
| TAGLN | NM_003186.2 | GATGGAGCAGGTGGCTCAGTTCCTGAAGGCGGCTGAGGACTCTGGGGTCAT CAAGACTGACATGTTCCAGACT | SEQ ID NO: 671 |
| TBP | NM_003194.1 | GCCCGAAACGCCGAATATAATCCCAAGCGGTTTGCTGCGGTAATCATGAGGAT AAGAGAGCCACG | SEQ ID NO: 672 |
| TCF-1 | NM_000545.3 | GAGGTCCTGAGCACTGCCAGGAGGGACAAAGGAGCCTGTGAACCCAGGAC AAGCATGGTCCCACATC | SEQ ID NO: 673 |
| TCF-7 | NM_003202.2 | GCAGCTGCAGTCAACAGTTCAAAGAAGTCATGGCCCAAATCCAGTGTGCACC CCTCCCCATTCACAG | SEQ ID NO: 674 |
| TCF7L1 | NM_031283.1 | CCGGGACACTTTCCAGAAGCCGCGGGACTATTTCGCCGAAGTGAGAAGGCCTC AGGACAGCGCGTTCT | SEQ ID NO: 675 |
| TCF7L2 | NM_030756.1 | CCAATCACGACAGGAGGATTCAGACACCCCTACCCCACAGCTCTGACCGTCAA TGCTTCCGTGTCCA | SEQ ID NO: 676 |
| TCFL4 | NM_170607.2 | CTGACTGCTCTGCTTAAAGGTGAAAGTAGCAGGAACAACAACAAAAGCCAACC AAAACAAGGTAGCCAGTGCAAGACAT | SEQ ID NO: 677 |
| TEK | NM_000459.1 | ACTTCGGTGCTACTTAACAACTTACATCCCAGGGAGCAGTACGTGGTCCG AGCTAGAGTCAACACCAAGGCCCAGG | SEQ ID NO: 678 |
| TERC | U86046.1 | AAGAGGAACGGAGCGAGTCCCCGCGCGCGGCGCGATTCCCTGAGCTGTGGGAC GTGCACCCAGGACTCGGCTCACACAT | SEQ ID NO: 679 |
| TERT | NM_003219.1 | GACATGGAGAACAAGCTGTTTGCGGGGATTCGGCGGGACGGGCTGCTCCT GCGTTTGGTGGATGATTTCTTGTTGGTGACACCTC | SEQ ID NO: 680 |
| TFF3 | NM_003226.1 | AGGCACTGTTCATCTCAGTTTTTCTGTCCCTTTGCTCCCGGCAAGCTTTC TGCTGAAAGTTCATATCTGGAGCCTGATG | SEQ ID NO: 681 |
| TGFA | NM_003236.1 | GGTGTGCCACAGACCTTCCTACTTGGCCTGTAATCACCTGTGCAGCCTTTT GTGGGCCTTCAAAACTCTGTCAAGAACTCCGT | SEQ ID NO: 682 |
| TGFB2 | NM_003238.1 | ACCAGTCCCCAGAAGACTATCCTGAGCCCGAGGAAGTCCCCCCGGAGGTGA TTTCCATCTACAACAGCACCAGG | SEQ ID NO: 683 |
| TGFB3 | NM_003239.1 | GGATCGAGCTCTTCCAGATCCTTCGGCCAGATGAGCACATTGCCAAACAGC GCTATATCGGTGGC | SEQ ID NO: 684 |
| TGFBI | NM_000358.1 | GCTACGAGTGCTGTCCTGGATATGAAAAGGTCCCTGGGGAGAAGGGCTGTC CAGCAGCCCTACCACT | SEQ ID NO: 685 |
| TGFBR1 | NM_004612.1 | GTCATCACCTGGCCTTGGTCCTGTGGAACTGGCAGCTGTCATTGCTGGA CCAGTGTGCTTCGTCTGC | SEQ ID NO: 686 |
| TGFBR2 | NM_003242.2 | AACACCAATGGGTTCCATCTTTCTGGGCTCCTGATTGCTCAAGCACAGTTT GGCCTGATGAAGAGG | SEQ ID NO: 687 |
| THBS1 | NM_003246.1 | CATCCGCAAAGTGACTGAAGAGAACAAAGAGTTGGCCAATGAGCTGAGGC GGCCTCCCCTATGCTATCACAACGGAGTTCAGTAC | SEQ ID NO: 688 |
| THY1 | NM_006288.2 | GGACAAGACCCTCTCAGGCTGTCCCAAGCTCCCAAGAGCTTCCAGAGCTCT GACCCACAGCCTCCAA | SEQ ID NO: 689 |
| TIMP1 | NM_003254.1 | TCCCTGCGGTCCCAGATAGCCTGAATCCTGCCCGGAGTGGAACTGAAGC CTGCACAGTGTCCACCCTGTTCCCAC | SEQ ID NO: 690 |
| TIMP2 | NM_003255.2 | TCACCCTCTGTGACTTCATCGTGCCCTGGGACACCCTGAGCACCACCCAG AAGAAGAGCTGAACCACA | SEQ ID NO: 691 |
| TIMP3 | NM_000362.2 | CTACCTGCCTTGCTTTGTGACTTCCAAGAACGAGTGTCTCTGGACCGACATG CTCTCCAATTTCGGT | SEQ ID NO: 692 |
| TJP1 | NM_003257.1 | ACTTTGCTGGGACAAAGGTCAACTGAAGAAGTGGGCAGGCCCGAGGCAGG AGAGATGCTGAGGAGTCCATGTG | SEQ ID NO: 693 |

TABLE B-continued

| Gene | Locus Link | Sequence | SEQ ID NO |
|---|---|---|---|
| TK1 | NM_003258.1 | GCCGGGAAGACCGTAATTGTGGCTGCACTGGATGGGACCTTCCAGAGGA<br>AGCCATTTGGGGCCATCCTGAACCTGGTGCCGCTG | SEQ ID NO: 694 |
| TLN1 | NM_006289.2 | AAGCAGAAGGGAGAGCGTAAGATCTTCCAGGCACACAAGAATTGTGGGC<br>AGATGAGTGAGATTGAGGCCAAGG | SEQ ID NO: 695 |
| TMEPAI | NM_020182.3 | CAGAAGGATGCCTGTGGCCCTCGGAGAGCACAGTGTCAGGCAACGGAATCC<br>CAGAGCCGCAGGTCTAC | SEQ ID NO: 696 |
| TMSB10 | NM_021103.2 | GAAATCGCCAGCTTCGATAAGGCCAAGCTGAAGAAAACGGAGACGCAGGAA<br>AAGAACACCCTGCCGAC | SEQ ID NO: 697 |
| TMSB4X | NM_021109.2 | CACATCAAAGAACTACTGACAACGAAGGCCGCGCCTGCCTTTCCCATCT<br>GTCTATCTATCTGGCTGGCAGG | SEQ ID NO: 698 |
| TNC | NM_002160.1 | AGCTCGGAACCTCACCGTGCCTGGCAGCCTTCGGGCTGTGGACATACCGG<br>GCCTCAAGGCTGCTAC | SEQ ID NO: 699 |
| TNF | NM_000594.1 | GGAGAAGGGTGACCGACTCAGCGCTGAGATCAATCGGCCCGACTATCTCG<br>ACTTTGCCGAGTCTGGGCA | SEQ ID NO: 700 |
| TNFRSF5 | NM_001250.3 | TCTCACCTCGCTATGGTTCGTCTGCCTCTGCAGTGCGTCCTCTGGGGCTGCTT<br>GCTGACCGCTGTCCATC | SEQ ID NO: 701 |
| TNFRSF6B | NM_003823.2 | CCTCAGCACCAGGGTACCAGGAGCTGAGGAGTGTGAGCGTGCCGTCATCG<br>ACTTTGTGGCTTTCCAGGACA | SEQ ID NO: 702 |
| TNFSF4 | NM_003326.2 | CTTCATCTTCCCTCTACCCAGATTGTGAAGATGGAAAGGGTCCAACCCCTGG<br>AAGAGAATGTGGGAAATGCAGC | SEQ ID NO: 703 |
| TOP2A | NM_001067.1 | AATCCAAGGGGAGAGTGATGACTTCCATATGGACTTTGACTCAGCTGTGG<br>CTCCTCGGGCAAAATCTGTAC | SEQ ID NO: 704 |
| TOP2B | NM_001068.1 | TGTGGACATCTTCCCCTCAGACTTCCCTACTGAGCCACCTTCTCTGCCACGA<br>ACCGGTCGGGCTAG | SEQ ID NO: 705 |
| TP | NM_001953.2 | CTATATGCAGCCAGAGATGTGACAGCCACCGTGGACAGCCTGCCACTCATC<br>ACAGCCTCCATTCTCAGTAAGAAACTCGTGG | SEQ ID NO: 706 |
| TP53BP1 | NM_005657.1 | TGCTGTTGCTGAGTCTGTTGCCAGTCCCCAGAAGACCATGTCTGTGTTGAGCT<br>GTATCTGTGAAGCCAGGCAAG | SEQ ID NO: 707 |
| TP53BP2 | NM_005426.1 | GGGCCAAATATTCAGAAGCTTTTATATCAGAGGACCACCATAGCGGCCAT<br>GGAGACCATCTCTGTCCCATCATACCCATCC | SEQ ID NO: 708 |
| TP53I3 | NM_004881.2 | GCGGACTTAATGCAGAGACAAGGCCAGTATGACCCACCTCCAGGAGCCAGC<br>AACATTTTGGGACTTGA | SEQ ID NO: 709 |
| TRAG3 | NM_004909.1 | GACGCTGGTCTGGTGAAGATGTCCAGGAAACCACGAGCCTCCAGCCCATTG<br>TCCAACAACCACCCA | SEQ ID NO: 710 |
| TRAIL | NM_003810.1 | CTTCACAGTGCTCCTGCAGTCTCTCTGTGTGGCTGTAACTTACGTGTACTTTAC<br>CAACGAGCTGAAGCAGATG | SEQ ID NO: 711 |
| TS | NM_001071.1 | GCCTCGGTGTGCCTTTCAACATCGCCAGCTACGCCCTGCTCACGTACATGAT<br>TGCGCACATCACG | SEQ ID NO: 712 |
| TST | NM_003312.4 | GGAGCCGGATGCAGTAGGACTGGACTCGGGCCATATCCGTGGTGCCGTC<br>AACATGCCTTTCATGGACTT | SEQ ID NO: 713 |
| TUBA1 | NM_006000.1 | TGTCACCCCGACTCAACGTGAGACGCACCGCCCGGACTCACCATGCGTGAAT<br>GCATCTCAGTCCACGT | SEQ ID NO: 714 |
| TUBB | NM_001069.1 | CGAGGACGAGGCTTAAAAACTTCTCAGATCAATCGTGCATCCTTAGTGAACT<br>TCTGTTGTCCTCAAGCATGGT | SEQ ID NO: 715 |
| TUFM | NM_003321.3 | GTATCACCATCAATGCGGCTCATGTGGAGTATAGCACTGCCGCCCGCCACT<br>ACGCCCACACAGACTG | SEQ ID NO: 716 |
| TULP3 | NM_003324.2 | TGTGTATAGTCCTGCCCCTCAAGGTGTCACAGTAAGATGTCGGATAATCCGGG<br>ATAAAAGGGGAATGGATCGGG | SEQ ID NO: 717 |
| tusc4 | NM_006545.4 | GGAGGAGCTAAATGCCTCAGGCCGGTGCACTCTGCCCATTGATGAGTCC<br>AACACCATCCACTTGAAGG | SEQ ID NO: 718 |

TABLE B-continued

| Gene | Locus Link | Sequence | SEQ ID NO |
|---|---|---|---|
| UBB | NM_018955.1 | GAGTCGACCCTGCACCTGGTCCTGCGTCTGAGAGGTGGTATGCAGATCTTC GTGAAGACCCTGACCGGCAAGACCATCACCCTGGAAGTGGAGCCCAGTGACACCAT CGAAAATGTGAAGGCCAAGATCCAGGATAAAGAAGGCATCCCTCCCGACCAGCAGAG GCTCATCTTTGCAGGCAAGCAGCTGGAAGATGGCCGCACTCTTTCTGACTACAACAT CCAGAAGGAGTCGACCCTGCACCTGGTCCTGCGTCTGAGAGGTGGTATGCAGATCT TCGTGAAGACCCTGACCGGCAAGACCATCACTCTGGAAGTGGAGCCCAGTGACACC ATCGAAAATGTGAAGGCCAAGATCCAAGATAAAGAAGGCATCCCTCCCGACCAGCAG AGGCTCATCTTTGCAGGCAAGCAGCTGGAAGATGGCCGCACTCTTTCTGACTACAA CATCCAGAAGGAGTCGACCCTGCACCTGGTCCTGCGCCTGAGGGGTGGCTGTTAAT TCTTCAGTCATGGCATTCGC | SEQ ID NO: 719 |
| UBC | NM_021009.2 | ACGCACCCTGTCTGACTACAACATCCAGAAAGAGTCCACCCTGCACCTG GTGCTCCGTCTTAGAGGT | SEQ ID NO: 720 |
| UBE2C | NM_007019.2 | TGTCTGGCGATAAAGGGATTTCTGCCTTCCCTGAATCAGACAACCTTTTCAAA TGGGTAGGGACCAT | SEQ ID NO: 721 |
| UBE2M | NM_003969.1 | CTCCATAATTTATGGCCTGCAGTATCTCTTCTTGGAGCCCAACCCCGAGGA CCCACTGAACAAGGAGGCCGCA | SEQ ID NO: 722 |
| UBL1 | NM_003352.3 | GTGAAGCCACCGTCATCATGTCTGACCAGGAGGCAAAACCTTCAACTGAGGAC TTGGGGGATAAGAAGGAAGG | SEQ ID NO: 723 |
| UCP2 | NM_003355.2 | ACCATGCTCCAGAAGGAGGGGCCCCGAGCCTTCTACAAAGGGTTCATGCCCTCC TTTCTCCGCTTGGGTT | SEQ ID NO: 724 |
| UGT1A1 | NM_000463.2 | CCATGCAGCCTGGAATTTGAGGCTACCCAGTGCCCCAACCCATTCTCCTACGTG CCCAGGCCTCTC | SEQ ID NO: 725 |
| UMPS | NM_000373.1 | TGCGGAAATGAGCTCCACCGGCTCCCTGGCCACTGGGGACTACACTAGAGC AGCGGTTAGAATGGCTGAGG | SEQ ID NO: 726 |
| UNC5A | XM_030300.7 | GACAGCTGATCCAGGAGCCACGGGTCCTGCACTTCAAGGACAGTTACCACAA CCTGCGCCTATCCAT | SEQ ID NO: 727 |
| UNC5B | NM_170744.2 | AGAACGGAGGCCGTGACTGCAGCGGGACGCTGCTCGACTCTAAGAACTGCA CAGATGGGCTGTGCATG | SEQ ID NO: 728 |
| UNC5C | NM_003728.2 | CTGAACACAGTGGAGCTGGTTTGCAAACTCTGTGTGCGGCAGGTGGAAGGA GAAGGGCAGATCTTCCAG | SEQ ID NO: 729 |
| upa | NM_002658.1 | GTGGATGTGCCCTGAAGGACAAGCCAGGCGTCTACACGAGAGTCTCACACT TCTTACCCTGGATCCGCAG | SEQ ID NO: 730 |
| UPP1 | NM_003364.2 | ACGGGTCCTGCCTCAGTTGGCGGAATGGCGGCCACGGGAGCCAATGCAGAG AAAGCTGAAAGTCACAATGATTGCCCCG | SEQ ID NO: 731 |
| VCAM1 | NM_001078.2 | TGGCTTCAGGAGCTGAATACCCTCCCAGGCACACACAGGTGGGACACAAA TAAGGGTTTTGGAACCACTATTTTCTCATCACGACAGCA | SEQ ID NO: 732 |
| VCL | NM_003373.2 | GATACCACAACTCCCATCAAGCTGTTGGCAGTGGCAGCCACGGCGCCTC CTGATGCGCCTAACAGGGA | SEQ ID NO: 733 |
| VCP | NM_007126.2 | GGCTTTGGCAGCTTCAGATTCCCTTCAGGGAACCAGGGTGGAGCTGGCCCC AGTCAGGGCAGTGGAG | SEQ ID NO: 734 |
| VDAC1 | NM_003374.1 | GCTGCGACATGGATTTCGACATTGCTGGGCCTTCCATCCGGGGTGCTCTGGTG CTAGGTTACGAGGGCTGG | SEQ ID NO: 735 |
| VDAC2 | NM_003375.2 | ACCCACGGACAGACTTGCGCGCGTCCAATGTGTATTCCTCCATCATATGC TGACCTTGGCAAAGCT | SEQ ID NO: 736 |
| VDR | NM_000376.1 | GCCCTGGATTTCAGAAAGAGCCAAGTCTGGATCTGGGACCCTTTCCTTCCT TCCCTGGCTTGTAACT | SEQ ID NO: 737 |
| VEGF | NM_003376.3 | CTGCTGTCTTGGGTGCATTGGAGCCTTGCCTTGCTGCTCTACCTCCACCATG CCAAGTGGTCCCAGGCTGC | SEQ ID NO: 738 |
| VEGF_altsplice1 | AF486837.1 | TGTGAATGCAGACCAAAGAAAGATAGAGCAAGACAAGAAAATCCCTGTG GGCCTTGCTCAGAGCGGAGAAAGC | SEQ ID NO: 739 |
| VEGF_altsplice2 | AF214570.1 | AGCTTCCTACAGCACAACAAATGTGAATGCAGACCAAAGAAAGATAGAG CAAGACAAGAAAATGTGACAAGCCGAG | SEQ ID NO: 740 |
| VEGFB | NM_003377.2 | TGACGATGGCCTGGAGTGTGTGCCCACTGGGCAGCACCAAGTCCGGATGC AGATCCTCATGATCCGGTACC | SEQ ID NO: 741 |

TABLE B-continued

| Gene | Locus Link | Sequence | SEQ ID NO |
|---|---|---|---|
| VEGFC | NM_005429.2 | CCTCAGCAAGACGTTATTTGAAATTACAGTGCCTCTCTCTCAAGGCCCCA AACCAGTAACAATCAGTTTTGCCAATCACACTT | SEQ ID NO: 742 |
| VIM | NM_003380.1 | TGCCCTTAAAGGAACCAATGAGTCCCTGGAACGCCAGATGCGTGAAA TGGAAGAGAACTTTGCCGTTGAAGC | SEQ ID NO: 743 |
| WIF | NM_007191.2 | TACAAGCTGAGTGCCCAGGCGGGTGCCGAAATGGAGGCTTTTGTAATGAAAG ACGCATCTGCGAGTG | SEQ ID NO: 744 |
| WISP1 | NM_003882.2 | AGAGGCATCCATGAACTTCACACTTGCGGGCTGCATCAGCACACGCTCCTAT CAACCCAAGTACTGTGGAGTTTG | SEQ ID NO: 745 |
| Wnt-3a | NM_033131.2 | ACAAAGCTACCAGGGAGTCGGCCTTTGTCCACGCCATTGCCTCAGCCGGTGT GGCCTTTGCAGTGACACGCTCA | SEQ ID NO: 746 |
| Wnt-5a | NM_003392.2 | GTATCAGGACCACATGCAGTACATCGGAGAAGGCGCGAAGACAGGCATCA AAGAATGCCAGTATCAATTCCGACA | SEQ ID NO: 747 |
| Wnt-5b | NM_032642.2 | TGTCTTCAGGGTCTTGTCCAGAATGTAGATGGGTTCCGTAAGAGGCCTGGT GCTCTCTTACTCTTTCATCCACGTGCAC | SEQ ID NO: 748 |
| WNT2 | NM_003391.1 | CGGTGGAATCTGGCTCTGGCTCCCTCTGCTCTTGACCTGGCTCACCCCCGA GGTCAACTCTTCATGG | SEQ ID NO: 749 |
| WWOX | NM_016373.1 | ATCGCAGCTGGTGGGTGTACACACTGCTGTTTACCTTGGCGAGGCCTTTCACC AAGTCCATGCAACAGGGAGCT | SEQ ID NO: 750 |
| XPA | NM_000380.2 | GGGTAGAGGGAAAAGGGTTCAACAAAGGCTGAACTGGATTCTTAACCAAG AAACAAATAATAGCAATGGTGGTGCA | SEQ ID NO: 751 |
| XPC | NM_004628.2 | GATACATCGTCTGCGAGGAATTCAAAGACGTGCTCCTGACTGCCTGGGA AAATGAGCAGGCAGTCATTGAAAG | SEQ ID NO: 752 |
| XRCC1 | NM_006297.1 | GGAGATGAAGCCCCCAAGCTTCCTCAGAAGCAACCCCAGACCAAAAC CAAGCCCACTCAGGCAGCTGGAC | SEQ ID NO: 753 |
| YB-1 | NM_004559.1 | AGACTGTGGAGTTTGATGTTGTTGAAGGAGAAAAGGGTGCGGAGGCAGCA AATGTTACAGGTCCTGGTGGTGTTCC | SEQ ID NO: 754 |
| YWHAH | NM_003405.2 | CATGGCCTCCGCTATGAAGGCGGTGACAGAGCTGAATGAACCTCTCTCCAA TGAAGATCGAAATCTCC | SEQ ID NO: 755 |
| zbtb7 | NM_015898.2 | CTGCGTTCACACCCCAGTGTCACAGGGCGAGCTGTTCTGGAGAGAAAACCAT CTGTCGTGGCTGAG | SEQ ID NO: 756 |
| ZG16 | NM_152338.1 | TGCTGAGCCTCCTCTCCTTGGCAGGGCACTGTGATGAGGAGTAAGAACTCC CTTATCACTAACCCCCATCC | SEQ ID NO: 757 |

TABLE C

| Variable | out1 | | out2 | | out3 | | out4 | | out5 | | out6 | |
|---|---|---|---|---|---|---|---|---|---|---|---|---|
| AMFR_1 | IGFBP7_1 | | AXIN1_1 | | HSPG2_1 | | VEGFB_1 | | GSK3B_2 | | THY1_1 | |
| ANXA1_1 | CTSB_1 | 0.3721 | PKR2_1 | 0.3298 | UPA_3 | 0.3072 | FAP_1 | 0.2993 | CTHRC1_1 | 0.2949 | CDX2_3 | 0.2857 |
| ANXA1_2 | ROCK1_1 | 0.5989 | TLN1_1 | 0.5649 | ITGB1_1 | 0.5216 | CSF1_1 | 0.516 | HIF1A_3 | 0.5157 | DAPK1_3 | -0.5141 |
| APC_4 | PLK_3 | 0.3982 | KIFC1_1 | 0.3672 | CDC20_1 | 0.365 | TS_1 | 0.3599 | CENPF_1 | 0.3591 | DHFR_2 | 0.3531 |
| AURKB_1 | NKD_1_1 | 0.5351 | CDX2_3 | 0.5327 | CRIPTO_TDGF1_OFFICIAL_1 | 0.5185 | EPHB2_1 | 0.4854 | PTCH_1 | 0.461 | ROCK2_1 | 0.4445 |
| AURKB_4 | | | | | | | | | | | | |
| AXIN_2_3 | COL1A1_1 | 0.7163 | SPARC_1 | 0.6605 | TIMP2_1 | 0.6388 | FAP_1 | 0.56 | ANTXR1_1 | 0.5044 | TGFB3_1 | 0.4941 |
| BGN_1 | TS_1 | 0.8986 | ATP5E_1 | 0.8711 | DHFR_2 | 0.8446 | MUC2_1 | 0.8177 | REG4_1 | 0.8159 | MUC1_2 | 0.8147 |
| BGN_1 | ITGB1_1 | 0.3266 | CREBBP_1 | -0.3247 | ITGAV_1 | 0.3132 | CDC42BPA_1 | 0.3079 | MYLK_1 | 0.2971 | AKT3_2 | 0.2771 |
| BIK_1 | AXIN_2_3 | 0.4156 | CDX2_3 | 0.4007 | REG4_1 | 0.3952 | RAB32_1 | 0.3855 | CRIPTO_TDGF1_OFFICIAL_1 | 0.3576 | TS_1 | 0.3574 |
| BIK_1 | | | | | | | | | | | | |
| BRAF_5 | | | | | | | | | | | | |
| BRAF_5 | | | | | | | | | | | | |
| BRAF_SNP1_6 | C20_ORF1_1 | -0.4564 | CLIC1_1 | -0.4561 | KIFC1_1 | 0.4075 | C_MYB_MYB_OFFICIAL_1 | -0.3921 | MYBL2_1 | -0.3901 | CDCA7_V2_1 | 0.378 |
| BRAF_SNP1_6 | | | | | | | | | | | | |
| BRCA2_2 | CDC2_1 | 0.3042 | CDC20_1 | 0.2484 | KI_67_2 | 0.2448 | H2AFZ_2 | 0.2432 | MAD2L1_1 | 0.2361 | LMNB1_1 | 0.2332 |
| BUB1_1 | CDC2_1 | 0.5865 | PTCH_1 | 0.5539 | NKD_1_1 | 0.5398 | TERC_2 | 0.5328 | NOTCH1_1 | 0.5271 | GSK3B_2 | 0.5245 |
| B_CATENIN_1 | | | | | | | | | | | | |
| B_CATENIN_3 | CSEL1_1 | 0.4659 | ATP5E_1 | 0.4524 | C20_ORF1_1 | 0.4522 | MUC1_2 | 0.4227 | EGLN3_1 | 0.4191 | PKR2_1 | 0.4076 |
| C20ORF126_1 | MYBL2_1 | 0.5815 | PLK_3 | 0.5313 | C20ORF126_1 | 0.5022 | STK15_2 | -0.4702 | E2F1_3 | -0.4675 | UBE2C_1 | -0.4551 |
| C20ORF126_1 | MYBL2_1 | 0.5644 | TAGLN_3 | 0.509 | CDH11_1 | 0.5022 | TIMP2_1 | 0.4949 | MYLK_1 | 0.4871 | PDGFC_3 | 0.4835 |
| C20_ORF1_1 | IGFBP5_1 | 0.7483 | TGFBR1_1 | 0.7452 | HSPG2_1 | 0.7339 | SPRY1_1 | 0.691 | RHOC_1 | 0.6846 | IGFBP7_1 | 0.6822 |
| C20_ORF1_1 | TAGLN_3 | 0.2373 | MCM2_2 | 0.2194 | BGN_1 | 0.2189 | TIMP2_1 | 0.2115 | CCNA2_1 | 0.2078 | ANTXR1_1 | 0.2067 |
| CALD1_2 | CCNE2_VARIANT_1_1 | | | | | | | | | | | |
| CALD1_2 | | | | | | | | | | | | |
| CASP9_1 | | | | | | | | | | | | |
| CASP9_1 | CCNE2_2 | 0.4225 | RRM2_1 | 0.3667 | MAD2L1_1 | -0.3646 | HSPE1_1 | -0.3627 | CCNB1_2 | 0.3526 | FBXO5_1 | -0.3382 |
| CCNE2_2 | CCNE2_2 | 0.4225 | | | | | | | | | | |
| CCNE2_2 | | | | | | | | | | | | |
| CCNE2_VARIANT_1_1 | | | | | | | | | | | | |
| CCNE2_VARIANT_1_1 | CD44V6_1 | 0.5418 | HNRPAB_3 | 0.4304 | RRM2_1 | 0.421 | SNRPF_2 | 0.4171 | RPS13_1 | 0.413 | HSPE1_1 | 0.3627 |
| CD44E_1 | | | | | | | | | | | | |
| CD44E_1 | MCP1_1 | 0.6091 | CTSL_2 | 0.6046 | SOD2_1 | 0.5965 | UPA_3 | 0.5919 | TLN1_1 | 0.5851 | THBS1_1 | 0.5824 |
| CD44S_1 | | | | | | | | | | | | |
| CD44S_1 | | | | | | | | | | | | |

TABLE C-continued

| | | | | | | | | | | |
|---|---|---|---|---|---|---|---|---|---|---|
| CD44V6_1 | CD44E_1 | | RBX1_1 | | HIF1A_3 | 0.3956 | MUC1_2 | 0.3886 | SNRPF_2 | 0.3631 | HNRPAB_3 | 0.3512 |
| CD44V6_1 | CTSL_2 | 0.5418 | CTSB_1 | | CD18_2 | 0.579 | TP_3 | 0.5754 | DPYD_2 | 0.538 | CD44S_1 | 0.534 |
| CD68_2 | KI_67_2 | 0.6148 | MAD2L1_1 | | BUB1_1 | 0.6217 | H2AFZ_2 | 0.5865 | CDC20_1 | 0.5658 | LMNB1_1 | 0.5426 |
| CDC2_1 | ITGAV_1 | 0.6905 | DPYD_2 | | PDGFRA_2 | 0.3128 | RBX1_1 | 0.2809 | CYR61_1 | 0.2745 | ITGB1_1 | 0.2745 |
| CDC2_1 | SPARC_1 | 0.3472 | TIMP2_1 | | IGFBP7_1 | 0.7629 | CALD1_2 | 0.7587 | TAGLN_3 | 0.7339 | IGFBP5_1 | 0.7338 |
| CDC4_1 | AXIN_2_3 | 0.7831 | CRIPTO_TDGF1_OFFICIAL_1 | | CAD17_1 | | EPHB2_1 | | C_MYB_MYB_OFFICIAL_1 | | PKR2_1 | 0.7319 |
| CDH11_1 | | | | | | | | | | | | |
| CDX2_3 | | | | | | | | | | | | |
| CDX2_3 | PLK_3 | 0.6605 | CKS2_2 | | BUB1_1 | 0.6374 | C20_ORF1_1 | 0.5944 | CDC2_1 | 0.5617 | AURKB_1 | 0.5296 |
| CENPA_1 | TOP2A_4 | 0.4964 | KIFC1_1 | | AURKB_1 | 0.4381 | NEK2_1 | 0.4355 | BUB1_1 | 0.4213 | PLK_3 | 0.3996 |
| CENPA_1 | TIMP2_1 | 0.4655 | TLN1_1 | | MYLK_1 | 0.4649 | DLC1_1 | 0.461 | CALD1_2 | 0.4607 | PDGFC_3 | 0.4578 |
| CENPF_1 | CCNA2_1 | 0.3942 | CCNB1_2 | | MCM2_2 | 0.3921 | MCM6_3 | 0.3912 | RRM1_2 | 0.3762 | CKS2_2 | 0.3762 |
| CHFR_1 | TMEPAI_1 | 0.5375 | MUC2_1 | | REG4_1 | 0.4769 | ATP5E_1 | 0.4596 | CRIPTO_TDGF1_OFFICIAL_1 | 0.4522 | ATP5A1_1 | 0.4487 |
| CHFR_1 | | | | | | | | | | | | |
| CHK1_2 | | | | | | | | | | | | |
| CLDN1_1 | KLF5_1 | 0.3493 | VEGF_ALTSPLICE2_1 | | CAD17_1 | -0.2952 | G_CATENIN_1 | -0.2935 | CLAUDIN_4_2 | 0.2804 | VEGF_ALTSPLICE_1 | 0.2714 |
| CLIC1_1 | HNRPD_1 | 0.4549 | GIT1_1 | | TMSB10_1 | 0.3923 | HES6_1 | 0.3693 | G_CATENIN_1 | 0.3686 | AURKB_1 | 0.3617 |
| CLIC1_1 | HSPE1_1 | 0.3483 | NME1_3 | | TERC_2 | 0.3445 | EREG_1 | 0.3217 | CXCR4_3 | 0.2959 | NME1_3 | 0.2938 |
| CLTC_1 | BGN_1 | 0.5511 | SPARC_1 | | TIMP2_1 | 0.4929 | FAP_1 | 0.4836 | AREG_2 | 0.4652 | NOTCH1_1 | 0.4599 |
| CLTC_1 | SPARC_1 | 0.8986 | MMP2_2 | | COL1A1_1 | 0.8713 | THBS1_1 | 0.8071 | ANTXR1_1 | 0.7833 | LOXL2_1 | 0.7796 |
| CMYC_3 | BRAF_5 | 0.8549 | ITGB1_1 | | ITGAV_1 | 0.7886 | TP53BP1_2 | 0.7642 | RAF1_1 | 0.7409 | CDH11_1 | 0.7368 |
| CMYC_3 | FAP_1 | 0.4007 | ANXA1_2 | | CTSL_2 | 0.3671 | CTHRC1_1 | 0.3516 | CXCR4_3 | 0.3439 | FZD1_1 | 0.3335 |
| COL1A1_1 | TP_3 | 0.6079 | SOD2_1 | | ITGA5_1 | 0.5989 | UPA_3 | 0.5926 | TIMP1_3 | 0.5907 | CD68_2 | 0.5813 |
| COL1A1_1 | BGN_1 | 0.6975 | CTGF_1 | | SFRP2_1 | 0.6913 | EREG_1 | 0.6748 | TIMP1_3 | 0.6558 | THBS1_1 | 0.6448 |
| COL1A2_1 | CTGF_1 | 0.6838 | DUSP1_1 | | THBS1_1 | 0.6683 | TIMP2_1 | 0.6649 | TGFB3_1 | 0.6334 | VIM_3 | 0.6254 |
| COL1A2_1 | TIMP2_1 | 0.8028 | CALD1_2 | | IGFBP5_1 | 0.7338 | PAI1_3 | 0.6623 | COL1A2_1 | 0.6477 | INHBA_1 | 0.6272 |
| CREBBP_1 | BGN_1 | 0.6783 | FOS_1 | | CTGF_1 | 0.6707 | CSEL1_1 | 0.653 | BGN_1 | 0.6465 | ANTXR1_1 | 0.6399 |
| CREBBP_1 | CYR61_1 | 0.7338 | DUSP1_1 | | SFRP2_1 | 0.7183 | PAI1_3 | 0.6632 | EGR1_1 | 0.6545 | NR4A1_1 | 0.6357 |
| CTSB_1 | | | | | | | | | | | | |
| CTSB_1 | | | | | | | | | | | | |
| CTSL_2 | | | | | | | | | | | | |
| CTSL_2 | MYBL2_1 | 0.548 | STK15_2 | | C20_ORF1_1 | 0.5117 | CSEL1_1 | 0.4871 | CMYC_3 | 0.4799 | UBE2C_1 | 0.4391 |
| CXCL12_1 | LAMC2_2 | 0.4628 | KLF5_1 | | SPRY2_2 | 0.426 | TMEPAI_1 | 0.4161 | MASPIN_2 | 0.3689 | RUNX1_2 | 0.3621 |
| CXCL12_1 | | | | | | | | | | | | |
| CYR61_1 | | | | | | | | | | | | |
| CYR61_1 | | | | | | | | | | | | |
| DLC1_1 | | | | | | | | | | | | |
| DLC1_1 | | | | | | | | | | | | |
| DUSP1_1 | | | | | | | | | | | | |
| DUSP1_1 | | | | | | | | | | | | |
| E2F1_3 | | | | | | | | | | | | |
| E2F1_3 | | | | | | | | | | | | |
| EFNB2_1 | | | | | | | | | | | | |
| EFNB2_1 | | | | | | | | | | | | |

TABLE C-continued

| | | | | | | | | | | | | | |
|---|---|---|---|---|---|---|---|---|---|---|---|---|---|
| EGR3_1 | NR4A1_1 | | EGR1_1 | | FOS_1 | 0.5943 | DUSP1_1 | 0.5672 | CYR61_1 | 0.5184 | HB_EGF_1 | 0.4565 | 0.4275 |
| EGR3_3 | H2AFZ_2 | 0.5977 | BAD_1 | | PRDX2_1 | 0.33 | KI_67_2 | 0.3296 | UMPS_2 | 0.3137 | MAD2L1_1 | 0.3104 | 0.309 |
| EI24_1 | TMSB10_1 | 0.3503 | PKR2_1 | | RCC1_1 | 0.5824 | CDC20_1 | 0.5401 | TK1_2 | 0.5181 | H2AFZ_2 | 0.5122 | 0.5104 |
| ENO1_1 | TLN1_1 | 0.6212 | CTGF_1 | | TAGLN_3 | 0.4978 | DLC1_1 | 0.4949 | MYLK_1 | 0.4927 | CDH11_1 | 0.4924 | 0.4886 |
| EPAS1_1 | BUB1_1 | 0.5073 | CDC2_1 | | CDC20_1 | 0.4762 | KI_67_2 | 0.4594 | LMNB1_1 | 0.4577 | PLK_3 | 0.457 | 0.4453 |
| ESPL1_1 | RRM2_1 | 0.5008 | CCNB1_2 | | MCM3_3 | 0.4526 | RBX1_1 | 0.4144 | CENPF_1 | 0.3819 | KIFC1_1 | 0.3819 | 0.3681 |
| ESPL1_3 | IGFBP3_3 | 0.4694 | NKD_1 | | MADH7_1 | 0.3172 | LEF_1 | 0.3068 | TGFB3_1 | 0.3058 | SFRP2_1 | 0.2956 | 0.2951 |
| FBXO5_1 | AKAP12_2 | 0.3258 | CAV1_1 | | MYH11_1 | 0.3882 | AKT3_2 | 0.3828 | CRYAB_1 | 0.3678 | TAGLN_3 | 0.3619 | 0.3568 |
| FGF18_2 | EGR1_1 | 0.3964 | NR4A1_1 | | DUSP1_1 | 0.7308 | CYR61_1 | 0.7183 | EGR3_1 | 0.5673 | HB_EGF_1 | 0.5672 | 0.5097 |
| FGF2_2 | NOTCH1_1 | 0.7448 | STAT5B_2 | | G_CATENIN_1 | 0.4285 | MYLK_1 | 0.4273 | MMP2_2 | 0.423 | ATP5E_1 | 0.4161 | 0.412 |
| FOS_1 | TGFBR2_3 | 0.457 | MADH4_1 | | CKS2_2 | 0.3167 | SFRP2_1 | 0.304 | SOS1_1 | -0.2981 | LEF_1 | 0.2922 | 0.29 |
| FOXO3A_1 | BGN_1 | 0.324 | CXCL12_1 | | TGFB3_1 | 0.4522 | SPARC_1 | 0.4392 | DLC1_1 | 0.4331 | TIMP2_1 | 0.4234 | 0.4116 |
| FPGS_1 | TIMP2_1 | 0.4544 | CDH11_1 | | PDGFC_3 | 0.6178 | LOX_1 | 0.5824 | IGFBP7_1 | 0.5755 | MMP2_2 | 0.5718 | 0.5708 |
| FST_1 | SPARC_1 | 0.642 | BGN_1 | | COL1A1_1 | 0.5861 | PGK1_1 | 0.5678 | TGFB3_1 | 0.5664 | INHBA_1 | 0.5082 | 0.5023 |
| FZD1_1 | THY1_1 | 0.5906 | IGFBP7_1 | | CAPG_1 | 0.4309 | CAPG_1 | 0.4164 | KLF6_1 | 0.4123 | BGN_1 | 0.3963 | 0.3957 |
| GJB2_1 | RHOB_1 | 0.514 | SHC1_1 | | HSPG2_1 | 0.271 | TGFBR2_3 | 0.263 | TK1_2 | 0.2471 | RRM2_1 | -0.2301 | -0.2298 |
| GPX1_2 | VCP_1 | 0.2712 | NOTCH1_1 | | CAPG_1 | 0.4861 | BAD_1 | 0.4596 | IGFBP7_1 | 0.4537 | TCF_1_1 | 0.4189 | 0.4085 |
| GRB10_1 | EPHB2_1 | 0.4936 | ANXA1_2 | | VCP_1 | | CIAP2_2 | | GSK3B_2 | | CRIPTO_TDGF1_OFFICIAL_1 | | 0.3251 |
| GSK3B_2 | ITGB1_1 | 0.4245 | SOD2_1 | | ITGA5_1 | -0.3618 | MCP1_1 | -0.3391 | CSF1_1 | 0.5464 | MMP2_2 | 0.5254 | 0.5156 |
| HES6_1 | PRKCB1_1 | 0.5905 | EIF4E_1 | | ITGA5_1 | 0.572 | MCP1_1 | 0.5647 | CSF1_1 | 0.5464 | MMP2_2 | 0.5254 | -0.1102 |
| HIF1A_3 | VIM_3 | 0.183 | CDC42BPA_1 | | MADH4_1 | 0.1662 | DPYD_2 | 0.1158 | CD3Z_1 | 0.1155 | RANBP2_3 | 0.1145 | 0.4401 |
| HLA_G_2 | CCNB1_2 | 0.5209 | C_MYB_MYB_OFFICIAL_1 | | HSPE1_1 | | CCNA2_1 | | RRM2_1 | | SLC25A3_2 | | 0.4401 |
| HNRPAB_3 | PLK_3 | 0.4549 | TMSB10_1 | | TMSB10_1 | 0.5053 | GIT1_1 | 0.5021 | FASN_1 | 0.4855 | ENO1_1 | 0.4497 | 0.3931 |
| HNRPD_1 | BRAF_5 | 0.3176 | IGFBP3_3 | | IGFBP3_3 | 0.4145 | TGFBR2_3 | 0.4125 | RAF1_3 | 0.3984 | CREBBP_1 | 0.3958 | 0.2981 |
| HOXA5_1 | PS2_2 | 0.2391 | SNRPF_1 | | SNRPF_1 | 0.3127 | REG4_1 | 0.3119 | CLDN7_2 | 0.307 | LGALS3_1 | 0.3009 | 0.1609 |
| HOXB13_1 | | 0.1996 | MASPIN_2 | | MASPIN_2 | 0.1989 | ANXA2_2 | 0.1949 | PS2_2 | | DAPK1_3 | 0.1847 | 0.4045 |
| HSD17B2_1 | REG4_1 | 0.5123 | SEMA4B_1 | | SEMA4B_1 | 0.4334 | REG4_1 | 0.4283 | RRM2_1 | 0.4182 | DAPK1_3 | 0.4129 | 0.4045 |

TABLE C-continued

| | | | | | | | | | | |
|---|---|---|---|---|---|---|---|---|---|---|
| HSPA1A_1 | FAP_1 | | BGN_1 | | INHBA_1 | | CTHRC1_1 | 0.3805 | GADD45B_1 | 0.3714 |
| HSPA1B_1 | VEGF_1 | 0.387 | HSPA1A_1 | 0.3843 | CLTC_1 | 0.3831 | MYH11_1 | 0.3773 | MUC2_1 | −0.2434 |
| HSPA1B_1 | CCNB1_2 | 0.3855 | CMYC_3 | 0.3521 | NME1_3 | −0.262 | HNRPAB_3 | 0.2604 | RRM2_1 | 0.4812 |
| HSPE1_1 | TIMP3_3 | 0.5716 | ANTXR1_1 | 0.5511 | SNRPF_2 | 0.5311 | PDGFC_3 | 0.5223 | FAP_1 | 0.5112 |
| HSPE1_1 | TAGLN_3 | 0.5674 | IGFBP7_1 | 0.5584 | SFRP4_1 | 0.5552 | TIMP2_1 | 0.5548 | SPARC_1 | 0.6781 |
| IGFBP3_3 | TAGLN_3 | 0.7829 | SPARC_1 | 0.764 | CALD1_2 | 0.7483 | THY1_1 | 0.7319 | HSPG2_1 | 0.7246 |
| IGFBP3_3 | AKT3_2 | 0.8225 | CXCL12_1 | 0.7715 | CDH11_1 | 0.764 | DLC1_1 | 0.7587 | ITGB3_1 | 0.4683 |
| IGFBP5_1 | CDC2_1 | 0.5231 | MAD2L1_1 | 0.5025 | MCP1_1 | 0.4968 | CDC20_1 | 0.4886 | SURV_2 | 0.5127 |
| IGFBP5_1 | PLK_3 | 0.6905 | KIFC1_1 | 0.5992 | H2AFZ_2 | 0.5801 | TUFM_1 | 0.5398 | MCM3_3 | 0.4297 |
| IGFBP7_1 | AURKB_1 | 0.4816 | CDC20_1 | 0.4811 | KI_67_2 | 0.4419 | PLK_3 | 0.4417 | KIF22_1 | 0.4811 |
| IL6ST_3 | SPRY2_2 | 0.5327 | LRP5_1 | 0.5047 | LMNB1_1 | 0.4837 | EFNB2_1 | 0.4831 | CAD17_1 | 0.424 |
| IL6ST_3 | KLK6_1 | 0.4836 | MASPIN_2 | 0.4552 | PI3K_2 | 0.4549 | ANXA2_2 | 0.436 | SEMA4B_1 | 0.3896 |
| KI_67_2 | KLK10_3 | 0.5431 | CDX2_3 | 0.5107 | PKR2_1 | 0.4727 | C_MYB_MYB_OFFICIAL_1 | 0.4679 | PKR2_1 | 0.436 |
| KI_67_2 | | 0.5431 | | | ANXA1_2 | | | | | |
| KIF22_1 | CD3Z_1 | 0.5431 | TP_3 | −0.3413 | CIAP2_2 | 0.3274 | CSF1_1 | 0.307 | PRKCB1_1 | −0.2976 |
| KIF22_1 | SNRPF_2 | 0.494 | ANXA2_2 | 0.4704 | GBP2_2 | 0.4453 | LGALS3_1 | 0.442 | BAD_1 | 0.4295 |
| KIFC1_1 | DPYD_2 | 0.5452 | FYN_3 | 0.5068 | GSTP_3 | 0.4753 | NRP2_2 | 0.4717 | CD18_2 | 0.4712 |
| KIFC1_1 | PDGFC_3 | 0.5009 | IGFBP7_1 | 0.4533 | TLN1_1 | 0.4411 | IGFBP3_3 | 0.4197 | FZD1_1 | 0.4096 |
| KLF5_1 | ROCK1_1 | 0.502 | TLN1_1 | 0.4981 | ANTXR1_1 | 0.4777 | RANBP2_3 | 0.4739 | VEGF_ALTSPLICE2_1 | 0.4645 |
| KLF5_1 | | | | | SFRP4_1 | | | | | |
| KLK10_3 | | | | | VIM_3 | | | | | |
| KLK10_3 | COL1A1_1 | 0.4447 | SPARC_1 | 0.4374 | COL1A2_1 | 0.3712 | TIMP2_1 | 0.3681 | ANTXR1_1 | 0.3433 |
| KLK6_1 | LOXL2_1 | 0.7724 | COL1A1_1 | 0.7606 | COL1A2_1 | 0.7415 | INHBA_1 | 0.7248 | LOXL2_1 | 0.6829 |
| KLRK1_2 | SPARC_1 | 0.7433 | BGN_1 | 0.7065 | TK1_2 | 0.695 | KI_67_2 | 0.62 | SURV_2 | 0.5981 |
| KLRK1_2 | H2AFZ_2 | 0.6365 | CDC_1 | 0.6217 | SNRPF_2 | 0.6053 | CALD1_2 | 0.6019 | TLN1_1 | 0.5841 |
| KRT8_3 | CDH11_1 | 0.5118 | MYLK_1 | 0.5073 | ID3_2 | 0.5064 | REG4_1 | 0.5055 | SEMA4B_1 | 0.5 |
| KRT8_3 | ANXA2_2 | 0.5431 | KLK10_3 | 0.5107 | LAMA3_1 | 0.5045 | PCNA_2 | 0.4999 | H2AFZ_2 | 0.4485 |
| LAT_1 | CDC2_1 | 0.496 | MAD2L1_1 | 0.491 | MCM2_2 | 0.4897 | KIFC1_1 | 0.4837 | | 0.45 |
| LAT_1 | CD44S_1 | 0.6091 | CXCL12_1 | 0.6022 | ITGA5_1 | 0.5939 | CTSL_2 | 0.5937 | FAP_1 | 0.5922 |
| LEF_1 | | | | | | | | | | |
| LEF_1 | | | | | | | | | | |
| LMYC_2 | | | | | | | | | | |
| LMYC_2 | | | | | | | | | | |
| LOXL2_1 | | | | | | | | | | |
| LOXL2_1 | | | | | | | | | | |
| LOX_1 | | | | | | | | | | |
| LOX_1 | | | | | | | | | | |
| MAD2L1_1 | | | | | | | | | | |
| MAD2L1_1 | | | | | | | | | | |
| MADH7_1 | | | | | | | | | | |
| MADH7_1 | | | | | | | | | | |
| MASPIN_2 | | | | | | | | | | |
| MASPIN_2 | | | | | | | | | | |
| MCM3_3 | | | | | | | | | | |
| MCM3_3 | | | | | | | | | | |
| MCP1_1 | | | | | | | | | | |
| MCP1_1 | | | | | | | | | | |

TABLE C-continued

| | | | | | | | | | | |
|---|---|---|---|---|---|---|---|---|---|---|
| MMP1_1 | SOD2_1 | 0.4786 | ITGA5_1 | 0.4474 | UPA_3 | 0.439 | CTSL_2 | 0.4101 | HIF1A_3 | 0.4086 | MMP2_2 | 0.4036 |
| MMP1_1 | COL1A2_1 | 0.7886 | SPARC_1 | 0.7229 | THBS1 | 0.7172 | CDH11_1 | 0.7019 | ITGA5 | 0.6969 | TAGLN_3 | 0.6663 |
| MMP2_2 | HNRPAB_3 | 0.4123 | HSPE1_1 | 0.4117 | MCM2_2 | 0.3967 | CHK1_2 | 0.3787 | RANBP2_3 | 0.3732 | CCNA2_1 | 0.3662 |
| MSH2_3 | PI3K_2 | | BRAF_5 | | RANBP2_3 | | CDC42BPA_1 | | CAD17 | | VEGF_ALTSPLICE2_1 | 0.2885 |
| MSH2_3 | | 0.3366 | | 0.3316 | | 0.3049 | | 0.2956 | | 0.2908 | | |
| MSH3_2 | FOS_1 | 0.7308 | EGR1_1 | 0.6946 | DUSP1_1 | 0.5993 | EGR3_1 | 0.5977 | HB_EGF_1 | 0.5041 | CYR61_1 | 0.4881 |
| NR4A1_1 | DPYD_2 | 0.6582 | TIMP1_3 | 0.6172 | MMP2_2 | 0.6168 | CTSL_2 | 0.6068 | SPARC_1 | 0.5989 | VIM_3 | 0.5925 |
| NR4A1_1 | TMEPAI_1 | 0.3884 | IGFBP5_1 | 0.3655 | TS_1 | −0.3617 | ANTXR1_1 | 0.3533 | IGFBP7_1 | 0.3519 | PTCH_1 | 0.3457 |
| NRP1_1 | TIMP2_1 | 0.707 | ANTXR1_1 | 0.6992 | SPARC_1 | 0.6961 | CDH11_1 | 0.6845 | CALD1_2 | 0.6822 | BGN_1 | 0.6788 |
| NRP1_1 | IGF1_2 | 0.4326 | CDH11_1 | 0.4256 | SPARC_1 | 0.42 | PDGFRA_2 | 0.4078 | IGFBP7_1 | 0.4048 | PDGFC_3 | 0.402 |
| PDGFA_3 | MMP2_2 | 0.6662 | IGFBP7_1 | 0.5972 | CDH11_1 | 0.5957 | MYLK_1 | 0.5934 | TAGLN_3 | 0.5926 | IGFBP5_1 | 0.5849 |
| PDGFA_3 | THBS1_1 | 0.3462 | NOTCH1_1 | 0.3219 | MYLK_1 | 0.3037 | MMP2_2 | 0.3005 | NME1_3 | 0.2977 | VIM_3 | 0.2945 |
| PDGFC_3 | SEMA4B_1 | 0.6153 | ANXA2_2 | 0.5857 | ENO1_1 | 0.5824 | ANXA1_2 | 0.5649 | CDX2_3 | −0.5224 | TMSB10_1 | 0.5159 |
| PDGFC_3 | H2AFZ_2 | 0.4369 | MAD2L1_1 | 0.4257 | KI_67_2 | 0.385 | CDC2_1 | 0.358 | ATP5A1_1 | 0.3566 | CLDN7_2 | 0.3468 |
| PDGFD_2 | CD24_1 | 0.4423 | BRAF_SNP1_6 | −0.3921 | STMY3_3 | 0.3889 | NOTCH1_1 | 0.3762 | PDGFRA_2 | 0.3749 | MYLK_1 | 0.3703 |
| PDGFD_2 | CDC20_1 | 0.5213 | CDC2_1 | 0.4949 | BUB1_1 | 0.459 | KIFC1_1 | 0.4585 | KI_67_2 | 0.458 | H2AFZ_2 | 0.4491 |
| PDGFRA_2 | HNRPAB_3 | 0.4152 | ROCK1_1 | 0.3988 | CDC42BPA_1 | 0.3974 | MSH2_3 | 0.3732 | TFF3_3 | 0.3711 | ODC1_3 | 0.3704 |
| PDGFRA_2 | H2AFZ_2 | 0.5801 | ENO1_1 | 0.5401 | TK1_2 | 0.4709 | SURV_2 | 0.4553 | NME1_3 | 0.458 | CDC2_1 | 0.4427 |
| PFN2_1 | EGR1_1 | 0.5108 | TIMP3_3 | 0.4698 | NR4A1_1 | 0.4623 | FOS_1 | 0.4315 | TGFBR2_3 | 0.4192 | DUSP1_1 | 0.4061 |
| PFN2_1 | AXIN_2_3 | 0.4123 | CDX2_3 | 0.4088 | CDH1_INTRON_2_2 | 0.3991 | TGFBR2_3 | 0.3798 | CRIPTO_TDGF1_OFFICIAL_1 | 0.398 | PTCH_1 | 0.3769 |
| PKR2_1 | | 0.4941 | TIMP2_1 | 0.4547 | PDGFC_3 | 0.4397 | ANTXR1_1 | 0.4064 | | | | |
| PKR2_1 | CDH11_1 | 0.5655 | REG4_1 | 0.5528 | MUC2_1 | 0.5419 | TFF3_3 | 0.5273 | BGN_1 | 0.5237 | CALD1_2 | 0.5186 |
| PRDX2_1 | PS2_1 | 0.4899 | SOD2_1 | 0.4734 | CSEL1_1 | 0.4089 | UPA_3 | 0.3989 | F3_1 | 0.371 | MASPIN_2 | 0.3674 |
| PRDX2_1 | TMSB10_1 | 0.3895 | ANXA2_2 | 0.3429 | REG4_1 | −0.3396 | F3_1 | 0.3315 | TP_3 | 0.3209 | LOX_1 | 0.3066 |
| RAB32_1 | PKR2_1 | 0.6153 | SOD2_1 | 0.5244 | REG4_1 | 0.4811 | F3_1 | 0.4508 | MASPIN_2 | 0.4485 | MUC1_2 | 0.4399 |
| RAB32_1 | TIMP2_1 | 0.4878 | BGN_1 | 0.4637 | WISP1_1 | 0.4428 | COL1A1_1 | 0.4426 | GADD45B_1 | 0.4426 | SPARC_1 | 0.4387 |
| RAD54L_1 | CENPF_1 | 0.4123 | RRM1_2 | | AURKB_1 | | CCNA2_1 | | CHK1_2 | | MCM2_2 | 0.3782 |
| RAD54L_1 | | | | | | | | | | | | |

TABLE C-continued

| Variable | | | | | | | | | | | | |
|---|---|---|---|---|---|---|---|---|---|---|---|---|
| SOD1_1 | CDC20_1 | | RCC1_1 | | SLC31A1_1 | | ENO1_1 | | DHFR_2 | | HSPA8_1 | 0.27 |
| SOD1_1 | RAF1_3 | 0.3141 | MADH4_1 | 0.3707 | IGFBP3_3 | 0.3331 | AKT3_2 | 0.2945 | IL6ST_3 | 0.2756 | MAD2L1_1 | −0.2938 |
| SOS1_1 | COL1A1_1 | | BGN_1 | | COL1A2_1 | 0.3091 | TIMP2_1 | 0.318 | CDH11_1 | 0.2941 | INHBA_1 | 0.774 |
| SOS1_1 | IGFBP7_1 | 0.8713 | NRP1_1 | | THBS1_1 | 0.8711 | TAGLN_3 | 0.8549 | CTGF_1 | 0.7831 | MMP2_2 | 0.461 |
| SPARC_1 | PTCH_1 | 0.4889 | KLF5_1 | | LRP5_1 | 0.4702 | EFNB2_1 | 0.47 | NOTCH1_1 | 0.4627 | B_CATENIN_3 | 0.3467 |
| SPARC_1 | UBE2C_1 | 0.4987 | CSEL1_1 | | E2F1_3 | 0.4836 | C20_ORF1_1 | 0.4261 | CDC2_1 | 0.3783 | MYBL2_1 | 0.4622 |
| SPRY1_1 | G_CATENIN_1 | 0.6551 | NOTCH1_1 | | GSK3B_2 | 0.6033 | PTCH_1 | 0.5117 | EPHB2_1 | 0.4653 | CDX2_3 | 0.384 |
| SPRY1_1 | CTGF_1 | 0.43 | COL1A2_1 | | SPARC_1 | 0.4202 | MMP2_2 | 0.4085 | ITGA5_1 | 0.3856 | PAI1_3 | 0.6802 |
| SPRY2_2 | SPARC_1 | 0.7694 | BGN_1 | | THBS1_1 | 0.7409 | COL1A2_1 | 0.7207 | CDH11_1 | 0.7058 | CTSL_2 | 0.6448 |
| SPRY2_2 | CDC6_1 | 0.7068 | CENPF_1 | | BRCA1_2 | 0.6713 | NME1_3 | 0.6534 | SURV_2 | 0.6452 | KIFC1_1 | 0.429 |
| STK15_2 | ITGB1_1 | 0.6143 | RANBP2_3 | | CREBBP_1 | 0.4655 | PI3K_2 | 0.4571 | BRAF_5 | 0.4375 | TP53BP2_2 | 0.3354 |
| STK15_2 | CSEL1_1 | 0.3646 | STK15_2 | | MYBL2_1 | 0.3596 | C20_ORF1_1 | 0.3439 | E2F1_3 | 0.336 | MCM2_2 | 0.411 |
| TCF_1 | NRP1_1 | 0.6581 | TP_3 | | DPYD_2 | 0.6551 | SOD2_1 | 0.5006 | KRT8_3 | 0.4385 | CTSL_2 | 0.3658 |
| TCF_1 | CAPG_1 | 0.3957 | BAD_1 | | NOTCH1_1 | 0.39 | GSK3B_2 | 0.3832 | H2AFZ_2 | 0.381 | MAD2L1_1 | 0.4564 |
| THBS1_1 | HDAC1_1 | 0.5823 | SLC25A3_2 | | HNRPAB_3 | 0.5384 | PKR2_1 | 0.4991 | TS_1 | 0.4724 | SEMA4B_1 | 0.3683 |
| THBS1_1 | | 0.5109 | | | | 0.4867 | | 0.4316 | | 0.4196 | | 0.3748 |

| Variable | out7 | | out8 | | out9 | | out10 | | out11 | | out12 | | out13 | |
|---|---|---|---|---|---|---|---|---|---|---|---|---|---|---|
| AMFR_1 | VCP_1 | | TUFM_1 | | LRP5_1 | | PTCH_1 | | NOTCH1_1 | | IGFBP5_1 | | TCF_1_1 | |
| AMFR_1 | TIMP2_1 | 0.2829 | CXCL12_1 | | BGN_1 | 0.2788 | ITGB1_1 | 0.2784 | TIMP3_3 | 0.2777 | KLK10_3 | 0.2713 | COL1A1_1 | 0.2701 |
| ANXA1_1 | | 0.5124 | | | | 0.5031 | | 0.4987 | | 0.488 | | 0.477 | | 0.4727 |
| ANXA1_2 | MADH2_1 | 0.3455 | ITGAV_1 | | FYN_3 | 0.3406 | CDC42BPA_1 | 0.3388 | RANBP2_3 | 0.3341 | CTGF_1 | 0.3282 | LMYC_2 | 0.3199 |
| APC_4 | BUB1_1 | | LMNB1_1 | | ESPL1_3 | 0.4337 | CHK1_2 | 0.4332 | RRM1_2 | 0.4285 | CDC6_1 | 0.4231 | RAD54L_1 | 0.4086 |
| APC_4 | | 0.4355 | | | | | | | | | | | | |
| AURKB_1 | TP_3 | −0.4647 | BRAF_SNP1_6 | | CAD17_1 | −0.4564 | PKR2_1 | −0.4454 | REG4_1 | −0.4449 | SEMA4B_1 | −0.4321 | CDCA7_V2_1 | −0.4193 |
| AURKB_1 | | | | | | | | | | | | | | |
| AXIN_2_3 | SFRP2_1 | 0.811 | INHBA_1 | | WISP1_1 | 0.7854 | CTHRC1_1 | 0.7682 | LOXL2_1 | 0.7668 | COL1A2_1 | 0.7415 | THY1_1 | 0.7368 |
| AXIN_2_3 | | | | | | | | | | | | | | |
| BGN_1 | SLC25A3_2 | 0.2713 | ATP5A1_1 | | VDAC2_1 | 0.2701 | VEGFB_1 | 0.255 | UBE2C_1 | −0.2501 | TMEPA1_1 | −0.2383 | SEMA4B_1 | −0.2382 |
| BGN_1 | | | | | | | | | | | | | | |
| BIK_1 | RAF1_3 | | RANBP2_3 | | TGFBR2_3 | | CAD17_1 | | C_MYB_MYB_ OFFICIAL_1 | | ABCC5_1 | | TP53BP1_2 | |
| BIK_1 | | | | | | | | | | | | | | |
| BRAF_5 | HSD17B2_1 | 0.3497 | PKR2_1 | | APG_1_1 | 0.3476 | MASPIN_2 | 0.3449 | AREG_2 | 0.3433 | | 0.3407 | | 0.3365 |
| BRAF_SNP1_6 | | 0.3757 | | | | 0.372 | | 0.3705 | | 0.3695 | | 0.3614 | | 0.3559 |
| BRAF_SNP1_6 | | | | | | | | | | | | | | −0.3209 |

TABLE C-continued

| Label | Gene | Value | Gene | Value | Gene | Value | Gene | Value | Gene | Value | Gene | Value | Gene | Value |
|---|---|---|---|---|---|---|---|---|---|---|---|---|---|---|
| BRCA2_2 | CHK1_2 | 0.2303 | CLDN1_1 | | CAPG_1 | 0.2196 | CENPF_1 | −0.2151 | C20ORF126_1 | 0.2132 | RAF1_3 | | CDX2_3 | 0.2047 |
| BRCA2_2 | ESPL1_3 | | NEK2_1 | | SURV_2 | 0.4929 | TK1_2 | 0.4923 | PLK_3 | 0.4803 | PCNA_2 | 0.4716 | KIFC1_1 | 0.4617 |
| BUB1_1 | KLF5_1 | 0.5008 | VEGFB_1 | | IGFBP7_1 | | TMEPAI_1 | 0.3679 | AXIN_2_3 | 0.3481 | SPRY2_2 | 0.3475 | FOXO3A_1 | 0.3467 |
| B_CATENIN_3 | EREG_1 | 0.38 | REG4_1 | | TMSB10_1 | 0.3684 | E2F1_3 | | SEMA4B_1 | | ANXA1_2 | | | 0.3442 |
| B_CATENIN_3 | | | | | | | | | | | | | CDH1_INTRON_2_2 | 0.3885 |
| C20ORF126_1 | CSEL1_1 | 0.4485 | CENPA_1 | | DPYD_2 | | TOP2A_4 | −0.4296 | CDCA7_V2_1 | 0.4259 | CDH1_INTRON_2_2 | −0.4054 | SGCB_1 | −0.3947 |
| C20_ORF1_1 | | 0.448 | ANTXR1_1 | | IGFBP7_1 | | SPARC_1 | −0.4108 | NRP2_2 | 0.3958 | BGN_1 | 0.3928 | COL1A2_1 | 0.3902 |
| CALD1_2 | DLC1_1 | 0.6707 | PDGFA_3 | | BAD_1 | 0.6524 | GSK3B_2 | 0.6494 | EPAS1_1 | 0.649 | P13K_2 | 0.6417 | COL1A2_1 | 0.6378 |
| CALD1_2 | | | | | | | | | | | | | PGK1_1 | 0.6362 |
| CASP9_1 | PDGFRA_2 | 0.2051 | THY1_1 | 0.38 | CKS2_2 | 0.2035 | IGFBP7_1 | 0.2033 | SPARC_1 | 0.2006 | GPX1_2 | 0.1962 | PDGFC_3 | 0.196 |
| CASP9_1 | | | | | | | | | | | | | | −0.1923 |
| CCNE2_2 | MCM6_3 | 0.3367 | CENPA_1 | −0.3216 | CKS2_2 | | | | | −0.2985 | | −0.2975 | | −0.2968 |
| CCNE2_2 | RBX1_1 | | SNRPF_2 | | CHK1_1 | | SURV_2 | 0.2999 | MCM3_3 | | CD44E_1 | | RRM1_2 | −0.2946 |
| CCNE2_VARIANT_1_1 | | | | | | | | | | | | | | 0.2946 |
| CD44E_1 | PI3K_2 | 0.3448 | RBX1_1 | | LGALS3_1 | 0.3294 | CCNB1_2 | 0.3273 | SLC25A3_2 | 0.3156 | ODC1_3 | 0.3125 | | 0.3014 |
| CD44E_1 | | | | | | | | | | | | | C_MYB_MYB_OFFICIAL_1 | 0.3716 |
| CD44S_1 | VIM_3 | 0.3992 | ITGA5_1 | | CTGF_1 | 0.3989 | COL1A2_1 | 0.3888 | TIMP1_3 | 0.3814 | MMP2_2 | 0.376 | CXCL12_1 | 0.3734 |
| CD44S_1 | ENO1_1 | 0.5817 | DAPK1_3 | | TMSB10_1 | 0.5815 | BRAF_5 | 0.5759 | VEGF_ALTSPLICE2_1 | 0.5643 | PS2_2 | 0.5624 | CCNB1_2 | 0.5612 |
| CD44V6_1 | | | | | | | | | | | | | | 0.5556 |
| CD44V6_1 | SOD2_1 | 0.3432 | NRP1_1 | | CSF1_1 | 0.3388 | MMP2_2 | 0.338 | PAI1_3 | 0.335 | VIM_3 | 0.3329 | COL1A2_1 | 0.3326 |
| CD68_2 | CCNB1_2 | 0.5168 | SURV_2 | | MCM3_3 | 0.5045 | CSF1_1 | 0.4849 | TK1_2 | 0.4758 | NEK2_1 | 0.4713 | MCM2_2 | 0.4683 |
| CD68_1 | AKT3_1 | 0.5255 | IL6ST_3 | | TP53BP2_2 | 0.5161 | BRAF_5 | 0.496 | HIF1A_3 | 0.4949 | CSF1_1 | 0.4933 | ROCK1_1 | 0.4928 |
| CDC2_2 | COL1A2_1 | 0.2707 | MYH11_1 | | MMP2_2 | 0.2704 | PDGFC_3 | 0.2692 | INHBA_1 | 0.2667 | SFRP4_1 | 0.2656 | ANTXR1_1 | 0.2588 |
| CDC2_1 | ANXA1_2 | 0.7272 | BGN_1 | | ST14_1 | 0.7265 | CDCA7_V2_1 | 0.7019 | FUT6_2 | 0.6845 | INHBA_1 | 0.6744 | ROCK2_1 | 0.6734 |
| CDC4_1 | CDC20_1 | −0.5141 | PTCH_1 | | ESPL1_3 | 0.4989 | KIF22_1 | 0.4834 | KIFC1_1 | 0.4609 | BRAF_SNP1_6 | 0.4566 | RAD54L_1 | 0.6665 |
| CDH11_1 | ESPL1_3 | 0.3792 | LMNB1_1 | | CDC20_1 | 0.3764 | CHK1_2 | 0.3671 | CCNA2_1 | 0.3575 | STK15_2 | 0.4566 | CCNB1_2 | −0.4561 |
| CDH11_1 | IGFBP5_1 | 0.4445 | RRM1_2 | | | 0.44 | ANTXR1_1 | 0.4269 | IGFBP7_1 | 0.4173 | IGFBP3_3 | 0.4134 | CDH11_1 | 0.4123 |
| CDX2_3 | | | | | MADH7_1 | 0.3625 | CENPF_1 | 0.3602 | HNRPAB_3 | 0.3559 | IGFBP3_3 | 0.3541 | TOP2A_4 | 0.3522 |
| CDX2_3 | KIFC1_1 | 0.3644 | AURKB_1 | | CDC20_1 | 0.4285 | CENPF_1 | 0.4206 | IGFBP3_3 | 0.4173 | IGFBP7_1 | 0.3988 | BRCA2_2 | −0.3928 |
| CENPA_1 | CDC20_1 | 0.4332 | PS2_2 | 0.269 | TS_1 | −0.253 | RUNX1_2 | −0.2498 | STMY3_3 | 0.2388 | | | CMYC_3 | 0.2313 |
| CENPA_1 | MGAT5_1 | | ST14_1 | | CDCA7_V2_1 | 0.3324 | C_SRC_1 | 0.3232 | KIFC1_1 | 0.318 | LRP5_1 | | | 0.2196 |
| CENPF_1 | MGAT5_1 | 0.3365 | | | | | | | | | | 0.3173 | | 0.3166 |
| CHFR_1 | | | | | | | | | | | | | | 0.3498 |
| CHK1_2 | | | | | | | | | | | | | | 0.3791 |
| CLDN1_1 | | | | | | | | | | | | | | 0.3137 |

TABLE C-continued

| | | | | | | | | | | |
|---|---|---|---|---|---|---|---|---|---|---|
| CLTC_1 | CSEL1_1 | | SBA2_1 | | MADH2_1 | | PRKCA_1 | | HSPA1B_1 | | THY1_1 | | EFP_3 | |
| CLTC_1 | MYBL2_1 | -0.2755 | C_SRC_1 | 0.2755 | SNRPF_2 | 0.2714 | E2F1_3 | 0.2651 | ATP5E_1 | -0.262 | UMPS_2 | 0.2597 |
| CMYC_3 | COL1A2_1 | 0.4543 | CSEL1_1 | 0.4539 | WISP1_1 | 0.4449 | SFRP2_1 | 0.4402 | THY1_1 | 0.4391 | INHBA_1 | 0.4255 |
| CMYC_3 | LOXL2_1 | 0.7642 | CTHRC1_1 | 0.7496 | TGFB3_1 | 0.7491 | VIM_3 | 0.7442 | CTGF_1 | 0.7263 | TIMP2_1 | 0.7202 |
| COL1A1_1 | GCNT1_1 | 0.7248 | ITGA5_1 | 0.7243 | CTHRC1_1 | 0.7112 | AKT3_2 | 0.7005 | TP53BP2_2 | 0.6897 | LEF_1 | 0.6874 |
| COL1A1_1 | BGN_1 | 0.32 | RUNX1_2 | 0.3194 | MYH11_1 | 0.3181 | TGFBR2_3 | 0.3168 | CYP1B1_3 | 0.3151 | WISP1_1 | 0.3042 |
| COL1A2_1 | PAI1_3 | 0.578 | COL1A1_1 | 0.5594 | UPA_3 | 0.5514 | TP_3 | 0.5461 | CD18_2 | 0.5281 | NRP1_1 | 0.519 |
| COL1A2_1 | COL1A1_1 | 0.6296 | COL1A2_1 | 0.6152 | DPYD_2 | 0.6151 | CD68_2 | 0.6148 | VIM_3 | 0.6109 | CTHRC1_1 | 0.6068 |
| CREBBP_1 | COL1A1_1 | 0.6206 | SPARC_1 | 0.6173 | CYR61_1 | 0.6149 | MCP1_1 | 0.6022 | WISP1_1 | 0.5972 | SPARC_1 | 0.5935 |
| CREBBP_1 | CXCL12_1 | 0.6149 | CTHRC1_1 | 0.5918 | VIM_3 | 0.576 | GADD45B_1 | 0.573 | SFRP2_1 | 0.5673 | VIM_3 | 0.5655 |
| CTSB_1 | TAGLN_3 | 0.6075 | THY1_1 | 0.6065 | HSPG2_1 | 0.6047 | FOS_1 | 0.5982 | CTGF_1 | 0.5964 | DLC1_1 | 0.5913 |
| CTSB_1 | GADD45B_1 | 0.5877 | THBS1_1 | 0.5827 | CXCL12_1 | 0.5262 | EGR3_1 | 0.5184 | ITGA5_1 | 0.5115 | NME1_3 | 0.507 |
| CTSL_2 | C20ORF126_1 | 0.4259 | ATP5E_1 | 0.4253 | BRCA1_2 | 0.4185 | ANXA1_2 | -0.411 | SURV_2 | 0.3813 | TERC_2 | 0.3583 |
| CTSL_2 | STMY3_3 | 0.3511 | EMP1_1 | 0.3446 | GSTP_3 | 0.3387 | IGFBP7_1 | 0.3235 | MRP3_1 | 0.3163 | TP53BP2_2 | 0.313 |
| CXCL12_1 | PLK3_1 | 0.3879 | RHOB_1 | 0.3764 | PAI1_3 | 0.3616 | GADD45B_1 | 0.3462 | CTGF_1 | 0.3455 | WISP1_1 | 0.3263 |
| CXCL12_1 | HSPA8_1 | | VCP_1 | | SNRPF_2 | | KRT8_3 | | TUFM_1 | | KIF22_1 | | K_RAS_SNP1_8 | -0.2915 |
| CYR61_1 | RRM2_1 | 0.3061 | BUB1_1 | 0.3054 | TGFBR2_3 | 0.3044 | UBE2M_2 | 0.3037 | ANXA2_2 | 0.2928 | NME1_3 | 0.2927 |
| CYR61_1 | IGFBP7_1 | 0.445 | TIMP2_1 | 0.4408 | HSPG2_1 | -0.4332 | SPARC_1 | 0.4328 | CXCL12_1 | 0.4262 | DUSP1_1 | 0.4166 |
| DLC1_1 | CENPF_1 | 0.4845 | AURKB_1 | 0.4802 | IL6ST_3 | 0.4794 | NEK2_1 | 0.477 | RAD54L_1 | 0.4748 | KIFC1_1 | 0.4673 |
| DLC1_1 | CCNE2_VARIANT_1_1 | 0.4445 | HSPE1_1 | 0.4332 | SURV_2 | 0.426 | ODC1_3 | 0.4239 | INHBA_1 | 0.4104 | MAD2L1_1 | 0.3994 |
| DUSP1_1 | UBB_1 | 0.3627 | TIMP3_3 | 0.3551 | CDC42BPA_1 | 0.3535 | PDGFC_3 | 0.352 | ANTXR1_1 | 0.3498 | CREBBP_1 | 0.3378 |
| DUSP1_1 | FGF18_2 | -0.2889 | ITGB3_1 | 0.2824 | IL6ST_3 | 0.2804 | IGFBP5_1 | 0.2749 | OSMR_1 | 0.2734 | AXIN_2_3 | 0.2601 |
| E2F1_3 | MYLK_1 | 0.3438 | PAI1_3 | 0.3421 | C8ORF4_1 | 0.3369 | TIMP2_1 | 0.3174 | PLK3_1 | 0.3146 | MCP1_1 | 0.3051 |
| EFNB2_1 | CTGF_1 | 0.478 | GSK3B_2 | 0.4715 | PTCH_1 | 0.4526 | GADD45B_1 | 0.4488 | KLF6_1 | 0.4469 | RHOB_1 | 0.4315 |
| EFNB2_1 | C_SRC_1 | 0.4066 | VDAC2_1 | 0.4026 | TLN1_1 | 0.4004 | IGFBP7_1 | 0.3998 | KLF5_1 | 0.3996 | HER2_3 | 0.3952 |
| EGR3_1 | MADH2_1 | 0.2809 | HOXB7_1 | 0.2803 | HDAC1_1 | 0.276 | HSPG2_1 | 0.2702 | SHC1_1 | 0.2608 | IGFBP3_3 | 0.2592 |
| EI24_1 | FAP_1 | 0.4052 | COL1A1_1 | 0.403 | WISP1_1 | 0.4017 | CYP1B1_3 | 0.3935 | ANTXR1_1 | 0.3895 | CTHRC1_1 | 0.3805 |

EI24_1
ENO1_1
ENO1_1
EPAS1_1
EPAS1_1
ESPL1_3
ESPL1_3
FBXO5_1
FBXO5_1
FBX18_2
FGF18_2
FGF2_2
FGF2_2
FOS_1
FOXO3A_1
FOXO3A_1
FPGS_1
FST_1
FST_1

TABLE C-continued

| | | | | | | | | | | | | | | |
|---|---|---|---|---|---|---|---|---|---|---|---|---|---|---|
| FZD1_1 | ANTXR1_1 | | NRP2_2 | | COL1A2_1 | | MYLK_1 | | TAGLN_3 | | BGN_1 | | CTHRC1_1 | 0.5458 |
| FZD1_1 | TIMP1_3 | 0.5671 | WISP1_1 | 0.5627 | TIMP2_1 | 0.5598 | SFRP2_1 | 0.5546 | THY1_1 | 0.5533 | UPA_3 | 0.5476 | CYP1B1_3 | 0.4759 |
| GJB2_1 | HNRPAB_3 | 0.4963 | HSPG2_1 | 0.4892 | SPARC_1 | 0.4817 | TIMP2_1 | 0.4813 | VEGFB_1 | 0.4812 | LOX_1 | 0.4796 | CCNA2_1 | −0.3771 |
| GJB2_1 | MAD2L1_1 | −0.3917 | CCNB1_2 | 0.3909 | TIMP2_1 | 0.3899 | EGR3_1 | 0.3807 | VEGFB_1 | 0.3796 | FAP_1 | 0.2168 | ANTXR1_1 | 0.2147 |
| GPX1_2 | GRB10_1 | −0.2283 | G_CATENIN_1 | −0.2247 | NEDD8_2 | 0.2221 | SBA2_1 | 0.218 | EMP1_1 | 0.2152 | FOXO3A_1 | 0.2168 | AXIN1_1 | 0.3841 |
| GPX1_2 | B_CATENIN_3 | 0.4076 | KLK10_3 | 0.4072 | CDX2_3 | −0.3229 | B_CATENIN_3 | −0.404 | FOXO3A_1 | 0.4038 | PTCH_1 | 0.4026 | ODC1_3 | 0.3963 |
| GRB10_1 | CTSB_1 | −0.324 | CD44S_1 | 0.3121 | CTGF_1 | 0.3191 | TFF3_1 | 0.3065 | CLTC_1 | 0.3017 | PAI1_3 | 0.01848 | |
| GRB10_1 | CTSL_2 | 0.5147 | VEGFB_1 | 0.5121 | SLC31A1_1 | 0.5057 | LAT_1 | 0.5049 | ITGAV_1 | 0.5024 | CYR61_1 | 0.4931 | SMARCA3_1 | 0.4902 |
| GSK3B_2 | WNT2_1 | 0.1098 | RBX1_1 | 0.1052 | CD44E_1 | 0.1046 | KLF6_1 | 0.098 | RHOC_1 | 0.0958 | SMARCA3_1 | 0.0951 | RALBP1_1 | 0.0948 |
| GSK3B_2 | VDAC2_1 | 0.4316 | RBX1_1 | 0.4314 | CD44E_1 | 0.4304 | ODC1_3 | 0.4196 | RANBP2_3 | 0.4152 | MSH2_3 | 0.4123 | NME1_3 | 0.4123 |
| HES6_1 | UBE2M_2 | 0.3866 | RCC1_1 | 0.3768 | H2AFZ_2 | 0.3749 | CDC6_1 | 0.3646 | LMNB1_1 | 0.3601 | CLTC_1 | 0.3483 | H2AFZ_2 | 0.3459 |
| HES6_1 | HOXB7_1 | −0.2301 | TK1_2 | −0.2779 | IL6ST_3 | 0.2753 | ITGB1_1 | 0.2705 | RCC1_1 | −0.2694 | EFNB2_1 | 0.2621 | IRS1_3 | −0.2577 |
| HIF1A_3 | C_SRC_1 | 0.2972 | CYP1B1_3 | 0.1596 | NME1_3 | −0.1595 | HOXA5_1 | 0.1574 | SLC31A1_1 | −0.1536 | MRP3_1 | 0.1532 | SL_1 | 0.1515 |
| HIF1A_3 | CYP3A4_2 | 0.3929 | BRAF_SNP1_6 | 0.3757 | MRP3_1 | 0.3732 | CYP2C8_2 | 0.3625 | SPARC_1 | 0.3566 | F3_1 | 0.3445 | TIMP3_3 | 0.3305 |
| HLA_G_2 | CYP1B1_3 | 0.3705 | COL1A1_1 | 0.3639 | ANXA1_2 | 0.3625 | CTSB_1 | 0.359 | SPARC_1 | 0.355 | CLAUDIN_4_2 | 0.3524 | STC1_1 | 0.355 |
| HNRPAB_3 | MYLK_1 | −0.2301 | STK15_2 | 0.3524 | CKS2_2 | 0.2288 | DLC1_1 | −0.2033 | TLN1_1 | 0.2066 | HSPA8_1 | −0.1995 | | |
| HNRPAB_3 | RBX1_1 | 0.4767 | ODC1_3 | 0.4647 | MAD2L1_1 | 0.458 | MSH2_3 | 0.4117 | AREG_2 | 0.4078 | CD44E_1 | 0.4061 | | |
| HNRPD_1 | BGN_1 | 0.5055 | FZD1_1 | 0.5019 | CTHRC1_1 | 0.4871 | IGFBP5_1 | 0.4784 | LEF_1 | 0.4674 | CALD1_2 | 0.4665 | CDH11_1 | 0.4614 |
| HNRPD_1 | MYLK_1 | 0.6532 | DLC1_1 | 0.653 | TIMP1_3 | 0.5019 | BGN_1 | 0.6403 | OSMR_1 | 0.6343 | HSPG2_1 | 0.6259 | TLN1_1 | 0.6221 |
| HOXA5_1 | TIMP2_1 | 0.7139 | SFRP4_1 | 0.6558 | ANTXR1_1 | 0.6558 | PDGFC_3 | 0.6538 | BGN_1 | 0.6494 | RUNX1_2 | 0.6467 | MYLK_1 | 0.6456 |
| HOXA5_1 | VIM_3 | −0.324 | EPAS1_1 | 0.6558 | ITGB1_1 | 0.4652 | CALD1_2 | 0.4617 | OSMR_1 | 0.4588 | CCNB1_2 | 0.4498 | CSF1_1 | 0.4438 |
| HOXB13_1 | TK1_2 | 0.466 | NEK2_1 | 0.5055 | LMNB1_1 | 0.4996 | RRM2_1 | 0.482 | LMNB1_1 | 0.4089 | SNRPF_2 | 0.4069 | | |
| HOXB13_1 | RAD54L_1 | 0.5071 | NEK2_1 | 0.4178 | CDC2_1 | 0.4112 | BUB1_1 | 0.4112 | LMNB1_1 | 0.4089 | CDC20_1 | 0.4678 | KIFC1_1 | 0.4614 |
| HSD17B2_1 | KIF22_1 | 0.4138 | NEK2_1 | 0.4178 | CDC2_1 | 0.4112 | BUB1_1 | 0.4112 | LMNB1_1 | 0.4089 | MCM2_2 | 0.4069 | PCNA_2 | 0.3983 |
| HSD17B2_1 | CDC2_1 | 0.4715 | CENPF_1 | 0.4649 | KL_67_2 | 0.4614 | BUB1_1 | 0.4614 | RAD54L_1 | 0.4599 | MRP3_1 | 0.4585 | CHK1_2 | 0.4332 |
| HSPA1A_1 | NOTCH1_1 | 0.4121 | C_SRC_1 | 0.4121 | CLAUDIN_4_2 | 0.4102 | G_CATENIN_1 | 0.4102 | FOXO3A_1 | 0.4017 | MRP3_1 | 0.3981 | TUFM_1 | 0.3891 |
| HSPA1A_1 | CDX2_3 | 0.4235 | CRIPTO_TDGF1_OFFICIAL_1 | | LAMA3_1 | | ATP5E_1 | | PLK3_1 | | HES6_1 | | | |
| HSPA1B_1 | | | | | | | | | | | | | | |
| HSPA1B_1 | LAMA3_1 | −0.3895 | −0.3884 | | 0.3542 | | −0.337 | | 0.3297 | | CTHRC1_1 | 0.3213 | | |
| HSPE1_1 | | | | | | | | | | | | | | |
| HSPE1_1 | | | | | | | | | | | | | | |
| IGFBP3_3 | | | | | | | | | | | | | | |
| IGFBP3_3 | | | | | | | | | | | | | | |
| IGFBP5_1 | | | | | | | | | | | | | | |
| IGFBP5_1 | | | | | | | | | | | | | | |
| IGFBP7_1 | | | | | | | | | | | | | | |
| IGFBP7_1 | | | | | | | | | | | | | | |
| IL6ST_3 | | | | | | | | | | | | | | |
| IL6ST_3 | | | | | | | | | | | | | | |
| KL_67_2 | | | | | | | | | | | | | | |
| KL_67_2 | | | | | | | | | | | | | | |
| KIF22_1 | | | | | | | | | | | | | | |
| KIF22_1 | | | | | | | | | | | | | | |
| KIFC1_1 | | | | | | | | | | | | | | |
| KIFC1_1 | | | | | | | | | | | | | | |
| KLF5_1 | | | | | | | | | | | | | | |
| KLF5_1 | | | | | | | | | | | | | | |
| KLK10_3 | | | | | | | | | | | | | | |
| KLK10_3 | | | | | | | | | | | | | | |
| KLK6_1 | LAMA3_1 | 0.2714 | ANXA2_2 | 0.2614 | MMP7_1 | 0.2568 | MASPIN_2 | 0.2493 | | | UPA_3 | 0.2471 | P21_3 | 0.2318 |
| KLK6_1 | | | | | | | | | | | | | | 0.2369 |

TABLE C-continued

| | | | | | | | | | | | | | | |
|---|---|---|---|---|---|---|---|---|---|---|---|---|---|---|
| KLRK1_2 | | | | | CD18_2 | 0.4214 | TRAIL_1 | 0.4121 | CRIPTO_TDGF1_OFFICIAL_1 | 0.4058 | ANXA1_2 | −0.3563 | LAT_1 | 0.3354 |
| KLRK1_3 | CTSB_1 | 0.4222 | | | | | | | | | | | | 0.3333 |
| KRT8_3 | MAD2L1_1 | 0.4427 | CAPG_1 | | ITGB4_2 | 0.4395 | LAMA3_1 | 0.4176 | VCP_1 | 0.4151 | IRS1_3 | 0.4132 | RRM2_1 | 0.3872 |
| KRT8_3 | NRP1_1 | 0.4074 | IGFBP7_1 | | VIM_3 | 0.4042 | GBP2_2 | 0.389 | TAGLN_3 | 0.3876 | CTSL_2 | 0.3769 | PRKCB1_1 | 0.3735 |
| LAT_1 | PTCH_1 | 0.4637 | TIMP2_1 | | CDH11_1 | 0.4554 | CALD1_2 | 0.4514 | MYLK_1 | 0.4488 | RUNX1_2 | 0.447 | MADH7_1 | 0.44 |
| LEF_1 | CYR61_1 | | CTGF_1 | | SBA2_1 | | DPYD_2 | | CALD1_2 | | ITGB1_1 | | VEGF_ALTSPLICE1_1 | |
| LMYC_2 | | | | | | | | | | | | | | 0.3104 |
| LOXL2_1 | CTHRC1_1 | 0.3381 | ADAMTS12_1 | | INHBA_1 | 0.3259 | FAP_1 | 0.3133 | WISP1_1 | 0.3114 | THY1_1 | 0.3112 | CDH11_1 | 0.6205 |
| LOXL2_1 | UPA_3 | 0.67 | THY1_1 | | GJB2_1 | 0.6679 | SFRP2_1 | 0.6613 | TGFB3_1 | 0.6439 | THY1_1 | 0.6237 | TIMP1_3 | 0.5524 |
| LOX_1 | | 0.5865 | | | | 0.5672 | | 0.5664 | | 0.5599 | | 0.5536 | | |
| MAD2L1_1 | CCNB1_2 | 0.5725 | RRM2_1 | | NEK2_1 | 0.558 | BUB1_1 | 0.5481 | NME1_3 | 0.5271 | MCM3_3 | 0.5143 | BAD_1 | 0.4674 |
| MADH7_1 | PDGFC_3 | 0.4952 | TAGLN_3 | | NRP2_2 | 0.4899 | IGFBP5_1 | 0.4682 | TIMP2_1 | 0.4592 | VIM_3 | 0.4532 | BGN_1 | 0.4422 |
| MASPIN_2 | LAMC2_2 | | HSD17B2_1 | | CDX2_3 | | ANXA1_2 | | PS2_2 | | DAPK1_3 | | F3_1 | |
| MASPIN_2 | | 0.433 | | | | 0.4283 | | −0.4216 | | 0.4196 | | 0.4193 | | 0.3972 |
| MCM3_2 | RAD54L_1 | 0.44 | RRM2_1 | | KI_67_2 | 0.4396 | BUB1_1 | 0.4331 | TK1_1 | 0.4321 | KIF22_1 | 0.4313 | TUFM_1 | 0.4289 |
| MCM3_3 | THBS1_1 | 0.5884 | VIM_3 | | UPA_3 | 0.5833 | CTGF_1 | 0.5797 | COLIA2_1 | 0.5796 | TIMP2_1 | 0.5787 | BGN_1 | 0.5688 |
| MCP1_1 | MCP1_1 | 0.4011 | SNAI2_1 | | CTSB_1 | 0.3891 | CD44S_1 | 0.3737 | COLIA2_1 | 0.36 | PAI1_3 | 0.3467 | COL1A1_1 | 0.336 |
| MMP1_1 | PDGFRA_2 | 0.6662 | VIM_3 | | NRP2_2 | 0.6556 | MCM6_3 | 0.6356 | SNAI2_1 | 0.6188 | NRP1_1 | 0.6175 | SOD2_1 | 0.6164 |
| MMP2_2 | C_MYB_MYB_OFFICIAL_1 | | TOP2A_4 | | CSEL1_1 | | PS2_2 | | RBX1_1 | | HDAC1_1 | | RAF1_3 | |
| MSH2_3 | HCRA_A_2 | 0.3632 | HNRPAB_3 | | CD44E_1 | 0.3305 | ITGAV_1 | 0.326 | ROCK1_1 | 0.3227 | RBX1_1 | 0.3158 | TP53BP2_2 | 0.3102 |
| MSH3_2 | RHOB_1 | 0.2878 | C8ORF4_1 | | KLF6_1 | 0.2862 | CTGF_1 | 0.2804 | GADD45B_1 | 0.2771 | PLK3_1 | 0.277 | PAI1_3 | 0.2682 |
| NR4A1_1 | COL1A2_1 | 0.4623 | THBS1_1 | | ITGA5_1 | 0.422 | TAGLN_3 | 0.3734 | NRP2_2 | 0.3655 | CTGF_1 | 0.3547 | PAI1_3 | 0.3396 |
| NRP1_1 | DLC1_1 | 0.5871 | HSPG2_1 | | CALD1_2 | 0.5846 | CCNB1_1 | 0.5836 | SFRP4_1 | 0.5771 | TGFBR2_3 | 0.5755 | STMY3_3 | 0.556 |
| PDGFA_3 | COL1A2_1 | 0.3453 | TAGLN_3 | | IGFBP7_1 | 0.3422 | SFRP4_1 | 0.3419 | NRP2_2 | −0.3389 | COL1A1_1 | 0.3308 | TGFB3_1 | 0.3279 |
| PDGFC_3 | COL1A2_1 | 0.6684 | COL1A2_1 | | CALD1_2 | 0.654 | SFRP4_1 | 0.6538 | TIMP2_1 | 0.6487 | CTGF_1 | 0.6436 | MYLK_1 | 0.6111 |
| PDGFD_2 | TAGLN_3 | 0.3986 | COL1A2_1 | | THBS1_1 | 0.3978 | SPARC_1 | 0.3865 | FZD1_1 | 0.3805 | PDGFC_3 | 0.3799 | VIM_3 | 0.3765 |
| PDGFRA_2 | CALD1_2 | 0.5564 | FOXO3A_1 | | CTGF_1 | 0.5392 | PRDX4_1 | 0.5358 | RBX1_1 | 0.5058 | BLMH_1 | 0.4929 | TP53BP2_2 | 0.4821 |
| PFN2_1 | GIT1_1 | 0.2905 | KLK10_3 | | CTSB_1 | 0.2848 | TS_1 | 0.2787 | C20ORF126_1 | 0.2783 | CRIPTO_TDGF1_OFFICIAL_1 | 0.2775 | AXIN_2_3 | 0.2737 |
| PKR2_1 | MASPIN_2 | | | | | | | | | | | | | |
| PKR2_1 | | 0.4999 | | | | 0.4679 | | 0.4635 | | 0.4591 | | −0.4551 | | −0.4512 |

TABLE C-continued

| | | | | | | | | | | | | | | |
|---|---|---|---|---|---|---|---|---|---|---|---|---|---|---|
| PRDX2_1 | SNRPF_2 | | EI24_1 | | CCNB1_2 | | LMNB1_1 | | PCNA_2 | | FAP_1 | | TIMP3_3 | −0.3171 |
| PRDX2_1 | MMP2_2 | 0.3366 | HSPE1_1 | | BAD_1 | 0.3296 | CRIPTO_TDGF1_OFFICIAL_1 | 0.3262 | PI3K_2 | 0.3222 | FOXO3A_1 | 0.319 | ID3_2 | −0.3178 |
| RAB32_1 | | | | | | | | | | | | | | 0.3219 |
| RAD54L_1 | LMNB1_1 | 0.3455 | MCM3_3 | | MCM2_2 | 0.3437 | TS_1 | 0.3392 | KIF22_1 | 0.333 | TK1_2 | 0.3224 | ESPL1_3 | 0.3219 |
| RAD54L_1 | RALBP1_1 | 0.4483 | HIF1A_3 | | DHFR_2 | 0.44 | TS_1 | 0.4353 | LMYC_2 | 0.4291 | BRAF_5 | 0.4178 | RAF1_3 | 0.4158 |
| RANBP2_3 | MAD2L1_1 | 0.3688 | CDC20_1 | | TP53BP1_2 | 0.3626 | LMYC_2 | 0.3596 | BRAF_5 | 0.3586 | MADH2_1 | 0.3476 | RAD54L_1 | 0.3417 |
| RANBP2_3 | | | | | | | | | | | | | | 0.4006 |
| RCC1_1 | MAD2L1_1 | 0.434 | CDC20_1 | | KI_67_2 | 0.4334 | BUB1_1 | 0.431 | ANTXR1_1 | 0.4281 | VCP_1 | 0.4176 | CDC2_1 | −0.4168 |
| RCC1_1 | AKAP12_2 | 0.3951 | CYR61_1 | | DLC1_1 | 0.4334 | ANTXR1_1 | 0.3926 | EPHB2_1 | 0.3908 | TGFBR2_3 | 0.3771 | CLAUDIN_4_2 | −0.3711 |
| RHOB_1 | | | | | | | | | | | | | | 0.3764 |
| RHOB_1 | NKD_1_1 | 0.3943 | TMEPAI_1 | | PKR2_1 | 0.3939 | INHBA_1 | 0.3702 | CAD17_1 | −0.3628 | EGR3_1 | 0.3613 | SFRP4_1 | −0.3259 |
| ROCK2_1 | FZD1_1 | 0.5114 | SPARC_1 | | IGFBP7_1 | 0.5078 | SEMA4B_1 | 0.501 | NRP2_2 | 0.4947 | ENO1_1 | 0.3528 | MRP3_1 | 0.4925 |
| ROCK2_1 | MUC1_2 | 0.3285 | HSD17B2_1 | | ANXA2_2 | 0.3061 | COL1A1_1 | 0.2873 | C20ORF126_1 | 0.287 | AKT3_2 | 0.4941 | CTSL_2 | 0.2751 |
| RUNX1_2 | ANXA2_2 | 0.2982 | GBP2_2 | | EGLN3_1 | 0.2852 | TS_1 | 0.2834 | P21_3 | 0.2795 | CD44S_1 | −0.2817 | EGLN3_1 | 0.2771 |
| RUNX1_2 | HSD17B2_1 | | AXIN_2_3 | | C20ORF126_1 | | | | CRIPTO_TDGF1_OFFICIAL_1 | | KLK10_3 | 0.2773 | | 0.275 |
| S100P_1 | | | | | | | | | | | | | | |
| S100P_1 | THY1_1 | 0.4334 | INHBA_1 | | FAP_1 | −0.4193 | UPA_3 | −0.4054 | TIMP1_3 | 0.402 | CTSB_1 | −0.4007 | | 0.387 |
| SAT_1 | CDC20_1 | 0.4375 | DHFR_2 | | PLK_3 | 0.427 | KIFC1_1 | 0.4246 | TOP2A_4 | 0.4198 | MCM3_3 | 0.4161 | TGFB3_1 | 0.3896 |
| SAT_1 | MUC1_2 | 0.3739 | H2AFZ_2 | | ANXA2_2 | 0.358 | KIFC1_1 | 0.3571 | APG_1_1 | 0.3544 | TK1_2 | 0.3486 | RAD54L_1 | 0.415 |
| SEMA4B_1 | FPGS_1 | 0.267 | CREBBP_1 | | ANXA2_2 | 0.2649 | ITGB1_1 | 0.2633 | TMSB10_1 | 0.2577 | CD44V6_1 | 0.2528 | CD44V6_1 | 0.3486 |
| SIAT4A_2 | MUC1_2 | 0.2922 | TAGLN_3 | | ITGB1_1 | 0.2877 | MADH7_1 | 0.272 | HOXA5_1 | 0.2624 | TRAIL_1 | 0.2574 | ANTXR1_1 | 0.2498 |
| SIAT4A_2 | IGFBP7_1 | 0.7715 | TLN1_1 | | LOXL2_1 | 0.7667 | THY1_1 | 0.7606 | LOX_1 | 0.7512 | ADAMTS12_1 | 0.7433 | MMP2_2 | 0.2542 |
| SKP2_1 | CDH11_1 | 0.4541 | CYP3A4_2 | | PAI1_3 | 0.4483 | PDGFRA_2 | 0.4369 | IGFBP5_1 | 0.4312 | COL1A2_1 | 0.4282 | VIM_3 | 0.7229 |
| SKP2_1 | SBA2_1 | 0.3463 | MCM2_2 | | CAD17_1 | 0.3451 | ANTXR1_1 | 0.3445 | NKD_1_1 | 0.3444 | MGAT5_1 | 0.3385 | GSK3B_2 | 0.4162 |
| SOD1_1 | BUB1_1 | 0.4311 | NEDD8_2 | | ANTXR1_1 | 0.4171 | BGN_1 | −0.414 | TGFB3_1 | −0.3956 | P21_3 | 0.3385 | DLC1_1 | 0.3297 |
| SOD1_1 | GIT1_1 | 0.3812 | CREBBP_1 | | CDCA7_V2_1 | −0.3754 | THY1_1 | −0.3706 | IRS1_3 | −0.3951 | TRAIL_1 | 0.3385 | DLC1_1 | −0.3935 |
| SOS1_1 | VIM_3 | 0.6723 | INHBA_1 | | NRP2_2 | 0.6685 | PDGFRA_2 | 0.6638 | CYR61_1 | 0.361 | ABCC6_1 | 0.3586 | AXIN1_1 | 0.3518 |
| SOS1_1 | IGFBP5_1 | 0.6403 | ITGA5_1 | | NRP2_2 | 0.6374 | CAD17_1 | 0.6172 | IGFBP7_1 | 0.6635 | CYR61_1 | 0.6623 | TIMP1_3 | 0.6534 |
| SPARC_1 | MYBL2_1 | 0.4194 | BUB1_1 | | AURKB_1 | 0.4151 | MADH2_1 | 0.6172 | CCNA2_1 | 0.6172 | IGFBP7_1 | 0.6157 | VIM_3 | 0.611 |
| SPARC_1 | MMP2_2 | 0.3255 | NOTCH1_1 | | LRP6_1 | 0.3247 | ROCK1_1 | 0.3232 | TGFB3_1 | 0.3212 | RAD54L_1 | 0.3937 | MCM3_3 | 0.3925 |
| SPRY1_1 | CDC2_1 | 0.4031 | EREG_1 | | C20ORF126_1 | 0.3927 | ATP5E_1 | 0.3874 | CMYC_3 | 0.378 | B_CATENIN_3 | 0.3183 | RBX1_1 | 0.3098 |
| UBE2C_1 | | | | | | | | | | | | | | 0.3561 |

TABLE C-continued

| | | | | | | | | | | | | |
|---|---|---|---|---|---|---|---|---|---|---|---|---|
| UPP1_1 | | | | | | | | | | | | 0.3279 |
| UPP1_1 | ITGA5_1 | 0.3457 | RHOC_1 | 0.339 | TIMP1_1 | 0.3349 | GBP2_2 | 0.3331 | CIAP2_2 | 0.3308 | TMSB10_1 | 0.3292 |
| VCP_1 | TUFM_1 | 0.437 | KI_67_2 | 0.4343 | RCC1_1 | 0.4286 | VEGFB_1 | 0.4176 | UMPS_2 | 0.4171 | KRT8_3 | 0.4166 | 0.4132 |
| VDAC2_1 | | | | | | | | | | | | |
| VDAC2_1 | CHK1_2 | 0.364 | CKS2_2 | 0.3575 | CCNB1_2 | 0.353 | ATP5A1_1 | 0.3506 | CDC20_1 | 0.3464 | ENO1_1 | 0.3448 | 0.3445 |

| Variable | out14 | | out15 | | out16 | | out17 | |
|---|---|---|---|---|---|---|---|---|
| AMFR_1 | PGK1_1 | | KCNH2_ISO_A_C_1 | | | | | |
| AMFR_1 | | | | | | | | |
| ANXA1_2 | CTSL_2 | | P21_3 | −0.2633 | KLF6_1 | 0.2554 | GIT1_1 | 0.2544 |
| ANXA1_2 | | | | | MCP1_1 | | | |
| APC_4 | FZD1_1 | 0.4678 | AKT3_2 | | CXCL12_1 | 0.4669 | ITGA5_1 | 0.4562 |
| APC_4 | | | | 0.3065 | | 0.3028 | CALD1_2 | |
| AURKB_1 | TOP2A_4 | 0.3996 | SKP2_1 | | CENPA_1 | 0.3991 | KIF22_1 | 0.2994 |
| AURKB_1 | | | | | | | | 0.3818 |
| AXIN_2_3 | MGAT5_1 | 0.4076 | PTP4A3_V2_1 | | TMEPAI_1 | 0.403 | ABCB1_5 | |
| AXIN_2_3 | | | | | | | | 0.3925 |
| BGN_1 | CDH11_1 | 0.7265 | TIMP3_3 | | ADAMTS12_1 | 0.7053 | LOX_1 | 0.695 |
| BGN_1 | | | | | | | | |
| BIK_1 | C20ORF126_1 | | PKR2_1 | −0.236 | KCNH2_ISO_A_C_1 | 0.2296 | EREG_1 | −0.2235 |
| BIK_1 | | | | | | | | |
| BRAF_5 | MYH11_1 | 0.3336 | MSH3_2 | | TP53BP2_2 | 0.3316 | CHFR_1 | 0.3257 |
| BRAF_5 | | | | | | | | |
| BRAF_SNP1_6 | DAPK1_3 | 0.3181 | EPHB2_1 | | ABCB1_5 | −0.3165 | NKD_1_1 | −0.304 |
| BRAF_SNP1_6 | | | | | | | | |
| BRCA2_2 | CUL4A_1 | 0.203 | CDH1_INTRON_2_2 | | RRM1_2 | 0.1978 | SKP2_1 | 0.1895 |
| BRCA2_2 | | | | | | | | |
| BUB1_1 | RAD54L_1 | 0.459 | CENPF_1 | | TGFBR2_3 | 0.4578 | RRM2_1 | 0.4494 |
| BUB1_1 | | | | | | | | |
| B_CATENIN_3 | CD24_1 | 0.3437 | EPHB2_1 | | C_SRC_1 | 0.329 | TCF_1 | 0.3261 |
| B_CATENIN_3 | | | | | | | | |
| C20ORF126_1 | UBE2C_1 | 0.3874 | ENO1_1 | | ANXA2_2 | −0.382 | STK15_2 | 0.3739 |
| C20ORF126_1 | | | | | | | | |
| C20_ORF1_1 | MUC1_2 | −0.3851 | KIFC1_1 | | DAPK1_3 | 0.3841 | RALBP1_1 | −0.3793 |
| C20_ORF1_1 | | | | | | | | |
| CALD1_2 | VIM_3 | 0.6359 | MMP2_2 | | TLN1_1 | 0.6356 | TGFB3_1 | 0.6208 |
| CALD1_2 | | | | | | | | |
| CASP9_1 | LMYC_2 | 0.1879 | PRKCA_1 | | CDC6_1 | 0.1878 | PTGER3_1 | 0.1811 |
| CCNE2_2 | EMP1_1 | −0.2934 | COL1A1_1 | | WISP1_1 | −0.2931 | HSPG2_1 | −0.2898 |
| CCNE2_2 | | | | | | | | |
| CCNE2_VARIANT_1_1 | E2F1_3 | 0.2934 | MCM2_2 | | MSH2_3 | 0.2929 | HNRPAB_3 | 0.2922 |
| CCNE2_VARIANT_1_1 | | | | | | | | |
| CD44E_1 | GCNT1_1 | 0.3712 | MRP3_1 | | VEGF_ALTSPLICE2_1 | 0.3625 | TP53BP2_2 | 0.3576 |
| CD44E_1 | | | | | | | | |
| CD44S_1 | TIMP2_1 | 0.551 | CSF1_1 | | CD18_2 | 0.5501 | NRP2_2 | 0.5451 |
| CD44S_1 | | | | | | | | |
| CD44V6_1 | TLN1_1 | 0.3281 | EFP_3 | | ODC1_3 | 0.3249 | RRM2_1 | 0.3161 |
| CD44V6_1 | | | | | | | | |

TABLE C-continued

| | | | | | | |
|---|---|---|---|---|---|---|
| CD68_2 | NRP2_2 | | CTGF_1 | 0.4613 | GBP2_2 | 0.4557 |
| CD68_2 | ESPL1_3 | 0.4629 | KIFC1_1 | 0.4715 | RRM2_1 | UPA_3 0.4653 |
| CDC2_1 | NFKBP50_3 | 0.4762 | CREBBP_1 | 0.2461 | MMP2_2 | STK15_2 0.2425 |
| CDC4_1 | THBS1_1 | 0.2504 | NRP2_2 | 0.6615 | COL1A1_1 | SGCB_1 0.647 |
| CDH11_1 | NKD_1_1 | 0.6635 | TP_3 | -0.436 | MASPIN_2 | ADAMTS12_1 -0.4153 |
| CDX2_3 | MCM2_2 | 0.4493 | TS_1 | 0.3254 | UBE2C_1 | CTSB_1 -0.3045 |
| CENPA_1 | LMNB1_1 | 0.3273 | MCM3_3 | 0.3979 | CDC25C_1 | PDGFC_3 0.3834 |
| CENPF_1 | FOXO3A_1 | 0.4011 | NRP2_2 | 0.3483 | PTCH_1 | KI_67_2 0.3348 |
| CHFR_1 | MSH2_3 | 0.3489 | SKP2_1 | 0.3782 | TS_1 | AKT3_2 0.3739 |
| CHK1_2 | NKD_1_1 | 0.3787 | CREBBP_1 | 0.2182 | VEGF_ALTSPLICE2_1 | MCM3_3 0.2141 |
| CLDN1_1 | EFNB2_1 | 0.2189 | TLN1_1 | 0.3117 | C_MYB_MYB_OFFICIAL_1 | AXIN_2_3 0.3091 |
| CLIC1_1 | PGK1_1 | 0.3132 | ITGB4_2 | 0.2559 | MAD2L1_1 | HER_2_3 0.2554 |
| CLTC_1 | PRDX4_1 | -0.2573 | CDX2_3 | 0.3997 | CDH11_1 | RHOC_1 0.3913 |
| CMYC_3 | ADAMTS12_1 | 0.4014 | LOX_1 | 0.7065 | TAGLN_3 | STK15_2 0.6306 |
| COL1A1_1 | SNAI2_1 | 0.7077 | PDGFC_3 | 0.6684 | VEGF_ALTSPLICE2_1 | TIMP3_3 0.6601 |
| COL1A2_1 | IL6ST_3 | 0.6764 | ABCC5_1 | 0.2983 | CXCL12_1 | NRP2_2 0.2981 |
| CREBBP_1 | OPN_OSTEOPONTIN_3 | 0.2994 | CSF1_1 | 0.5143 | MCP1_1 | HOXA5_1 0.5067 |
| CTSB_1 | CD44S_1 | 0.5168 | MMP2_2 | 0.5971 | IGF1_2 | INHBA_1 0.5926 |
| CTSL_2 | FAP_1 | 0.6046 | COL1A2_1 | 0.5786 | DLC1_1 | CTSB_1 0.5731 |
| CXCL12_1 | MMP2_2 | 0.5903 | ITGA5_1 | 0.5564 | COL1A1_1 | THBS1_1 0.5467 |
| CYR6L_1 | SPARC_1 | 0.563 | CDH11_1 | 0.5872 | SPARC_1 | EGR1_1 0.577 |
| DLC1_1 | HB_EGF_1 | 0.5903 | VIM_3 | 0.4985 | EREG_1 | SFRP2_1 0.4901 |
| DUSP1_1 | MAD2L1_1 | 0.5018 | CDC2_1 | 0.3502 | LAMA3_1 | COL1A2_1 0.3493 |
| E2F1_3 | MADH7_1 | 0.3517 | LEF_1 | 0.305 | COL1A1_1 | TCF_1_1 0.3014 |
| EFNB2_1 | DLC1_1 | 0.3057 | FAP_1 | 0.3083 | ODC1_3 | KRT8_3 0.3004 |
| EGR3_1 | SURV_2 | 0.3193 | PCNA_2 | 0.2837 | | CXCL12_1 0.278 |
| EI24_1 | | 0.2886 | | | | MCM3_3 |

TABLE C-continued

| | | | | | |
|---|---|---|---|---|---|
| ENO1_1 | MAD2L1_1 | | EGLN3_1 | 0.4046 | TS_1 | 0.4037 | SURV_2 | 0.3952 |
| ENO1_1 | IL6ST_3 | 0.4147 | FZD1_1 | 0.4637 | TGFBR1_1 | 0.4635 | IGFBP5_1 | 0.463 |
| EPAS1_1 | KIF22_1 | 0.4652 | CENPA_1 | 0.3671 | RCC1_1 | 0.3665 | MAD2L1_1 | 0.3627 |
| ESPL1_3 | CCNA2_1 | 0.3918 | RRM1_2 | 0.3342 | TP53BP2_2 | 0.3335 | SURV_2 | 0.333 |
| FBXO5_1 | AKT3_2 | 0.3364 | CALD1_2 | 0.2564 | BRAF_5 | 0.2553 | SFRP4_1 | 0.2532 |
| FGF18_2 | CALD1_2 | 0.2565 | PTGER3_1 | 0.2934 | NRP2_2 | 0.2928 | DLC1_1 | 0.2855 |
| FGF2_2 | THBS1_1 | 0.2937 | INHBA_1 | 0.3762 | CXCL12_1 | 0.3614 | EMP1_1 | 0.3524 |
| FOS_1 | TP53BP2_2 | 0.3766 | MYH11_1 | 0.3886 | CMYC_3 | 0.387 | STMY3_3 | 0.3786 |
| FOXO3A_1 | FUT6_2 | 0.3893 | TGFBR1_1 | 0.2549 | RAF1_3 | 0.252 | HOXA5_1 | 0.2512 |
| FPGS_1 | CTGF_1 | 0.2561 | CALD1_2 | 0.3627 | AKAP12_2 | 0.3468 | FABP4_1 | 0.3372 |
| FST_1 | SFRP4_1 | 0.3685 | CALD1_2 | 0.5383 | IGFBP5_1 | 0.5304 | THBS1_1 | 0.5254 |
| FZD1_1 | COL1A2_1 | 0.5429 | ADAMTS12_1 | 0.4719 | LOXL2_1 | 0.4622 | CDH11_1 | 0.4508 |
| GJB2_1 | CD18_2 | 0.4748 | NEDD8_2 | -0.3654 | UNC5B_1 | 0.3585 | ANTXR1_1 | 0.3426 |
| GPX1_2 | GADD45B_1 | 0.3763 | PLK3_1 | 0.2094 | DLC1_1 | 0.2041 | IGFBP3_3 | 0.2028 |
| GRB10_1 | TUFM_1 | 0.21 | CMYC_3 | 0.3772 | KLF5_1 | 0.3724 | VEGFB_1 | 0.3711 |
| GSK3B_2 | CXCR4_3 | 0.3797 | PTCH_1 | 0.29 | SURV_2 | 0.2898 | CEBPB_1 | -0.2843 |
| HES6_1 | UPA_3 | -0.2925 | FYN_3 | 0.4783 | COL1A2_1 | 0.478 | SNAI2_1 | 0.4749 |
| HIF1A_3 | HSPA1A_1 | 0.4892 | UPA_1 | 0.0933 | UPP1_1 | 0.0928 | GPX1_2 | 0.0923 |
| HLA_G_2 | HDAC1_1 | 0.0946 | CHK1_2 | 0.3988 | GPX1_2 | -0.3917 | THY1_1 | -0.3892 |
| HNRPAB_3 | DHFR_2 | 0.3994 | EFP_3 | 0.3367 | ST14_1 | 0.3435 | AURKB_1 | 0.3142 |
| HNRPD_1 | MGAT5_1 | 0.3451 | SOS1_1 | 0.2574 | ITGAV_1 | 0.3189 | FPGS_1 | 0.2512 |
| HOXA5_1 | F3_1 | 0.2576 | WISP1_1 | -0.1501 | BRCA1_2 | 0.1477 | PI3K_2 | 0.1475 |
| HOXB13_1 | MUC2_1 | 0.1509 | AXIN_2_3 | -0.3248 | CRIPTO_TDGF1_OFFICIAL_1 | -0.3206 | KRT8_3 | 0.3193 |
| HSD17B2_1 | HSPA1A_1 | 0.3261 | PLK3_1 | 0.3446 | WISP1_1 | 0.3435 | ITGB1_1 | 0.3426 |
| HSPA1A_1 | CENPA_1 | 0.3521 | SBA2_1 | -0.1883 | CDC2_1 | 0.1862 | VEGF_ALTSPLICE1_1 | 0.186 |
| HSPA1B_1 | THY1_1 | 0.1905 | EREG_1 | 0.3909 | CCNE2_VARIANT_1_1 | 0.3882 | CSEL1_1 | 0.3881 |
| HSPE1_1 | | -0.4037 | | | | | | |

TABLE C-continued

| Label | Gene A | Val A | Gene B | Val B | Gene C | Val C | Gene D | Val D |
|---|---|---|---|---|---|---|---|---|
| IGFBP3_3 | RUNX1_2 | 0.4596 | TGFB3_1 | 0.4561 | AKT3_2 | 0.4539 | WISP1_1 | 0.4518 |
| IGFBP5_1 | THY1_1 | 0.622 | ADAMTS12_1 | 0.6219 | THBS1_1 | 0.6177 | TGFB3_1 | 0.6165 |
| IGFBP7_1 | ADAMTS12_1 | 0.6433 | NRP2_2 | 0.6374 | VEGFB_1 | 0.6369 | COL1A2_1 | 0.616 |
| IL6ST_3 | MYLK_1 | 0.4413 | FAP_1 | 0.4408 | MYH11_1 | 0.439 | FZD1_1 | 0.4346 |
| KL_67_2 | RAD54L_1 | 0.458 | ESPL1_3 | 0.4577 | PCNA_2 | 0.4482 | KIF22_1 | 0.4417 |
| KIF22_1 | CDC25C_1 | 0.3962 | ESPL1_3 | 0.3918 | SURV_2 | 0.3909 | AURKB_1 | 0.3818 |
| KIFC1_1 | TOP2A_4 | 0.429 | PCNA_2 | 0.4097 | CDC25C_1 | 0.404 | NEK2_1 | 0.4033 |
| KLF5_1 | GSTP_3 | 0.3846 | HER2_3 | 0.3818 | AXIN1_1 | 0.3818 | B_CATENIN_3 | 0.38 |
| KLK10_3 | C20ORF126_1 | -0.3166 | LAMC2_2 | 0.3161 | E2F1_3 | -0.3127 | CDCA7_V2_1 | -0.3053 |
| KLK6_1 | AKAP12_2 | 0.2316 | LAMC2_2 | 0.2265 | CDC25C_1 | -0.2255 | EPHB6_1 | 0.2251 |
| KLRK1_2 | CDX2_3 | -0.3299 | IL6ST_3 | 0.3216 | FYN_3 | 0.3098 | DPYD_2 | 0.3097 |
| KRT8_3 | RHOC_1 | 0.3866 | RBX1_1 | 0.3849 | H2AFZ_2 | 0.3828 | UPP1_1 | 0.381 |
| LAT_1 | CAPG_1 | 0.3629 | CD68_2 | 0.3496 | ANXA5_1 | 0.3487 | CDH11_1 | 0.3424 |
| LEF_1 | IGFBP5_1 | 0.4348 | HSPG2_1 | 0.4259 | MYH11_1 | 0.4157 | DLC1_1 | 0.4014 |
| LMYC_2 | P53R2_3 | 0.3076 | APC_4 | 0.3067 | ITGA5_1 | 0.3059 | SOD2_1 | 0.2981 |
| LOXL2_1 | ITGA5_1 | 0.6129 | TIMP3_3 | 0.6125 | LOX_1 | 0.5981 | TGFB3_1 | 0.5957 |
| LOX_1 | TIMP2_1 | 0.5512 | ADAMTS12_1 | 0.5512 | WISP1_1 | 0.5504 | PAI1_3 | 0.5407 |
| MAD2L1_1 | HSPE1_1 | 0.458 | VCP_1 | 0.4564 | TGFBR2_3 | -0.4486 | KRT8_3 | 0.4427 |
| MADH7_1 | CTGF_1 | 0.4413 | LEF_1 | 0.44 | SPARC_1 | 0.4336 | THBS1_1 | 0.43 |
| MASPIN_2 | CRIPTO_TDGF1_OFFICIAL_1 | -0.3952 | BRAF_SNP1_6 | 0.3695 | MADH2_1 | 0.3679 | S100P_1 | 0.3674 |
| MCM3_3 | FBXO5_1 | 0.4144 | CCNB1_2 | 0.4117 | CDC25C_1 | 0.4058 | LMNB1_1 | 0.4042 |
| MCP1_1 | CTHRC1_1 | 0.5633 | MMP2_2 | 0.5618 | WISP1_1 | 0.5532 | INHBA_1 | 0.5514 |
| MMP1_1 | CTHRC1_1 | 0.3333 | FAP_1 | 0.3281 | TIMP1_3 | 0.3168 | TP_3 | 0.3146 |
| MMP2_2 | IGFBP5_1 | 0.6159 | TIMP2_1 | 0.6096 | CTGF_1 | 0.6026 | IGFBP7_1 | 0.5986 |
| MSH2_3 | FBXO5_1 | 0.3091 | CCNB1_2 | 0.3083 | VEGF_ALTSPLICE_1 | 0.3027 | ODC1_3 | 0.297 |
| MSH3_2 | ITGB1_1 | 0.2659 | EFP_3 | 0.2658 | TLN1_1 | 0.2634 | APC_4 | 0.2603 |

TABLE C-continued

| | | | | | | |
|---|---|---|---|---|---|---|
| NR4A1_1 | THBS1_1 | | INHBA_1 | EMP1_1 | | DLC1_1 | |
| NR4A1_1 | | 0.318 | | | 0.2957 | | 0.2866 |
| NRP1_1 | IGFBP7_1 | | ANXA5_1 | SNAI2_1 | | CDH11_1 | |
| NRP1_1 | | 0.5447 | | | 0.5423 | | 0.5303 |
| PDGFA_3 | CRYAB_1 | | MYLK_1 | ENO1_1 | | CEBPB_1 | |
| PDGFA_3 | | 0.3255 | | | 0.3217 | | 0.3184 |
| PDGFC_3 | INHBA_1 | | TIMP3_3 | ADAMTS12_1 | | CTHRC1_1 | |
| PDGFC_3 | | 0.6108 | | | 0.6098 | | 0.6067 |
| PDGFD_2 | TGFB3_1 | | IGFBP5_1 | OSMR_1 | | CXCL12_1 | |
| PDGFD_2 | | 0.3705 | | | 0.3678 | | 0.3589 |
| PDGFRA_2 | NRP1_1 | | TIMP2_1 | TLN1_1 | | DPYD_2 | |
| PDGFRA_2 | | 0.4776 | | | 0.4692 | | 0.4672 |
| PFN2_1 | BAD_1 | | HSPE1_1 | TAGLN_3 | | SNRPF_2 | |
| PFN2_1 | | 0.2731 | | | 0.2691 | | 0.2662 |
| PKR2_1 | HIF1A_3 | | CTSL_2 | EGLN3_1 | | P21_3 | |
| PKR2_1 | | 0.4442 | | | 0.4435 | | 0.4307 |
| PRDX2_1 | ANTXR1_1 | | UBB_1 | MCM2_2 | | STK15_2 | |
| PRDX2_1 | | −0.3086 | | | 0.3085 | | 0.3021 |
| RAB32_1 | GSK3B_2 | | IGFBP7_1 | TAGLN_3 | | CDH11_1 | |
| RAB32_1 | | 0.3192 | | | 0.3176 | | 0.3145 |
| RAD54L_1 | PLK_3 | | SURV_2 | CDC6_1 | | AURKB_1 | |
| RAD54L_1 | | 0.4095 | | | 0.4057 | | 0.4048 |
| RANBP2_3 | HDAC1_1 | | APC_4 | MGAT5_1 | | TP53BP2_2 | |
| RANBP2_3 | | 0.3297 | | | 0.3282 | | 0.32 |
| RCC1_1 | PCNA_2 | | LMNB1_1 | NEK2_1 | | SNRPF_2 | |
| RCC1_1 | | 0.3966 | | | 0.3942 | | 0.3843 |
| RHOB_1 | MAD2L1_1 | | TIMP2_1 | CDC42BPA_1 | | ITGB1_1 | |
| RHOB_1 | | −0.3705 | | | 0.3565 | | 0.3452 |
| ROCK2_1 | PTP4A3_V2_1 | | TGFBI_1 | RHOB_1 | | APG_1_1 | |
| ROCK2_1 | | 0.3235 | | | 0.3231 | | 0.314 |
| RUNX1_2 | COL1A2_1 | | CTHRC1_1 | FAP_1 | | WISP1_1 | |
| RUNX1_2 | | 0.4883 | | | 0.4825 | | 0.482 |
| S100P_1 | SLPI_1 | | APG_1_1 | EGLN3_1 | | LGALS3_1 | |
| S100P_1 | | 0.2655 | | | 0.257 | | 0.257 |
| SAT_1 | BGN_1 | | CAD17_1 | C20ORF126_1 | | TLN1_1 | |
| SAT_1 | | 0.2684 | | | −0.2621 | | −0.2575 |
| SEMA4B_1 | P21_3 | | PS2_2 | CDX2_3 | | PLK3_1 | |
| SEMA4B_1 | | 0.3866 | | | 0.3864 | | −0.3826 |
| SIAT4A_2 | HSPG2_1 | | ITGA5_1 | PLK3_1 | | LOX_1 | |
| SIAT4A_2 | | 0.4082 | | | 0.3906 | | 0.3905 |
| SKP2_1 | TS_1 | | CCNB1_2 | C_MYB_MYB_OFFICIAL_1 | | C20_ORF1_1 | |
| SKP2_1 | | 0.3348 | | | 0.3306 | | 0.3291 |
| SOD1_1 | TMEPAI_1 | | HOXB7_1 | EI24_1 | | REG4_1 | |
| SOD1_1 | | −0.2457 | | | 0.233 | | 0.2277 |
| SOS1_1 | TGFBR2_3 | | FAP_1 | BRAF_5 | | TIMP3_3 | |
| SOS1_1 | | 0.2537 | | | 0.253 | | 0.2524 |
| SPARC_1 | THBS1_1 | | ANTXR1_1 | TGFB3_1 | | TIMP1_3 | |
| SPARC_1 | | 0.7207 | | | 0.7138 | | 0.7095 |
| SPRY1_1 | SPARC_1 | | TIMP1_3 | FYN_3 | | ITGA5_1 | |
| SPRY1_1 | | 0.4152 | | | 0.4138 | | 0.4125 |
| SPRY2_2 | TGFBI_1 | | LEF_1 | PI3K_2 | | CUL4A_1 | |
| SPRY2_2 | | 0.3209 | | | 0.315 | | 0.3058 |

TABLE C-continued

| | | | | | | |
|---|---|---|---|---|---|---|
| STK15_2 | CMYC_3 | | FAP_1 | | TIMP2_1 | |
| STK15_2 | E2F1_3 | 0.3913 | ANXA1_2 | -0.3863 | C_SRC_1 | |
| TCF_1_1 | TLN1_1 | 0.3493 | UPA_3 | -0.3475 | CTSL_2 | |
| TCF_1_1 | TIMP2_1 | 0.64 | PAI1_3 | 0.639 | UPA_3 | |
| THBS1_1 | RRM2_1 | 0.6022 | CDC2_1 | 0.6019 | CHK1_2 | |
| THBS1_1 | ITGAV_1 | 0.3887 | MGAT5_1 | 0.3809 | AKT3_2 | |
| TIMP1_3 | P21_3 | 0.3095 | AREG_2 | 0.309 | BUB1_1 | |
| TIMP1_3 | UPA_3 | -0.3471 | CAPG_1 | 0.3458 | CD18_2 | |
| TOP2A_4 | SNRPF_2 | 0.3277 | PCNA_2 | 0.3228 | SLC31A1_1 | |
| TOP2A_4 | CCNA2_1 | 0.4076 | DHFR_2 | 0.4072 | DR4_2 | |
| TP53BP1_2 | | 0.3424 | | 0.3417 | | |

| Variable | out18 | | out19 | | out20 | _lstyle |
|---|---|---|---|---|---|---|
| AMFR_1 | TAGLN_3 | | FOXO3A_1 | | CHFR_1 | 1 |
| AMFR_1 | | | | 0.2535 | | 0.2474 | 2 |
| ANXA1_2 | CXCR4_3 | | INHBA_1 | 0.454 | WISP1_1 | 0.4497 | 2 |
| ANXA1_2 | MMP2_2 | | EPAS1_1 | 0.2911 | VIM_3 | 0.2884 | 1 |
| APC_4 | CDC2_1 | | TK1_2 | 0.3799 | C20_ORF1_1 | 0.3655 | 2 |
| APC_4 | AREG_2 | | CTSL_2 | 0.3911 | TGFBI_1 | 0.3851 | 1 |
| AURKB_1 | CTGF_1 | | CXCL12_1 | 0.6912 | PDGFC_3 | 0.6788 | 2 |
| AURKB_1 | S100P_1 | | APG_1_1 | 0.2117 | EGLN3_1 | 0.211 | 1 |
| AXIN_2_3 | MGAT5_1 | | GCNT1_1 | 0.3249 | TLN1_1 | 0.323 | 2 |
| AXIN_2_3 | EPHB6_1 | | EREG_1 | 0.3038 | ROCK2_1 | -0.289 | 1 |
| BGN_1 | CRIPTO_TDGF1_OFFICIAL_1 | | VEGF_ALTSPLICE2_1 | | AURKB_1 | 2 |
| BGN_1 | | | | 0.1884 | | 0.1879 | 0.1843 | 1 |
| BIK_1 | CCNB1_2 | | ENO1_1 | 0.4432 | CENPA_1 | 0.4355 | 2 |
| BIK_1 | TGFBI_1 | | TP53BP1_2 | 0.3177 | AXIN1_1 | 0.313 | 1 |
| BRAF_5 | P21_3 | | AXIN_2_3 | -0.3673 | CDX2_3 | 0.3627 | 2 |
| BRAF_5 | CENPF_1 | | REG4_1 | 0.3773 | PS2_2 | -0.3674 | 1 |
| BRAF_SNP1_6 | THBS1_1 | | AKT3_2 | 0.6188 | CTGF_1 | 0.595 | 2 |
| BRAF_SNP1_6 | | | | | | 0.6145 | |
| BRCA2_2 | | | | | | | |
| BUB1_1 | | | | | | | |
| BUB1_1 | | | | | | | |
| B_CATENIN_3 | | | | | | | |
| B_CATENIN_3 | | | | | | | |
| C20ORF126_1 | | | | | | | |
| C20ORF126_1 | | | | | | | |
| C20_ORF1_1 | | | | | | | |
| C20_ORF1_1 | | | | | | | |
| CALD1_2 | | | | | | | |
| CALD1_2 | | | | | | | |

TABLE C-continued

| | | | | | | |
|---|---|---|---|---|---|---|
| CASP9_1 | CRYAB_1 | | VEGFB_1 | 0.1781 | CCNA2_1 | 1 |
| CASP9_1 | | 0.181 | | | | 2 |
| CCNE2_2 | NRP2_2 | | CHK1_2 | 0.28 | NEDD8_2 | 2 |
| CCNE2_2 | EFP_3 | -0.2801 | CDC2_1 | | | 1 |
| CCNE2_VARIANT_1_1 | | | | | MCM6_3 | 2 |
| CCNE2_VARIANT_1_1 | | 0.2868 | | 0.2859 | | 2 |
| CD44E_1 | CMYC_3 | 0.3463 | MAD2L1_1 | 0.3318 | EIF4E_1 | 1 |
| CD44E_1 | BGN_1 | | CD68_2 | | SPARC_1 | 2 |
| CD44S_1 | | 0.5448 | EGLN3_1 | 0.534 | | 1 |
| CD44V6_1 | PKR2_1 | 0.3123 | | 0.3118 | SLC25A3_2 | 2 |
| CD44V6_1 | TIMP1_3 | | FYN_3 | | SNAI2_1 | 1 |
| CD68_2 | | 0.4491 | | 0.449 | | 2 |
| CDC2_1 | SNRPF_2 | 0.4625 | PCNA_2 | 0.4446 | CDC25C_1 | 1 |
| CDC2_1 | P53R2_3 | | PI3K_2 | | RANBP2_3 | 2 |
| CDC4_1 | | 0.2415 | | 0.2412 | | 1 |
| CDH11_1 | TIMP1_3 | 0.6452 | VIM_3 | 0.6376 | CTGF_1 | 2 |
| CDH11_1 | CDH1_INTRON_2_2 | | CD24_1 | | CMYC_3 | 1 |
| CDX2_3 | | 0.409 | | 0.4051 | | 2 |
| CENPA_1 | CENPF_1 | 0.3016 | MMP2_2 | -0.3012 | CYR61_1 | 1 |
| CENPA_1 | FBXO5_1 | | C20_ORF1_1 | | MCM2_2 | 2 |
| CENPF_1 | | 0.3819 | | 0.3773 | | 1 |
| CHFR_1 | ITGB3_1 | 0.3346 | VIM_3 | 0.3306 | CXCL12_1 | 2 |
| CHFR_1 | CDC6_1 | | SLC25A3_2 | | C_MYB_MYB_OFFICIAL_1 | 1 |
| CHK1_2 | | 0.3707 | | 0.3672 | | 2 |
| CHK1_2 | C20ORF126_1 | 0.2128 | CLIC1_1 | 0.2119 | EFNB2_1 | 1 |
| CLDN1_1 | TMSB10_1 | | HCRA_A_2 | | FOXO3A_1 | 2 |
| CLDN1_1 | | 0.309 | | 0.3081 | | 1 |
| CLIC1_1 | NOTCH1_1 | 0.2509 | UNC5B_1 | 0.24 | DLC1_1 | 2 |
| CLIC1_1 | CMET_2 | | ODC1_1 | | C_MYB_MYB_OFFICIAL_1 | 2 |
| CLTC_1 | | 0.3894 | | 0.3882 | | 1 |
| CLTC_1 | PDGFC_3 | 0.6281 | CXCL12_1 | 0.6206 | HSPG2_1 | 2 |
| CMYC_3 | SFRP2_1 | | TIMP1_3 | | ADAMTS12_1 | 2 |
| CMYC_3 | | 0.6536 | | 0.6518 | | 1 |
| COL1A1_1 | MYLK_1 | 0.2954 | KLF5_1 | 0.2953 | HCRA_A_2 | 2 |
| COL1A1_1 | TIMP2_1 | | SFRP2_1 | | MCP1_1 | 2 |
| COL1A2_1 | | 0.5016 | | 0.5015 | | 1 |
| COL1A2_1 | OPN_OSTEOPONTIN_3 | 0.5915 | NRP2_2 | 0.5813 | SPARC_1 | 2 |
| CREBBP_1 | DLC1_1 | | TLN1_1 | | CD44S_1 | 2 |
| CREBBP_1 | | 0.5611 | | 0.5583 | | 1 |
| CTSB_1 | | | | | | 2 |
| CTSB_1 | | | | | | 2 |
| CTSL_2 | | | | | | 1 |
| CTSL_2 | | | | | | 2 |
| CXCL12_1 | | | | | | 1 |
| CXCL12_1 | | | | | | 2 |

TABLE C-continued

| | | | | | |
|---|---|---|---|---|---|
| CYR61_1 | BGN_1 | | MCP1_1 | | WISP1_1 | 1 |
| CYR61_1 | | 0.5458 | | 0.5436 | | 1 |
| DLC1_1 | ADAMTS12_1 | | IGFBP7_1 | | CXCL12_1 | 2 |
| DLC1_1 | | 0.5642 | | 0.564 | | 1 |
| DUSP1_1 | KLF6_1 | | BGN_1 | | EPAS1_1 | 2 |
| DUSP1_1 | | 0.4868 | | 0.4773 | | 1 |
| E2F1_3 | CTSB_1 | | FAP_1 | | TOP2A_4 | 2 |
| E2F1_3 | | −0.3492 | | −0.3434 | | 1 |
| EFNB2_1 | CUL4A_1 | | CLAUDIN_4_2 | | B_CATENIN_3 | 2 |
| EFNB2_1 | | 0.2961 | | 0.2958 | | 1 |
| EGR3_1 | KLF6_1 | | EMP1_1 | | BGN_1 | 2 |
| EGR3_1 | | 0.2997 | | 0.2978 | | 1 |
| EI24_1 | KLF5_1 | | RRM2_1 | | HRAS_1 | 2 |
| EI24_1 | | 0.2735 | | 0.2724 | | 1 |
| ENO1_1 | EIF4E_1 | | HNRPD_1 | | CCNB1_2 | 2 |
| ENO1_1 | | 0.395 | | 0.3931 | | 1 |
| EPAS1_1 | ITGB3_1 | | COL1A2_1 | | CALD1_2 | 2 |
| EPAS1_1 | | 0.4622 | | 0.4607 | | 1 |
| ESPL1_3 | TS_1 | | PCNA_1 | | C20_ORF1_1 | 2 |
| ESPL1_3 | | 0.356 | | 0.3534 | | 1 |
| FBXO5_1 | CDC2_1 | | MCM6_3 | | MYBL2_1 | 2 |
| FBXO5_1 | | 0.3287 | | 0.3234 | | 1 |
| FGF18_2 | BGN_1 | | DLC1_1 | | TGFB2_2 | 2 |
| FGF18_2 | | 0.253 | | 0.25 | | 1 |
| FGF2_2 | IGFBP7_1 | | ITGA5_1 | | ITGB1_1 | 2 |
| FGF2_2 | | 0.2841 | | 0.2812 | | 1 |
| FOS_1 | DLC1_1 | | VCL_1 | | CXCR4_3 | 2 |
| FOS_1 | | 0.3491 | | 0.3409 | | 1 |
| FOXO3A_1 | LRP5_1 | | GSTP_3 | | THBS1_1 | 2 |
| FOXO3A_1 | | 0.3785 | | 0.3775 | | 1 |
| FPGS_1 | NEDD8_2 | | CMYC_3 | | ANXA1_2 | 2 |
| FPGS_1 | | 0.2493 | | −0.2475 | | 1 |
| FST_1 | INHBA_1 | | IGFBP3_3 | | CYR61_1 | 2 |
| FST_1 | | 0.3353 | | 0.3352 | | 1 |
| FZD1_1 | AKT3_2 | | CTGF_1 | | RUNX1_2 | 2 |
| FZD1_1 | | 0.5202 | | 0.5168 | | 1 |
| GJB2_1 | CTHRC1_1 | | FAP_1 | | SNAI2_1 | 2 |
| GJB2_1 | | 0.4475 | | 0.4401 | | 1 |
| GPX1_2 | PLK3_1 | | TGFB3_1 | | TP_3 | 2 |
| GPX1_2 | | 0.3404 | | 0.3396 | | 1 |
| GRB10_1 | TGFB3_1 | | HSPE1_1 | | SURV_2 | 2 |
| GRB10_1 | | 0.2026 | | −0.2017 | | 1 |
| GSK3B_2 | GIT1_1 | | TAGLN_3 | | SNRPF_2 | 2 |
| GSK3B_2 | | 0.3639 | | 0.362 | | 1 |
| HES6_1 | TCF_1_1 | | NOTCH1_1 | | H2AFZ_2 | 2 |
| HES6_1 | | 0.2824 | | 0.28 | | 1 |
| HIF1A_3 | CXCL12_1 | | ROCK1_1 | | RBX1_1 | 2 |
| HIF1A_3 | | 0.4727 | | 0.4665 | | 1 |
| HLA_G_2 | CXCL12_1 | | C20ORF126_1 | | TGFBR1_1 | 2 |
| HLA_G_2 | | 0.0919 | | −0.0903 | | 1 |
| HNRPAB_3 | MCM6_3 | | ITGAV_1 | | HSPG2_1 | 2 |
| HNRPAB_3 | | 0.3728 | | 0.3664 | | 2 |

TABLE C-continued

| | | | | | | |
|---|---|---|---|---|---|---|
| HNRPD_1 | GPX1_2 | | ESPL1_3 | | BUB1_1 | 1 |
| HNRPD_1 | NME1_3 | 0.3129 | RANBP2_3 | 0.3115 | MADH4_1 | 1 |
| HOXA5_1 | CTSB_1 | -0.25 | KLF5_1 | 0.2467 | BAX_1 | 2 |
| HOXA5_1 | | -0.1472 | S100P_1 | 0.1469 | EREG_1 | 1 |
| HOXB13_1 | LGALS3_1 | 0.3131 | CD44S_1 | 0.3061 | SFRP2_1 | 2 |
| HOXB13_1 | LOXL2_1 | 0.3347 | CMET_2 | 0.3311 | CALD1_2 | 1 |
| HSD17B2_1 | NR4A1_1 | 0.1761 | CCNA2_1 | 0.175 | SURV_2 | 2 |
| HSD17B2_1 | HSPG2_1 | -0.3878 | IGFBP7_1 | 0.3821 | DLC1_1 | 1 |
| HSPA1A_1 | ITGB1_1 | 0.4444 | ANTXR1_1 | 0.4437 | NRP2_2 | 2 |
| HSPA1A_1 | MMP2_2 | 0.6159 | MMP2_2 | 0.6115 | PDGFRA_2 | 1 |
| HSPA1B_1 | TIMP1_3 | 0.6157 | ITGAV_1 | 0.5986 | IGFBP5_1 | 2 |
| HSPA1B_1 | TIMP3_3 | 0.4307 | VCP_1 | 0.426 | MCM3_3 | 2 |
| HSPE1_1 | CDC25C_1 | 0.4369 | RCC1_1 | 0.4343 | CENPA_1 | 1 |
| HSPE1_1 | TK1_2 | 0.3733 | ESPL1_3 | 0.3731 | RRM2_1 | 2 |
| IGFBP3_3 | KIF22_1 | 0.3998 | PTCH_1 | 0.3996 | GSK3B_2 | 2 |
| IGFBP3_3 | KIFC1_1 | 0.3783 | MYBL2_1 | 0.3781 | CTSB_1 | 1 |
| IGFBP5_1 | ST14_1 | 0.3039 | P14ARF_1 | -0.2978 | CRIPTO_TDGF1_OFFICIAL_1 | 1 |
| IGFBP5_1 | F3_1 | -0.2134 | EPHB2_1 | 0.212 | CCR7_1 | -0.2119 | 2 |
| IGFBP7_1 | CAD17_1 | 0.309 | CMET_2 | -0.3045 | LAMC2_2 | 0.3004 | 2 |
| IL6ST_3 | CD68_2 | 0.378 | IGFBP5_1 | 0.3738 | KLRK1_2 | 0.3723 | 1 |
| IL6ST_3 | SBA2_1 | 0.3366 | NRP2_2 | 0.3363 | TAGLN_3 | 0.3333 | 2 |
| KL_67_2 | MYLK_1 | 0.3957 | COL1A2_1 | 0.3855 | HIF1A_3 | 0.3848 | 2 |
| KL_67_2 | THY1_1 | 0.2931 | CALD1_2 | 0.2863 | SFRP2_1 | 0.2853 | 1 |
| KIF22_1 | CDC42BPA_1 | 0.5923 | CTGF_1 | 0.5833 | VIM_3 | 0.5714 | 2 |
| KIF22_1 | PDGFC_3 | 0.5365 | CDC20_1 | 0.5297 | RCC1_1 | 0.5285 | 2 |
| KIFC1_1 | CTHRC1_1 | 0.4403 | RUNX1_2 | 0.4398 | INHBA_1 | 0.434 | 1 |
| KIFC1_1 | PCNA_2 | | | | | 2 |
| KLF5_1 | COL1A2_1 | 0.4249 | | 0.422 | | 0.4169 | 2 |
| KLF5_1 | | | | | | | |
| KLK10_3 | | | | | | | |
| KLK10_3 | | | | | | | |
| KLK6_1 | | | | | | | |
| KLK6_1 | | | | | | | |
| KLRK1_2 | | | | | | | |
| KLRK1_2 | | | | | | | |
| KRT8_3 | | | | | | | |
| KRT8_3 | | | | | | | |
| LAT_1 | | | | | | | |
| LAT_1 | | | | | | | |
| LEF_1 | | | | | | | |
| LEF_1 | | | | | | | |
| LMYC_2 | | | | | | | |
| LMYC_2 | | | | | | | |
| LOXL2_1 | | | | | | | |
| LOXL2_1 | | | | | | | |
| LOX_1 | | | | | | | |
| LOX_1 | | | | | | | |
| MAD2L1_1 | | | | | | | |
| MAD2L1_1 | | | | | | | |
| MADH7_1 | | | | | | | |
| MADH7_1 | | | | | | | |

TABLE C-continued

| | | | | | |
|---|---|---|---|---|---|
| MASPIN_2 | PTP4A3_V2_1 | | EFNB2_1 | 0.3621 | ATP5A1_1 | 0.3601 | 1
| MASPIN_2 | | -0.3648 | TOP2A_4 | | PLK_3 | 0.3864 | 1
| MCM3_3 | CENPF_1 | 0.3979 | HIF1A_3 | 0.39 | CYR61_1 | 0.5436 | 2
| MCP1_1 | IGFBP5_1 | 0.5511 | LOXL2_1 | 0.5464 | SPARC_1 | 0.2972 | 1
| MCP1_1 | ITGAV_1 | 0.3087 | TIMP1_3 | 0.3064 | MYLK_1 | 0.5897 | 2
| MMP1_1 | CTSL_2 | 0.5971 | CENPF_1 | 0.5962 | BRAF_5 | 0.2867 | 1
| MMP2_2 | CCNE2_VARIANT_1_1 | 0.2926 | CTGF_1 | 0.2893 | MGAT5_1 | 0.2538 | 2
| MSH2_3 | CLIC1_1 | 0.2594 | PDGFA_3 | 0.2563 | TIMP3_3 | 0.2506 | 1
| MSH3_2 | CXCR4_3 | 0.276 | SOD2_1 | 0.2626 | TP_3 | 0.5083 | 2
| NR4A1_1 | CD18_2 | 0.5172 | TAGLN_3 | 0.5163 | RHOB_1 | 0.3139 | 1
| NRP1_1 | TGFBR1_1 | 0.3153 | SFRP2_1 | 0.3152 | IGFBP5_1 | 0.6005 | 2
| PDGFA_3 | WISP1_1 | 0.606 | AKT3_2 | 0.6006 | BGN_1 | 0.3536 | 2
| PDGFC_3 | VIM_3 | 0.3581 | GJA1_1 | 0.357 | SFRP4_1 | 0.4582 | 1
| PDGFD_2 | CTGF_1 | 0.4666 | ODC1_3 | 0.4657 | CKS2_2 | -0.2632 | 2
| PDGFRA_2 | ITGA5_1 | 0.2653 | LAMA3_1 | 0.2643 | VDAC2_1 | 0.4196 | 2
| PFN2_1 | OPN_OSTEOPONTIN_3 | 0.4289 | TUFM_1 | 0.4249 | TK1_1 | 0.2937 | 1
| PKR2_1 | MCM3_3 | 0.301 | CMYC_3 | 0.2956 | TERC_2 | 0.3064 | 2
| PRDX2_1 | THBS1_1 | 0.3133 | RCC1_1 | 0.3082 | CDC25C_1 | 0.394 | 2
| RAB32_1 | MAD2L1_1 | 0.4022 | REG4_1 | 0.4006 | ITGAV_1 | 0.3188 | 1
| RAD54L_1 | K_RAS_10 | 0.3199 | HNRPD_1 | 0.3191 | KIF22_1 | 0.3731 | 2
| RANBP2_3 | UBE2M_2 | 0.3837 | PDGFC_3 | 0.3768 | FAP_1 | 0.3377 | 1
| RCC1_1 | ITGB3_1 | 0.3446 | PDGFA_3 | 0.3394 | MASPIN_2 | -0.2938 | 2
| RHOB_1 | MGAT5_1 | 0.3001 | TAGLN_3 | 0.2957 | TIMP3_3 | 0.4708 | 1
| ROCK2_1 | TGFB3_1 | 0.4743 | KLF5_1 | 0.4742 | CYP3A4_2 | 0.2433 | 2
| RUNX1_2 | EREG_1 | -0.2478 | GADD45B_1 | 0.2473 | CTSB_1 | 0.2505 | 1
| S100P_1 | ENO1_1 | 0.2533 | VDAC2_1 | 0.2523 | MUC2_1 | 0.3645 | 2
| SAT_1 | LAMA3_1 | 0.3748 | | 0.3683 | | |

TABLE C-continued

| | | | | | |
|---|---|---|---|---|---|
| SIAT4A_2 | SFRP2_1 | | IGFBP7_1 | | CD44S_1 | |
| SIAT4A_2 | | | | 0.386 | | 0.3833 | 0.3826 | 1 |
| SKP2_1 | ODC1_3 | | HDAC1_1 | | CDC25C_1 | |
| SKP2_1 | | | | 0.3224 | | 0.3143 | 0.3053 | 2 |
| SOD1_1 | VDAC2_1 | | NME1_3 | | MUC2_1 | |
| SOD1_1 | | | | 0.2227 | | 0.2203 | 0.2185 | 2 |
| SOS1_1 | CDC2_1 | | WISP1_1 | | VCP_1 | |
| SOS1_1 | | | | −0.2507 | | 0.2479 | −0.2473 | 1 |
| SPARC_1 | SFRP2_1 | | CTHRC1_1 | | PDGFC_3 | |
| SPARC_1 | | | | 0.6994 | | 0.6964 | 0.6961 | 1 |
| SPRY1_1 | BAD_1 | | DPYD_2 | | SGCB_1 | |
| SPRY1_1 | | | | 0.4051 | | 0.4046 | 0.4012 | 2 |
| SPRY2_2 | KCNH2_ISO_A_C_1 | | TLN1_1 | | CRIPTO_TDGF1_OFFICIAL_1 | |
| SPRY2_2 | | | | 0.2923 | | 0.2825 | 0.2821 | 1 |
| STK15_2 | MAD2L1_1 | | C20ORF126_1 | | TIMP3_3 | |
| STK15_2 | | | | 0.3755 | | 0.3739 | −0.3732 | 2 |
| TCF_1_1 | VCP_1 | | CXCR4_3 | | VEGFB_1 | |
| TCF_1_1 | | | | 0.3407 | | −0.3387 | 0.338 | 1 |
| THBS1_1 | CALD1_2 | | IGFBP5_1 | | CTHRC1_1 | |
| THBS1_1 | | | | 0.6188 | | 0.6177 | 0.5994 | 2 |
| TIMP1_3 | INHBA_1 | | MCP1_1 | | COL1A1_1 | |
| TIMP1_3 | | | | 0.5947 | | 0.5922 | 0.5731 | 2 |
| TOP2A_4 | CDC20_1 | | CCNB1_1 | | HSPE1_1 | |
| TOP2A_4 | | | | 0.3724 | | 0.3692 | 0.3686 | 1 |
| TP53BP1_2 | MADH2_1 | | PDGFRA_2 | | FZD1_1 | |
| TP53BP1_2 | | | | 0.2951 | | 0.2892 | 0.2882 | 2 |
| UBE2C_1 | CENPF_1 | | CDC25C_1 | | MAD2L1_1 | |
| UBE2C_1 | | | | 0.3286 | | 0.3254 | 0.3219 | 1 |
| UPP1_1 | ENO1_1 | | ANXA2_2 | | LAMA3_1 | |
| UPP1_1 | | | | 0.306 | | 0.3042 | 0.299 | 2 |
| VCP_1 | NEDD8_2 | | CLDN7_2 | | BUB1_1 | |
| VCP_1 | | | | −0.388 | | 0.3854 | 0.3796 | 1 |
| VDAC2_1 | MADH4_1 | | PLK_3 | | ITGB1_1 | |
| VDAC2_1 | | | | 0.3017 | | 0.3017 | 0.2988 | 2 |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08632980B2). An electronic copy of the "Sequence Listing" will also be available from the USPTO upon request and payment of the fee set forth in 37 CFR 1.19(b)(3).

What is claimed:

1. A method of predicting whether a human patient diagnosed with colorectal cancer has an increased or decreased likelihood of a positive clinical response to treatment with chemotherapy, comprising:
    extracting RNA from a fixed, paraffin-embedded colorectal cancer tissue sample obtained from the patient;
    quantitatively measuring a level of an RNA transcript of HNRPD;
    normalizing the level of the RNA transcript of HNRPD to obtain a normalized HNRPD expression level;
    using a computer-implemented program to compare the normalized HNRPD expression level to a statistical model-predicted relationship between normalized HNRPD expression level and likelihood of positive response to treatment with chemotherapy determined from a population of at least 679 patients with colorectal cancer treated with chemotherapy and with known clinical outcome and a population of at least 578 patients with colorectal cancer not treated with chemotherapy and with known clinical outcome; and
    generating a report comprising a prediction whether the patient has an increased or decreased likelihood of exhibiting a positive response to chemotherapy.

2. The method of claim 1, wherein the measuring is done by a PCR-based method.

3. The method of claim 1, wherein the measuring is done by an array-based method.

4. The method of claim 1, wherein the measuring is done by a sequencing-based method.

5. The method of claim 1, wherein the colorectal cancer is Dukes B (stage II) or Dukes C (stage III) colorectal cancer.

6. The method of claim 1, wherein the colorectal cancer is colon cancer.

7. The method of claim 6, wherein the colon cancer is Duke B (stage II) or Dukes C (stage III) colon cancer.

8. The method of claim 1, wherein the chemotherapy is a 5-fluorouracil (5-FU) therapy.

9. The method of claim 8, wherein the 5-FU therapy is leucovorin-mediated fluorouracil (5-FU/LV) therapy.

10. The method of claim 1, wherein the clinical response is expressed in terms of Recurrence-Free Interval (RFI), Overall Survival (OS), Disease-Free Survival (DFS), or Distant Recurrence-Free Interval (DRFI).

11. The method of claim 1, wherein the level of the RNA transcript of HNRPD is quantitative measured using about 1 nanogram of the extracted RNA.

12. A method of predicting whether a human patient diagnosed with colorectal cancer has an increased or decreased likelihood of a positive clinical response to treatment with chemotherapy, comprising:
    extracting RNA from a fixed, paraffin-embedded colorectal cancer tissue sample obtained from the human patient;
    reverse transcribing an RNA transcript of HNRPD to produce a cDNA of HNRPD;
    amplifying the cDNA of HNRPD;
    producing an amplicon of the RNA transcript of HNRPD;
    quantitatively assaying a level of the amplicon of the RNA transcript of HNRPD;
    normalizing the level of the amplicon of the RNA transcript of HNRPD against a level of an amplicon of at least one reference RNA transcript in the tissue sample to provide a normalized HNRPD amplicon level;
    using a computer-implemented program to compare the normalized HNRPD amplicon level to a statistical model-predicted relationship between normalized HNRPD amplicon level and likelihood of positive response to treatment with chemotherapy determined from a population of at least 679 patients with colorectal cancer treated with chemotherapy and with known clinical outcome and a population of at least 578 patients with colorectal cancer not treated with chemotherapy and with known clinical outcome; and
    generating a report comprising a prediction whether the human patient diagnosed with colorectal cancer has an increased or decreased likelihood of a positive clinical response to treatment with chemotherapy, wherein the clinical response is expressed in terms of Recurrence-Free Interval (RFI), Overall Survival (OS), Disease-Free Survival (DFS), or Distant Recurrence-Free Interval (DRFI).

13. The method of claim 12, wherein the level of the amplicon of the RNA transcript of HNRPD is a threshold cycle ($C_t$) value and the normalized HNRPD amplicon level is a normalized $C_t$ value.

14. The method of claim 12, wherein the colorectal cancer is Dukes B (stage II) or Dukes C (stage III) colorectal cancer.

15. The method of claim 12, wherein said colorectal cancer is colon cancer.

16. The method of claim 15, wherein said colon cancer is Duke B (stage II) or Dukes C (stage III) colon cancer.

17. The method of claim 12, wherein the chemotherapy is a 5-fluorouracil (5-FU) therapy.

18. The method of claim 12, wherein the RNA transcript of HNRPD is reverse transcribed using about 1 nanogram of the extracted RNA.

* * * * *